(12) United States Patent
Fecteau et al.

(10) Patent No.: US 11,866,505 B2
(45) Date of Patent: Jan. 9, 2024

(54) ANTI-CD30L ANTIBODIES AND USES THEREOF

(71) Applicants: PROMETHEUS BIOSCIENCES, INC., San Diego, CA (US); DR. FALK PHARMA GMBH, Freiburg im Breisgau (DE)

(72) Inventors: Jessie-Farah Fecteau, Escondido, CA (US); Mark Renshaw, San Diego, CA (US); Johan Fransson, San Diego, CA (US); Olivier Laurent, San Diego, CA (US); Burton Barnett, Poway, CA (US)

(73) Assignees: PROMETHEUS BIOSCIENCES, INC., San Diego, CA (US); DR. FALK PHARMA GMBH, Freiburg im Breisgau (DE)

( * ) Notice: Subject to any disclaimer, the term of this patent is extended or adjusted under 35 U.S.C. 154(b) by 0 days.

(21) Appl. No.: 17/822,598

(22) Filed: Aug. 26, 2022

(65) Prior Publication Data

US 2023/0060624 A1    Mar. 2, 2023

Related U.S. Application Data

(63) Continuation of application No. PCT/US2022/016565, filed on Feb. 16, 2022.
(Continued)

(51) Int. Cl.
C07K 16/24 (2006.01)
C07K 16/28 (2006.01)
(Continued)

(52) U.S. Cl.
CPC .......... *C07K 16/2878* (2013.01); *A61P 37/06* (2018.01); *C07K 16/2875* (2013.01);
(Continued)

(58) Field of Classification Search
None
See application file for complete search history.

(56) References Cited

U.S. PATENT DOCUMENTS

| 5,500,362 A | 3/1996 | Robinson et al. |
| 5,624,821 A | 4/1997 | Winter et al. |

(Continued)

FOREIGN PATENT DOCUMENTS

| WO | WO-9324135 A1 | 12/1993 |
| WO | WO-9429351 A2 | 12/1994 |

(Continued)

OTHER PUBLICATIONS

Herold et al., Determinants of the assembly and function of antibody variable domains, Scientific Reports, 7:12276, DOI:10.1038/s41598-017-12519-9, Sep. 2017.*

(Continued)

*Primary Examiner* — Claire Kaufman
(74) *Attorney, Agent, or Firm* — Wilson Sonsini Goodrich & Rosati

(57) ABSTRACT

Described herein are anti-CD30L antibodies and pharmaceutical compositions for the treatment of autoimmune diseases and disorders such inflammatory bowel disease (IBD), including Crohn's Disease (CD) and ulcerative colitis (UC).

30 Claims, 9 Drawing Sheets

Specification includes a Sequence Listing.

Related U.S. Application Data

(60) Provisional application No. 63/150,373, filed on Feb. 17, 2021.

(51) Int. Cl.
*A61P 37/06* (2006.01)
*A61K 39/00* (2006.01)

(52) U.S. Cl.
CPC .... *A61K 2039/505* (2013.01); *C07K 2317/24* (2013.01); *C07K 2317/565* (2013.01); *C07K 2317/732* (2013.01); *C07K 2317/92* (2013.01)

(56) References Cited

U.S. PATENT DOCUMENTS

| | | | |
|---|---|---|---|
| 5,648,260 | A | 7/1997 | Winter et al. |
| 5,821,337 | A | 10/1998 | Carter et al. |
| 6,194,551 | B1 | 2/2001 | Idusogie et al. |
| 6,602,684 | B1 | 8/2003 | Umana et al. |
| 7,273,609 | B2 * | 9/2007 | Mohler .............. C07K 16/2875 530/387.3 |
| 7,371,826 | B2 | 5/2008 | Presta |
| 9,926,373 | B2 * | 3/2018 | Andersen ................ A61P 25/00 |
| 2005/0014934 | A1 | 1/2005 | Hinton et al. |
| 2008/0003221 | A1 | 1/2008 | Podack |
| 2017/0088620 | A1 * | 3/2017 | Nioi .................... A61K 39/3955 |

FOREIGN PATENT DOCUMENTS

| | | |
|---|---|---|
| WO | WO-9951642 A1 | 10/1999 |
| WO | WO-0211767 A2 | 2/2002 |
| WO | WO-2013059732 A1 | 4/2013 |
| WO | WO-2013163377 A1 | 10/2013 |
| WO | WO-2017127537 A1 | 7/2017 |
| WO | WO-2019212899 A1 | 11/2019 |
| WO | WO-2020096046 A1 | 5/2020 |
| WO | WO-2022177963 A1 | 8/2022 |

OTHER PUBLICATIONS

Dondelinger et al., Understanding the Significance and Implications of Antibody Numbering and Antigen-Binding Surface/Residue Definition, Front. Immunol. 9:2278, doi.org/10.3389/fimmu.2018.02278, Oct. 16, 2018.*
Al-Lazikani et al.: Standard conformations for the canonical structures of immunoglobulins. J. Molec. Biol. 273:927-948, 1997.
Altschul et al.: Basic Local Alignment Search Tool. J. Mol. Biol. 215: 403-410 (1990).
Bich et al.: Reactivity and applications of new amine reactive cross-linkers for mass spectrometric detection of protein-protein complexes. Anal. Chem. 82(1):172-179 (2010).
Bracher et al.: Three-colour flow cytometric method to measure antibody-dependent tumour cell killing by cytotoxicity and phagocytosis. J. Immunol. Methods 323(2):160-171 (2007).
Bruggemann et al.: Comparison of the Effector Functions of Human Immunoglobulins Using a Matched Set of Chimeric Antibodies, J. Exp. Med. 166 (1987) 1351-1361).
Chowdhury: Engineering hot spots for affinity enhancement of antibodies. Methods Mol. Biol. 207:179-196, 2008.
Clackson et al.: Making antibody fragments using phage display libraries. Nature 352(6336):624-628 (1991).
Clynes et al.: Fc receptors are required in passive and active immunity to melanoma. Proc Natl Acad Sci U S A. 95(2):652-656 (1998).
Cunningham et al. High-Resolution Epitope Mapping of hGH-Receptor Interactions by Alanine-Scanning Mutagenesis. Science 244:1081-1085 (1989).
Duncan et al. The binding site for C1q on IgG. Nature 332(6166):738-40 (1988).
Gazzano-Santoro et al.: A non-radioactive complement-dependent cytotoxicity assay for anti-CD20 monoclonal antibody. J Immunol Methods 202(2):163-171 (Mar. 28, 1997).
Hargreaves et al.: Soluble CD30 binds to CD153 with high affinity and blocks transmembrane signaling by CD30. European Journal of Immunology. 32:163-173 (2002).
Hombach et al.: Blocking CD30 on T Cells by a Dual Specific CAR for CD30 and Colon Cancer Antigens Improves the CAR T Cell Response against CD30. Tumors. Molecular Therapy. 27(10):1825-1835 (2019).
Honegger et al.: Yet another numbering scheme for immunoglobulin variable domains: an automatic modeling and analysis tool. J Mol Biol 309(3):657-70 (2001).
Hoogenboom et al.: Overview of antibody phage-display technology and its applications. In: Methods in Molecular Biology. 178:1-37 (2001).
Idusogie et al.: Mapping of the C1q binding site on rituxan, a chimeric antibody with a human IgG1 Fc. J Immunol. Apr. 15, 2000;164(8):4178-84.
Kabat et al.: Sequences of Proteins of Immunological Interest. NIH Pub. No. 91-3242. Public Health Service, National Institutes of Health. 1:647-669 (1991).
Kanda et al.: Comparison of cell lines for stable production of fucose-negative antibodies with enhanced ADCC. Biotechnol. Bioeng. 94(4):680-688 (2006).
Karlin et al.: Applications and statistics for multiple high-scoring segments in molecular sequences. PNAS USA 90(12):5873-5787 (1993).
Lefranc et al.: IMGT unique numbering for immunoglobulin and T cell receptor variable domains and Ig superfamily V-like domains. Dev Comp Immunol 27(1):55-77 (2003).
Li et al.: Cell culture processes for monoclonal antibody production. Mabs. 2(5):466-477 (2010).
MacCallum et al.: Antibody-antigen interactions: contact analysis and binding site topography. J Mol Biol. 262(5):732-745 (1996).
Patel et al.: An improved assay for antibody dependent cellular cytotoxicity based on time resolved fluorometry. J Immunol Methods. Jul. 17, 1995;184(1):29-38.
Paul: Chapter 19. Fundamental Immunology 4th edition pp. 663-665 (1998).
PCT/US2022/016565 International Search Report and Written Opinion dated Apr. 14, 2022.
Portolano et al.: Lack of promiscuity in autoantigen-specific H and L chain combinations as revealed by human H and L chain "roulette". J. Immunol. 150:880-887 (1993).
Powell et al.: Construction and expression of a soluble form of human CD30 ligand with functional activity. Journal of Leukocyte Biology. 63:752-757 (1998).
Prometheus Biosciences, Inc. Form S-1 Registration Statement as filed with the Securities and Exchange Commission on Feb. 19, 2021 (246 pages).
Ravetch et al.: Fc receptors. Annu Rev Immunol. 9:457-92 (1991).
Ripka et al.: Two Chinese hamster ovary glycosylation mutants affected in the conversion of GDP-mannose to GDP-fucose. Arch Biochem Biophys. 249(2):533-545 (Sep. 1986).
Wallace et al.: Bispecific antibody-targeted phagocytosis of HER-2/neu expressing tumor cells by myeloid cells activated in vivo. J. Immunol. Methods 248:167-82 (2001).
Whitelegg et al. : WAM: an improved algorithm for modelling antibodies on the WEB. Protein Eng. 13:819-24 (2000).
Wiley et al.: Reverse signaling via CD30 ligand. Journal of Immunology. 157:3653-3639 (1996).
Wilkinson et al.: Antibody-dependent cell-mediated cytotoxicity: a flow cytometry-based assay using fluorophores. J Immunol Methods. Dec. 1, 2001;258(1-2):183-91.
Wisecarver et al.: A method for determination of antibody-dependent cellular cytotoxicity (ADCC) of human peripheral mononuclear cells. J Immunol Methods. May 23, 1985;79(2):277-82.
Wright et al.: Effect of glycosylation on antibody function: implications for genetic engineering TIBTECH 15(1):26-32 (1997).
Yamane-Ohnuki et al.: Establishment of FUT8 knockout Chinese hamster ovary cells: An ideal host cell line for producing completely

(56) References Cited

OTHER PUBLICATIONS defucosylated antibodies with enhanced antibody-dependent cellular cytotoxicity. Biotech. Bioeng. 87:614-622 (2004).

* cited by examiner

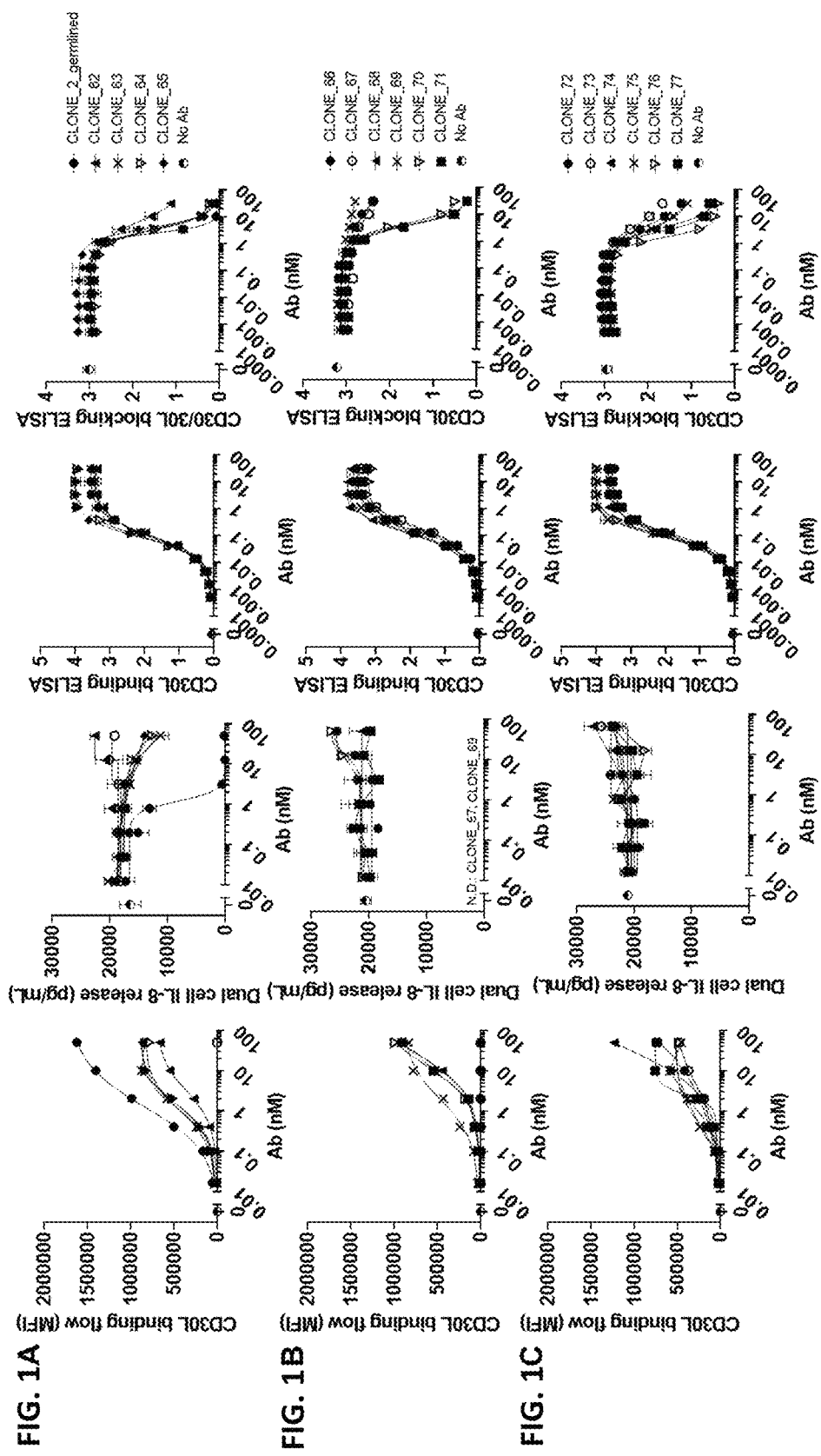

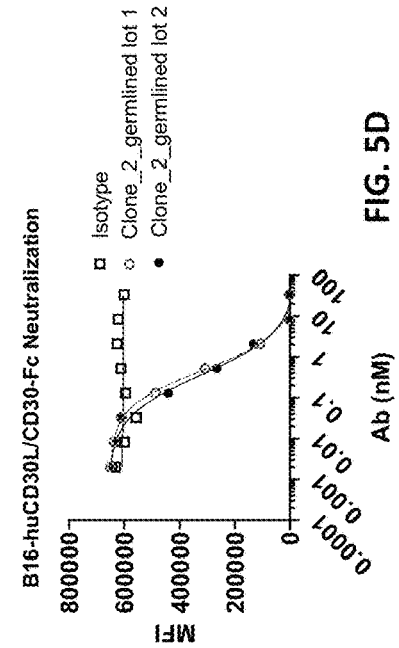
FIG. 5B
FIG. 5D
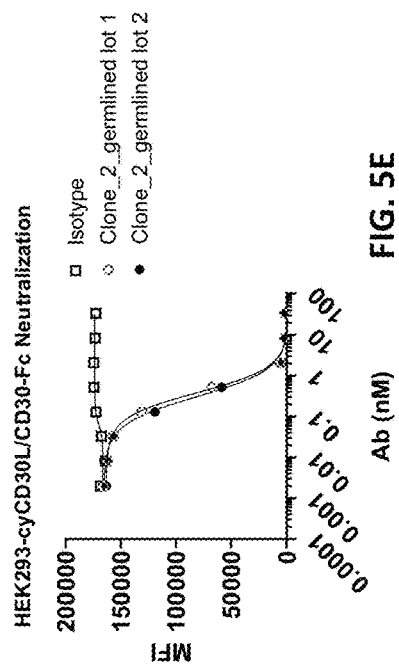
FIG. 5C
FIG. 5E
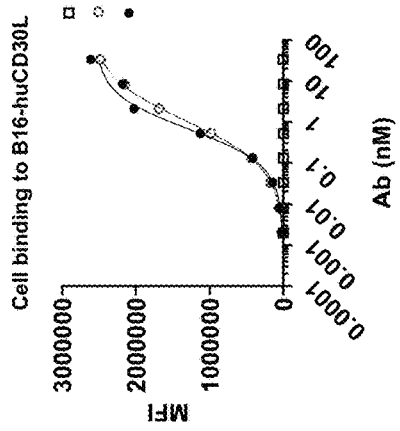
FIG. 5A

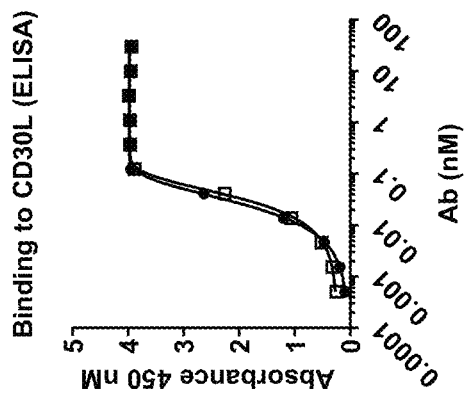
FIG. 5H
FIG. 5I
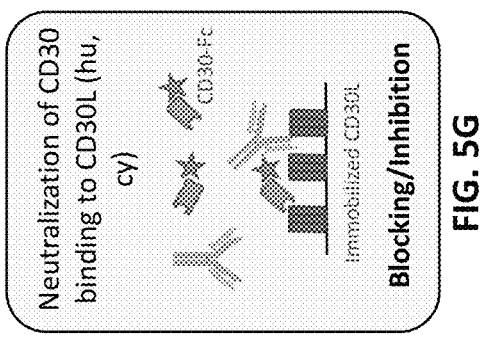
FIG. 5F
FIG. 5G

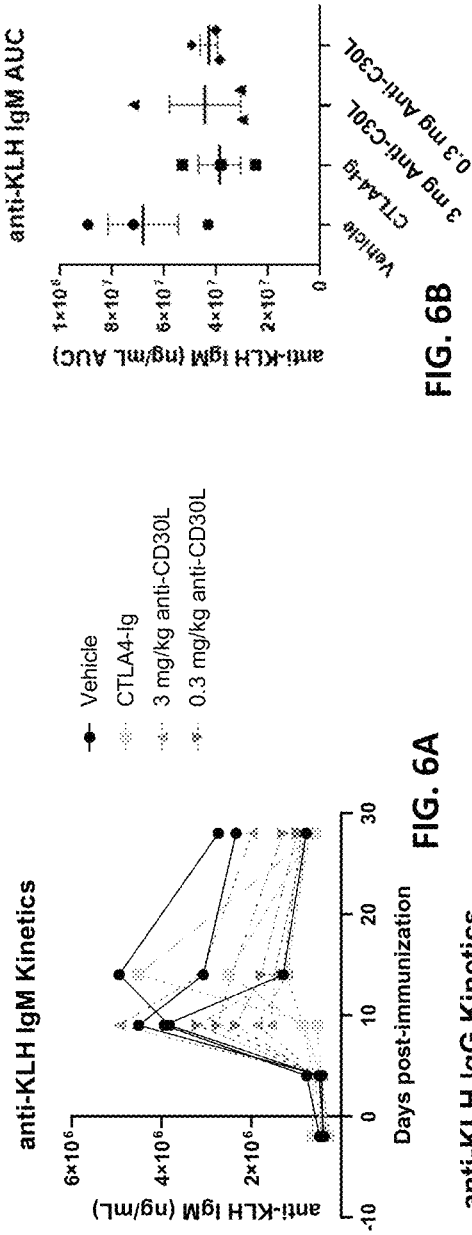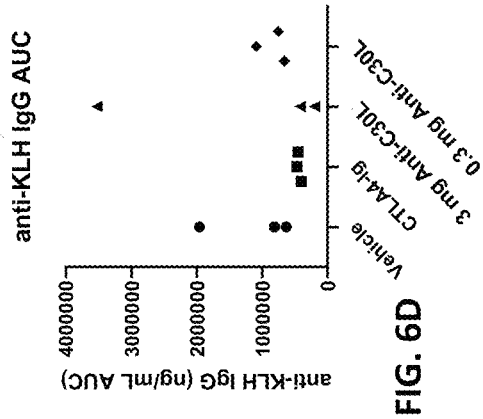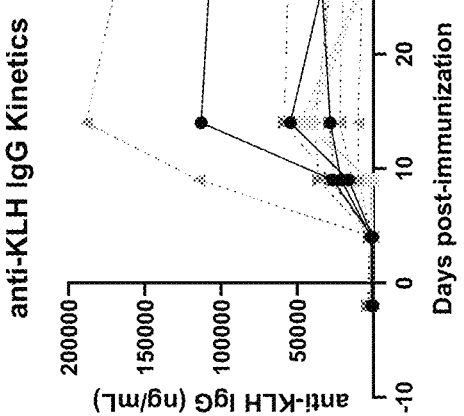

ANTI-CD30L ANTIBODIES AND USES THEREOF

CROSS-REFERENCE

This is a continuation of International Application No. PCT/US2022/016565, filed Feb. 16, 2022, which claims the benefit of U.S. Provisional Patent Application Ser. No. 63/150,373 filed Feb. 17, 2021, which is incorporated by reference herein in its entirety.

SEQUENCE LISTING

The instant application contains a Sequence Listing which has been submitted electronically and is hereby incorporated by reference in its entirety. Said copy, created on Jul. 21, 2023, is named 56884-786-301_Replacement_SL.xml and is 867,896 bytes in size.

1. BACKGROUND

Autoimmune disease occurs when the immune system attacks self-molecules as a result of a breakdown of immunologic tolerance to autoreactive immune cells. Many autoimmune disorders have been strongly associated with genetic, infectious, and/or environmental predisposing factors yielding multiple disorders and symptoms ranging from organ-specific dysfunction to systemic dysfunction. Inflammatory bowel disease (IBD) refers to a collection of intestinal disorders causing inflammatory conditions in the gastrointestinal tract. The primary types of IBD are ulcerative colitis (UC) and Crohn's Disease (CD). These diseases are prevalent, with about 1.86 million people diagnosed globally with UC, and about 1.3 million people diagnosed globally with CD. Severe forms of IBD may result in or be characterized by intestinal fibrosis, which is the accumulation of scar tissue in the intestinal wall. The pathogenesis of IBD is thought to involve an uncontrolled immune response that may be triggered by certain environmental factors in a genetically susceptible host. The heterogeneity of disease pathogenesis and clinical course, combined with the variable response to treatment and its associated side effects, suggests a targeted therapeutic approach to treating these diseases is a desirable treatment strategy. Yet there are very few targeted therapies available to IBD patients, especially those patients who may be non-responsive or lose response to existing IBD therapies.

2. SUMMARY

Provided herein are antibodies that bind CD30 ligand (also referred to as CD30L, CD153, TNFSF8) and are useful in the treatment of autoimmune disorders such as IBD. Generally, in an aspect, the antibodies described herein effectively inhibit an interaction between CD30L and CD30 in order to effectively reduce, inhibit, or prevent immune activation (for example, an inflammatory response). Furthermore, the anti-CD30L antibodies described herein also comprise properties useful for therapeutic application, including, for example, reduced and/or low immunogenicity. The antibodies described herein also inhibit expression/secretion of certain inflammatory cytokines (e.g., interleukin-6 and interleukin-8) that play a key role in inflammatory and autoimmune diseases such as inflammatory bowel disease, Crohn's disease, and ulcerative colitis.

Accordingly, in one aspect, provided herein is an antibody or antigen binding fragment thereof that binds CD30L, wherein the antibody or antigen binding fragment thereof comprises: (a) an immunoglobulin heavy chain CDR1 (CDR-H1) comprising the amino acid sequence set forth in any one of SEQ ID NOs: 100-139, 220-234, 465-489, 628-641, and 712-723; (b) an immunoglobulin heavy chain CDR2 (CDR-H2) comprising the amino acid sequence set forth in any one of SEQ ID NOs: 140-179, 235-249, 490-499, 513-527, 642-655, and 724-735; (c) an immunoglobulin heavy chain CDR3 (CDR-H3) comprising the amino acid sequence set forth in any one of SEQ ID NOs: 180-219, 250-264, 528-552, 656-669, and 736-743; (d) an immunoglobulin light chain CDR1 (CDR-L1) comprising the amino acid sequence set forth in any one of SEQ ID NOs: 300-339, 420-434, 553-577, 670-683, and 744-751; (d) an immunoglobulin light chain CDR2 (CDR-L2) comprising the amino acid sequence set forth in any one of SEQ ID NOs: 340-379, 435-449, 578-602, 684-697, and 752-759; and/or (e) an immunoglobulin light chain CDR3 (CDR-L3) comprising the amino acid sequence set forth in any one of SEQ ID NOs: 380-419, 450-464, 603-627, 698-711, and 760-765.

In some embodiments, the antibody or antigen binding fragment thereof comprises: (a) a CDR-H1 comprising the amino acid sequence set forth in any one of SEQ ID NOs: 100-109, 628, 635, and 712-723; (b) a CDR-H2 comprising the amino acid sequence set forth in any one of SEQ ID NOs: 140-149, 642, 649, and 724-735; (c) a CDR-H3 comprising the amino acid sequence set forth in any one of SEQ ID NOs: 180-189, 656, 663, and 736-743; (d) a CDR-L1 comprising the amino acid sequence set forth in any one of SEQ ID NOs: 300-309, 670, 677, and 744-751; (e) a CDR-L2 comprising the amino acid sequence set forth in any one of SEQ ID NOs: 340-349, 684, 691, and 752-759; and/or (f) a CDR-L3 comprising the amino acid sequence set forth in any one of SEQ ID Nos: 380-389, 698, 705, and 760-765.

In some embodiments, the antibody or antigen binding fragment thereof comprises: (a) a CDR-H1 comprising the amino acid sequence set forth in any one of SEQ ID NOs: 105-109, 628, 635, and 712-723; (b) a CDR-H2 comprising the amino acid sequence set forth in any one of SEQ ID NOs: 145-149, 642, 649, and 724-735; (c) a CDR-H3 comprising the amino acid sequence set forth in any one of SEQ ID NOs: 185-189, 656, 663, and 736-743; (d) a CDR-L1 comprising the amino acid sequence set forth in any one of SEQ ID NOs: 305-309, 670, 677, and 744-751; (e) a CDR-L2 comprising the amino acid sequence set forth in any one of SEQ ID NOs: 345-349, 684, 691, and 752-759; and/or (f) a CDR-L3 comprising the amino acid sequence set forth in any one of SEQ ID NOs: 385-389, 698, 705, and 760-765.

In one aspect, provided herein is an antibody or antigen binding fragment thereof that binds CD30L, wherein the antibody or antigen binding fragment thereof binds to an epitope comprising one or more amino acids in CD30L selected from the group consisting of K16, S21, R30, K48, R63, and Y64, wherein the amino acids are numbered according to the amino acid sequence of CD30L as set forth in SEQ ID NO:34.

In some embodiments, the antibody or antigen binding fragment thereof binds to an epitope comprising: (i) any one amino acid in CD30L selected from the group consisting of K16, S21, R30, K48, R63, and Y64; (ii) any two amino acids in CD30L selected from the group consisting of K16, S21, R30, K48, R63, and Y64; (iii) any three amino acids in CD30L selected from the group consisting of K16, S21, R30, K48, R63, and Y64; (iv) any four amino acids in CD30L selected from the group consisting of K16, S21, R30, K48, R63, and Y64; (ii) any five amino acids in CD30L selected from the group consisting of K16, S21, R30, K48, R63, and Y64; or (ii) K16, S21, R30, K48, R63, and Y64 in CD30L; wherein the amino acids are numbered according to the amino acid sequence of CD30L as set forth in SEQ ID NO:34.

In some embodiments, the antibody or antigen binding fragment thereof binds to an epitope comprising K16 in CD30L, wherein the amino acids are numbered according to the amino acid sequence of CD30L as set forth in SEQ ID NO:34. In some embodiments, the epitope further comprises S21 in CD30L, wherein the amino acids are numbered according to the amino acid sequence of CD30L as set forth in SEQ ID NO:34. In some embodiments, the epitope further comprises R30 in CD30L, wherein the amino acids are numbered according to the amino acid sequence of CD30L as set forth in SEQ ID NO:34. In some embodiments, the epitope further comprises K48 in CD30L, wherein the amino acids are numbered according to the amino acid sequence of CD30L as set forth in SEQ ID NO:34. In some embodiments, the epitope further comprises R63 in CD30L, wherein the amino acids are numbered according to the amino acid sequence of CD30L as set forth in SEQ ID NO:34. In some embodiments, the epitope further comprises Y64 in CD30L, wherein the amino acids are numbered according to the amino acid sequence of CD30L as set forth in SEQ ID NO:34.

In some embodiments, the antibody or antigen binding fragment thereof comprises: (a) a CDR-H1 comprising the amino acid sequence set forth in any one of SEQ ID NOs: 110-119, 629, 636, and 712-723; (b) a CDR-H2 comprising the amino acid sequence set forth in any one of SEQ ID NOs: 150-159, 643, 650, and 724-735; (c) a CDR-H3 comprising the amino acid sequence set forth in any one of SEQ ID NOs: 190-199, 657, 664, and 736-743; (d) a CDR-L1 comprising the amino acid sequence set forth in any one of SEQ ID NOs: 310-319, 671, 678, and 744-751; (e) a CDR-L2 comprising the amino acid sequence set forth in any one of SEQ ID NOs: 350-359, 685, 692, and 752-759; and/or (f) a CDR-L3 comprising the amino acid sequence set forth in any one of SEQ ID NOs: 390-399, 699, 706, and 760-765.

In some embodiments, the antibody or antigen binding fragment thereof comprises: (a) a CDR-H1 comprising the amino acid sequence set forth in any one of SEQ ID NOs: 115-119, 629, 636, and 712-723; (b) a CDR-H2 comprising the amino acid sequence set forth in any one of SEQ ID NOs: 155-159, 643, 650, and 724-735; (c) a CDR-H3 comprising the amino acid sequence set forth in any one of SEQ ID NOs: 195-199, 657, 664, and 736-743; (d) a CDR-L1 comprising the amino acid sequence set forth in any one of SEQ ID NOs: 315-319, 671, 678, and 744-751; (e) a CDR-L2 comprising the amino acid sequence set forth in any one of SEQ ID NOs: 355-359, 685, 692, and 752-759; and/or (f) a CDR-L3 comprising the amino acid sequence set forth in any one of SEQ ID NOs: 395-399, 699, 706, and 760-765.

In some embodiments, the antibody or antigen binding fragment thereof comprises: (a) a CDR-H1 comprising the amino acid sequence set forth in any one of SEQ ID NOs: 120-129, and 712-723; (b) a CDR-H2 comprising the amino acid sequence set forth in any one of SEQ ID NOs: 160-169, and 724-735; (c) a CDR-H3 comprising the amino acid sequence set forth in any one of SEQ ID NOs: 200-209, and 736-743; (d) a CDR-L1 comprising the amino acid sequence set forth in any one of SEQ ID NOs: 320-329, and 744-751; (e) a CDR-L2 comprising the amino acid sequence set forth in any one of SEQ ID NOs: 360-369, and 752-759; and/or (f) a CDR-L3 comprising the amino acid sequence set forth in any one of SEQ ID NOs: 400-409, and 760-765.

In some embodiments, the antibody or antigen binding fragment thereof comprises: (a) a CDR-H1 comprising the amino acid sequence set forth in any one of SEQ ID NOs: 125-129, and 712-723; (b) a CDR-H2 comprising the amino acid sequence set forth in any one of SEQ ID NOs: 165-169, and 724-735; (c) a CDR-H3 comprising the amino acid sequence set forth in any one of SEQ ID NOs: 205-209, and 736-743; (d) a CDR-L1 comprising the amino acid sequence set forth in any one of SEQ ID NOs: 325-329, and 744-751; (e) a CDR-L2 comprising the amino acid sequence set forth in any one of SEQ ID NOs: 365-369, and 752-759; and/or (f) a CDR-L3 comprising the amino acid sequence set forth in any one of SEQ ID NOs: 405-409, and 760-765.

In some embodiments, the antibody or antigen binding fragment thereof comprises: (a) a CDR-H1 comprising the amino acid sequence set forth in any one of SEQ ID NOs: 130-139, and 712-723; (b) a CDR-H2 comprising the amino acid sequence set forth in any one of SEQ ID NOs: 170-179, and 724-735; (c) a CDR-H3 comprising the amino acid sequence set forth in any one of SEQ ID NOs: 210-219, and 736-743; (d) a CDR-L1 comprising the amino acid sequence set forth in any one of SEQ ID NOs: 330-339, and 744-751; (e) a CDR-L2 comprising the amino acid sequence set forth in any one of SEQ ID NOs: 370-379, and 752-759; and/or (f) a CDR-L3 comprising the amino acid sequence set forth in any one of SEQ ID NOs: 410-419, and 760-765.

In some embodiments, the antibody or antigen binding fragment thereof comprises: (a) a CDR-H1 comprising the amino acid sequence set forth in any one of SEQ ID NOs: 130-134; (b) a CDR-H2 comprising the amino acid sequence set forth in any one of SEQ ID NOs: 170-174; (c) a CDR-H3 comprising the amino acid sequence set forth in any one of SEQ ID NOs: 210-214; (d) a CDR-L1 comprising the amino acid sequence set forth in any one of SEQ ID NOs: 330-334; (e) a CDR-L2 comprising the amino acid sequence set forth in any one of SEQ ID NOs: 370-374; and/or (f) a CDR-L3 comprising the amino acid sequence set forth in any one of SEQ ID NOs: 410-414.

In some embodiments, the antibody or antigen binding fragment thereof comprises: (a) a CDR-H1 comprising the amino acid sequence set forth in any one of SEQ ID NOs: 135-139, and 712-723; (b) a CDR-H2 comprising the amino acid sequence set forth in any one of SEQ ID NOs: 175-179, and 724-735; (c) a CDR-H3 comprising the amino acid sequence set forth in any one of SEQ ID NOs: 215-219, and 736-743; (d) a CDR-L1 comprising the amino acid sequence set forth in any one of SEQ ID NOs: 335-339, and 744-751; (e) a CDR-L2 comprising the amino acid sequence set forth in any one of SEQ ID NOs: 375-379, and 752-759; and/or (f) a CDR-L3 comprising the amino acid sequence set forth in any one of SEQ ID NOs: 415-419, and 760-765.

In some embodiments, the antibody or antigen binding fragment thereof comprises: (a) a CDR-H1 comprising the amino acid sequence set forth in any one of SEQ ID NOs: 220-224, and 712-723; (b) a CDR-H2 comprising the amino acid sequence set forth in any one of SEQ ID NOs: 235-239, and 724-735; (c) a CDR-H3 comprising the amino acid sequence set forth in any one of SEQ ID NOs: 250-254, and 736-743; (d) a CDR-L1 comprising the amino acid sequence set forth in any one of SEQ ID NOs: 420-424, and 744-751; (e) a CDR-L2 comprising the amino acid sequence set forth in any one of SEQ ID NOs: 435-439, and 752-759; and/or (f) a CDR-L3 comprising the amino acid sequence set forth in any one of SEQ ID NOs: 450-454, and 760-765.

In some embodiments, the antibody or antigen binding fragment thereof comprises an immunoglobulin variable region heavy chain and an immunoglobulin variable region light chain, wherein: (a) the immunoglobulin variable region heavy chain (VH) comprises an amino acid sequence having at least about 90, 95, 97, 98, 99, or 100% sequence identity to SEQ ID NO: 17; and/or (b) the immunoglobulin variable region light chain (VL) comprises an amino acid sequence having at least about 90, 95, 97, 98, 99, or 100% sequence identity to SEQ ID NO: 18.

In some embodiments, the antibody or antigen binding fragment thereof comprises: (a) a CDR-H1 comprising the amino acid sequence set forth in any one of SEQ ID NOs: 225-229, and 712-723; (b) a CDR-H2 comprising the amino acid sequence set forth in any one of SEQ ID NOs: 240-244, and 724-735; (c) a CDR-H3 comprising the amino acid sequence set forth in any one of SEQ ID NOs: 255-259, and 736-743; (d) a CDR-L1 comprising the amino acid sequence set forth in any one of SEQ ID NOs: 425-429, and 744-751; (e) a CDR-L2 comprising the amino acid sequence set forth in any one of SEQ ID NOs: 440-444, and 752-759; and/or (f) a CDR-L3 comprising the amino acid sequence set forth in any one of SEQ ID NOs: 455-459, and 760-765.

In some embodiments, the antibody or antigen binding fragment thereof comprises an immunoglobulin variable region heavy chain and an immunoglobulin variable region light chain, wherein: (a) VH comprises an amino acid sequence having at least about 90, 95, 97, 98, 99, or 100% sequence identity to SEQ ID NO: 19; and/or (b) VL comprises an amino acid sequence having at least about 90, 95, 97, 98, 99, or 100% sequence identity to SEQ ID NO: 20.

In some embodiments, the antibody or antigen binding fragment thereof comprises: (a) a CDR-H1 comprising the amino acid sequence set forth in any one of SEQ ID NOs: 230-234, and 712-723; (b) a CDR-H2 comprising the amino acid sequence set forth in any one of SEQ ID NOs: 245-249, and 724-735; (c) a CDR-H3 comprising the amino acid sequence set forth in any one of SEQ ID NOs: 260-264, and 736-743; (d) a CDR-L1 comprising the amino acid sequence set forth in any one of SEQ ID NOs: 430-434, and 744-751; (e) a CDR-L2 comprising the amino acid sequence set forth in any one of SEQ ID NOs: 445-449, and 752-759; and/or (f) a CDR-L3 comprising the amino acid sequence set forth in any one of SEQ ID NOs: 460-464, and 760-765.

In some embodiments, the antibody or antigen binding fragment thereof comprises an immunoglobulin variable region heavy chain and an immunoglobulin variable region light chain, wherein: (a) VH comprises an amino acid sequence having at least about 90, 95, 97, 98, 99, or 100% sequence identity to SEQ ID NO: 21; and/or (b) VL comprises an amino acid sequence having at least about 90, 95, 97, 98, 99, or 100% sequence identity to SEQ ID NO: 22.

In some embodiments, the antibody or antigen binding fragment thereof comprises: (a) a CDR-H1 comprising the amino acid sequence set forth in any one of SEQ ID NOs: 465-469, 631, 638, and 712-723; (b) a CDR-H2 comprising the amino acid sequence set forth in any one of SEQ ID NOs: 490-494, 645, 652, and 724-735; (c) a CDR-H3 comprising the amino acid sequence set forth in any one of SEQ ID NOs: 528-532, 659, 666, and 736-743; (d) a CDR-L1 comprising the amino acid sequence set forth in any one of SEQ ID NOs: 553-557, 673, 680, and 744-751; (e) a CDR-L2 comprising the amino acid sequence set forth in any one of SEQ ID NOs: 578-582, 687, 694, and 752-759; and/or (f) a CDR-L3 comprising the amino acid sequence set forth in any one of SEQ ID NOs: 603-607, 701, 708, and 760-765. In some embodiments, the antibody or antigen binding fragment thereof comprises: (a) a CDR-H1 comprising the amino acid sequence set forth in any one of SEQ ID NOs: 470-474, 632, 639, and 712-723; (b) a CDR-H2 comprising the amino acid sequence set forth in any one of SEQ ID NOs: 495-499, 646, 653, and 724-735; (c) a CDR-H3 comprising the amino acid sequence set forth in any one of SEQ ID NOs: 533-537, 660, 667, and 736-743; (d) a CDR-L1 comprising the amino acid sequence set forth in any one of SEQ ID NOs: 558-562, 674, 681, and 744-751; (e) a CDR-L2 comprising the amino acid sequence set forth in any one of SEQ ID NOs: 583-587, 688, 695, and 752-759; and/or (f) a CDR-L3 comprising the amino acid sequence set forth in any one of SEQ ID NOs: 608-612, 702, 709, and 760-765. In some embodiments, the antibody or antigen binding fragment thereof comprises: (a) a CDR-H1 comprising the amino acid sequence set forth in any one of SEQ ID NOs: 475-479, 633, 640, and 712-723; (b) a CDR-H2 comprising the amino acid sequence set forth in any one of SEQ ID NOs: 513-517, 647, 654, and 724-735; (c) a CDR-H3 comprising the amino acid sequence set forth in any one of SEQ ID NOs: 538-542, 661, 668, and 736-743; (d) a CDR-L1 comprising the amino acid sequence set forth in any one of SEQ ID NOs: 563-567, 675, 682, and 744-751; (e) a CDR-L2 comprising the amino acid sequence set forth in any one of SEQ ID NOs: 588-592, 689, 696, and 752-759; and/or (f) a CDR-L3 comprising the amino acid sequence set forth in any one of SEQ ID NOs: 613-617, 703, 710, and 760-765. In some embodiments, the antibody or antigen binding fragment thereof comprises: (a) a CDR-H1 comprising the amino acid sequence set forth in any one of SEQ ID NOs: 480-484, 630, 637, and 712-723; (b) a CDR-H2 comprising the amino acid sequence set forth in any one of SEQ ID NOs: 518-522, 644, 651, and 724-735; (c) a CDR-H3 comprising the amino acid sequence set forth in any one of SEQ ID NOs: 543-547, 658, 665, and 736-743; (d) a CDR-L1 comprising the amino acid sequence set forth in any one of SEQ ID NOs: 568-572, 672, 679, and 744-751; (e) a CDR-L2 comprising the amino acid sequence set forth in any one of SEQ ID NOs: 593-597, 686, 693, and 752-759; and/or (f) a CDR-L3 comprising the amino acid sequence set forth in any one of SEQ ID NOs: 618-622, 700, 707, and 760-765. In some embodiments, the antibody or antigen binding fragment thereof comprises: (a) a CDR-H1 comprising the amino acid sequence set forth in any one of SEQ ID NOs: 485-489, 634, 641, and 712-723; (b) a CDR-H2 comprising the amino acid sequence set forth in any one of SEQ ID NOs: 523-527, 648, 655, and 724-735; (c) a CDR-H3 comprising the amino acid sequence set forth in any one of SEQ ID NOs: 548-552, 662, 669, and 736-743; (d) a CDR-L1 comprising the amino acid sequence set forth in any one of SEQ ID NOs: 573-577, 676, 683, and 744-751; (e) a CDR-L2 comprising the amino acid sequence set forth in any one of SEQ ID NOs: 598-602, 690, 697, and 752-759; and/or (f) a CDR-L3 comprising the amino acid sequence set forth in any one of SEQ ID NOs: 623-627, 704, 711, and 760-765.

In some embodiments, the antibody or antigen binding fragment thereof comprises: (a) a CDR-H1 comprising the amino acid sequence set forth in any one of SEQ ID NOs: 712-723; (b) a CDR-H2 comprising the amino acid sequence set forth in any one of SEQ ID NOs: 724-735; (c) a CDR-H3 comprising the amino acid sequence set forth in any one of SEQ ID NOs: 736-743; (d) a CDR-L1 comprising the amino acid sequence set forth in any one of SEQ ID NOs: 744-751; (e) a CDR-L2 comprising the amino acid sequence set forth in any one of SEQ ID NOs: 752-759; and/or (f) a CDR-L3 comprising the amino acid sequence set forth in any one of SEQ ID NOs: 760-765. In some embodiments, the antibody or antigen binding fragment thereof comprises: (a) a CDR-H1 comprising the amino acid sequence set forth in any one of SEQ ID NOs: 712, 714, 716, 718, 720, and 722; (b) a CDR-H2 comprising the amino acid sequence set forth in any one of SEQ ID NOs: 724, 726, 728, 730, 732, and 734; (c) a CDR-H3 comprising the amino acid sequence set forth in any one of SEQ ID NOs: 736, 738, 740, and 742; (d) a CDR-L1 comprising the amino acid sequence set forth in any one of SEQ ID NOs: 744, 746, 748, and 750; (e) a CDR-L2 comprising the amino acid sequence set forth in any one of SEQ ID NOs: 752, 754, 756, and 758; and/or (f) a CDR-L3 comprising the amino acid sequence set forth in any one of SEQ ID NOs: 760, 762, and 764. In some embodiments, the antibody or antigen binding fragment thereof comprises: (a) a CDR-H1 comprising the amino acid sequence set forth in any one of SEQ ID NOs: 713, 715, 717, 719, 721, and 723; (b) a CDR-H2 comprising the amino acid sequence set forth in any one of SEQ ID NOs: 725, 727, 729, 731, 733, and 735; (c) a CDR-H3 comprising the amino acid sequence set forth in any one of SEQ ID NOs: 737, 739, 741, and 743; (d) a CDR-L1 comprising the amino acid sequence set forth in any one of SEQ ID NOs: 745, 747, 749, and 751; (e) a CDR-L2 comprising the amino acid sequence set forth in any one of SEQ ID NOs: 753, 755, 757, and 759; and/or (f) a CDR-L3 comprising the amino acid sequence set forth in any one of SEQ ID NOs: 761, 763, and 765. In some embodiments, the antibody or antigen binding fragment thereof comprises: (a) a CDR-H1 comprising the amino acid sequence set forth in SEQ ID NO: 712; (b) a CDR-H2 comprising the amino acid sequence set forth in SEQ ID NO: 730; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In some embodiments, the antibody or antigen binding fragment thereof comprises: (v)(a) a CDR-H1 comprising the amino acid sequence set forth in SEQ ID NO: 713; (b) a CDR-H2 comprising the amino acid sequence set forth in SEQ ID NO: 731; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In some embodiments, the antibody or antigen binding fragment thereof comprises: (a) a CDR-H1 comprising the amino acid sequence set forth in SEQ ID NO: 712; (b) a CDR-H2 comprising the amino acid sequence set forth in SEQ ID NO: 724; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In some embodiments, the antibody or antigen binding fragment thereof comprises: (a) a CDR-H1 comprising the amino acid sequence set forth in SEQ ID NO: 713; (b) a CDR-H2 comprising the amino acid sequence set forth in SEQ ID NO: 725; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In some embodiments, the antibody or antigen binding fragment thereof comprises: (a) a CDR-H1 comprising the amino acid sequence set forth in SEQ ID NO: 714; (b) a CDR-H2 comprising the amino acid sequence set forth in SEQ ID NO: 726; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In some embodiments, the antibody or antigen binding fragment thereof comprises: (a) a CDR-H1 comprising the amino acid sequence set forth in SEQ ID NO: 715; (b) a CDR-H2 comprising the amino acid sequence set forth in SEQ ID NO: 727; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In some embodiments, the antibody or antigen binding fragment thereof comprises: (a) a CDR-H1 comprising the amino acid sequence set forth in SEQ ID NO: 716; (b) a CDR-H2 comprising the amino acid sequence set forth in SEQ ID NO: 728; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In some embodiments, the antibody or antigen binding fragment thereof comprises: (a) a CDR-H1 comprising the amino acid sequence set forth in SEQ ID NO: 717; (b) a CDR-H2 comprising the amino acid sequence set forth in SEQ ID NO: 729; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In some embodiments, the antibody or antigen binding fragment thereof comprises: (a) a CDR-H1 comprising the amino acid sequence set forth in SEQ ID NO: 718; (b) a CDR-H2 comprising the amino acid sequence set forth in SEQ ID NO: 730; (c) a CDR-H3 comprising the amino acid sequence set forth in SEQ ID NO: 738; (d) a CDR-L1 comprising the amino acid sequence set forth in SEQ ID NO: 746; (e) a CDR-L2 comprising the amino acid sequence set forth SEQ ID NO: 754; and/or (f) a CDR-L3 comprising the amino acid sequence set forth SEQ ID NO: 762. In some embodiments, the antibody or antigen binding fragment thereof comprises: (a) a CDR-H1 comprising the amino acid sequence set forth in SEQ ID NO: 719; (b) a CDR-H2 comprising the amino acid sequence set forth in SEQ ID NO: 731; (c) a CDR-H3 comprising the amino acid sequence set forth in SEQ ID NO: 739; (d) a CDR-L1 comprising the amino acid sequence set forth in SEQ ID NO: 747; (e) a CDR-L2 comprising the amino acid sequence set forth SEQ ID NO: 755; and/or (f) a CDR-L3 comprising the amino acid sequence set forth SEQ ID NO: 763. In some embodiments, the antibody or antigen binding fragment thereof comprises: (a) a CDR-H1 comprising the amino acid sequence set forth in SEQ ID NO: 720; (b) a CDR-H2 comprising the amino acid sequence set forth in SEQ ID NO: 732; (c) a CDR-H3 comprising the amino acid sequence set forth in SEQ ID NO: 740; (d) a CDR-L1 comprising the amino acid sequence set forth in SEQ ID NO: 748; (e) a CDR-L2 comprising the amino acid sequence set forth SEQ ID NO: 756; and/or (f) a CDR-L3 comprising the amino acid sequence set forth SEQ ID NO: 760. In some embodiments, the antibody or antigen binding fragment thereof comprises: (a) a CDR-H1 comprising the amino acid sequence set forth in SEQ ID NO: 721; (b) a CDR-H2 comprising the amino acid sequence set forth in SEQ ID NO: 733; (c) a CDR-H3 comprising the amino acid sequence set forth in SEQ ID NO: 741; (d) a CDR-L1 comprising the amino acid sequence set forth in SEQ ID NO: 749; (e) a CDR-L2 comprising the amino acid sequence set forth SEQ ID NO: 757; and/or (f) a CDR-L3 comprising the amino acid sequence set forth SEQ ID NO: 761. In some embodiments, the antibody or antigen binding fragment thereof comprises: (a) a CDR-H1 comprising the amino acid sequence set forth in SEQ ID NO: 722; (b) a CDR-H2 comprising the amino acid sequence set forth in SEQ ID NO: 734; (c) a CDR-H3 comprising the amino acid sequence set forth in SEQ ID NO: 742; (d) a CDR-L1 comprising the amino acid sequence set forth in SEQ ID NO: 750; (e) a CDR-L2 comprising the amino acid sequence set forth SEQ ID NO: 758; and/or (f) a CDR-L3 comprising the amino acid sequence set forth SEQ ID NO: 764. In some embodiments, the antibody or antigen binding fragment thereof comprises: (a) a CDR-H1 comprising the amino acid sequence set forth in SEQ ID NO: 723; (b) a CDR-H2 comprising the amino acid sequence set forth in SEQ ID NO: 735; (c) a CDR-H3 comprising the amino acid sequence set forth in SEQ ID NO: 743; (d) a CDR-L1 comprising the amino acid sequence set forth in SEQ ID NO: 751; (e) a CDR-L2 comprising the amino acid sequence set forth SEQ ID NO: 759; and/or (f) a CDR-L3 comprising the amino acid sequence set forth SEQ ID NO: 765.

In some embodiments, the antibody or antigen binding fragment thereof comprises: (a) a CDR-H1 comprising the amino acid sequence set forth in SEQ ID NO: 635; (b) a CDR-H2 comprising the amino acid sequence set forth in SEQ ID NO: 649; (c) a CDR-H3 comprising the amino acid sequence set forth in SEQ ID NO: 663; (d) a CDR-L1 comprising the amino acid sequence set forth in SEQ ID NO: 677; (e) a CDR-L2 comprising the amino acid sequence set forth SEQ ID NO: 691; and/or (f) a CDR-L3 comprising the amino acid sequence set forth SEQ ID NO: 705. In some embodiments, the antibody or antigen binding fragment thereof comprises: (a) a CDR-H1 comprising the amino acid sequence set forth in SEQ ID NO: 107; (b) a CDR-H2 comprising the amino acid sequence set forth in SEQ ID NO: 147; (c) a CDR-H3 comprising the amino acid sequence set forth in SEQ ID NO: 187; (d) a CDR-L1 comprising the amino acid sequence set forth in SEQ ID NO: 307; (e) a CDR-L2 comprising the amino acid sequence set forth SEQ ID NO: 347; and/or (f) a CDR-L3 comprising the amino acid sequence set forth SEQ ID NO: 387. In some embodiments, the antibody or antigen binding fragment thereof comprises: (a) a CDR-H1 comprising the amino acid sequence set forth in SEQ ID NO: 105; (b) a CDR-H2 comprising the amino acid sequence set forth in SEQ ID NO: 145; (c) a CDR-H3 comprising the amino acid sequence set forth in SEQ ID NO: 185; (d) a CDR-L1 comprising the amino acid sequence set forth in SEQ ID NO: 305; (e) a CDR-L2 comprising the amino acid sequence set forth SEQ ID NO: 345; and/or (f) a CDR-L3 comprising the amino acid sequence set forth SEQ ID NO: 385. In some embodiments, the antibody or antigen binding fragment thereof comprises: (a) a CDR-H1 comprising the amino acid sequence set forth in SEQ ID NO: 106; (b) a CDR-H2 comprising the amino acid sequence set forth in SEQ ID NO: 146; (c) a CDR-H3 comprising the amino acid sequence set forth in SEQ ID NO: 186; (d) a CDR-L1 comprising the amino acid sequence set forth in SEQ ID NO: 306; (e) a CDR-L2 comprising the amino acid sequence set forth SEQ ID NO: 346; and/or (f) a CDR-L3 comprising the amino acid sequence set forth SEQ ID NO: 386. In some embodiments, the antibody or antigen binding fragment thereof comprises: (a) a CDR-H1 comprising the amino acid sequence set forth in SEQ ID NO: 108; (b) a CDR-H2 comprising the amino acid sequence set forth in SEQ ID NO: 148; (c) a CDR-H3 comprising the amino acid sequence set forth in SEQ ID NO: 188; (d) a CDR-L1 comprising the amino acid sequence set forth in SEQ ID NO: 308; (e) a CDR-L2 comprising the amino acid sequence set forth SEQ ID NO: 348; and/or (f) a CDR-L3 comprising the amino acid sequence set forth SEQ ID NO: 388. In some embodiments, the antibody or antigen binding fragment thereof comprises: (a) a CDR-H1 comprising the amino acid sequence set forth in SEQ ID NO: 109; (b) a CDR-H2 comprising the amino acid sequence set forth in SEQ ID NO: 149; (c) a CDR-H3 comprising the amino acid sequence set forth in SEQ ID NO: 189; (d) a CDR-L1 comprising the amino acid sequence set forth in SEQ ID NO: 309; (e) a CDR-L2 comprising the amino acid sequence set forth SEQ ID NO: 349; and/or (f) a CDR-L3 comprising the amino acid sequence set forth SEQ ID NO: 389. In some embodiments, the antibody or antigen binding fragment thereof comprises: (a) a CDR-H1 comprising the amino acid sequence set forth in SEQ ID NO: 628; (b) a CDR-H2 comprising the amino acid sequence set forth in SEQ ID NO: 642; (c) a CDR-H3 comprising the amino acid sequence set forth in SEQ ID NO: 656; (d) a CDR-L1 comprising the amino acid sequence set forth in SEQ ID NO: 670; (e) a CDR-L2 comprising the amino acid sequence set forth SEQ ID NO: 684; and/or (f) a CDR-L3 comprising the amino acid sequence set forth SEQ ID NO: 698.

In some embodiments, the antibody or antigen binding fragment thereof comprises: (a) a CDR-H1 comprising the amino acid sequence set forth in SEQ ID NO: 636; (b) a CDR-H2 comprising the amino acid sequence set forth in SEQ ID NO: 650; (c) a CDR-H3 comprising the amino acid sequence set forth in SEQ ID NO: 664; (d) a CDR-L1 comprising the amino acid sequence set forth in SEQ ID NO: 678; (e) a CDR-L2 comprising the amino acid sequence set forth SEQ ID NO: 692; and/or (f) a CDR-L3 comprising the amino acid sequence set forth SEQ ID NO: 706. In some embodiments, the antibody or antigen binding fragment thereof comprises: (a) a CDR-H1 comprising the amino acid sequence set forth in SEQ ID NO: 117; (b) a CDR-H2 comprising the amino acid sequence set forth in SEQ ID NO: 157; (c) a CDR-H3 comprising the amino acid sequence set forth in SEQ ID NO: 197; (d) a CDR-L1 comprising the amino acid sequence set forth in SEQ ID NO: 317; (e) a CDR-L2 comprising the amino acid sequence set forth SEQ ID NO: 357; and/or (f) a CDR-L3 comprising the amino acid sequence set forth SEQ ID NO: 397. In some embodiments, the antibody or antigen binding fragment thereof comprises: (a) a CDR-H1 comprising the amino acid sequence set forth in SEQ ID NO: 115; (b) a CDR-H2 comprising the amino acid sequence set forth in SEQ ID NO: 155; (c) a CDR-H3 comprising the amino acid sequence set forth in SEQ ID NO: 195; (d) a CDR-L1 comprising the amino acid sequence set forth in SEQ ID NO: 315; (e) a CDR-L2 comprising the amino acid sequence set forth SEQ ID NO: 355; and/or (f) a CDR-L3 comprising the amino acid sequence set forth SEQ ID NO: 395. In some embodiments, the antibody or antigen binding fragment thereof comprises: (a) a CDR-H1 comprising the amino acid sequence set forth in SEQ ID NO: 116; (b) a CDR-H2 comprising the amino acid sequence set forth in SEQ ID NO: 156; (c) a CDR-H3 comprising the amino acid sequence set forth in SEQ ID NO: 196; (d) a CDR-L1 comprising the amino acid sequence set forth in SEQ ID NO: 316; (e) a CDR-L2 comprising the amino acid sequence set forth SEQ ID NO: 356; and/or (f) a CDR-L3 comprising the amino acid sequence set forth SEQ ID NO: 396. In some embodiments, the antibody or antigen binding fragment thereof comprises: (a) a CDR-H1 comprising the amino acid sequence set forth in SEQ ID NO: 118; (b) a CDR-H2 comprising the amino acid sequence set forth in SEQ ID NO: 158; (c) a CDR-H3 comprising the amino acid sequence set forth in SEQ ID NO: 198; (d) a CDR-L1 comprising the amino acid sequence set forth in SEQ ID NO: 318; (e) a CDR-L2 comprising the amino acid sequence set forth SEQ ID NO: 358; and/or (f) a CDR-L3 comprising the amino acid sequence set forth SEQ ID NO: 398. In some embodiments, the antibody or antigen binding fragment thereof comprises: (a) a CDR-H1 comprising the amino acid sequence set forth in SEQ ID NO: 119; (b) a CDR-H2 comprising the amino acid sequence set forth in SEQ ID NO: 159; (c) a CDR-H3 comprising the amino acid sequence set forth in SEQ ID NO: 199; (d) a CDR-L1 comprising the amino acid sequence set forth in SEQ ID NO: 319; (e) a CDR-L2 comprising the amino acid sequence set forth SEQ ID NO: 359; and/or (f) a CDR-L3 comprising the amino acid sequence set forth SEQ ID NO: 399. In some embodiments, the antibody or antigen binding fragment thereof comprises: (a) a CDR-H1 comprising the amino acid sequence set forth in SEQ ID NO: 629; (b) a CDR-H2 comprising the amino acid sequence set forth in SEQ ID NO: 643; (c) a CDR-H3 comprising the amino acid sequence set forth in SEQ ID NO: 657; (d) a CDR-L1 comprising the amino acid sequence set forth in SEQ ID NO: 671; (e) a CDR-L2 comprising the amino acid sequence set forth SEQ ID NO: 685; and/or (f) a CDR-L3 comprising the amino acid sequence set forth SEQ ID NO: 699.

In some embodiments, the antibody or antigen binding fragment thereof comprises: (a) a CDR-H1 comprising the amino acid sequence set forth in SEQ ID NO: 637; (b) a CDR-H2 comprising the amino acid sequence set forth in SEQ ID NO: 651; (c) a CDR-H3 comprising the amino acid sequence set forth in SEQ ID NO: 665; (d) a CDR-L1 comprising the amino acid sequence set forth in SEQ ID NO: 679; (e) a CDR-L2 comprising the amino acid sequence set forth SEQ ID NO: 693; and/or (f) a CDR-L3 comprising the amino acid sequence set forth SEQ ID NO: 707. In some embodiments, the antibody or antigen binding fragment thereof comprises: (a) a CDR-H1 comprising the amino acid sequence set forth in SEQ ID NO: 482; (b) a CDR-H2 comprising the amino acid sequence set forth in SEQ ID NO: 520; (c) a CDR-H3 comprising the amino acid sequence set forth in SEQ ID NO: 545; (d) a CDR-L1 comprising the amino acid sequence set forth in SEQ ID NO: 570; (e) a CDR-L2 comprising the amino acid sequence set forth SEQ ID NO: 595; and/or (f) a CDR-L3 comprising the amino acid sequence set forth SEQ ID NO: 620. In some embodiments, the antibody or antigen binding fragment thereof comprises: (a) a CDR-H1 comprising the amino acid sequence set forth in SEQ ID NO: 480; (b) a CDR-H2 comprising the amino acid sequence set forth in SEQ ID NO: 518; (c) a CDR-H3 comprising the amino acid sequence set forth in SEQ ID NO: 543; (d) a CDR-L1 comprising the amino acid sequence set forth in SEQ ID NO: 568; (e) a CDR-L2 comprising the amino acid sequence set forth SEQ ID NO: 593; and/or (f) a CDR-L3 comprising the amino acid sequence set forth SEQ ID NO: 618. In some embodiments, the antibody or antigen binding fragment thereof comprises: (a) a CDR-H1 comprising the amino acid sequence set forth in SEQ ID NO: 481; (b) a CDR-H2 comprising the amino acid sequence set forth in SEQ ID NO: 519; (c) a CDR-H3 comprising the amino acid sequence set forth in SEQ ID NO: 544; (d) a CDR-L1 comprising the amino acid sequence set forth in SEQ ID NO: 569; (e) a CDR-L2 comprising the amino acid sequence set forth SEQ ID NO: 594; and/or (f) a CDR-L3 comprising the amino acid sequence set forth SEQ ID NO: 619. In some embodiments, the antibody or antigen binding fragment thereof comprises: (a) a CDR-H1 comprising the amino acid sequence set forth in SEQ ID NO: 483; (b) a CDR-H2 comprising the amino acid sequence set forth in SEQ ID NO: 521; (c) a CDR-H3 comprising the amino acid sequence set forth in SEQ ID NO: 546; (d) a CDR-L1 comprising the amino acid sequence set forth in SEQ ID NO: 571; (e) a CDR-L2 comprising the amino acid sequence set forth SEQ ID NO: 596; and/or (f) a CDR-L3 comprising the amino acid sequence set forth SEQ ID NO: 621. In some embodiments, the antibody or antigen binding fragment thereof comprises: (a) a CDR-H1 comprising the amino acid sequence set forth in SEQ ID NO: 484; (b) a CDR-H2 comprising the amino acid sequence set forth in SEQ ID NO: 522; (c) a CDR-H3 comprising the amino acid sequence set forth in SEQ ID NO: 547; (d) a CDR-L1 comprising the amino acid sequence set forth in SEQ ID NO: 572; (e) a CDR-L2 comprising the amino acid sequence set forth SEQ ID NO: 597; and/or (f) a CDR-L3 comprising the amino acid sequence set forth SEQ ID NO: 622. In some embodiments, the antibody or antigen binding fragment thereof comprises: (a) a CDR-H1 comprising the amino acid sequence set forth in SEQ ID NO: 630; (b) a CDR-H2 comprising the amino acid sequence set forth in SEQ ID NO: 644; (c) a CDR-H3 comprising the amino acid sequence set forth in SEQ ID NO: 658; (d) a CDR-L1 comprising the amino acid sequence set forth in SEQ ID NO: 672; (e) a CDR-L2 comprising the amino acid sequence set forth SEQ ID NO: 686; and/or (f) a CDR-L3 comprising the amino acid sequence set forth SEQ ID NO: 700.

In some embodiments, the antibody or antigen binding fragment thereof comprises: (a) a CDR-H1 comprising the amino acid sequence set forth in SEQ ID NO: 638; (b) a CDR-H2 comprising the amino acid sequence set forth in SEQ ID NO: 652; (c) a CDR-H3 comprising the amino acid sequence set forth in SEQ ID NO: 666; (d) a CDR-L1 comprising the amino acid sequence set forth in SEQ ID NO: 680; (e) a CDR-L2 comprising the amino acid sequence set forth SEQ ID NO: 694; and/or (f) a CDR-L3 comprising the amino acid sequence set forth SEQ ID NO: 708. In some embodiments, the antibody or antigen binding fragment thereof comprises: (a) a CDR-H1 comprising the amino acid sequence set forth in SEQ ID NO: 467; (b) a CDR-H2 comprising the amino acid sequence set forth in SEQ ID NO: 492; (c) a CDR-H3 comprising the amino acid sequence set forth in SEQ ID NO: 530; (d) a CDR-L1 comprising the amino acid sequence set forth in SEQ ID NO: 555; (e) a CDR-L2 comprising the amino acid sequence set forth SEQ ID NO: 580; and/or (f) a CDR-L3 comprising the amino acid sequence set forth SEQ ID NO: 605. In some embodiments, the antibody or antigen binding fragment thereof comprises: (a) a CDR-H1 comprising the amino acid sequence set forth in SEQ ID NO: 465; (b) a CDR-H2 comprising the amino acid sequence set forth in SEQ ID NO: 490; (c) a CDR-H3 comprising the amino acid sequence set forth in SEQ ID NO: 528; (d) a CDR-L1 comprising the amino acid sequence set forth in SEQ ID NO: 553; (e) a CDR-L2 comprising the amino acid sequence set forth SEQ ID NO: 578; and/or (f) a CDR-L3 comprising the amino acid sequence set forth SEQ ID NO: 603. In some embodiments, the antibody or antigen binding fragment thereof comprises: (a) a CDR-H1 comprising the amino acid sequence set forth in SEQ ID NO: 466; (b) a CDR-H2 comprising the amino acid sequence set forth in SEQ ID NO: 491; (c) a CDR-H3 comprising the amino acid sequence set forth in SEQ ID NO: 529; (d) a CDR-L1 comprising the amino acid sequence set forth in SEQ ID NO: 554; (e) a CDR-L2 comprising the amino acid sequence set forth SEQ ID NO: 579; and/or (f) a CDR-L3 comprising the amino acid sequence set forth SEQ ID NO: 604. In some embodiments, the antibody or antigen binding fragment thereof comprises: (a) a CDR-H1 comprising the amino acid sequence set forth in SEQ ID NO: 468; (b) a CDR-H2 comprising the amino acid sequence set forth in SEQ ID NO: 493; (c) a CDR-H3 comprising the amino acid sequence set forth in SEQ ID NO: 531; (d) a CDR-L1 comprising the amino acid sequence set forth in SEQ ID NO: 556; (e) a CDR-L2 comprising the amino acid sequence set forth SEQ ID NO: 581; and/or (f) a CDR-L3 comprising the amino acid sequence set forth SEQ ID NO: 606. In some embodiments, the antibody or antigen binding fragment thereof comprises: (a) a CDR-H1 comprising the amino acid sequence set forth in SEQ ID NO: 469; (b) a CDR-H2 comprising the amino acid sequence set forth in SEQ ID NO: 494; (c) a CDR-H3 comprising the amino acid sequence set forth in SEQ ID NO: 532; (d) a CDR-L1 comprising the amino acid sequence set forth in SEQ ID NO: 557; (e) a CDR-L2 comprising the amino acid sequence set forth SEQ ID NO: 582; and/or (f) a CDR-L3 comprising the amino acid sequence set forth SEQ ID NO: 607. In some embodiments, the antibody or antigen binding fragment thereof comprises: (a) a CDR-H1 comprising the amino acid sequence set forth in SEQ ID NO: 631; (b) a CDR-H2 comprising the amino acid sequence set forth in SEQ ID NO: 645; (c) a CDR-H3 comprising the amino acid sequence set forth in SEQ ID NO: 659; (d) a CDR-L1 comprising the amino acid sequence set forth in SEQ ID NO: 673; (e) a CDR-L2 comprising the amino acid sequence set forth SEQ ID NO: 687; and/or (f) a CDR-L3 comprising the amino acid sequence set forth SEQ ID NO: 701.

In some embodiments, the antibody or antigen binding fragment thereof comprises: (a) a CDR-H1 comprising the amino acid sequence set forth in SEQ ID NO: 639; (b) a CDR-H2 comprising the amino acid sequence set forth in SEQ ID NO: 653; (c) a CDR-H3 comprising the amino acid sequence set forth in SEQ ID NO: 667; (d) a CDR-L1 comprising the amino acid sequence set forth in SEQ ID NO: 681; (e) a CDR-L2 comprising the amino acid sequence set forth SEQ ID NO: 695; and/or (f) a CDR-L3 comprising the amino acid sequence set forth SEQ ID NO: 709. In some embodiments, the antibody or antigen binding fragment thereof comprises: (a) a CDR-H1 comprising the amino acid sequence set forth in SEQ ID NO: 472; (b) a CDR-H2 comprising the amino acid sequence set forth in SEQ ID NO: 497; (c) a CDR-H3 comprising the amino acid sequence set forth in SEQ ID NO: 535; (d) a CDR-L1 comprising the amino acid sequence set forth in SEQ ID NO: 560; (e) a CDR-L2 comprising the amino acid sequence set forth SEQ ID NO: 585; and/or (f) a CDR-L3 comprising the amino acid sequence set forth SEQ ID NO: 610. In some embodiments, the antibody or antigen binding fragment thereof comprises: (a) a CDR-H1 comprising the amino acid sequence set forth in SEQ ID NO: 470; (b) a CDR-H2 comprising the amino acid sequence set forth in SEQ ID NO: 495; (c) a CDR-H3 comprising the amino acid sequence set forth in SEQ ID NO: 533; (d) a CDR-L1 comprising the amino acid sequence set forth in SEQ ID NO: 558; (e) a CDR-L2 comprising the amino acid sequence set forth SEQ ID NO: 583; and/or (f) a CDR-L3 comprising the amino acid sequence set forth SEQ ID NO: 608. In some embodiments, the antibody or antigen binding fragment thereof comprises: (a) a CDR-H1 comprising the amino acid sequence set forth in SEQ ID NO: 471; (b) a CDR-H2 comprising the amino acid sequence set forth in SEQ ID NO: 496; (c) a CDR-H3 comprising the amino acid sequence set forth in SEQ ID NO: 534; (d) a CDR-L1 comprising the amino acid sequence set forth in SEQ ID NO: 559; (e) a CDR-L2 comprising the amino acid sequence set forth SEQ ID NO: 584; and/or (f) a CDR-L3 comprising the amino acid sequence set forth SEQ ID NO: 609. In some embodiments, the antibody or antigen binding fragment thereof comprises: (a) a CDR-H1 comprising the amino acid sequence set forth in SEQ ID NO: 473; (b) a CDR-H2 comprising the amino acid sequence set forth in SEQ ID NO: 498; (c) a CDR-H3 comprising the amino acid sequence set forth in SEQ ID NO: 536; (d) a CDR-L1 comprising the amino acid sequence set forth in SEQ ID NO: 561; (e) a CDR-L2 comprising the amino acid sequence set forth SEQ ID NO: 586; and/or (f) a CDR-L3 comprising the amino acid sequence set forth SEQ ID NO: 611. In some embodiments, the antibody or antigen binding fragment thereof comprises: (a) a CDR-H1 comprising the amino acid sequence set forth in SEQ ID NO: 474; (b) a CDR-H2 comprising the amino acid sequence set forth in SEQ ID NO: 499; (c) a CDR-H3 comprising the amino acid sequence set forth in SEQ ID NO: 537; (d) a CDR-L1 comprising the amino acid sequence set forth in SEQ ID NO: 562; (e) a CDR-L2 comprising the amino acid sequence set forth SEQ ID NO: 587; and/or (f) a CDR-L3 comprising the amino acid sequence set forth SEQ ID NO: 612. In some embodiments, the antibody or antigen binding fragment thereof comprises: (a) a CDR-H1 comprising the amino acid sequence set forth in SEQ ID NO: 632; (b) a CDR-H2 comprising the amino acid sequence set forth in SEQ ID NO: 646; (c) a CDR-H3 comprising the amino acid sequence set forth in SEQ ID NO: 660; (d) a CDR-L1 comprising the amino acid sequence set forth in SEQ ID NO: 674; (e) a CDR-L2 comprising the amino acid sequence set forth SEQ ID NO: 688; and/or (f) a CDR-L3 comprising the amino acid sequence set forth SEQ ID NO: 702.

In some embodiments, the antibody or antigen binding fragment thereof comprises: (a) a CDR-H1 comprising the amino acid sequence set forth in SEQ ID NO: 640; (b) a CDR-H2 comprising the amino acid sequence set forth in SEQ ID NO: 654; (c) a CDR-H3 comprising the amino acid sequence set forth in SEQ ID NO: 668; (d) a CDR-L1 comprising the amino acid sequence set forth in SEQ ID NO: 682; (e) a CDR-L2 comprising the amino acid sequence set forth SEQ ID NO: 696; and/or (f) a CDR-L3 comprising the amino acid sequence set forth SEQ ID NO: 710. In some embodiments, the antibody or antigen binding fragment thereof comprises: (a) a CDR-H1 comprising the amino acid sequence set forth in SEQ ID NO: 477; (b) a CDR-H2 comprising the amino acid sequence set forth in SEQ ID NO: 515; (c) a CDR-H3 comprising the amino acid sequence set forth in SEQ ID NO: 540; (d) a CDR-L1 comprising the amino acid sequence set forth in SEQ ID NO: 565; (e) a CDR-L2 comprising the amino acid sequence set forth SEQ ID NO: 590; and/or (f) a CDR-L3 comprising the amino acid sequence set forth SEQ ID NO: 615. In some embodiments, the antibody or antigen binding fragment thereof comprises: (a) a CDR-H1 comprising the amino acid sequence set forth in SEQ ID NO: 475; (b) a CDR-H2 comprising the amino acid sequence set forth in SEQ ID NO: 513; (c) a CDR-H3 comprising the amino acid sequence set forth in SEQ ID NO: 538; (d) a CDR-L1 comprising the amino acid sequence set forth in SEQ ID NO: 563; (e) a CDR-L2 comprising the amino acid sequence set forth SEQ ID NO: 588; and/or (f) a CDR-L3 comprising the amino acid sequence set forth SEQ ID NO: 613. In some embodiments, the antibody or antigen binding fragment thereof comprises: (a) a CDR-H1 comprising the amino acid sequence set forth in SEQ ID NO: 476; (b) a CDR-H2 comprising the amino acid sequence set forth in SEQ ID NO: 514; (c) a CDR-H3 comprising the amino acid sequence set forth in SEQ ID NO: 539; (d) a CDR-L1 comprising the amino acid sequence set forth in SEQ ID NO: 564; (e) a CDR-L2 comprising the amino acid sequence set forth SEQ ID NO: 589; and/or (f) a CDR-L3 comprising the amino acid sequence set forth SEQ ID NO: 614. In some embodiments, the antibody or antigen binding fragment thereof comprises: (a) a CDR-H1 comprising the amino acid sequence set forth in SEQ ID NO: 478; (b) a CDR-H2 comprising the amino acid sequence set forth in SEQ ID NO: 516; (c) a CDR-H3 comprising the amino acid sequence set forth in SEQ ID NO: 541; (d) a CDR-L1 comprising the amino acid sequence set forth in SEQ ID NO: 566; (e) a CDR-L2 comprising the amino acid sequence set forth SEQ ID NO: 591; and/or (f) a CDR-L3 comprising the amino acid sequence set forth SEQ ID NO: 616. In some embodiments, the antibody or antigen binding fragment thereof comprises: (a) a CDR-H1 comprising the amino acid sequence set forth in SEQ ID NO: 479; (b) a CDR-H2 comprising the amino acid sequence set forth in SEQ ID NO: 517; (c) a CDR-H3 comprising the amino acid sequence set forth in SEQ ID NO: 542; (d) a CDR-L1 comprising the amino acid sequence set forth in SEQ ID NO: 567; (e) a CDR-L2 comprising the amino acid sequence set forth SEQ ID NO: 592; and/or (f) a CDR-L3 comprising the amino acid sequence set forth SEQ ID NO: 617. In some embodiments, the antibody or antigen binding fragment thereof comprises: (a) a CDR-H1 comprising the amino acid sequence set forth in SEQ ID NO: 633; (b) a CDR-H2 comprising the amino acid sequence set forth in SEQ ID NO: 647; (c) a CDR-H3 comprising the amino acid sequence set forth in SEQ ID NO: 661; (d) a CDR-L1 comprising the amino acid sequence set forth in SEQ ID NO: 675; (e) a CDR-L2 comprising the amino acid sequence set forth SEQ ID NO: 689; and/or (f) a CDR-L3 comprising the amino acid sequence set forth SEQ ID NO: 703.

In some embodiments, the antibody or antigen binding fragment thereof comprises: (a) a CDR-H1 comprising the amino acid sequence set forth in SEQ ID NO: 641; (b) a CDR-H2 comprising the amino acid sequence set forth in SEQ ID NO: 655; (c) a CDR-H3 comprising the amino acid sequence set forth in SEQ ID NO: 669; (d) a CDR-L1 comprising the amino acid sequence set forth in SEQ ID NO: 683; (e) a CDR-L2 comprising the amino acid sequence set forth SEQ ID NO: 697; and/or (f) a CDR-L3 comprising the amino acid sequence set forth SEQ ID NO: 711. In some embodiments, the antibody or antigen binding fragment thereof comprises: (a) a CDR-H1 comprising the amino acid sequence set forth in SEQ ID NO: 487; (b) a CDR-H2 comprising the amino acid sequence set forth in SEQ ID NO: 525; (c) a CDR-H3 comprising the amino acid sequence set forth in SEQ ID NO: 550; (d) a CDR-L1 comprising the amino acid sequence set forth in SEQ ID NO: 575; (e) a CDR-L2 comprising the amino acid sequence set forth SEQ ID NO: 600; and/or (f) a CDR-L3 comprising the amino acid sequence set forth SEQ ID NO: 625. In some embodiments, the antibody or antigen binding fragment thereof comprises: (a) a CDR-H1 comprising the amino acid sequence set forth in SEQ ID NO: 485; (b) a CDR-H2 comprising the amino acid sequence set forth in SEQ ID NO: 523; (c) a CDR-H3 comprising the amino acid sequence set forth in SEQ ID NO: 548; (d) a CDR-L1 comprising the amino acid sequence set forth in SEQ ID NO: 573; (e) a CDR-L2 comprising the amino acid sequence set forth SEQ ID NO: 598; and/or (f) a CDR-L3 comprising the amino acid sequence set forth SEQ ID NO: 623. In some embodiments, the antibody or antigen binding fragment thereof comprises: (a) a CDR-H1 comprising the amino acid sequence set forth in SEQ ID NO: 486; (b) a CDR-H2 comprising the amino acid sequence set forth in SEQ ID NO: 524; (c) a CDR-H3 comprising the amino acid sequence set forth in SEQ ID NO: 549; (d) a CDR-L1 comprising the amino acid sequence set forth in SEQ ID NO: 574; (e) a CDR-L2 comprising the amino acid sequence set forth SEQ ID NO: 599; and/or (f) a CDR-L3 comprising the amino acid sequence set forth SEQ ID NO: 624. In some embodiments, the antibody or antigen binding fragment thereof comprises: (a) a CDR-H1 comprising the amino acid sequence set forth in SEQ ID NO: 488; (b) a CDR-H2 comprising the amino acid sequence set forth in SEQ ID NO: 526; (c) a CDR-H3 comprising the amino acid sequence set forth in SEQ ID NO: 551; (d) a CDR-L1 comprising the amino acid sequence set forth in SEQ ID NO: 576; (e) a CDR-L2 comprising the amino acid sequence set forth SEQ ID NO: 601; and/or (f) a CDR-L3 comprising the amino acid sequence set forth SEQ ID NO: 626. In some embodiments, the antibody or antigen binding fragment thereof comprises: (a) a CDR-H1 comprising the amino acid sequence set forth in SEQ ID NO: 489; (b) a CDR-H2 comprising the amino acid sequence set forth in SEQ ID NO: 527; (c) a CDR-H3 comprising the amino acid sequence set forth in SEQ ID NO: 552; (d) a CDR-L1 comprising the amino acid sequence set forth in SEQ ID NO: 577; (e) a CDR-L2 comprising the amino acid sequence set forth SEQ ID NO: 602; and/or (f) a CDR-L3 comprising the amino acid sequence set forth SEQ ID NO: 627. In some embodiments, the antibody or antigen binding fragment thereof comprises: (a) a CDR-H1 comprising the amino acid sequence set forth in SEQ ID NO: 634; (b) a CDR-H2 comprising the amino acid sequence set forth in SEQ ID NO: 648; (c) a CDR-H3 comprising the amino acid sequence set forth in SEQ ID NO: 662; (d) a CDR-L1 comprising the amino acid sequence set forth in SEQ ID NO: 676; (e) a CDR-L2 comprising the amino acid sequence set forth SEQ ID NO: 690; and/or (f) a CDR-L3 comprising the amino acid sequence set forth SEQ ID NO: 704.

In some embodiments, the antibody or antigen binding fragment thereof comprises: (a) an immunoglobulin variable region heavy chain (VH) comprising an amino acid sequence having at least about 90, 95, 97, 98, 99, or 100% sequence identity to any one of SEQ ID NOs: 1, 2, 5, 6, 9, 10, 13, 14, 17, 19, 21, 23, 25, 27, 29, and 31; and/or (b) an immunoglobulin variable region light chain (VL) comprising an amino acid sequence having at least about 90, 95, 97, 98, 99, or 100% sequence identity to any one of SEQ ID NOs: 3, 4, 7, 8, 11, 12, 15, 16, 18, 20, 22, 24, 26, 28, and 30. In some embodiments, the antibody or antigen binding fragment thereof comprises: (a) a VH comprising an amino acid sequence having at least about 90, 95, 97, 98, 99, or 100% sequence identity to SEQ ID NO: 1; and/or (b) a VL comprising an amino acid sequence having at least about 90, 95, 97, 98, 99, or 100% sequence identity to SEQ ID NO: 3. In some embodiments, the antibody or antigen binding fragment thereof comprises: (a) a VH comprising an amino acid sequence having at least about 90, 95, 97, 98, 99, or 100% sequence identity to SEQ ID NO: 2; and/or (b) a VL comprising an amino acid sequence having at least about 90, 95, 97, 98, 99, or 100% sequence identity to SEQ ID NO: 4. In some embodiments, the antibody or antigen binding fragment thereof comprises: (a) a VH comprising an amino acid sequence having at least about 90, 95, 97, 98, 99, or 100% sequence identity to SEQ ID NO: 5; and/or (b) a VL comprising an amino acid sequence having at least about 90, 95, 97, 98, 99, or 100% sequence identity to SEQ ID NO: 7. In some embodiments, the antibody or antigen binding fragment thereof comprises: (a) a VH comprising an amino acid sequence having at least about 90, 95, 97, 98, 99, or 100% sequence identity to SEQ ID NO: 6; and/or (b) a VL comprising an amino acid sequence having at least about 90, 95, 97, 98, 99, or 100% sequence identity to SEQ ID NO: 8. In some embodiments, the antibody or antigen binding fragment thereof comprises: (a) a VH comprising an amino acid sequence having at least about 90, 95, 97, 98, 99, or 100% sequence identity to SEQ ID NO: 9; and/or (b) a VL comprising an amino acid sequence having at least about 90, 95, 97, 98, 99, or 100% sequence identity to SEQ ID NO: 11. In some embodiments, the antibody or antigen binding fragment thereof comprises: (a) a VH comprising an amino acid sequence having at least about 90, 95, 97, 98, 99, or 100% sequence identity to SEQ ID NO: 10; and/or (b) a VL comprising an amino acid sequence having at least about 90, 95, 97, 98, 99, or 100% sequence identity to SEQ ID NO: 12. In some embodiments, the antibody or antigen binding fragment thereof comprises: (a) a VH comprising an amino acid sequence having at least about 90, 95, 97, 98, 99, or 100% sequence identity to SEQ ID NO: 13; and/or (b) a VL comprising an amino acid sequence having at least about 90, 95, 97, 98, 99, or 100% sequence identity to SEQ ID NO: 15. In some embodiments, the antibody or antigen binding fragment thereof comprises: (a) a VH comprising an amino acid sequence having at least about 90, 95, 97, 98, 99, or 100% sequence identity to SEQ ID NO: 14; and/or (b) a VL comprising an amino acid sequence having at least about 90, 95, 97, 98, 99, or 100% sequence identity to SEQ ID NO: 16. In some embodiments, the antibody or antigen binding fragment thereof comprises: (a) a VH comprising an amino acid sequence having at least about 90, 95, 97, 98, 99, or 100% sequence identity to SEQ ID NO: 23; and/or (b) a VL comprising an amino acid sequence having at least about 90, 95, 97, 98, 99, or 100% sequence identity to SEQ ID NO: 24. In some embodiments, the antibody or antigen binding fragment thereof comprises: (a) a VH comprising an amino acid sequence having at least about 90, 95, 97, 98, 99, or 100% sequence identity to SEQ ID NO: 25; and/or (b) a VL comprising an amino acid sequence having at least about 90, 95, 97, 98, 99, or 100% sequence identity to SEQ ID NO: 26. In some embodiments, the antibody or antigen binding fragment thereof comprises: (a) a VH comprising an amino acid sequence having at least about 90, 95, 97, 98, 99, or 100% sequence identity to SEQ ID NO: 27; and/or (b) a VL comprising an amino acid sequence having at least about 90, 95, 97, 98, 99, or 100% sequence identity to SEQ ID NO: 28. In some embodiments, the antibody or antigen binding fragment thereof comprises: (a) a VH comprising an amino acid sequence having at least about 90, 95, 97, 98, 99, or 100% sequence identity to SEQ ID NO: 29; and/or (b) a VL comprising an amino acid sequence having at least about 90, 95, 97, 98, 99, or 100% sequence identity to SEQ ID NO: 30. In some embodiments, the antibody or antigen binding fragment thereof comprises: (a) a VH comprising an amino acid sequence having at least about 90, 95, 97, 98, 99, or 100% sequence identity to SEQ ID NO: 31; and/or (b) a VL comprising an amino acid sequence having at least about 90, 95, 97, 98, 99, or 100% sequence identity to SEQ ID NO: 32.

In some embodiments, the antibody or antigen binding fragment thereof comprises: (a) a VH comprising an amino acid sequence set forth in any one of SEQ ID NOs: 1, 2, 5, 6, 9, 10, 13, 14, 17, 19, 21, 23, 25, 27, 29, and 31; and/or (b) a VL comprising an amino acid sequence set forth in any one of SEQ ID NOs: 3, 4, 7, 8, 11, 12, 15, 16, 18, 20, 22, 24, 26, 28, and 30. In some embodiments, the antibody or antigen binding fragment thereof comprises: (a) a VH comprising an amino acid sequence set forth in SEQ ID NO: 1; and/or (b) a VL comprising an amino acid sequence set forth in SEQ ID NO: 3. In some embodiments, the antibody or antigen binding fragment thereof comprises: (a) a VH comprising an amino acid sequence set forth in SEQ ID NO: 2; and/or (b) a VL comprising an amino acid sequence set forth in SEQ ID NO: 4. In some embodiments, the antibody or antigen binding fragment thereof comprises: (a) a VH comprising an amino acid sequence set forth in SEQ ID NO: 5; and/or (b) a VL comprising an amino acid sequence set forth in SEQ ID NO: 7. In some embodiments, the antibody or antigen binding fragment thereof comprises: (a) a VH comprising an amino acid sequence set forth in SEQ ID NO: 6; and/or (b) a VL comprising an amino acid sequence set forth in SEQ ID NO: 8. In some embodiments, the antibody or antigen binding fragment thereof comprises: (a) a VH comprising an amino acid sequence set forth in SEQ ID NO: 9; and/or (b) a VL comprising an amino acid sequence set forth in SEQ ID NO: 11. In some embodiments, the antibody or antigen binding fragment thereof comprises: (a) a VH comprising an amino acid sequence set forth in SEQ ID NO: 10; and/or (b) a VL comprising an amino acid sequence set forth in SEQ ID NO: 12. In some embodiments, the antibody or antigen binding fragment thereof comprises: (a) a VH comprising an amino acid sequence set forth in SEQ ID NO: 13; and/or (b) a VL comprising an amino acid sequence set forth in SEQ ID NO: 15. In some embodiments, the antibody or antigen binding fragment thereof comprises: (a) a VH comprising an amino acid sequence set forth in SEQ ID NO: 14; and/or (b) a VL comprising an amino acid sequence set forth in SEQ ID NO: 16. In some embodiments, the antibody or antigen binding fragment thereof comprises: (a) a VH comprising an amino acid sequence set forth in SEQ ID NO: 23; and/or (b) a VL comprising an amino acid sequence set forth in SEQ ID NO: 24. In some embodiments, the antibody or antigen binding fragment thereof comprises: (a) a VH comprising an amino acid sequence set forth in SEQ ID NO: 25; and/or (b) a VL comprising an amino acid sequence set forth in SEQ ID NO: 26. In some embodiments, the antibody or antigen binding fragment thereof comprises: (a) a VH comprising an amino acid sequence set forth in SEQ ID NO: 27; and/or (b) a VL comprising an amino acid sequence set forth in SEQ ID NO: 28. In some embodiments, the antibody or antigen binding fragment thereof comprises: (a) a VH comprising an amino acid sequence set forth in SEQ ID NO: 29; and/or (b) a VL comprising an amino acid sequence set forth in SEQ ID NO: 30. In some embodiments, the antibody or antigen binding fragment thereof comprises: (a) a VH comprising an amino acid sequence set forth in SEQ ID NO: 31; and/or (b) a VL comprising an amino acid sequence set forth in SEQ ID NO: 32.

In some embodiments, the antibody or antigen binding fragment thereof further comprises an IgG constant region. In some embodiments, the antibody or antigen binding fragment thereof further comprises an IgG constant region having reduced antibody-dependent cell-mediated cytotoxicity (ADCC) function as compared to human IgG and/or reduced complement-dependent cytotoxicity (CDC) as compared to human IgG. In some embodiments, the constant region comprises an amino acid sequence having 80, 85, 90, 95, 97, 98, 99, or 100% sequence identity to the amino acid sequence set forth by any one of SEQ ID NOs: 500-512. In some embodiments, the constant region comprises the amino acid sequence set forth by any one of SEQ ID NOs: 500-512.

In some embodiments, the antibody or antigen binding fragment thereof further comprises a constant region having an amino acid sequence variant corresponding to (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331 S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265 S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328Y, (gg) 330R, (hh) 339E or 339L, (ii) 343I or 343V, (jj) 373A, 373G, or 373S, (kk) 376E, 376W, or 376Y, (ll) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa) L234A, L235E, G237A, and P331 S (bbb) L234A, L235A, G237A, P238S, H268A, A330S, and P331 S, (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (lll) A330L, (mmm) P331A or P331S, or (nnn) any combination of (a)-(mmm), per EU numbering.

In some embodiments, the antibody or antigen binding fragment thereof is an IgG antibody. In some embodiments, the IgG antibody is IgG1, IgG2, IgG3, or IgG4.

In some embodiments, the antibody or antigen binding fragment thereof is human, chimeric, or humanized.

In some embodiments, the antigen binding fragment thereof is a Fab, F(ab')2, a single-domain antibody, or a single chain variable fragment (scFv).

In some embodiments, the antibody or antigen binding fragment thereof binds one or more amino acids residues of CD30L that interact with CD30.

In some embodiments, the antibody or antigen binding fragment thereof inhibits a binding interaction between CD30L and CD30. In some embodiments, the antibody or antigen binding fragment thereof blocks a binding interaction between CD30L and CD30. In some embodiments, the inhibition or blocking is determined in an ELISA assay, a cell binding assay with CD30L expressing cells, or a surface plasmon resonance (SPR) assay.

In some embodiments, the antibody or antigen binding fragment thereof specifically binds to CD30L.

In some embodiments, the antibody or antigen binding fragment thereof (i) inhibits interleukin-8 secretion in a cell-based assay, (ii) inhibits interleukin-6 secretion in a cell-based assay, or (iii) both (i) and (ii). In some embodiments, the antibody or antigen binding fragment thereof (i) blocks interleukin-8 secretion in a cell-based assay, (ii) blocks interleukin-6 secretion in a cell-based assay, or (iii) both (i) and (ii). In some embodiments, the cell-based assay is a dual cell assay with a cell expressing CD30 and a cell expressing CD30L.

In some embodiments, the antibody or antigen binding fragment thereof binds to (i) human CD30L, (ii) cynomolgus CD30L, or (iii) both human CD30L and cynomolgus CD30L.

In some embodiments, the antibody or antigen binding fragment thereof binds to CD30L with a dissociation equilibrium constant ($K_D$) of no more than 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, or 1000 pM. In some embodiments, the antibody or antigen binding fragment thereof binds to CD30L with an association rate constant ($k_{on}$) of at least $0.1 \times 10^6$, $0.2 \times 10^6$, $0.3 \times 10^6$, $0.4 \times 10^6$, $0.5 \times 10^6$, $0.6 \times 10^6$, $0.7 \times 10^6$, $0.8 \times 10^6$, $0.9 \times 10^6$, $1.0 \times 10^6$, $1.1 \times 10^6$, $1.2 \times 10^6$, $1.3 \times 10^6$, $1.4 \times 10^6$, $1.5 \times 10^6$, or $1.55 \times 10^6$ $M^{-1}S^{-1}$. In some embodiments, the antibody or antigen binding fragment thereof binds to CD30L with a dissociation rate constant ($k_{off}$) of no more than $1.4 \times 10^{-4}$, $1.41 \times 10^{-4}$, $1.5 \times 10^{-4}$, $1.6 \times 10^{-4}$, $1.7 \times 10^{-4}$, $1.8 \times 10^{-4}$, $1.9 \times 10^{-4}$, $2.0 \times 10^{-4}$, $2.1 \times 10^{-4}$, $2.2 \times 10^{-4}$, $2.3 \times 10^{-4}$, $2.4 \times 10^{-4}$, $2.5 \times 10^{-4}$, $2.6 \times 10^{-4}$, $2.7 \times 10^{-4}$, $2.8 \times 10^{-4}$, $2.9 \times 10^{-4}$, $3.0 \times 10^{-4}$, $3.1 \times 10^{-4}$, $3.2 \times 10^{-4}$, $3.3 \times 10^{-4}$, $3.4 \times 10^{-4}$, or $3.5 \times 10^{-4}$ $S^{-1}$.

In some embodiments, the antibody or antigen binding fragment thereof is recombinant antibody or antigen binding fragment thereof.

In some embodiments, the antibody or antigen binding fragment thereof is isolated antibody or antigen binding fragment thereof.

In one aspect, provided herein are recombinant antibodies and/or antigen binding fragments thereof that binds CD30L, wherein the antibody or antigen binding fragment thereof comprises: (a) an immunoglobulin heavy chain CDR1 (CDR-H1) comprising the amino acid sequence set forth in any one of SEQ ID NOs: 100-139 or 220-234; (b) an immunoglobulin heavy chain CDR2 (CDR-H2) comprising the amino acid sequence set forth in any one of SEQ ID NOs: 140-179 or 235-249; (c) an immunoglobulin heavy chain CDR3 (CDR-H3) comprising the amino acid sequence set forth in any one of SEQ ID NOs: 180-219 or 250-264; (d) an immunoglobulin light chain CDR1 (CDR-L1) comprising the amino acid sequence set forth in any one of SEQ ID NOs: 300-339 or 420-434; (e) an immunoglobulin light chain CDR2 (CDR-L2) comprising the amino acid sequence set forth in any one of SEQ ID NOs: 340-379 or 435-449; and/or (f) an immunoglobulin light chain CDR3 (CDR-L3) comprising the amino acid sequence set forth in any one of SEQ ID NOs: 380-419 or 450-464.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 100-109; (b) an immunoglobulin heavy chain CDR2 (CDR-H2) comprising the amino acid sequence set forth in any one of SEQ ID NOs: 140-149; (c) an immunoglobulin heavy chain CDR3 (CDR- H3) comprising the amino acid sequence set forth in any one of SEQ ID NOs: 180-189; (d) an immunoglobulin light chain CDR1 (CDR-L1) comprising the amino acid sequence set forth in any one of SEQ ID NOs: 300-309; (e) an immunoglobulin light chain CDR2 (CDR-L2) comprising the amino acid sequence set forth in any one of SEQ ID NOs: 340-349; and/or (f) an immunoglobulin light chain CDR3 (CDR-L3) comprising the amino acid sequence set forth in any one of SEQ ID NOs: 380-389.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 100-104; (b) an immunoglobulin heavy chain CDR2 (CDR-H2) comprising the amino acid sequence set forth in any one of SEQ ID NOs: 140-144; (c) an immunoglobulin heavy chain CDR3 (CDR-H3) comprising the amino acid sequence set forth in any one of SEQ ID NOs: 180-184; (d) an immunoglobulin light chain CDR1 (CDR-L1) comprising the amino acid sequence set forth in any one of SEQ ID NOs: 300-304; (e) an immunoglobulin light chain CDR2 (CDR-L2) comprising the amino acid sequence set forth in any one of SEQ ID NOs: 340-344; and/or (f) an immunoglobulin light chain CDR3 (CDR-L3) comprising the amino acid sequence set forth in any one of SEQ ID NOs: 380-384.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 105-109; (b) an immunoglobulin heavy chain CDR2 (CDR-H2) comprising the amino acid sequence set forth in any one of SEQ ID NOs: 145-149; (c) an immunoglobulin heavy chain CDR3 (CDR-H3) comprising the amino acid sequence set forth in any one of SEQ ID NOs: 185-189; (d) an immunoglobulin light chain CDR1 (CDR-L1) comprising the amino acid sequence set forth in any one of SEQ ID NOs: 305-309; (e) an immunoglobulin light chain CDR2 (CDR-L2) comprising the amino acid sequence set forth in any one of SEQ ID NOs: 345-349; and/or (f) an immunoglobulin light chain CDR3 (CDR-L3) comprising the amino acid sequence set forth in any one of SEQ ID NOs: 385-389.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 1 and 2; and/or (b) the immunoglobulin variable region light chain comprises an amino acid sequence having at least about 90, 95, 97, 98, 99, or 100% sequence identity to any one of SEQ ID NOs: 3 and 4.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 110-119; (b) an immunoglobulin heavy chain CDR2 (CDR-H2) comprising the amino acid sequence set forth in any one of SEQ ID NOs: 150-159; (c) an immunoglobulin heavy chain CDR3 (CDR-H3) comprising the amino acid sequence set forth in any one of SEQ ID NOs: 190-199; (d) an immunoglobulin light chain CDR1 (CDR-L1) comprising the amino acid sequence set forth in any one of SEQ ID NOs: 310-319; (e) an immunoglobulin light chain CDR2 (CDR-L2) comprising the amino acid sequence set forth in any one of SEQ ID NOs: 350-359; and/or (e) an immunoglobulin light chain CDR3 (CDR-L3) comprising the amino acid sequence set forth in any one of SEQ ID NOs: 390-399.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 110-114; (b) an immunoglobulin heavy chain CDR2 (CDR-H2) comprising the amino acid sequence set forth in any one of SEQ ID NOs: 150-154; (c) an immunoglobulin heavy chain CDR3 (CDR-H3) comprising the amino acid sequence set forth in any one of SEQ ID NOs: 190-194; (d) an immunoglobulin light chain CDR1 (CDR-L1) comprising the amino acid sequence set forth in any one of SEQ ID NOs: 310-314; (e) an immunoglobulin light chain CDR2 (CDR-L2) comprising the amino acid sequence set forth in any one of SEQ ID NOs: 350-354; and/or (e) an immunoglobulin light chain CDR3 (CDR-L3) comprising the amino acid sequence set forth in any one of SEQ ID NOs: 390-394.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 115-119; (b) an immunoglobulin heavy chain CDR2 (CDR-H2) comprising the amino acid sequence set forth in any one of SEQ ID NOs: 155-159; (c) an immunoglobulin heavy chain CDR3 (CDR-H3) comprising the amino acid sequence set forth in any one of SEQ ID NOs: 195-199; (d) an immunoglobulin light chain CDR1 (CDR-L1) comprising the amino acid sequence set forth in any one of SEQ ID NOs: 315-319; (e) an immunoglobulin light chain CDR2 (CDR-L2) comprising the amino acid sequence set forth in any one of SEQ ID NOs: 355-359; and/or (f) an immunoglobulin light chain CDR3 (CDR-L3) comprising the amino acid sequence set forth in any one of SEQ ID NOs: 395-399.

In some embodiments, provided is an antibody or antigen binding fragment thereof of any of the preceding embodiments, comprising an immunoglobulin variable region heavy chain and an immunoglobulin variable region light chain, wherein (a) the immunoglobulin variable region heavy chain comprises an amino acid sequence having at least about 90, 95, 97, 98, 99, or 100% sequence identity to any one of SEQ ID NOs: 5 and 6; and/or (b) the immunoglobulin variable region light chain comprises an amino acid sequence having at least about 90, 95, 97, 98, 99, or 100% sequence identity to any one of SEQ ID NOs: 7 and 8.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 120-129; (b) an immunoglobulin heavy chain CDR2 (CDR-H2) comprising the amino acid sequence set forth in any one of SEQ ID NOs: 160-169; (c) an immunoglobulin heavy chain CDR3 (CDR-H3) comprising the amino acid sequence set forth in any one of SEQ ID NOs: 200-209; (d) an immunoglobulin light chain CDR1 (CDR-L1) comprising the amino acid sequence set forth in any one of SEQ ID NOs: 320-329; (e) an immunoglobulin light chain CDR2 (CDR-L2) comprising the amino acid sequence set forth in any one of SEQ ID NOs: 360-369; and/or (f) an immunoglobulin light chain CDR3 (CDR-L3) comprising the amino acid sequence set forth in any one of SEQ ID NOs: 400-409.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 120-124; (b) an immunoglobulin heavy chain CDR2 (CDR-H2) comprising the amino acid sequence set forth in any one of SEQ ID NOs: 160-164; (c) an immunoglobulin heavy chain CDR3 (CDR-H3) comprising the amino acid sequence set forth in any one of SEQ ID NOs: 200-204; (d) an immunoglobulin light chain CDR1 (CDR-L1) comprising the amino acid sequence set forth in any one of SEQ ID NOs: 320-324; (e) an immunoglobulin light chain CDR2 (CDR-L2) comprising the amino acid sequence set forth in any one of SEQ ID NOs: 360-364; and/or (f) an immunoglobulin light chain CDR3 (CDR-L3) comprising the amino acid sequence set forth in any one of SEQ ID NOs: 400-404.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 125-129; (b) an immunoglobulin heavy chain CDR2 (CDR-H2) comprising the amino acid sequence set forth in any one of SEQ ID NOs: 165-169; (c) an immunoglobulin heavy chain CDR3 (CDR-H3) comprising the amino acid sequence set forth in any one of SEQ ID NOs: 205-209; (d) an immunoglobulin light chain CDR1 (CDR-L1) comprising the amino acid sequence set forth in any one of SEQ ID NOs: 325-329; (e) an immunoglobulin light chain CDR2 (CDR-L2) comprising the amino acid sequence set forth in any one of SEQ ID NOs: 365-369; and/or (f) an immunoglobulin light chain CDR3 (CDR-L3) comprising the amino acid sequence set forth in any one of SEQ ID NOs: 405-409.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 9 and 10; and/or (b) the immunoglobulin variable region light chain comprises an amino acid sequence having at least about 90, 95, 97, 98, 99, or 100% sequence identity to any one of SEQ ID NOs: 11 and 12.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 130-139; (b) an immunoglobulin heavy chain CDR2 (CDR-H2) comprising the amino acid sequence set forth in any one of SEQ ID NOs: 170-179; (c) an immunoglobulin heavy chain CDR3 (CDR-H3) comprising the amino acid sequence set forth in any one of SEQ ID NOs: 210-219; (d) an immunoglobulin light chain CDR1 (CDR-L1) comprising the amino acid sequence set forth in any one of SEQ ID NOs: 330-339; (e) an immunoglobulin light chain CDR2 (CDR-L2) comprising the amino acid sequence set forth in any one of SEQ ID NOs: 370-379; and/or (f) an immunoglobulin light chain CDR3 (CDR-L3) comprising the amino acid sequence set forth in any one of SEQ ID NOs: 410-419.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 130-134; (b) an immunoglobulin heavy chain CDR2 (CDR-H2) comprising the amino acid sequence set forth in any one of SEQ ID NOs: 170-174; (c) an immunoglobulin heavy chain CDR3 (CDR-H3) comprising the amino acid sequence set forth in any one of SEQ ID NOs: 210-214; (d) an immunoglobulin light chain CDR1 (CDR-L1) comprising the amino acid sequence set forth in any one of SEQ ID NOs: 330-334; (e) an immunoglobulin light chain CDR2 (CDR-L2) comprising the amino acid sequence set forth in any one of SEQ ID NOs: 370-374; and/or (f) an immunoglobulin light chain CDR3 (CDR-L3) comprising the amino acid sequence set forth in any one of SEQ ID NOs: 410-414.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 135-139; (b) an immunoglobulin heavy chain CDR2 (CDR-H2) comprising the amino acid sequence set forth in any one of SEQ ID NOs: 175-179; (c) an immunoglobulin heavy chain CDR3 (CDR-H3) comprising the amino acid sequence set forth in any one of SEQ ID NOs: 215-219; (d) an immunoglobulin light chain CDR1 (CDR-L1) comprising the amino acid sequence set forth in any one of SEQ ID NOs: 335-339; (e) an immunoglobulin light chain CDR2 (CDR-L2) comprising the amino acid sequence set forth in any one of SEQ ID NOs: 375-379; and/or (f) an immunoglobulin light chain CDR3 (CDR-L3) comprising the amino acid sequence set forth in any one of SEQ ID NOs: 415-419.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 13 and 14; and/or (b) the immunoglobulin variable region light chain comprises an amino acid sequence having at least about 90, 95, 97, 98, 99, or 100% sequence identity to any one of SEQ ID NOs: 15 and 16.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 220-224; (b) an immunoglobulin heavy chain CDR2 (CDR-H2) comprising the amino acid sequence set forth in any one of SEQ ID NOs: 235-239; (c) an immunoglobulin heavy chain CDR3 (CDR-H3) comprising the amino acid sequence set forth in any one of SEQ ID NOs: 250-254; (d) an immunoglobulin light chain CDR1 (CDR-L1) comprising the amino acid sequence set forth in any one of SEQ ID NOs: 420-424; (e) an immunoglobulin light chain CDR2 (CDR-L2) comprising the amino acid sequence set forth in any one of SEQ ID NOs: 435-439; and/or (f) an immunoglobulin light chain CDR3 (CDR-L3) comprising the amino acid sequence set forth in any one of SEQ ID NOs: 450-454.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NO: 17; and/or (b) the immunoglobulin variable region light chain comprises an amino acid sequence having at least about 90, 95, 97, 98, 99, or 100% sequence identity to any one of SEQ ID NO: 15 and 18.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 225-229; (b) an immunoglobulin heavy chain CDR2 (CDR-H2) comprising the amino acid sequence set forth in any one of SEQ ID NOs: 240-244; (c) an immunoglobulin heavy chain CDR3 (CDR-H3) comprising the amino acid sequence set forth in any one of SEQ ID NOs: 255-259; (d) an immunoglobulin light chain CDR1 (CDR-L1) comprising the amino acid sequence set forth in any one of SEQ ID NOs: 425-429; (e) an immunoglobulin light chain CDR2 (CDR-L2) comprising the amino acid sequence set forth in any one of SEQ ID NOs: 440-444; and/or (f) an immunoglobulin light chain CDR3 (CDR-L3) comprising the amino acid sequence set forth in any one of SEQ ID NOs: 455-459.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NO: 19; and/or (b) the immunoglobulin variable region light chain comprises an amino acid sequence having at least about 90, 95, 97, 98, 99, or 100% sequence identity to any one of SEQ ID NO: 15 and 20.

In some embodiments, provided is an antibody or antigen binding fragment thereof of any of the preceding embodiments, wherein the antibody or antigen binding fragment thereof comprises: (a) an immunoglobulin heavy chain CDR1 (CDR-H1) comprising the amino acid sequence set forth in any one of SEQ ID NOs: 230-234; (b) an immunoglobulin heavy chain CDR2 (CDR-H2) comprising the amino acid sequence set forth in any one of SEQ ID NOs: 245-249; (c) an immunoglobulin heavy chain CDR3 (CDR-H3) comprising the amino acid sequence set forth in any one of SEQ ID NOs: 260-264; (d) an immunoglobulin light chain CDR1 (CDR-L1) comprising the amino acid sequence set forth in any one of SEQ ID NOs: 430-434; (e) an immunoglobulin light chain CDR2 (CDR-L2) comprising the amino acid sequence set forth in any one of SEQ ID NOs: 445-449; and/or (f) an immunoglobulin light chain CDR3 (CDR-L3) comprising the amino acid sequence set forth in any one of SEQ ID NOs: 460-464.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NO: 21; and/or (b) the immunoglobulin variable region light chain comprises an amino acid sequence having at least about 90, 95, 97, 98, 99, or 100% sequence identity to any one of SEQ ID NO: 15 and 22.

In some embodiments, provided is an antibody or antigen binding fragment thereof of any of the preceding embodiments, comprising a constant region (e.g. a fragment crystallizable (Fc) region) having reduced antibody-dependent cell-mediated cytotoxicity (ADCC) function as compared to human IgG1 and/or reduced complement-dependent cytotoxicity (CDC) as compared to human IgG1. In some embodiments, provided is an antibody or antigen binding fragment thereof of any of the preceding embodiments, wherein the Constant region comprises an amino acid sequence having 80, 85, 90, 95, 97, 98, 99, or 100% sequence identity to the amino acid sequence set forth by any one of SEQ ID NOs: 500-512. In some embodiments, provided is an antibody or antigen binding fragment thereof of any of the preceding embodiments, wherein the Constant region comprises the amino acid sequence set forth by any one of SEQ ID NOs: 500-512.

In some embodiments, provided is an antibody or antigen binding fragment thereof of any of the preceding embodiments, comprising a constant region having an amino acid sequence variant corresponding to (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331 S, (1) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (11) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331S, (zz) L234A, L235E, and G237A, (aaa), L234A, L235E, G237A, and P331 S (bbb) L234A, L235A, G237A, P238S, H268A, A330S, and P331 S, (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (111) A330L, (mmm) P331A or P331 S, or (nnn) any combination of (a)-(mmm), per EU numbering.

In some embodiments, provided is an antibody or antigen binding fragment thereof of any of the preceding embodiments, wherein the recombinant antibody or antigen binding fragment thereof is an IgG antibody. In some embodiments, provided is an antibody or antigen binding fragment thereof of any of the preceding embodiments, wherein the IgG antibody is IgG1, IgG2, IgG3, or IgG4. In some embodiments, provided is an antibody or antigen binding fragment thereof of any of the preceding embodiments, wherein the recombinant antibody or antigen binding fragment thereof is human, chimeric, or humanized.

In some embodiments, provided is an antibody or antigen binding fragment thereof of any of the preceding embodiments, wherein the recombinant antibody or antigen binding fragment thereof is a Fab, F(ab)'$_2$, a single-domain antibody, or a single chain variable fragment (scFv). In some embodiments, provided is an antibody or antigen binding fragment thereof of any of the preceding embodiments, wherein the recombinant antibody or antigen binding fragment thereof is a bispecific or multispecific antibody.

In some embodiments, provided is an antibody or antigen binding fragment thereof of any of the preceding embodiments, wherein the recombinant antibody or antigen binding fragment thereof inhibits a binding interaction between CD30L and CD30.

In an aspect, further provided are nucleic acids encoding the recombinant antibody or antigen binding fragment thereof of any of the preceding embodiments. Also provided are cells comprising the recombinant antibody or antigen binding fragment thereof of any of the preceding embodiments. In some embodiments, the cell is a eukaryotic cell. In some embodiments, the cell is a prokaryotic cell.

In an aspect, provided are recombinant antibodies or antigen binding fragments thereof of any the preceding embodiments for use in a method of inhibiting binding of CD30L to CD30. Further provided are recombinant antibodies or antigen binding fragments thereof of any the preceding embodiments for use in a method of inhibiting activation of CD30 signaling in a cell. Also provided are recombinant antibodies or antigen binding fragments thereof of any the preceding embodiments for use in a method of inhibiting activation, expression, and/or secretion of a pro-inflammatory cytokine protein.

In an aspect, provided are recombinant antibodies or antigen binding fragments thereof of any the preceding embodiments for use in treating an autoimmune disease in an individual in need thereof. In some embodiments, the autoimmune disease is irritable bowel disease. In some embodiments, the irritable bowel disease comprises ulcerative colitis (UC) or Crohn's Disease (CD).

In an aspect, provided are methods of treating or ameliorating an autoimmune disease in an individual in need thereof, the method comprising administering to the individual the recombinant antibody or antigen binding fragment thereof of any of the preceding embodiments, thereby treating or ameliorating the autoimmune disease. Also provided are methods for inhibiting and/or reducing binding of CD30L to CD30 in an individual with an inflammatory or autoimmune disorder, the method comprising administering to an individual afflicted with the inflammatory or autoimmune disorder the recombinant antibody or antigen binding fragment thereof of the preceding embodiments, thereby inhibiting and/or reducing the binding of CD30L to CD30. Further provided are methods of reducing and/or inhibiting inflammation in an individual, the method comprising administering to the individual the recombinant antibody or antigen binding fragment thereof of any of the preceding embodiments, thereby reducing and/or inhibiting inflammation.

In some embodiments, the provided are methods of any of the preceding embodiments, wherein the individual has an autoimmune disease. In some embodiments, the provided are methods of any of the preceding embodiments, wherein the autoimmune disease is irritable bowel disease. In some embodiments, the provided are methods of any of the preceding embodiments, wherein the irritable bowel disease comprises ulcerative colitis (UC) or Crohn's Disease (CD).

In some embodiments, the provided are methods of any of the preceding embodiments, wherein reducing and/or inhibiting inflammation comprises reducing an amount of pro-inflammatory cytokine expression or secretion in the individual or a tissue of the individual. In some embodiments, the provided are methods of any of the preceding embodiments, wherein the pro-inflammatory cytokine comprises interleukin 8 and/or interleukin 6. In some embodiments, the provided are methods of any of the preceding embodiments, wherein the individual has an autoimmune disease. In some embodiments, the provided are methods of any of the preceding embodiments, wherein the autoimmune disease is irritable bowel disease. In some embodiments, the provided are methods of any of the preceding embodiments, wherein the irritable bowel disease comprises ulcerative colitis (UC) or Crohn's Disease (CD).

3. BRIEF DESCRIPTION OF THE DRAWINGS

FIGS. 1A-1E depict dose dependent curve of various anti-CD30L antibodies in B16-huCD30L cell binding assay (1st left column), inhibition/blocking of IL-8 release in a dual cell assay (B16-huCD30L cells and K299 cells) (2nd column from the left), ELISA assay of binding to rhCD30L (3rd column from the left), and ELISA assay of antibody-mediated blocking of CD30-Fc binding to huCD30L (4th column from the left). Units for ELISA are OD 450 nm; and units for cell binding assays are mean fluorescence intensity (MFI). FIG. 1A: results for clones 2_germlined, 62, 63, 64 and 65; FIG. 1B: results for clones 66, 67, 68, 69, 70 and 71; FIG. 1C: results for clones 72, 73, 74, 75, 76 and 77; FIG. 1D: results for clones 78, 79 80 and 8; FIG. 1E: results for clones 82, 83, 84 and 85.

FIGS. 4A-4J depict the 3 dimensional structure of the epitope on CD30L as identified. CD30L amino acids colored in dark gray are corresponding to 16-30 (KGGNCSEDLL-CILKR; SEQ ID NO: 770) and 48-64 (KTKLSWNKDG-ILHGVRY; SEQ ID NO: 771) of SEQ ID NO: 34. FIGS. 4A-4E: ribbon/surface representation of front view (4A); back view (4B), side view 1 (4C), side view 2 (4D) and top view (4E). FIGS. 4F-4J: ribbon representation of front view (4F); back view (4G), side view 1 (411), side view 2 (4I) and top view (4J).

Figure 5K:
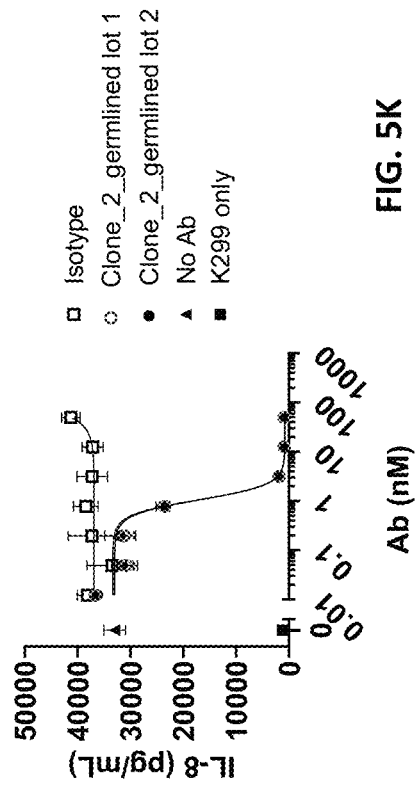
Figure 5L:
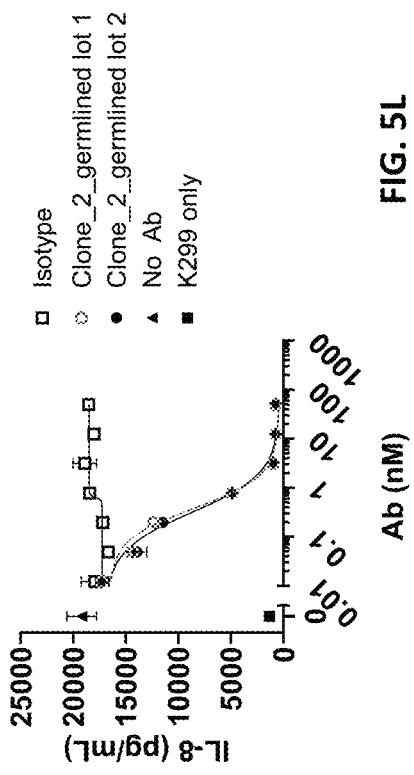
Figure 5J:
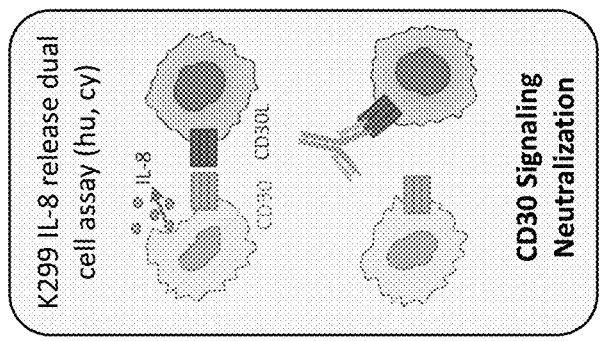

FIG. 5A depicts the cell binding assays for determining anti-CD30L binding to CD30L expressing cells and for determining the blocking/inhibition of CD30 binding to CD30L expressing cells by anti-CD30L. FIG. 5B and FIG. 5C depict representative binding curves for germlined clone 2 from cell binding assay shown in FIG. 5A, with 5B showing binding to human CD30L expressing B16 cells and 5C showing binding to cynoCD30L expressing HEK293 cells. FIG. 5D and FIG. 5E depict representative blocking curves for germlined clone 2 from cell binding assay shown in FIG. 5A, with 5D showing blocking curves against humanCD30L expressing B16 cells and 5E showing blocking curves against cynoCD30L expressing HEK293 cells. FIG. 5F depicts the ELISA configuration for determining anti-CD30L binding to purified CD30L and FIG. 5G depicts the ELISA configuration for determining the blocking/inhibition of CD30L to CD30 by anti-CD30L. FIG. 5H depicts representative binding curve for germlined clone 2 with ELISA assay shown in FIG. 5F and FIG. 5I depicts representative blocking curve for germlined clone 2 with ELISA assay shown in FIG. 5G. FIG. 5J depicts the dual cell IL-8 release assay in which CD30 expressing cells release IL-8 upon signaling by ligation with CD30L expressing cells via the CD30-CD30L interaction. FIG. 5K and FIG. 5L depict representative IL-8 release curves for germlined clone 2 from dual cell assay shown in FIG. 5J, with 5K showing IL-8 release curves with humanCD30L expressing B16 cells and 5L showing IL-8 release curves with cynoCD30L expressing HEK293 cells.

FIGS. 6A-6D depict the effect of anti-CD30l in cynomolgus T cell-dependent antibody responses in vivo. FIG. 6A depicts the time course of the KLH-specific IgM levels in the serum of various treated animals as indicated. FIG. 6B depicts the overall anti-KLH IgM levels (area under the curve) after various treatment based on the curve of FIG. 6A. FIG. 6C depicts the time course of the KLH-specific IgG levels in the serum of various treated animals as indicated. FIG. 6D depicts the overall anti-KLH IgG levels (area under the curve) after various treatment based on the curve of FIG. 6C.

4. DETAILED DESCRIPTION

There are a limited number of therapies available for autoimmune disorders such as IBD, and the development of new therapeutics presents a challenge in the treatment autoimmune diseases, disorders, and symptoms associated therewith. A notable number anti-inflammatory therapies either do not result in an effective therapeutic response to or fail to provide a lasting response. Furthermore, for the time that a patient is treated with an ineffective anti-inflammatory therapy, the disease worsens. For such non-responding patients, the only treatment is surgery, generally in the form of strictureplasty (reshaping of the intestine) or resection (removal of the intestine). Surgical treatments for IBD are invasive, causing post-operative risks for an estimated one-third of patients undergoing surgery, such as anastomotic leak, infection, and bleeding. Accordingly, the heterogeneity of disease pathogenesis and clinical course, combined with the variable and/or inconsistent response to treatment, suggests a targeted therapeutic approach to treating autoimmune disorders such as IBD is a desirable treatment strategy. Yet very few targeted therapies have been identified and effective in IBD patients, especially those patients who may be non-responsive to existing IBD anti-inflammatory therapies. Thus, there is a need for novel therapeutics to treat autoimmune diseases such as IBD that specifically target IBD pathogenesis.

Described herein are antibodies that target and bind CD30 µligand (CD30L) and, in certain instances, provide an effective targeted therapy approach for the treatment of autoimmune disorders such as IBD. Generally, in an aspect, the antibodies described herein effectively inhibit an interaction between CD30L and CD30 in order to effectively reduce, inhibit, or prevent immune activation (for example, an inflammatory response). The CD30 ligand (also referred to as CD30L, CD153 or TNFSF8) is a member of the tumor necrosis factor (TNF) family. CD30L is a transmembrane protein expressed on immune cells, including activated T and B cells. Generally, after interaction with its receptor CD30, CD30L may induce signal transduction through modulation of TNF receptor-associated factor 1 (TRAF1), TRAF2, 3 and 5. Interaction between CD30-CD30L results in the triggering of immune cell (for example, T cell) activation (for example, stimulating immune cell proliferation, release of cytokines, etc.) and the activation of an inflammatory response. Accordingly, the antibodies described here that target CD30L are useful in preventing, inhibiting, or reducing CD30-CD30L-mediated immune cell activation and/or activation of an inflammatory response in an individual. In certain instances, preventing, inhibiting, or reducing CD30-CD30L-mediated immune cell activation and/or activation of an inflammatory response in an individual is useful for the treatment of autoimmune disorders such as IBD.

4.1 anti-CD30L Antibodies

Described herein are recombinant antibodies or antigen binding fragments thereof that bind CD30 µligand (CD30L). CD30 µligand or CD30L or human CD30L (also known and referred to as Tumor necrosis factor ligand superfamily member 8, CD153; CD30L; CD30LG; TNLG3A) as used herein refers to any protein that comprises the expressed and processed forms of the human (*Homo sapiens*) CD30L gene which, in certain embodiments, is designated as UniProtKB/Swiss-Prot P32971 (NCBI Reference Sequence: NM_001244.4→NP_001235.1 or NM_001252290.1→NP_001239219.1) The term "CD30L" as used herein includes the wild type protein and all naturally occurring variants and/or isoforms thereof, and all transcriptional variants, post-translationally-modified variants (for example, as described as part of the record in UniProtKB/Swiss-Prot P32971). The antibodies further block an interaction between CD30L and CD30 and inhibit pro-inflammatory cytokine release.

The term "and/or" as used in a phrase with a list of members is intended to include all members individually and all combination of full or partial list of members. For example, a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The disclosure provides that wherever embodiments are provided herein with the term "comprising," the analogous embodiments described in terms of "consisting of" and/or "consisting essentially of" are also provided, if such analogous embodiments are not explicitly provided. The disclosure further provides that wherever embodiments are described herein with the phrase "consisting essentially of," the analogous embodiments described in terms of "consisting of" are also provided. The disclosure also provides that wherever embodiments are described herein with the phrase "consisting of," the analogous embodiments described in terms of "consisting essentially of" are also provided.

All applications, publications, patents and other references, GenBank citations and ATCC citations cited herein are incorporated by reference in their entirety. In case of conflict, the specification, including definitions, will control.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1,000, 1,000-2,500, 2,500-5,000, 5,000-25,000, 25,000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges includes combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

In some embodiments, the term "about" means mean within 10%, within 9%, within 8%, within 7%, within 6%, within 5%, within 4%, within 3%, within 2%, within 1%, or less of a given value, amount, or range. For instance, an antibody variable region comprising about 90% identity to a reference variable region may comprise 82% to 98% identity to the reference variable region.

The terms "specifically bind to," "specific binding," and analogous terms when used in the context of one molecule binding to the other, means that one molecule binds to the other molecule with significantly higher affinity than to any cross-reactive antigen or off-target antigen (together as non-target antigen) as determined using experimental techniques, such as Surface Plasmon Resonance (SPR), fluorescence activated cell sorting (FACS) analysis, Kinetic Exclusion Assay (KinExA), isothermal titration calorimetry (ITC), radioimmunoassays (RIA) and enzyme linked immunosorbent assays (ELISAs). Typically, a specific or selective reaction will be at least twice non-target signal or noise of non-target binding and may be more than 10 times non-target binding. See, e.g., *Fundamental Immunology* 332-36 (Paul ed., 2d ed. 1989) for a discussion regarding antibody specificity. An antibody or antigen binding fragment which binds a target of interest (e.g., a target CD30L) is one that binds the target with sufficient affinity such that the antibody or antigen binding fragment is useful as a therapeutic agent in targeting a cell or tissue expressing the target, and does not significantly cross-react with other proteins. In such embodiments, the extent of binding of the antibody or antigen binding fragment to a "non-target" protein will be less than about 10% of the binding of the antibody or antigen binding fragment to its particular target protein, for example, as determined by FACS analysis, SPR, KinExA, ITC, ELISA, or RIA. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. As such, the term "specific binding," "specifically binds to," "specifically inhibits," "specifically blocks" or "is specific for" a particular target as used herein refers to binding, blocking, or inhibition where a molecule binds to, blocks, or inhibits a particular target without substantially binding to or inhibiting a non-target. In certain embodiments, the antiCD30L antibody or antigen binding fragment provided herein specifically binds to CD30L. In some embodiments, an antiCD30L antibody or antigen binding fragment that specifically binds to CD30L indicates that the antibody reacts or associates more frequently, more rapidly, with greater duration, with greater affinity, or with some combination of the above to the CD30L than with alternative substances, including unrelated proteins.

As used herein, the term "inhibit," "inhibiting," or "inhibition" when used in reference to CD30-CD30L binding or interaction, CD30L-mediated CD30 signaling, or other CD30L biochemical or biological functions, is intended to mean decreasing, attenuating, lowering, reducing, or completely abolishing the CD30-CD30L binding or interaction, CD30L-mediated CD30 signaling, or other CD30L biochemical or biological functions (such as CD30L-mediated IL-8 release in CD30 expressing cells). For example, such inhibition of the CD30-CD30L binding or interaction, CD30L-mediated CD30 signaling, or other CD30L biochemical or biological functions can be a reduction of 10%, 20%, 30%, 40%, 50%, 60%, 70%, 80%, 90%, 95%, or 99% of the CD30-CD30L binding or interaction, CD30L-mediated CD30 signaling, or other CD30L biochemical or biological functions. In other examples, such inhibition of the CD30-CD30L binding or interaction, CD30L-mediated CD30 signaling, or other CD30L biochemical or biological functions can be complete elimination of the CD30-CD30L binding or interaction, CD30L-mediated CD30 signaling, or other CD30L biochemical or biological functions. In one embodiment, the anti-CD30L antibody or antigen binding fragment provided herein inhibited the CD30-CD30L binding or interaction, CD30L-mediated CD30 signaling, or other CD30L biochemical or biological functions by at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In another embodiment, the anti-CD30L antibody or antigen binding fragment provided herein inhibited the CD30-CD30L binding or interaction, CD30L-mediated CD30 signaling, or other CD30L biochemical or biological functions by about 30%, about 35%, about 40%, about 45%, about 50%, about 55%, about 60%, about 65%, about 70%, about 75%, about 80%, about 85%, about 90%, about 95%, or about 99%. In yet another embodiment, the anti-CD30L antibody or antigen binding fragment provided herein completely abolished the CD30-CD30L binding or interaction, CD30L-mediated CD30 signaling, or other CD30L biochemical or biological functions.

As used herein, the term "block," or "blocking," when used in reference to CD30-CD30L binding or interaction, CD30L-mediated CD30 signaling, or other CD30L biochemical or biological functions, is intended to mean decreasing, attenuating, lowering, reducing, or completely abolishing the CD30-CD30L binding or interaction, CD30L-mediated CD30 signaling, or other CD30L biochemical or biological functions (such as CD30L-mediated IL-8 release in CD30 expressing cells), to such a degree that the remaining the CD30-CD30L binding or interaction, CD30L-mediated CD30 signaling, or other CD30L biochemical or biological functions are no longer biologically significant. For example, such blocking of the CD30-CD30L binding or interaction, CD30L-mediated CD30 signaling, or other CD30L biochemical or biological functions can be a reduction of 60%, 65%, 70%, 75%, 80%, 85%, 90%, 95%, or 99% of the CD30-CD30L binding or interaction, CD30L-mediated CD30 signaling, or other CD30L biochemical or biological functions. In other examples, such blocking of the CD30-CD30L binding or interaction, CD30L-mediated CD30 signaling, or other CD30L biochemical or biological functions can be complete elimination of the CD30-CD30L binding or interaction, CD30L-mediated CD30 signaling, or other CD30L biochemical or biological functions. In one embodiment, the anti-CD30L antibody or antigen binding fragment provided herein blocks the CD30-CD30L binding or interaction, CD30L-mediated CD30 signaling, or other CD30L biochemical or biological functions by decreasing at least 60%, at least 65%, at least 70%, at least 75%, at least 80%, at least 85%, at least 90%, at least 95%, or at least 99% of the CD30-CD30L binding or interaction, CD30L-mediated CD30 signaling, or other CD30L biochemical or biological functions, such that the remaining CD30-CD30L binding or interaction, CD30L-mediated CD30 signaling, or other CD30L biochemical or biological functions are no longer biologically significant. In another embodiment, the anti-CD30L antibody or antigen binding fragment provided herein blocks the CD30-CD30L binding or interaction, CD30L-mediated CD30 signaling, or other CD30L biochemical or biological functions by about 60%, about 65%, about 70%, about 75%, about 80%, about 85%, about 90%, about 95%, or about 99% of the CD30-CD30L binding or interaction, CD30L-mediated CD30 signaling, or other CD30L biochemical or biological functions, such that the remaining CD30-CD30L binding or interaction, CD30L-mediated CD30 signaling, or other CD30L biochemical or biological functions are no longer biologically significant. In yet another embodiment, the anti-CD30L antibody or antigen binding fragment provided herein completely blocks, e.g. completely abolishes the CD30-CD30L binding or interaction, CD30L-mediated CD30 signaling, or other CD30L biochemical or biological functions.

"Antibody-dependent cell-mediated cytotoxicity" or "ADCC" refers to a form of cytotoxicity in which secreted immunoglobulin bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. NK cells, the primary cells for mediating ADCC, express FcγRIII only, whereas monocytes express FcγRI, FcγRII, and FcγRIII. FcR expression on hematopoietic cells is known (see, e.g., Ravetch and Kinet, 1991, Annu. Rev. Immunol. 9:457-92). To assess ADCC activity of a molecule of interest, an in vitro ADCC assay (see, e.g., U.S. Pat. Nos. 5,500,362 and 5,821,337) can be performed. Useful effector cells for such assays include peripheral blood mononuclear cells (PBMC) and Natural Killer (NK) cells. Alternatively, or additionally, ADCC activity of the molecule of interest may be assessed in vivo, for example, in an animal model (see, e.g., Clynes et al., 1998, Proc. Natl. Acad. Sci. USA 95:652-56). Antibodies with little or no ADCC activity can be selected for use.

"Antibody-dependent cellular phagocytosis" or "ADCP" refers to the destruction of target cells via monocyte or macrophage-mediated phagocytosis when immunoglobulin bound onto Fc receptors (FcRs) present on certain phagocytotic cells (e.g., neutrophils, monocytes, and macrophages) enable these phagocytotic cells to bind specifically to an antigen-bearing target cell and subsequently kill the target cell. To assess ADCP activity of a molecule of interest, an in vitro ADCP assay (see, e.g., Bracher et al., 2007, J. Immunol. Methods 323:160-71) can be performed. Useful phagocytotic cells for such assays include peripheral blood mononuclear cells (PBMC), purified monocytes from PBMC, or U937 cells differentiated to the mononuclear type. Alternatively, or additionally, ADCP activity of the molecule of interest may be assessed in vivo, for example, in an animal model (see, e.g., Wallace et al., 2001, J. Immunol. Methods 248:167-82). Antibodies with little or no ADCP activity can be selected for use.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay (see, e.g., Gazzano-Santoro et al., 1996, J. Immunol. Methods 202:163) may be performed. Polypeptide variants with altered Fc region amino acid sequences (polypeptides with a variant Fc region) and increased or decreased C1q binding capability have been described (see, e.g., U.S. Pat. No. 6,194,551; WO 1999/51642; Idusogie et al., 2000, J. Immunol. 164: 4178-84). Antibodies with little or no CDC activity can be selected for use.

As provided herein, the term "antibody" is used in the broadest sense and includes polyclonal and monoclonal antibodies, including intact antibodies and functional (antigen-binding) antibody fragments thereof, including fragment antigen binding (Fab) fragments, F(ab')$_2$ fragments, Fab' fragments, Fv fragments, recombinant IgG (rIgG) fragments, single chain antibody fragments, including single chain variable fragments (sFv or scFv), and single domain antibodies (for example, sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, for example, bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. The antibody can comprise a human IgG1 constant region. The antibody can comprise a human IgG4 constant region.

The provided antibodies are useful as monoclonal antibodies, in polyclonal antibody compositions, as multispecific antibodies (for example, bispecific antibodies and polyreactive antibodies), and as antibody fragments (for example, scFv formats). The antibodies provided herein also include antibody-conjugates and molecules comprising the antibodies, such as chimeric molecules. Thus, an antibody includes, but is not limited to, full-length and native antibodies, as well as fragments and portions thereof retaining the binding specificities thereof, such as any specific binding portion thereof including those having any number of, immunoglobulin classes and/or isotypes (for example, IgG1, IgG2, IgG3, IgG4, IgA, IgD, IgE and IgM); and biologically relevant (antigen-binding) fragments or specific binding portions thereof, including but not limited to Fab, F(ab')2, Fv, and scFv (single chain or related entity). A monoclonal antibody is generally one within a composition of substantially homogeneous antibodies; thus, any individual antibodies comprised within the monoclonal antibody composition are identical except for possible naturally occurring mutations that may be present in minor amounts. A polyclonal antibody is a preparation that includes different antibodies of varying sequences that generally are directed against two or more different determinants (epitopes). The monoclonal antibody can comprise a human IgG1 constant region. The monoclonal antibody can comprise a human IgG4 constant region.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745. ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme); and Whitelegg N R and Rees A R, "WAM: an improved algorithm for modelling antibodies on the WEB," Protein Eng. 2000 December; 13(12):819-24 ("AbM" numbering scheme). The CDRs of the antibodies described herein may be defined by the Kabat, IMGT, Chothia, AbM, Aho, contact numbering scheme, or any combination thereof.

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The various numbering schemes and the CDR boundaries according to each numbering schemes are summarized below in Table 26.

TABLE 26

CDR boundaries according to various numbering schemes

|  | IMGT | Kabat | AbM | Chothia | Contact | Aho |
|---|---|---|---|---|---|---|
| CDR-H1 (VH CDR1) | 27-38 | 31-35 | 26-35 | 26-32 | 30-35 | 25-40 |
| CDR-H2 (VH CDR2) | 56-65 | 50-65 | 50-58 | 52-56 | 47-58 | 58-77 |
| CDR-H3 (VH CDR3) | 105-117 | 95-102 | 95-102 | 96-101 | 93-101 | 109-137 |
| CDR-L1 (VL CDR1) | 27-38 | 24-34 | 24-34 | 26-32 | 30-36 | 25-40 |
| CDR-L2 (VL CDR2) | 56-65 | 50-56 | 50-56 | 50-52 | 46-55 | 58-77 |
| CDR-L3 (VL CDR3) | 105-117 | 89-97 | 89-97 | 91-96 | 89-96 | 109-137 |

Accordingly, the term "variable region residue numbering as in Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHo.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs (See for example, Kindt et al. Kuby Immunology, 6th ed., W. H. Freeman and Co., page 91(2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (See for example, Portolano et al., J. Immunol. 150:880-887 (1993); Clarkson et al., Nature 352: 624-628 (1991)).

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (a), delta (6), epsilon (F), gamma (γ), and mu (ρ), based on the amino acid sequence of the heavy chain constant region. The distinct heavy chains differ in size: α, δ, and γ contain approximately 450 amino acids, while ρ and F contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4. A heavy chain canbe a human heavy chain.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (x) or lambda (k) based on the amino acid sequence of the constant domains. Light chain amino acid sequences are well known in the art. A light chain can be a human light chain.

Among the provided antibodies are antibody fragments. An "antibody fragment," "antigen-binding fragment," "antigen-binding domain," "antigen-binding region," "antigen binding fragment," "antigen binding domain," "antigen binding region," and similar terms refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; diabodies; linear antibodies; single-chain antibody molecules (for example, scFv or sFv); and multispecific antibodies formed from antibody fragments. In particular embodiments, the antibodies are single-chain antibody fragments comprising a variable heavy chain region and/or a variable light chain region, such as scFvs. Generally, an antibody fragment or antigen-binding fragment will comprise one or more CDRs from a parental antibody that are sufficient to confer binding specificity.

As used herein the term "contact" or "contacts" in reference to an antibody binding or being bound to a specific target refers to an amino acid residue of variable region or a CDR coming within 5, 4, 3 or fewer angstroms of the recited contacted residue. Contact includes hydrogen bonding, Van der Waal's interactions and salt bridge formation between an amino acid residue of the variable region or CDR of the antibody and the recited residue.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, for example, polypeptide linkers, and/or those that are not produced by enzyme digestion of a naturally-occurring intact antibody. In some aspects, the antibody fragments are scFvs.

Generally, a humanized antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (for example, the antibody from which the CDR residues are derived), for example, to restore or improve antibody specificity or affinity. In some embodiments, a humanized antibody refers to forms of non-human (for example, murine) or not fully humanized antibodies having specific immunoglobulin chains, chimeric immunoglobulins, or fragments thereof that contain minimal non-human (for example, murine) sequences. In a non-limiting example, a humanized antibody comprises less than about 40% non-human sequence in the variable region. In some embodiments, a humanized antibody comprises less than about 20% non-human sequence in a full-length antibody sequence. In a further non-limiting example, a humanized antibody comprises less than about 20% non-human sequence in the framework region of each of the heavy chain and light chain variable regions. For instance, the humanized antibody comprises less than about 20%, 19%, 18%, 17%, 16%, 15%, 14%, 13%, 12%, 11%, 10%, 9%, 8%, 7%, 6%, 5%, 4%, 3%, 2%, or 1% non-human sequence in the framework region of each of the heavy chain and light chain variable regions. As another example, the humanized antibody comprises about or less than about 15, 14, 13, 12, 11, 10, 9, 8, 7, 6, 5, 4, 3, 2, or 1 non-human sequences in the framework region of each of the heavy chain and light chain variable regions. In some embodiments, humanized antibodies are human immunoglobulins in which residues from the complementarity determining region (CDR) are replaced by residues from the CDR of a non-human species (for example, mouse, rat, rabbit, hamster) that have the desired specificity, affinity, and capability. These humanized antibodies may contain one or more non-human species mutations, for example, the heavy chain comprises about 1, 2, 3, 4, 5, 6, 7, 8, 9, 10, 11, 12, 13, 14, or 15 non-human species mutations in the framework region, and the light chain comprises about 1, 2, 3, 4, 5, 6, 7, 8, 9, 10, 11, 12, 13, 14, or 15 non-human species mutations in the framework region. The humanized heavy chain variable domain may comprise a IGHV3-9, IGHV4-59, or IGHV3-33 framework with no or fewer than about 10, 9, 8, 7, 6, 5, 4, 3, 2, or 1 amino acid mutations. In some embodiments, the heavy chain variable domain comprises a IGHV3-9 framework. n some embodiments, the heavy chain variable domain comprises a IGHV4-59 framework. n some embodiments, the heavy chain variable domain comprises a IGHV3-33 framework. The humanized light chain variable domain may comprise IGKV1-16, IGKV1-6, or IGKV2-28 framework with no or fewer than about 10, 9, 8, 7, 6, 5, 4, 3, 2, or 1 amino acid mutations.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived or selected from human antibody libraries, including phage display and cell-free libraries, containing antibody-encoding sequences derived from a human repertoire. In certain embodiments, a human antibody can have sequence liabilities removed or its affinity increased by successive rounds of selection by a method such as phage display.

The terms "polypeptide" and "protein" are used interchangeably to refer to a polymer of amino acid residues and are not limited to a minimum length. Polypeptides, including the provided antibodies and antibody chains and other peptides, for example, linkers and binding peptides, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known for instance, using publicly available computer software such as BLAST, BLAST-2, ALIGN or Megalign (DNASTAR) software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source co de has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In some embodiments, antibody variants having one or more amino acid substitutions are provided. Sites of interest for mutagenesis by substitution include the CDRs and FRs. Amino acid substitutions may be introduced into an antibody of interest and the products screened for a desired activity, for example, retained/improved antigen binding, decreased immunogenicity such as reduced ADCC or CDC. In some embodiments, substitutions, insertions, or deletions may occur within one or more CDRs, wherein the substitutions, insertions, or deletions do not substantially reduce antibody binding to antigen. For example, conservative substitutions that do not substantially reduce binding affinity may be made in CDRs. Such alterations may be outside of CDR "hotspots." In some embodiments of the variant VH and VL sequences, each CDR is unaltered.

Alterations (for example, substitutions) may be made in CDRs, for example, to improve antibody affinity. Such alterations may be made in CDR encoding codons with a high mutation rate during somatic maturation (See for example, Chowdhury, Methods Mol. Biol. 207:179-196 (2008)), and the resulting variant can be tested for binding affinity. Affinity maturation (for example, using error-prone PCR, chain shuffling, randomization of CDRs, or oligonucleotide-directed mutagenesis) can be used to improve antibody affinity (See for example, Hoogenboom et al. in Methods in Molecular Biology 178:1-37 (2001)). CDR residues involved in antigen binding may be specifically identified, for example, using alanine scanning mutagenesis or modeling (See for example, Cunningham and Wells Science, 244:1081-1085 (1989)). CDR-H3 and CDR-L3 in particular are often targeted. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions and deletions include amino- and/or carboxyl-terminal fusions ranging in length from one residue to polypeptides containing a hundred or more residues, as well as intrasequence insertions and deletions of single or multiple amino acid residues. Examples of terminal insertions include an antibody with an N-terminal methionyl residue. Other insertional variants of the antibody molecule include the fusion to the N- or C-terminus of the antibody to an enzyme (for example, for ADEPT) or a polypeptide which increases the serum half-life of the antibody. Examples of intrasequence insertion variants of the antibody molecules include an insertion of 3 amino acids in the light chain. Examples of terminal deletions include an antibody with a deletion of 7 or less amino acids at an end of the light chain.

In some embodiments, the antibodies are altered to increase or decrease their glycosylation (for example, by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to Asn297 of the CH2 domain of the Fc region (See for example, Wright et al. TIBTECH 15:26-32 (1997)). The oligosaccharide can be various carbohydrates, for example, mannose, N-acetyl glucosamine (GlcNAc), galactose, sialic acid, fucose attached to a GlcNAc in the stem of the biantennar oligosaccharide structure. Modifications of the oligosaccharidein an antibody can be made, for example, to create antibody variants with certain improved properties. Antibody glycosylation variants can alter ADCC and/or CDC function. Cell lines, for example, knockout cell lines and methods of their use can be used to produce defucosylated antibodies, for example, Lec13 CHO cells deficient in protein fucosylation and alpha-1,6-fucosyltransferase gene (FUT8) knockout CHO cells (See for example, Ripka et al. Arch. Biochem. Biophys. 249:533-545 (1986); Yamane-Ohnuki et al. Biotech. Bioeng. 87: 614 (2004); Kand a, Y. et al., Biotechnol. Bioeng., 94(4):680-688 (2006)). Other antibody glycosylation variants are also included (See for example, U.S. Pat. No. 6,602,684).

In some embodiments, one or more amino acid modifications may be introduced into the Fc region of an antibody provided herein, thereby generating an Fc region variant. An Fc region herein is a C-terminal region of an immunoglobulin heavy chain that contains at least a portion of the constant region. An Fc region includes native sequence Fc regions and variant Fc regions. The Fc region variant may comprise a human Fc region sequence (for example, a human IgG1, IgG2, IgG3 or IgG4 Fc region) comprising an amino acid modification (for example, a substitution) at one or more amino acid positions.

In some embodiments, the antibodies of this disclosure are variants that possess some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity). Non-limiting examples of in vitro assays to assess ADCC activity of a molecule of interest is described in U.S. Pat. Nos. 5,500,362 and 5,821,337. Alternatively, non-radioactive assays methods may be employed (for example, ACTI™ and CytoTox 96® non-radioactive cytotoxicity assays). Useful effector cells for such assays include peripheral blood mononuclear cells (PBMC), monocytes, macrophages, and Natural Killer (NK) cells.

Antibodies can have increased half-lives and improved binding to the neonatal Fc receptor (FcRn) (See for example, US 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 or 434 according to the EU numbering system (See for example, U.S. Pat. No. 7,371,826). Other examples of Fc region variants are also contemplated (See for example, Duncan & Winter, Nature 322:738-40 (1988); U.S. Pat. Nos. 5,648,260 and 5,624,821; and WO94/29351).

Reactive groups can be positioned at sites for conjugation to other moieties, such as drug moieties or linker drug moieties, to create an immunoconjugate. In certain embodiments, the recombinant anti-CD30L antibody provided herein may be further modified to contain additional non-proteinaceous moieties that are known and available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n vinyl pyrrolidone) polyethylene glycol, polypropylene glycol homopolymers, polypropylen oxide/ethylene oxide co-polymers, poly oxyethylated polyols (for example, glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if two or more polymers are attached, they can be the same or different molecules.

The antibodies described herein can be encoded by a nucleic acid. A nucleic acid is a type of polynucleotide comprising two or more nucleotide bases. In certain embodiments, the nucleic acid is a component of a vector that can be used to transfer the polypeptide encoding polynucleotide into a cell. As used herein, the term "vector" refers to a nucleic acid molecule capable of transporting another nucleic acid to which it has been linked. One type of vector is a genomic integrated vector, or "integrated vector," which can become integrated into the chromosomal DNA of the host cell. Another type of vector is an "episomal" vector, for example, a nucleic acid capable of extra-chromosomal replication. Vectors capable of directing the expression of genes to which they are operatively linked are referred to herein as "expression vectors." Suitable vectors comprise plasmids, bacterial artificial chromosomes, yeast artificial chromosomes, viral vectors and the like. In the expression vectors regulatory elements such as promoters, enhancers, polyadenylation signals for use in controlling transcription can be derived from mammalian, microbial, viral or insect genes. The ability to replicate in a host, usually conferred by an origin of replication, and a selection gene to facilitate recognition of transformants may additionally be incorporated. Vectors derived from viruses, such as lentiviruses, retroviruses, adenoviruses, adeno-associated viruses, and the like, may be employed. Plasmid vectors can be linearized for integration into a chromosomal location. Vectors can comprise sequences that direct site-specific integration into a defined location or restricted set of sites in the genome (for example, AttP-AttB recombination). Additionally, vectors can comprise sequences derived from transposable elements.

As used herein, the terms "homologous," "homology," or "percent homology" when used herein to describe to an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

The nucleic acids encoding the antibodies described herein can be used to infect, transfect, transform, or otherwise render a suitable cell transgenic for the nucleic acid, thus enabling the production of antibodies for commercial or therapeutic uses. Stand ard cell lines and methods for the production of antibodies from a large-scale cell culture are known in the art. See for example, Li et al., "Cell culture processes for monoclonal antibody production." Mabs. 2010 September-October; 2(5): 466-477. In certain embodiments, the cell is a Eukaryotic cell. In certain embodiments, the Eukaryotic cell is a mammalian cell. In certain embodiments, the mammalian cell is a Chines Hamster Ovary cell (CHO) cell, an NS0 murine myeloma cell, a HEK293 (Human Embryonic Kidney 293) cell or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

In certain embodiments, described herein, is a master cell bank comprising: (a) a mammalian cell line comprising one or more nucleic acids encoding an antibody described herein integrated at a genomic location; and (b) a cryoprotectant. In certain embodiments, the cryoprotectant comprises glycerol, DMSO, or a combination thereof. In certain embodiments, the master cell bank comprises: (a) a CHO cell line comprising a nucleic acid encoding an antibody with (i) a heavy chain variable region amino acid sequence at least 90% identical to that set forth by SEQ ID NO: 1, 2, 5, 6, 9, 10, 13, 14, 17, 19, 21, 23, 25, 27, 29, or 31; and (ii) a light chain amino acid sequence at least 90% identical to that set forth by SEQ ID NO: 3, 4, 7, 8, 11, 12, 15, 16, 18, 20, 22, 24, 26, 28, 30, or 32, integrated at a genomic location; and (b) a cryoprotectant. In certain embodiments, the cryoprotectant comprises glycerol, DMSO, or a combination thereof. In certain embodiments, the master cell bank is contained in a suitable vial or container able to withstand freezing by liquid nitrogen.

Also described herein are methods of making an antibody described herein. Such methods comprise incubating a cell or cell-line comprising a nucleic acid encoding the antibody in a cell culture medium under conditions sufficient to allow for expression and secretion of the antibody, and further harvesting the antibody from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, dialysis, desalting, protein A, protein G, protein A/G, or protein L purification, and/or ion exchange chromatography.

The recombinant antibodies or antibody fragments thereof disclosed herein, specifically bind CD30L and are marked by a high affinity for CD30L. Accordingly, the antibodies disclosed herein are useful for targeting (i.e. binding) CD30L. In some embodiments, the anti-CD30L antibodies provided comprise a heavy chain comprising four heavy chain framework regions (HCFR) and three heavy chain complementarity-determining regions (HCDR): HCFR1, HCDR1, HCFR2, HCDR2, HCFR3, HCDR3, and HCFR4; and a light chain comprising four light chain framework regions (LCFR) and three light chain complementarity-determining regions (LCDR): LCFR1, LCDR1, LCFR2, LCDR2, LCFR3, LCDR3, and LCFR4.

In one aspect, provided herein is an antibody or antigen binding fragment thereof that binds CD30L, wherein the antibody or antigen binding fragment thereof comprises: (a) an immunoglobulin heavy chain CDR1 (CDR-H1) comprising the amino acid sequence set forth in any one of SEQ ID NOs: 100-139, 220-234, 465-489, 628-641, and 712-723; (b) an immunoglobulin heavy chain CDR2 (CDR-H2) comprising the amino acid sequence set forth in any one of SEQ ID NOs: 140-179, 235-249, 490-499, 513-527, 642-655, and 724-735; (c) an immunoglobulin heavy chain CDR3 (CDR-H3) comprising the amino acid sequence set forth in any one of SEQ Id NOs: 180-219, 250-264, 528-552, 656-669, and 736-743; (d) an immunoglobulin light chain CDR1 (CDR-L1) comprising the amino acid sequence set forth in any one of SEQ ID NOs: 300-339, 420-434, 553-577, 670-683, and 744-751; (d) an immunoglobulin light chain CDR2 (CDR-L2) comprising the amino acid sequence set forth in any one of SEQ ID NOs: 340-379, 435-449, 578-602, 684-697, and 752-759; and/or (e) an immunoglobulin light chain CDR3 (CDR-L3) comprising the amino acid sequence set forth in any one of SEQ ID NOs: 380-419, 450-464, 603-627, 698-711, and 760-765.

Consistent with the above aspect, in one embodiment, the Antibody or antigen binding fragment thereof comprises or consists of a CDR-H1 comprising the amino acid sequence set forth in any one of SEQ ID NOs: 100-139, 220-234, 465-489, 628-641, and 712-723. In some embodiments, the Antibody or antigen binding fragment thereof comprises or consists of a CDR-H2 comprising the amino acid sequence set forth in any one of SEQ ID NOs: 140-179, 235-249, 490-499, 513-527, 642-655, and 724-735. In certain embodiments, the Antibody or antigen binding fragment thereof comprises or consists of a CDR-H3 comprising the amino acid sequence set forth in any one of SEQ Id NOs: 180-219, 250-264, 528-552, 656-669, and 736-743. In other embodiments, the Antibody or antigen binding fragment thereof comprises or consists of a CDR-L1 comprising the amino acid sequence set forth in any one of SEQ ID NOs: 300-339, 420-434, 553-577, 670-683, and 744-751. In yet other embodiments, the antibody or antigen binding fragment thereof comprises or consists of a CDR-L2 comprising the amino acid sequence set forth in any one of SEQ ID NOs: 340-379, 435-449, 578-602, 684-697, and 752-759. In another embodiment, the antibody or antigen binding fragment thereof comprises or consists of a CDR-L3 comprising the amino acid sequence set forth in any one of SEQ ID NOs: 380-419, 450-464, 603-627, 698-711, and 760-765. In one embodiment, the antibody or antigen binding fragment thereof comprises or consists of a CDR-H1 comprising the amino acid sequence set forth in any one of SEQ ID NOs: 100-139, 220-234, 465-489, 628-641, and 712-723 and a CDR-H2 comprising the amino acid sequence set forth in any one of SEQ ID NOs: 140-179, 235-249, 490-499, 513-527, 642-655, and 724-735. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723 and a CDR-H3 comprising the amino acid sequence set forth in any one of SEQ Id NOs: 180-219, 250-264, 528-552, 656-669, and 736-743. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723 and a CDR-L1 comprising the amino acid sequence set forth in any one of SEQ ID NOs: 300-339, 420-434, 553-577, 670-683, and 744-751. In other embodiments, the antibody or antigen binding fragment thereof comprises or consists of a CDR-H1 comprising the amino acid sequence set forth in any one of SEQ ID NOs: 100-139, 220-234, 465-489, 628-641, and 712-723 and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723 and a CDR-L3 comprising the amino acid sequence set forth in any one of SEQ ID NOs: 380-419, 450-464, 603-627, 698-711, and 760-765. In further embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735 and a CDR-H3 comprising the amino acid sequence set forth in any one of SEQ Id NOs: 180-219, 250-264, 528-552, 656-669, and 736-743. In one embodiment, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735 and a CDR-L1 comprising the amino acid sequence set forth in any one of SEQ ID NOs: 300-339, 420434, 553-577, 670-683, and 744-751. In some embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735 and a CDR-L2 comprising the amino acid sequence set forth in any one of SEQ ID NOs: 340-379, 435-449, 578-602, 684-697, and 752-759. In certain embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735 and a CDR-L3 comprising the amino acid sequence set forth in any one of SEQ ID NOs: 380-419, 450-464, 603-627, 698-711, and 760-765. In other embodiments, the antibody or antigen binding fragment thereof comprises or consists of a CDR-H3 comprising the amino acid sequence set forth in any one of SEQ Id NOs: 180-219, 250-264, 528-552, 656-669, and 736-743 and a CDR-L1 comprising the amino acid sequence set forth in any one of SEQ ID NOs: 300-339, 420-434, 553-577, 670-683, and 744-751. In yet other embodiments, the antibody or antigen binding fragment thereof comprises or consists of a CDR-H3 comprising the amino acid sequence set forth in any one of SEQ Id NOs: 180-219, 250-264, 528-552, 656-669, and 736-743 and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H3 comprising the amino acid sequence set forth in any one of SEQ Id NOs: 180-219, 250-264, 528-552, 656-669, and 736-743 and a CDR-L3 comprising the amino acid sequence set forth in any one of SEQ ID NOs: 380-419, 450-464, 603-627, 698-711, and 760-765. In one embodiment, the antibody or antigen binding fragment thereof comprises or consists of a CDR-L1 comprising the amino acid sequence set forth in any one of SEQ ID NOs: 300-339, 420-434, 553-577, 670-683, and 744-751 and a CDR-L2 comprising the amino acid sequence set forth in any one of SEQ ID NOs: 340-379, 435-449, 578-602, 684-697, and 752-759. In another embodiment, the antibody or antigen binding fragment thereof comprises or consists of a CDR-L1 comprising the amino acid sequence set forth in any one of SEQ ID NOs: 300-339, 420-434, 553-577, 670-683, and 744-751 and a CDR-L3 comprising the amino acid sequence set forth in any one of SEQ ID NOs: 380-419, 450-464, 603-627, 698-711, and 760-765. In another embodiment, the antibody or antigen binding fragment thereof comprises or consists of a CDR-L2 comprising the amino acid sequence set forth in any one of SEQ ID NOs: 340-379, 435-449, 578-602, 684-697, and 752-759 and a CDR-L3 comprising the amino acid sequence set forth in any one of SEQ ID NOs: 380-419, 450-464, 603-627, 698-711, and 760-765. In other embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, and a CDR-H3 comprising the amino acid sequence set forth in any one of SEQ Id NOs: 180-219, 250-264, 528-552, 656-669, and 736-743. In yet other embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, and a CDR-L1 comprising the amino acid sequence set forth in any one of SEQ ID NOs: 300-339, 420-434, 553-577, 670-683, and 744-751. In further embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H3 comprising the amino acid sequence set forth in any one of SEQ Id NOs: 180-219, 250-264, 528-552, 656-669, and 736-743 and a CDR-L1 comprising the amino acid sequence set forth in any one of SEQ ID NOs: 300-339, 420-434, 553-577, 670-683, and 744-751. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H3 comprising the amino acid sequence set forth in any one of SEQ Id NOs: 180-219, 250-264, 528-552, 656-669, and 736-743, and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H3 comprising the amino acid sequence set forth in any one of SEQ Id NOs: 180-219, 250-264, 528-552, 656-669, and 736-743, and a CDR-L3 comprising the amino acid sequence set forth in any one of SEQ ID NOs: 380-419, 450-464, 603-627, 698-711, and 760-765. In yet other embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-L1 comprising the amino acid sequence set forth in any one of SEQ ID NOs: 300-339, 420-434, 553-577, 670-683, and 744-751 and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-L1 comprising the amino acid sequence set forth in any one of SEQ ID NOs: 300-339, 420-434, 553-577, 670-683, and 744-751 and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-L2 comprising the amino acid sequence set forth in any one of SEQ ID NOs: 340-379, 435-449, 578-602, 684-697, and 752-759 and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743 and a CDR-L1 comprising the amino acid sequence set forth in any one of SEQ ID NOs: 300-339, 420434, 553-577, 670-683, and 744-751. In certain embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, and a CDR-L3 comprising the amino acid sequence set forth in any one of SEQ ID NOs: 380-419, 450-464, 603-627, 698-711, and 760-765. In other embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-L1 comprising the amino acid sequence set forth in any one of SEQ ID NOs: 300-339, 420-434, 553-577, 670-683, and 744-751 and a CDR-L2 comprising the amino acid sequence set forth in any one of SEQ ID NOs: 340-379, 435-449, 578-602, 684-697, and 752-759. In yet other embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-L1 comprising the amino acid sequence set forth in any one of SEQ ID NOs: 300-339, 420434, 553-577, 670-683, and 744-751 and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-L2 comprising the amino acid sequence set forth in any one of SEQ ID NOs: 340-379, 435-449, 578-602, 684-697, and 752-759 and a CDR-L3 comprising the amino acid sequence set forth in any one of SEQ ID NOs: 380-419, 450-464, 603-627, 698-711, and 760-765. In yet other embodiments, the antibody or antigen binding fragment thereof comprises or consists of a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751 and a CDR-L2 comprising the amino acid sequence set forth in any one of SEQ ID NOs: 340-379, 435-449, 578-602, 684-697, and 752-759. In other embodiments, the antibody or antigen binding fragment thereof comprises or consists of a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751 and a CDR-L3 comprising the amino acid sequence set forth in any one of SEQ ID NOs: 380-419, 450-464, 603-627, 698-711, and 760-765. In certain embodiments, the antibody or antigen binding fragment thereof comprises or consists of a CDR-H3 comprising the amino acid sequence set forth in any one of SEQ Id NOs: 180-219, 250-264, 528-552, 656-669, and 736-743, a CDR-L2 comprising the amino acid sequence set forth in any one of SEQ ID NOs: 340-379, 435-449, 578-602, 684-697, and 752-759 and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759 and a CDR-L3 comprising the amino acid sequence set forth in any one of SEQ ID NOs: 380-419, 450-464, 603-627, 698-711, and 760-765. In other embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, and a CDR-L1 comprising the amino acid sequence set forth in any one of SEQ ID NOs: 300-339, 420-434, 553-577, 670-683, and 744-751. In further embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-L1 comprising the amino acid sequence set forth in any one of SEQ ID NOs: 300-339, 420-434, 553-577, 670-683, and 744-751, and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, and a CDR-L2 comprising the amino acid sequence set forth in any one of SEQ ID NOs: 340-379, 435-449, 578-602, 684-697, and 752-759. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, and a CDR-L3 comprising the amino acid sequence set forth in any one of SEQ ID NOs: 380-419, 450-464, 603-627, 698-711, and 760-765. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H3 comprising the amino acid sequence set forth in any one of SEQ Id NOs: 180-219, 250-264, 528-552, 656-669, and 736-743, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In yet other embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In further embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, and a CDR-L3 comprising the amino acid sequence set forth in any one of SEQ ID NOs: 380-419, 450-464, 603-627, 698-711, and 760-765. In further embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, and a CDR-L2 comprising the amino acid sequence set forth in any one of SEQ ID NOs: 340-379, 435-449, 578-602, 684-697, and 752-759. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In certain embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of any one of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765. In some embodiments, the antibody or antigen binding fragment thereof comprises or consists of any two of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765, in any combination or permutation. In some embodiments, the antibody or antigen binding fragment thereof comprises or consists of any three of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765, in any combination or permutation. In some embodiments, the antibody or antigen binding fragment thereof comprises or consists of any four of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765, in any combination or permutation. In some embodiments, the antibody or antigen binding fragment thereof comprises or consists of any five of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765, in any combination or permutation. In some embodiments, the Antibody or antigen binding fragment thereof comprises or consists of all six of a CDR-H1 comprising the amino acid sequence set forth in any one of SEQ ID NOs: 100-139, 220-234, 465-489, 628-641, and 712-723, a CDR-H2 comprising the amino acid sequence set forth in any one of SEQ ID NOs: 140-179, 235-249, 490-499, 513-527, 642-655, and 724-735, a CDR-H3 comprising the amino acid sequence set forth in any one of SEQ Id NOs: 180-219, 250-264, 528-552, 656-669, and 736-743, a CDR-L1 comprising the amino acid sequence set forth in any one of SEQ ID NOs: 300-339, 420-434, 553-577, 670-683, and 744-751, a CDR-L2 comprising the amino acid sequence set forth in any one of SEQ ID NOs: 340-379, 435-449, 578-602, 684-697, and 752-759, and a CDR-L3 comprising the amino acid sequence set forth in any one of SEQ ID NOs: 380-419, 450-464, 603-627, 698-711, and 760-765.

In some embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 100-109, 628, 635, and 712-723; (b) a CDR-H2 comprising the amino acid sequence set forth in any one of SEQ ID NOs: 140-149, 642, 649, and 724-735; (c) a CDR-H3 comprising the amino acid sequence set forth in any one of SEQ ID NOs: 180-189, 656, 663, and 736-743; (d) a CDR-L1 comprising the amino acid sequence set forth in any one of SEQ ID NOs: 300-309, 670, 677, and 744-751; (e) a CDR-L2 comprising the amino acid sequence set forth in any one of SEQ ID NOs: 340-349, 684, 691, and 752-759; and/or (f) a CDR-L3 comprising the amino acid sequence set forth in any one of SEQ ID Nos: 380-389, 698, 705, and 760-765.

In certain embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 100-109, 628, 635, and 712-723; (b) a CDR-H2 comprising the amino acid sequence set forth in any one of SEQ ID NOs: 140-149, 642, 649, and 724-735; (c) a CDR-H3 comprising the amino acid sequence set forth in any one of SEQ ID NOs: 180-189, 656, 663, and 736-743; (d) a CDR-L1 comprising the amino acid sequence set forth in any one of SEQ ID NOs: 300-309, 670, 677, and 744-751; (e) a CDR-L2 comprising the amino acid sequence set forth in any one of SEQ ID NOs: 340-349, 684, 691, and 752-759;

and/or (f) a CDR-L3 comprising the amino acid sequence set forth in any one of SEQ ID Nos: 380-389, 698, 705, and 760-765.

In certain embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 105-109, 628, 635, and 712-723; (b) a CDR-H2 comprising the amino acid sequence set forth in any one of SEQ ID NOs: 145-149, 642, 649, and 724-735; (c) a CDR-H3 comprising the amino acid sequence set forth in any one of SEQ ID NOs: 185-189, 656, 663, and 736-743; (d) a CDR-L1 comprising the amino acid sequence set forth in any one of SEQ ID NOs: 305-309,670,677, and 744-751; (e) a CDR-L2 comprising the amino acid sequence set forth in any one of SEQ ID NOs: 345-349, 684, 691, and 752-759; and/or (f) a CDR-L3 comprising the amino acid sequence set forth in any one of SEQ ID NOs: 385-389, 698, 705, and 760-765.

In one aspect, provided herein is an antibody or antigen binding fragment thereof that binds CD30L, wherein the antibody or antigen binding fragment thereof binds to an epitope comprising one or more amino acids in CD30L selected from the group consisting of K16, S21, R30, K48, R63, and Y64, wherein the amino acids are numbered according to the amino acid sequence of CD30L as set forth in SEQ ID NO:34.

The anti-CD30L antibody provided herein can binds to epitope of various combinations of amino acids on CD30L as described herein. Accordingly, in one embodiment of the anti-CD30L antibody or antigen binding fragment provided herein, including in Section 2 and this Section (Section 4.1), the antibody or antigen binding fragment thereof binds to an epitope comprising any one amino acid in CD30L selected from the group consisting of K16, S21, R30, K48, R63, and Y64. In another embodiment of the anti-CD30L antibody or antigen binding fragment provided herein, including in Section 2 and this Section (Section 4.1), the antibody or antigen binding fragment thereof binds to an epitope comprising any two amino acid in CD30L selected from the group consisting of K16, S21, R30, K48, R63, and Y64. In a further embodiment of the anti-CD30L antibody or antigen binding fragment provided herein, including in Section 2 and this Section (Section 4.1), the antibody or antigen binding fragment thereof binds to an epitope comprising any three amino acid in CD30L selected from the group consisting of K16, S21, R30, K48, R63, and Y64. In yet another embodiment of the anti-CD30L antibody or antigen binding fragment provided herein, including in Section 2 and this Section (Section 4.1), the antibody or antigen binding fragment thereof binds to an epitope comprising any four amino acid in CD30L selected from the group consisting of K16, S21, R30, K48, R63, and Y64. In a further embodiment of the anti-CD30L antibody or antigen binding fragment provided herein, including in Section 2 and this Section (Section 4.1), the antibody or antigen binding fragment thereof binds to an epitope comprising any five amino acid in CD30L selected from the group consisting of K16, S21, R30, K48, R63, and Y64. In one embodiment of the anti-CD30L antibody or antigen binding fragment provided herein, including in Section 2 and this Section (Section 4.1), the antibody or antigen binding fragment thereof binds to an epitope comprising K16, S21, R30, K48, R63, and Y64. The position of the amino acids in this paragraph are numbered according to the amino acid sequence of CD30L as set forth in SEQ ID NO:34.

Furthermore, the anti-CD30L antibody provided herein including in Section 2 and this Section (Section 4.1) can bind to certain specific epitope of specific combinations of amino acids on CD30L as described herein and such epitopes are further provided in this paragraph. Accordingly, in one embodiment, the epitope for the anti-CD30L provided herein comprises or consists of K16. In some embodiments, the epitope for the anti-CD30L provided herein comprises or consists of S21. In certain embodiments, the epitope for the anti-CD30L provided herein comprises or consists of R30. In other embodiments, the epitope for the anti-CD30L provided herein comprises or consists of K48. In yet other embodiments, the epitope for the anti-CD30L provided herein comprises or consists of R63. In another embodiment, the epitope for the anti-CD30L provided herein comprises or consists of Y64. In one embodiment, the epitope for the anti-CD30L provided herein comprises or consists of K16 and S21. In some embodiments, the epitope for the anti-CD30L provided herein comprises or consists of K16 and R30. In certain embodiments, the epitope for the anti-CD30L provided herein comprises or consists of K16 and K48. In other embodiments, the epitope for the anti-CD30L provided herein comprises or consists of K16 and R63. In some embodiments, the epitope for the anti-CD30L provided herein comprises or consists of K16 and Y64. In further embodiments, the epitope for the anti-CD30L provided herein comprises or consists of S21 and R30. In one embodiment, the epitope for the anti-CD30L provided herein comprises or consists of S21 and K48. In some embodiments, the epitope for the anti-CD30L provided herein comprises or consists of S21 and R63. In certain embodiments, the epitope for the anti-CD30L provided herein comprises or consists of S21 and Y64. In other embodiments, the epitope for the anti-CD30L provided herein comprises or consists of R30 and K48. In yet other embodiments, the epitope for the anti-CD30L provided herein comprises or consists of R30 and R63. In some embodiments, the epitope for the anti-CD30L provided herein comprises or consists of R30 and Y64. In one embodiment, the epitope for the anti-CD30L provided herein comprises or consists of K48 and R63. In another embodiment, the epitope for the anti-CD30L provided herein comprises or consists of K48 and Y64. In another embodiment, the epitope for the anti-CD30L provided herein comprises or consists of R63 and Y64. In other embodiments, the epitope for the anti-CD30L provided herein comprises or consists of K16, S21, and R30. In yet other embodiments, the epitope for the anti-CD30L provided herein comprises or consists of K16, S21 and K48. In further embodiments, the epitope for the anti-CD30L provided herein comprises or consists of K16, S21, and R63. In some embodiments, the epitope for the anti-CD30L provided herein comprises or consists of K16, S21, and Y64. In some embodiments, the epitope for the anti-CD30L provided herein comprises or consists of K16, R30 and K48. In certain embodiments, the epitope for the anti-CD30L provided herein comprises or consists of K16, R30, and R63. In some embodiments, the epitope for the anti-CD30L provided herein comprises or consists of K16, R30, and Y64. In yet other embodiments, the epitope for the anti-CD30L provided herein comprises or consists of K16, K48 and R63. In some embodiments, the epitope for the anti-CD30L provided herein comprises or consists of K16, K48 and Y64. In some embodiments, the epitope for the anti-CD30L provided herein comprises or consists of K16, R63 and Y64. In some embodiments, the epitope for the anti-CD30L provided herein comprises or consists of S21, R30 and K48. In certain embodiments, the epitope for the anti-CD30L provided herein comprises or consists of S21, R30, and R63. In some embodiments, the epitope for the anti-CD30L provided herein comprises or consists of S21, R30, and Y64. In other embodiments, the epitope for the anti-CD30L provided herein comprises or consists of S21, K48 and R63. In yet other embodiments, the epitope for the anti-CD30L provided herein comprises or consists of S21, K48 and Y64. In some embodiments, the epitope for the anti-CD30L provided herein comprises or consists of S21, R63 and Y64. In yet other embodiments, the epitope for the anti-CD30L provided herein comprises or consists of R30, K48 and R63. In other embodiments, the epitope for the anti-CD30L provided herein comprises or consists of R30, K48 and Y64. In certain embodiments, the epitope for the anti-CD30L provided herein comprises or consists of R30, R63 and Y64. In some embodiments, the epitope for the anti-CD30L provided herein comprises or consists of K48, R63 and Y64. In other embodiments, the epitope for the anti-CD30L provided herein comprises or consists of K16, S21, R30, and K48. In further embodiments, the epitope for the anti-CD30L provided herein comprises or consists of K16, S21, R30, and R63. In some embodiments, the epitope for the anti-CD30L provided herein comprises or consists of K16, S21, R30, and Y64. In some embodiments, the epitope for the anti-CD30L provided herein comprises or consists of K16, S21, K48, and R63. In some embodiments, the epitope for the anti-CD30L provided herein comprises or consists of K16, S21, K48, and Y64. In some embodiments, the epitope for the anti-CD30L provided herein comprises or consists of K16, S21, R63, and Y64. In certain embodiments, the epitope for the anti-CD30L provided herein comprises or consists of K16, R30, K48, and R63. In certain embodiments, the epitope for the anti-CD30L provided herein comprises or consists of K16, R30, K48, and Y64. In certain embodiments, the epitope for the anti-CD30L provided herein comprises or consists of K16, R30, R63, and Y64. In yet other embodiments, the epitope for the anti-CD30L provided herein comprises or consists of K16, K48, R63, and Y64. In further embodiments, the epitope for the anti-CD30L provided herein comprises or consists of S21, R30, K48, and R63. In some embodiments, the epitope for the anti-CD30L provided herein comprises or consists of S21, R30, K48, and Y64. In further embodiments, the epitope for the anti-CD30L provided herein comprises or consists of S21, R30, R63, and Y64. In some embodiments, the epitope for the anti-CD30L provided herein comprises or consists of S21, K48, R63, and Y64. In some embodiments, the epitope for the anti-CD30L provided herein comprises or consists of R30, K48, R63, and Y64. In certain embodiments, the epitope for the anti-CD30L provided herein comprises or consists of K16, S21, R30, K48, and R63. In some embodiments, the epitope for the anti-CD30L provided herein comprises or consists of K16, S21, R30, K48, and Y64. In some embodiments, the epitope for the anti-CD30L provided herein comprises or consists of K16, S21, R30, R63, and Y64. In certain embodiments, the epitope for the anti-CD30L provided herein comprises or consists of K16, S21, K48, R63, and Y64. In certain embodiments, the epitope for the anti-CD30L provided herein comprises or consists of K16, R30, K48, R63, and Y64. In some embodiments, the epitope for the anti-CD30L provided herein comprises or consists of S21, R30, K48, R63, and Y64. In some embodiments, the epitope for the anti-CD30L provided herein comprises or consists of K16, S21, R30, K48, R63, and Y64. In some embodiments, the epitope for the anti-CD30L provided herein comprises or consists of any one of K16, S21, R30, K48, R63, and Y64.

In some embodiments, the epitope for the anti-CD30L provided herein comprises or consists of any two of K16, S21, R30, K48, R63, and Y64, in any combination or permutation. In some embodiments, the epitope for the anti-CD30L provided herein comprises or consists of any three of K16, S21, R30, K48, R63, and Y64, in any combination or permutation. In some embodiments, the epitope for the anti-CD30L provided herein comprises or consists of any four of K16, S21, R30, K48, R63, and Y64, in any combination or permutation. In some embodiments, the epitope for the anti-CD30L provided herein comprises or consists of any five of K16, S21, R30, K48, R63, and Y64, in any combination or permutation. In some embodiments, the epitope for the anti-CD30L provided herein comprises or consists of all six of K16, S21, R30, K48, R63, and Y64. The position of the amino acids in this paragraph are numbered according to the amino acid sequence of CD30L as set forth in SEQ ID NO:34.

In some embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 110-119, 629, 636, and 712-723; (b) a CDR-H2 comprising the amino acid sequence set forth in any one of SEQ ID NOs: 150-159, 643, 650, and 724-735; (c) a CDR-H3 comprising the amino acid sequence set forth in any one of SEQ ID NOs: 190-199, 657, 664, and 736-743; (d) a CDR-L1 comprising the amino acid sequence set forth in any one of SEQ ID NOs: 310-319, 671, 678, and 744-751; (e) a CDR-L2 comprising the amino acid sequence set forth in any one of SEQ ID NOs: 350-359, 685, 692, and 752-759; and/or (f) a CDR-L3 comprising the amino acid sequence set forth in any one of SEQ ID NOs: 390-399, 699, 706, and 760-765.

In certain embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 110-114, 629, 636, and 712-723; (b) a CDR-H2 comprising the amino acid sequence set forth in any one of SEQ ID NOs: 150-154, 643, 650, and 724-735; (c) a CDR-H3 comprising the amino acid sequence set forth in any one of SEQ ID NOs: 190-194, 657, 664, and 736-743; (d) a CDR-L1 comprising the amino acid sequence set forth in any one of SEQ ID NOs: 310-314, 671, 678, and 744-751; (e) a CDR-L2 comprising the amino acid sequence set forth in any one of SEQ ID NOs: 350-354, 685, 692, and 752-759; and/or (f) a CDR-L3 comprising the amino acid sequence set forth in any one of SEQ ID NOs: 390-394, 699, 706, and 760-765.

In other embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 115-119, 629, 636, and 712-723; (b) a CDR-H2 comprising the amino acid sequence set forth in any one of SEQ ID NOs: 155-159, 643, 650, and 724-735; (c) a CDR-H3 comprising the amino acid sequence set forth in any one of SEQ ID NOs: 195-199, 657, 664, and 736-743; (d) a CDR-L1 comprising the amino acid sequence set forth in any one of SEQ ID NOs: 315-319, 671, 678, and 744-751; (e) a CDR-L2 comprising the amino acid sequence set forth in any one of SEQ ID NOs: 355-359, 685, 692, and 752-759;

and/or (f) a CDR-L3 comprising the amino acid sequence set forth in any one of SEQ ID NOs: 395-399, 699, 706, and 760-765.

In some embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 120-129, and 712-723; (b) a CDR-H2 comprising the amino acid sequence set forth in any one of SEQ ID NOs: 160-169, and 724-735; (c) a CDR-H3 comprising the amino acid sequence set forth in any one of SEQ ID NOs: 200-209, and 736-743; (d) a CDR-L1 comprising the amino acid sequence set forth in any one of SEQ ID NOs: 320-329, and 744-751; (e) a CDR-L2 comprising the amino acid sequence set forth in any one of SEQ ID NOs: 360-369, and 752-759; and/or (f) a CDR-L3 comprising the amino acid sequence set forth in any one of SEQ ID NOs: 400-409, and 760-765.

In certain embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 120-124, and 712-723; (b) a CDR-H2 comprising the amino acid sequence set forth in any one of SEQ ID NOs: 160-164, and 724-735; (c) a CDR-H3 comprising the amino acid sequence set forth in any one of SEQ ID NOs: 200-204, and 736-743; (d) a CDR-L1 comprising the amino acid sequence set forth in any one of SEQ ID NOs: 320-324, and 744-751; (e) a CDR-L2 comprising the amino acid sequence set forth in any one of SEQ ID NOs: 360-364, and 752-759; and/or (f) a CDR-L3 comprising the amino acid sequence set forth in any one of SEQ ID NOs: 400-404, and 760-765.

In other embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 125-129, and 712-723; (b) a CDR-H2 comprising the amino acid sequence set forth in any one of SEQ ID NOs: 165-169, and 724-735; (c) a CDR-H3 comprising the amino acid sequence set forth in any one of SEQ ID NOs: 205-209, and 736-743; (d) a CDR-L1 comprising the amino acid sequence set forth in any one of SEQ ID NOs: 325-329, and 744-751; (e) a CDR-L2 comprising the amino acid sequence set forth in any one of SEQ ID NOs: 365-369, and 752-759; and/or (f) a CDR-L3 comprising the amino acid sequence set forth in any one of SEQ ID NOs: 405-409, and 760-765.

In some embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 130-139, and 712-723; (b) a CDR-H2 comprising the amino acid sequence set forth in any one of SEQ ID NOs: 170-179, and 724-735; (c) a CDR-H3 comprising the amino acid sequence set forth in any one of SEQ ID NOs: 210-219, and 736-743; (d) a CDR-L1 comprising the amino acid sequence set forth in any one of SEQ ID NOs: 330-339, and 744-751; (e) a CDR-L2 comprising the amino acid sequence set forth in any one of SEQ ID NOs: 370-379, and 752-759; and/or (f) a CDR-L3 comprising the amino acid sequence set forth in any one of SEQ ID NOs: 410-419, and 760-765.

In certain embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 130-134, and 712-723; (b) a CDR-H2 comprising the amino acid sequence set forth in any one of SEQ ID NOs: 170-174, and 724-735; (c) a CDR-H3 comprising the amino acid sequence set forth in any one of SEQ ID NOs: 210-214, and 736-743; (d) a CDR-L1 comprising the amino acid sequence set forth in any one of SEQ ID NOs: 330-334, and 744-751; (e) a CDR-L2 comprising the amino acid sequence set forth in any one of SEQ ID NOs: 370-374, and 752-759; and/or (f) a CDR-L3 comprising the amino acid sequence set forth in any one of SEQ ID NOs: $410^{-414}$, and 760-765.

In other embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 135-139, and 712-723; (b) a CDR-H2 comprising the amino acid sequence set forth in any one of SEQ ID NOs: 175-179, and 724-735; (c) a CDR-H3 comprising the amino acid sequence set forth in any one of SEQ ID NOs: 215-219, and 736-743; (d) a CDR-L1 comprising the amino acid sequence set forth in any one of SEQ ID NOs: 335-339, and 744-751; (e) a CDR-L2 comprising the amino acid sequence set forth in any one of SEQ ID NOs: 375-379, and 752-759; and/or (f) a CDR-L3 comprising the amino acid sequence set forth in any one of SEQ ID NOs: 415-419, and 760-765.

In some embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 220-224, and 712-723; (b) a CDR-H2 comprising the amino acid sequence set forth in any one of SEQ ID NOs: 235-239, and 724-735; (c) a CDR-H3 comprising the amino acid sequence set forth in any one of SEQ ID NOs: 250-254, and 736-743; (d) a CDR-L1 comprising the amino acid sequence set forth in any one of SEQ ID NOs: 420-424, and 744-751; (e) a CDR-L2 comprising the amino acid sequence set forth in any one of SEQ ID NOs: 435-439, and 752-759; and/or (f) a CDR-L3 comprising the amino acid sequence set forth in any one of SEQ ID NOs: 450-454, and 760-765.

In certain embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 225-229, and 712-723; (b) a CDR-H2 comprising the amino acid sequence set forth in any one of SEQ ID NOs: 240-244, and 724-735; (c) a CDR-H3 comprising the amino acid sequence set forth in any one of SEQ ID NOs: 255-259, and 736-743; (d) a CDR-L1 comprising the amino acid sequence set forth in any one of SEQ ID NOs: 425-429, and 744-751; (e) a CDR-L2 comprising the amino acid sequence set forth in any one of SEQ ID NOs: 440-444, and 752-759; and/or (f) a CDR-L3 comprising the amino acid sequence set forth in any one of SEQ ID NOs: 455-459, and 760-765.

In other embodiments of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 230-234, and 712-723; (b) a CDR-H2 comprising the amino acid sequence set forth in any one of SEQ ID NOs: 245-249, and 724-735; (c) a CDR-H3 comprising the amino acid sequence set forth in any one of SEQ ID NOs: 260-264, and 736-743; (d) a CDR-L1 comprising the amino acid sequence set forth in any one of SEQ ID NOs: 430-434, and 744-751; (e) a CDR-L2 comprising the amino acid sequence set forth in any one of SEQ ID NOs: 445-449, and 752-759; and/or (f) a CDR-L3 comprising the amino acid sequence set forth in any one of SEQ ID NOs: 460-464, and 760-765.

In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 465-469,631,638, and 712-723; (b) a CDR-H2 comprising the amino acid sequence set forth in any one of SEQ ID NOs: 490-494, 645, 652, and 724-735; (c) a CDR-H3 comprising the amino acid sequence set forth in any one of SEQ ID NOs: 528-532, 659, 666, and 736-743; (d) a CDR-L1 comprising the amino acid sequence set forth in any one of SEQ ID NOs: 553-557, 673, 680, and 744-751; (e) a CDR-L2 comprising the amino acid sequence set forth in any one of SEQ ID NOs: 578-582, 687, 694, and 752-759; and/or (f) a CDR-L3 comprising the amino acid sequence set forth in any one of SEQ ID NOs: 603-607, 701, 708, and 760-765;

In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 470-474, 632, 639, and 712-723; (b) a CDR-H2 comprising the amino acid sequence set forth in any one of SEQ ID NOs: 495-499, 646, 653, and 724-735; (c) a CDR-H3 comprising the amino acid sequence set forth in any one of SEQ ID NOs: 533-537, 660, 667, and 736-743; (d) a CDR-L1 comprising the amino acid sequence set forth in any one of SEQ ID NOs: 558-562,674,681, and 744-751; (e) a CDR-L2 comprising the amino acid sequence set forth in any one of SEQ ID NOs: 583-587, 688, 695, and 752-759; and/or (f) a CDR-L3 comprising the amino acid sequence set forth in any one of SEQ ID NOs: 608-612, 702, 709, and 760-765;

In a further embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 475-479, 633, 640, and 712-723; (b) a CDR-H2 comprising the amino acid sequence set forth in any one of SEQ ID NOs: 513-517, 647, 654, and 724-735; (c) a CDR-H3 comprising the amino acid sequence set forth in any one of SEQ ID NOs: 538-542, 661, 668, and 736-743; (d) a CDR-L1 comprising the amino acid sequence set forth in any one of SEQ ID NOs: 563-567,675,682, and 744-751; (e) a CDR-L2 comprising the amino acid sequence set forth in any one of SEQ ID NOs: 588-592, 689, 696, and 752-759; and/or (f) a CDR-L3 comprising the amino acid sequence set forth in any one of SEQ ID NOs: 613-617, 703, 710, and 760-765;

In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 480-484, 630, 637, and 712-723; (b) a CDR-H2 comprising the amino acid sequence set forth in any one of SEQ ID NOs: 518-522, 644, 651, and 724-735; (c) a CDR-H3 comprising the amino acid sequence set forth in any one of SEQ ID NOs: 543-547, 658, 665, and 736-743; (d) a CDR-L1 comprising the amino acid sequence set forth in any one of SEQ ID NOs: 568-572, 672, 679, and 744-751; (e) a CDR-L2 comprising the amino acid sequence set forth in any one of SEQ ID NOs: 593-597, 686, 693, and 752-759; and/or (f) a CDR-L3 comprising the amino acid sequence set forth in any one of SEQ ID NOs: 618-622, 700, 707, and 760-765; or In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID Nos: 485-489, 634, 641, and 712-723; (b) a CDR-H2 comprising the amino acid sequence set forth in any one of SEQ ID Nos: 523-527, 648, 655, and 724-735; (c) a CDR-H3 comprising the amino acid sequence set forth in any one of SEQ ID Nos: 548-552, 662, 669, and 736-743; (d) a CDR-L1 comprising the amino acid sequence set forth in any one of SEQ ID Nos: 573-577, 676, 683, and 744-751; E a CDR-L2 comprising the amino acid sequence set forth in any one of SEQ ID Nos: 598-602, 690, 697, and 752-759; and/or (f) a CDR-L3 comprising the amino acid sequence set forth in any one of SEQ ID Nos: 623-627, 704, 711, and 760-765.

The disclosure further provides that the sequence and structural features in the CDR sequences common to the antibodies that confer the anti-CD30L antibody the binding affinity, specificity, and the capacity to functionally block both the CD30-CD30L interaction and the CD30L-mediated CD30 signaling and IL-8 releasing. Accordingly, also provided herein are anti-CD30L antibodies with consensus CDR sequences that confer the anti-CD30L antibody the binding affinity, specificity, and the capacity to functionally block both the CD30-CD30L interaction and the CD30L-mediated CD30 signaling and IL-8 releasing. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 712-723; (b) a CDR-H2 comprising the amino acid sequence set forth in any one of SEQ ID NOs: 724-735; (c) a CDR-H3 comprising the amino acid sequence set forth in any one of SEQ ID NOs: 736-743; (d) a CDR-L1 comprising the amino acid sequence set forth in any one of SEQ ID NOs: 744-751; (e) a CDR-L2 comprising the amino acid sequence set forth in any one of SEQ ID NOs: 752-759; and/or (f) a CDR-L3 comprising the amino acid sequence set forth in any one of SEQ ID NOs: 760-765. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 712, 714, 716, 718, 720, and 722; (b) a CDR-H2 comprising the amino acid sequence set forth in any one of SEQ ID NOs: 724, 726, 728, 730, 732, and 734; (c) a CDR-H3 comprising the amino acid sequence set forth in any one of SEQ ID NOs: 736, 738, 740, and 742; (d) a CDR-L1 comprising the amino acid sequence set forth in any one of SEQ ID NOs: 744, 746, 748, and 750; (e) a CDR-L2 comprising the amino acid sequence set forth in any one of SEQ ID NOs: 752, 754, 756, and 758; and/or (f) a CDR-L3 comprising the amino acid sequence set forth in any one of SEQ ID NOs: 760, 762, and 764. In a further embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in any one of SEQ ID NOs: 713, 715, 717, 719, 721, and 723; (b) a CDR-H2 comprising the amino acid sequence set forth in any one of SEQ ID NOs: 725, 727, 729, 731, 733, and 735; (c) a CDR-H3 comprising the amino acid sequence set forth in any one of SEQ ID NOs: 737, 739, 741, and 743; (d) a CDR-L1 comprising the amino acid sequence set forth in any one of SEQ ID NOs: 745, 747, 749, and 751; (e) a CDR-L2 comprising the amino acid sequence set forth in any one of SEQ ID NOs: 753, 755, 757, and 759; and/or (f) a CDR-L3 comprising the amino acid sequence set forth in any one of SEQ ID NOs: 761, 763, and 765. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 712; (b) a CDR-H2 comprising the amino acid sequence set forth in SEQ ID NO: 730; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 713; (b) a CDR-H2 comprising the amino acid sequence set forth in SEQ ID NO: 731; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 712; (b) a CDR-H2 comprising the amino acid sequence set forth in SEQ ID NO: 724; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In a further embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 713; (b) a CDR-H2 comprising the amino acid sequence set forth in SEQ ID NO: 725; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 714; (b) a CDR-H2 comprising the amino acid sequence set forth in SEQ ID NO: 726; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 715; (b) a CDR-H2 comprising the amino acid sequence set forth in SEQ ID NO: 727; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 716; (b) a CDR-H2 comprising the amino acid sequence set forth in SEQ ID NO: 728; (c) a CDR-H3 comprising the amino acid sequence set forth in SEQ ID NO: 736; (d) a CDR-L1 comprising the amino acid sequence set forth in SEQ ID NO: 744; (e) a CDR-L2 comprising the amino acid sequence set forth SEQ ID NO: 752; and/or (f) a CDR-L3 comprising the amino acid sequence set forth SEQ ID NO: 760. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 717; (b) a CDR-H2 comprising the amino acid sequence set forth in SEQ ID NO: 729; (c) a CDR-H3 comprising the amino acid sequence set forth in SEQ ID NO: 737; (d) a CDR-L1 comprising the amino acid sequence set forth in SEQ ID NO: 745; (e) a CDR-L2 comprising the amino acid sequence set forth SEQ ID NO: 753; and/or (f) a CDR-L3 comprising the amino acid sequence set forth SEQ ID NO: 761. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 718; (b) a CDR-H2 comprising the amino acid sequence set forth in SEQ ID NO: 730; (c) a CDR-H3 comprising the amino acid sequence set forth in SEQ ID NO: 738; (d) a CDR-L1 comprising the amino acid sequence set forth in SEQ ID NO: 746; (e) a CDR-L2 comprising the amino acid sequence set forth SEQ ID NO: 754; and/or (f) a CDR-L3 comprising the amino acid sequence set forth SEQ ID NO: 762. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 719; (b) a CDR-H2 comprising the amino acid sequence set forth in SEQ ID NO: 731; (c) a CDR-H3 comprising the amino acid sequence set forth in SEQ ID NO: 739; (d) a CDR-L1 comprising the amino acid sequence set forth in SEQ ID NO: 747; (e) a CDR-L2 comprising the amino acid sequence set forth SEQ ID NO: 755; and/or (f) a CDR-L3 comprising the amino acid sequence set forth SEQ ID NO: 763. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 720; (b) a CDR-H2 comprising the amino acid sequence set forth in SEQ ID NO: 732; (c) a CDR-H3 comprising the amino acid sequence set forth in SEQ ID NO: 740; (d) a CDR-L1 comprising the amino acid sequence set forth in SEQ ID NO: 748; (e) a CDR-L2 comprising the amino acid sequence set forth SEQ ID NO: 756; and/or (f) a CDR-L3 comprising the amino acid sequence set forth SEQ ID NO: 760. In a further embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 721; (b) a CDR-H2 comprising the amino acid sequence set forth in SEQ ID NO: 733; (c) a CDR-H3 comprising the amino acid sequence set forth in SEQ ID NO: 741; (d) a CDR-L1 comprising the amino acid sequence set forth in SEQ ID NO: 749; (e) a CDR-L2 comprising the amino acid sequence set forth SEQ ID NO: 757; and/or (f) a CDR-L3 comprising the amino acid sequence set forth SEQ ID NO: 761. In a further embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 722; (b) a CDR-H2 comprising the amino acid sequence set forth in SEQ ID NO: 734; (c) a CDR-H3 comprising the amino acid sequence set forth in SEQ ID NO: 742; (d) a CDR-L1 comprising the amino acid sequence set forth in SEQ ID NO: 750; (e) a CDR-L2 comprising the amino acid sequence set forth SEQ ID NO: 758; and/or (f) a CDR-L3 comprising the amino acid sequence set forth SEQ ID NO: 764. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 723; (b) a CDR-H2 comprising the amino acid sequence set forth in SEQ ID NO: 735; (c) a CDR-H3 comprising the amino acid sequence set forth in SEQ ID NO: 743; (d) a CDR-L1 comprising the amino acid sequence set forth in SEQ ID NO: 751; (e) a CDR-L2 comprising the amino acid sequence set forth SEQ ID NO: 759; and/or (f) a CDR-L3 comprising the amino acid sequence set forth SEQ ID NO: 765. In some embodiments of the anti-CD30L provided herein including in Section 2 and this Section 4.1 (such as those of this paragraph), the CDR-H1 comprises the amino acid sequence set forth in any one of SEQ ID NOs: 105-109, 628, 635, 115-119, 629, 636, 480-484, 630, 637, 465-469, 631, 638, 470-474, 632, 639, 475-479, 633, 640, 485-489,634, and 641. In some embodiments of the anti-CD30L provided herein including in Section 2 and this Section 4.1 (such as those of this paragraph), the CDR-H2 comprises the amino acid sequence set forth in any one of SEQ ID NOs: 145-149, 642, 649, 155-159, 643, 650, 518-522, 644, 651, 490-494, 645, 652, 495-499, 646, 653, 513-517, 647, 654, 523-527, 648, and 655. In some embodiments of the anti-CD30L provided herein including in Section 2 and this Section 4.1 (such as those of this paragraph), the CDR-H3 comprises the amino acid sequence set forth in any one of SEQ ID NOs: 185-189, 656, 663, 195-199, 657, 664, 543-547, 658, 665, 528-532, 659, 666, 533-537, 660, 667, 538-542, 661, 668, 548-552, 662, and 669. In some embodiments of the anti-CD30L provided herein including in Section 2 and this Section 4.1 (such as those of this paragraph), the CDR-L1 comprises the amino acid sequence set forth in any one of SEQ ID NOs: 305-309, 670, 677, 315-319, 671, 678, 568-572, 672, 679, 553-557, 673, 680, 558-562, 674, 681, 563-567, 675, 682, 573-577, 676, and 683. In some embodiments of the anti-CD30L provided herein including in Section 2 and this Section 4.1 (such as those of this paragraph), the CDR-L2 comprises the amino acid sequence set forth in any one of SEQ ID NOs: 345-349, 684, 691, 355-359, 685, 692, 593-597, 686, 693, 578-582, 687, 694, 583-587, 688, 695, 588-592, 689, 696, 598-602, 690, and 697. In some embodiments of the anti-CD30L provided herein including in Section 2 and this Section 4.1 (such as those of this paragraph), the CDR-L3 comprises the amino acid sequence set forth in any one of SEQ ID NOs: 385-389, 698, 705, 395-399, 699, 706, 618-622, 700,707, 603-607, 701,708, 608-612, 702, 709, 613-617, 703, 710, 623-627, 704, and 711. In certain embodiments of the anti-CD30L provided herein including in Section 2 and this Section 4.1 (such as those of this paragraph), the CDR-H1 comprises the amino acid sequence set forth in any one of SEQ ID NOs: 105-109, 628, 635, 115-119, 629, 636, 480-484, 630, and 637. In certain embodiments of the anti-CD30L provided herein including in Section 2 and this Section 4.1 (such as those of this paragraph), the CDR-H2 comprises the amino acid sequence set forth in any one of SEQ ID NOs: 145-149, 642, 649, 155-159, 643, 650, 518-522, 644, and 651. In certain embodiments of the anti-CD30L provided herein including in Section 2 and this Section 4.1 (such as those of this paragraph), the CDR-H3 comprises the amino acid sequence set forth in any one of SEQ ID NOs: 185-189, 656, 663, 195-199, 657, 664, 543-547, 658, and 665. In certain embodiments of the anti-CD30L provided herein including in Section 2 and this Section 4.1 (such as those of this paragraph), the CDR-L1 comprises the amino acid sequence set forth in any one of SEQ ID NOs: 305-309, 670, 677, 315-319, 671, 678, 568-572, 672, and 679. In certain embodiments of the anti-CD30L provided herein including in Section 2 and this Section 4.1 (such as those of this paragraph), the CDR-L2 comprises the amino acid sequence set forth in any one of SEQ ID NOs: 345-349, 684, 691, 355-359, 685, 692, 593-597, 686, and 693. In certain embodiments of the anti-CD30L provided herein including in Section 2 and this Section 4.1 (such as those of this paragraph), the CDR-L3 comprises the amino acid sequence set forth in any one of SEQ ID NOs: 385-389,698,705, 395-399, 699, 706, 618-622,700, and 707.

Further to the anti-CD30L antibody provided herein including in Section 2 and this Section 4.1 (such as those of the preceding paragraph), in one embodiment, the anti-CD30L antibody or antigen binding fragment provided herein comprises or consists of a CDR-H1 comprising the amino acid sequence set forth in any one of SEQ ID NOs: 712-723. In some embodiments, the anti-CD30L antibody or antigen binding fragment provided herein comprises or consists of a CDR-H2 comprising the amino acid sequence set forth in any one of SEQ ID NOs: 724-735. In certain embodiments, the anti-CD30L antibody or antigen binding fragment provided herein comprises or consists of a CDR- H3 comprising the amino acid sequence set forth in any one of SEQ ID NOs: 736-743. In other embodiments, the anti-CD30L antibody or antigen binding fragment provided herein comprises or consists of a CDR-L1 comprising the amino acid sequence set forth in any one of SEQ ID NOs: 744-751. In yet other embodiments, the anti-CD30L antibody or antigen binding fragment provided herein comprises or consists of a CDR-L2 comprising the amino acid sequence set forth in any one of SEQ ID NOs: 752-759. In another embodiment, the anti-CD30L antibody or antigen binding fragment provided herein comprises or consists of a CDR-L3 comprising the amino acid sequence set forth in any one of SEQ ID NOs: 760-765. In one embodiment, the anti-CD30L antibody or antigen binding fragment provided herein comprises or consists of a CDR-H1 comprising the amino acid sequence set forth in any one of SEQ ID NOs: 712-723 and a CDR-H2 comprising the amino acid sequence set forth in any one of SEQ ID NOs: 724-735. In some embodiments, the anti-CD30L antibody or antigen binding fragment provided herein comprises or consists of a CDR-H1 comprising the amino acid sequence set forth in any one of SEQ ID NOs: 712-723 and a CDR-H3 comprising the amino acid sequence set forth in any one of SEQ ID NOs: 736-743. In certain embodiments, the anti-CD30L antibody or antigen binding fragment provided herein comprises or consists of a CDR-H1 comprising the amino acid sequence set forth in any one of SEQ ID NOs: 712-723 and a CDR-L1 comprising the amino acid sequence set forth in any one of SEQ ID NOs: 744-751. In other embodiments, the anti-CD30L antibody or antigen binding fragment provided herein comprises or consists of a CDR-H1 comprising the amino acid sequence set forth in any one of SEQ ID NOs: 712-723 and a CDR-L2 comprising the amino acid sequence set forth in any one of SEQ ID NOs: 752-759. In some embodiments, the anti-CD30L antibody or antigen binding fragment provided herein comprises or consists of a CDR-H1 comprising the amino acid sequence set forth in any one of SEQ ID NOs: 712-723 and a CDR-L3 comprising the amino acid sequence set forth in any one of SEQ ID NOs: 760-765. In further embodiments, the anti-CD30L antibody or antigen binding fragment provided herein comprises or consists of a CDR-H2 comprising the amino acid sequence set forth in any one of SEQ ID NOs: 724-735 and a CDR-H3 comprising the amino acid sequence set forth in any one of SEQ ID NOs: 736-743. In one embodiment, the anti-CD30L antibody or antigen binding fragment provided herein comprises or consists of a CDR-H2 comprising the amino acid sequence set forth in any one of SEQ ID NOs: 724-735 and a CDR-L1 comprising the amino acid sequence set forth in any one of SEQ ID NOs: 744-751. In some embodiments, the anti-CD30L antibody or antigen binding fragment provided herein comprises or consists of a CDR-H2 comprising the amino acid sequence set forth in any one of SEQ ID NOs: 724-735 and a CDR-L2 comprising the amino acid sequence set forth in any one of SEQ ID NOs: 752-759. In certain embodiments, the anti-CD30L antibody or antigen binding fragment provided herein comprises or consists of a CDR-H2 comprising the amino acid sequence set forth in any one of SEQ ID NOs: 724-735 and a CDR-L3 comprising the amino acid sequence set forth in any one of SEQ ID NOs: 760-765. In other embodiments, the anti-CD30L antibody or antigen binding fragment provided herein comprises or consists of a CDR-H3 comprising the amino acid sequence set forth in any one of SEQ ID NOs: 736-743 and a CDR-L1 comprising the amino acid sequence set forth in any one of SEQ ID NOs: 744-751. In yet other embodiments, the anti-CD30L antibody or antigen binding fragment provided herein comprises or consists of a CDR-H3 comprising the amino acid sequence set forth in any one of SEQ ID NOs: 736-743 and a CDR-L2 comprising the amino acid sequence set forth in any one of SEQ ID NOs: 752-759. In some embodiments, the anti-CD30L antibody or antigen binding fragment provided herein comprises or consists of a CDR-H3 comprising the amino acid sequence set forth in any one of SEQ ID NOs: 736-743 and a CDR-L3 comprising the amino acid sequence set forth in any one of SEQ ID NOs: 760-765. In one embodiment, the anti-CD30L antibody or antigen binding fragment provided herein comprises or consists of a CDR-L1 comprising the amino acid sequence set forth in any one of SEQ ID NOs: 744-751 and a CDR-L2 comprising the amino acid sequence set forth in any one of SEQ ID NOs: 752-759. In another embodiment, the anti-CD30L antibody or antigen binding fragment provided herein comprises or consists of a CDR-L1 comprising the amino acid sequence set forth in any one of SEQ ID NOs: 744-751 and a CDR-L3 comprising the amino acid sequence set forth in any one of SEQ ID NOs: 760-765. In another embodiment, the anti-CD30L antibody or antigen binding fragment provided herein comprises or consists of a CDR-L2 comprising the amino acid sequence set forth in any one of SEQ ID NOs: 752-759 and a CDR-L3 comprising the amino acid sequence set forth in any one of SEQ ID NOs: 760-765. In other embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, and a CDR-H3 comprising the amino acid sequence set forth in any one of SEQ ID NOs: 736-743. In yet other embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735 and a CDR-L1 comprising the amino acid sequence set forth in any one of SEQ ID NOs: 744-751. In further embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, and a CDR-L2 comprising the amino acid sequence set forth in any one of SEQ ID NOs: 752-759. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, and a CDR-L3 comprising the amino acid sequence set forth in any one of SEQ ID NOs: 760-765. In some embodiments, the anti-CD30L antibody or antigen binding fragment provided herein comprises or consists of a CDR-H1 comprising the amino acid sequence set forth in any one of SEQ ID NOs: 712-723, a CDR-H3 comprising the amino acid sequence set forth in any one of SEQ ID NOs: 736-743 and a CDR-L1 comprising the amino acid sequence set forth in any one of SEQ ID NOs: 744-751. In certain embodiments, the anti-CD30L antibody or antigen binding fragment provided herein comprises or consists of a CDR-H1 comprising the amino acid sequence set forth in any one of SEQ ID NOs: 712-723, a CDR-H3 comprising the amino acid sequence set forth in any one of SEQ ID NOs: 736-743, and a CDR-L2 comprising the amino acid sequence set forth in any one of SEQ ID NOs: 752-759. In some embodiments, the anti-CD30L antibody or antigen binding fragment provided herein comprises or consists of a CDR-H1 comprising the amino acid sequence set forth in any one of SEQ ID NOs: 712-723, a CDR-H3 comprising the amino acid sequence set forth in any one of SEQ ID NOs: 736-743, and a CDR-L3 comprising the amino acid sequence set forth in any one of SEQ ID NOs: 760-765. In yet other embodiments, the anti-CD30L antibody or antigen binding fragment provided herein comprises or consists of a CDR-H1 comprising the amino acid sequence set forth in any one of SEQ ID NOs: 712-723, a CDR-L1 comprising the amino acid sequence set forth in any one of SEQ ID NOs: 744-751 and a CDR-L2 comprising the amino acid sequence set forth in any one of SEQ ID NOs: 752-759. In some embodiments, the anti-CD30L antibody or antigen binding fragment provided herein comprises or consists of a CDR-H1 comprising the amino acid sequence set forth in any one of SEQ ID NOs: 712-723, a CDR-L1 comprising the amino acid sequence set forth in any one of SEQ ID NOs: 744-751 and a CDR-L3 comprising the amino acid sequence set forth in any one of SEQ ID NOs: 760-765. In some embodiments, the anti-CD30L antibody or antigen binding fragment provided herein comprises or consists of a CDR-H1 comprising the amino acid sequence set forth in any one of SEQ ID NOs: 712-723, a CDR-L2 comprising the amino acid sequence set forth in any one of SEQ ID NOs: 752-759 and a CDR-L3 comprising the amino acid sequence set forth in any one of SEQ ID NOs: 760-765. In some embodiments, the anti-CD30L antibody or antigen binding fragment provided herein comprises or consists of a CDR-H2 comprising the amino acid sequence set forth in any one of SEQ ID NOs: 724-735, a CDR-H3 comprising the amino acid sequence set forth in any one of SEQ ID NOs: 736-743 and a CDR-L1 comprising the amino acid sequence set forth in any one of SEQ ID NOs: 744-751. In certain embodiments, the anti-CD30L antibody or antigen binding fragment provided herein comprises or consists of a CDR-H2 comprising the amino acid sequence set forth in any one of SEQ ID NOs: 724-735, a CDR-H3 comprising the amino acid sequence set forth in any one of SEQ ID NOs: 736-743, and a CDR-L2 comprising the amino acid sequence set forth in any one of SEQ ID NOs: 752-759. In some embodiments, the anti-CD30L antibody or antigen binding fragment provided herein comprises or consists of a CDR-H2 comprising the amino acid sequence set forth in any one of SEQ ID NOs: 724-735, a CDR-H3 comprising the amino acid sequence set forth in any one of SEQ ID NOs: 736-743, and a CDR-L3 comprising the amino acid sequence set forth in any one of SEQ ID NOs: 760-765. In other embodiments, the anti-CD30L antibody or antigen binding fragment provided herein comprises or consists of a CDR-H2 comprising the amino acid sequence set forth in any one of SEQ ID NOs: 724-735, a CDR-L1 comprising the amino acid sequence set forth in any one of SEQ ID NOs: 744-751 and a CDR-L2 comprising the amino acid sequence set forth in any one of SEQ ID NOs: 752-759. In yet other embodiments, the anti-CD30L antibody or antigen binding fragment provided herein comprises or consists of a CDR-H2 comprising the amino acid sequence set forth in any one of SEQ ID NOs: 724-735, a CDR-L1 comprising the amino acid sequence set forth in any one of SEQ ID NOs: 744-751 and a CDR-L3 comprising the amino acid sequence set forth in any one of SEQ ID NOs: 760-765. In some embodiments, the anti-CD30L antibody or antigen binding fragment provided herein comprises or consists of a CDR-H2 comprising the amino acid sequence set forth in any one of SEQ ID NOs: 724-735, a CDR-L2 comprising the amino acid sequence set forth in any one of SEQ ID NOs: 752-759 and a CDR-L3 comprising the amino acid sequence set forth in any one of SEQ ID NOs: 760-765. In yet other embodiments, the anti-CD30L antibody or antigen binding fragment provided herein comprises or consists of a CDR-H3 comprising the amino acid sequence set forth in any one of SEQ ID NOs: 736-743, a CDR-L1 comprising the amino acid sequence set forth in any one of SEQ ID NOs: 744-751 and a CDR-L2 comprising the amino acid sequence set forth in any one of SEQ ID NOs: 752-759. In other embodiments, the anti-CD30L antibody or antigen binding fragment provided herein comprises or consists of a CDR-H3 comprising the amino acid sequence set forth in any one of SEQ ID NOs: 736-743, a CDR-L1 comprising the amino acid sequence set forth in any one of SEQ ID NOs: 744-751 and a CDR-L3 comprising the amino acid sequence set forth in any one of SEQ ID NOs: 760-765. In certain embodiments, the anti-CD30L antibody or antigen binding fragment provided herein comprises or consists of a CDR-H3 comprising the amino acid sequence set forth in any one of SEQ ID NOs: 736-743, a CDR-L2 comprising the amino acid sequence set forth in any one of SEQ ID NOs: 752-759 and a CDR-L3 comprising the amino acid sequence set forth in any one of SEQ ID NOs: 760-765. In some embodiments, the anti-CD30L antibody or antigen binding fragment provided herein comprises or consists of a CDR-L1 comprising the amino acid sequence set forth in any one of SEQ ID NOs: 744-751, a CDR-L2 comprising the amino acid sequence set forth in any one of SEQ ID NOs: 752-759 and a CDR-L3 comprising the amino acid sequence set forth in any one of SEQ ID NOs: 760-765. In other embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, and a CDR-L1 comprising the amino acid sequence set forth in any one of SEQ ID NOs: 744-751. In further embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, and a CDR-L2 comprising the amino acid sequence set forth in any one of SEQ ID NOs: 752-759. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, and a CDR-L3 comprising the amino acid sequence set forth in any one of SEQ ID NOs: 760-765. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-L1 comprising the amino acid sequence set forth in any one of SEQ ID NOs: 744-751, and a CDR-L2 comprising the amino acid sequence set forth in any one of SEQ ID NOs: 752-759. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-L1 comprising the amino acid sequence set forth in any one of SEQ ID NOs: 744-751, and a CDR-L3 comprising the amino acid sequence set forth in any one of SEQ ID NOs: 760-765. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-L2 comprising the amino acid sequence set forth in any one of SEQ ID NOs: 752-759, and a CDR-L3 comprising the amino acid sequence set forth in any one of SEQ ID NOs: 760-765. In certain embodiments, the anti-CD30L antibody or antigen binding fragment provided herein comprises or consists of a CDR-H1 comprising the amino acid sequence set forth in any one of SEQ ID NOs: 712-723, a CDR-H3 comprising the amino acid sequence set forth in any one of SEQ ID NOs: 736-743, a CDR-L1 comprising the amino acid sequence set forth in any one of SEQ ID NOs: 744-751, and a CDR-L2 comprising the amino acid sequence set forth in any one of SEQ ID NOs: 752-759. In certain embodiments, the anti-CD30L antibody or antigen binding fragment provided herein comprises or consists of a CDR-H1 comprising the amino acid sequence set forth in any one of SEQ ID NOs: 712-723, a CDR-H3 comprising the amino acid sequence set forth in any one of SEQ ID NOs: 736-743, a CDR-L1 comprising the amino acid sequence set forth in any one of SEQ ID NOs: 744-751, and a CDR-L3 comprising the amino acid sequence set forth in any one of SEQ ID NOs: 760-765. In certain embodiments, the anti-CD30L antibody or antigen binding fragment provided herein comprises or consists of a CDR-H1 comprising the amino acid sequence set forth in any one of SEQ ID NOs: 712-723, a CDR-H3 comprising the amino acid sequence set forth in any one of SEQ ID NOs: 736-743, a CDR-L2 comprising the amino acid sequence set forth in any one of SEQ ID NOs: 752-759, and a CDR-L3 comprising the amino acid sequence set forth in any one of SEQ ID NOs: 760-765. In yet other embodiments, the anti-CD30L antibody or antigen binding fragment provided herein comprises or consists of a CDR-H1 comprising the amino acid sequence set forth in any one of SEQ ID NOs: 712-723, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In further embodiments, the anti-CD30L antibody or antigen binding fragment provided herein comprises or consists of a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, and a CDR-L2 comprising the amino acid sequence set forth in any one of SEQ ID NOs: 752-759. In some embodiments, the anti-CD30L antibody or antigen binding fragment provided herein comprises or consists of a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, and a CDR-L3 compris-ing the amino acid sequence set forth in any one of SEQ ID NOs: 760-765. In further embodiments, the anti-CD30L antibody or antigen binding fragment provided herein comprises or consists of a CDR-H2 comprising the amino acid sequence set forth in any one of SEQ ID NOs: 724-735, a CDR-H3 comprising the amino acid sequence set forth in any one of SEQ ID NOs: 736-743, a CDR-L2 comprising the amino acid sequence set forth in any one of SEQ ID NOs: 752-759, and a CDR-L3 comprising the amino acid sequence set forth in any one of SEQ ID NOs: 760-765. In some embodiments, the anti-CD30L antibody or antigen binding fragment provided herein comprises or consists of a CDR-H2 comprising the amino acid sequence set forth in any one of SEQ ID NOs: 724-735, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In some embodiments, the anti-CD30L antibody or antigen binding fragment provided herein comprises or consists of a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In certain embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, and a CDR-L2 comprising the amino acid sequence set forth in any one of SEQ ID NOs: 752-759. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, and a CDR-L3 comprising the amino acid sequence set forth in any one of SEQ ID NOs: 760-765. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L2 comprising the amino acid sequence set forth in any one of SEQ ID NOs: 752-759, and a CDR-L3 comprising the amino acid sequence set forth in any one of SEQ ID NOs: 760-765. In certain embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In certain embodiments, the anti-CD30L antibody or antigen binding fragment provided herein comprises or consists of a CDR-H1 comprising the amino acid sequence set forth in any one of SEQ ID NOs: 712-723, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In some embodiments, the anti-CD30L antibody or antigen binding fragment provided herein comprises or consists of a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In some embodiments, the anti-CD30L antibody or antigen binding fragment provided herein comprises or consists of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In some embodiments, the anti-CD30L antibody or antigen binding fragment provided herein comprises or consists of any one of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In some embodiments, the anti-CD30L antibody or antigen binding fragment provided herein comprises or consists of any two of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and aCDR-L3 comprising the amino acid sequence set forth in any one of SEQ ID NOs: 760-765, in any combination or permutation. In some embodiments, the anti-CD30L antibody or antigen binding fragment provided herein comprises or consists of any three of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765, in any combination or permutation. In some embodiments, the anti-CD30L antibody or antigen binding fragment provided herein comprises or consists of any four of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765, in any combination or permutation. In some embodiments, the anti-CD30L antibody or antigen binding fragment provided herein comprises or consists of any five of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765, in any combination or permutation. In some embodiments, the anti-CD30L antibody or antigen binding fragment provided herein comprises or consists of all six of a CDR-H1 comprising the amino acid sequence set forth in any one of SEQ ID NOs: 712-723, a CDR-H2 comprising the amino acid sequence set forth in any one of SEQ ID NOs: 724-735, a CDR-H3 comprising the amino acid sequence set forth in any one of SEQ ID NOs: 736-743, a CDR-L1 comprising the amino acid sequence set forth in any one of SEQ ID NOs: 744-751, a CDR-L2 comprising the amino acid sequence set forth in any one of SEQ ID NOs: 752-759, and a CDR-L3 comprising the amino acid sequence set forth in any one of SEQ ID NOs: 760-765. In some embodiments of the anti-CD30L provided herein including in Section 2 and this Section 4.1 (such as those of this paragraph), the CDR-H1 comprises the amino acid sequence set forth in any one of SEQ ID NOs: 105-109, 628, 635, 115-119, 629, 636, 480-484, 630, 637, 465-469, 631, 638, 470-474, 632, 639, 475-479, 633, 640, 485-489, 634, and 641. In some embodiments of the anti-CD30L provided herein including in Section 2 and this Section 4.1 (such as those of this paragraph), the CDR-H2 comprises the amino acid sequence set forth in any one of SEQ ID NOs: 145-149, 642, 649, 155-159, 643, 650, 518-522, 644, 651, 490-494, 645, 652, 495499, 646, 653, 513-517, 647, 654, 523-527, 648, and 655. In some embodiments of the anti-CD30L provided herein including in Section 2 and this Section 4.1 (such as those of this paragraph), the CDR-H3 comprises the amino acid sequence set forth in any one of SEQ ID NOs: 185-189, 656, 663, 195-199, 657, 664, 543-547, 658, 665, 528-532, 659, 666, 533-537, 660, 667, 538-542, 661, 668, 548-552, 662, and 669. In some embodiments of the anti-CD30L provided herein including in Section 2 and this Section 4.1 (such as those of this paragraph), the CDR-L1 comprises the amino acid sequence set forth in any one of SEQ ID NOs: 305-309, 670, 677, 315-319, 671, 678, 568-572, 672,679, 553-557, 673,680, 558-562, 674, 681, 563-567, 675, 682, 573-577, 676, and 683. In some embodiments of the anti-CD30L provided herein including in Section 2 and this Section 4.1 (such as those of this paragraph), the CDR-L2 comprises the amino acid sequence set forth in any one of SEQ ID NOs: 345-349, 684, 691, 355-359, 685, 692, 593-597, 686,693, 578-582, 687,694, 583-587, 688, 695, 588-592, 689, 696, 598-602, 690, and 697. In some embodiments of the anti-CD30L provided herein including in Section 2 and this Section 4.1 (such as those of this paragraph), the CDR-L3 comprises the amino acid sequence set forth in any one of SEQ ID NOs: 385-389, 698, 705, 395-399, 699, 706, 618-622, 700,707, 603-607, 701,708, 608-612, 702, 709, 613-617, 703, 710, 623-627, 704, and 711. In certain embodiments of the anti-CD30L provided herein including in Section 2 and this Section 4.1 (such as those of this paragraph), the CDR-H1 comprises the amino acid sequence set forth in any one of SEQ ID NOs: 105-109, 628, 635, 115-119, 629, 636, 480-484, 630, and 637. In certain embodiments of the anti-CD30L provided herein including in Section 2 and this Section 4.1 (such as those of this paragraph), the CDR-H2 comprises the amino acid sequence set forth in any one of SEQ ID NOs: 145-149, 642, 649, 155-159, 643, 650, 518-522, 644, and 651. In certain embodiments of the anti-CD30L provided herein including in Section 2 and this Section 4.1 (such as those of this paragraph), the CDR-H3 comprises the amino acid sequence set forth in any one of SEQ ID NOs: 185-189, 656, 663, 195-199, 657, 664, 543-547, 658, and 665. In certain embodiments of the anti-CD30L provided herein including in Section 2 and this Section 4.1 (such as those of this paragraph), the CDR-L1 comprises the amino acid sequence set forth in any one of SEQ ID NOs: 305-309, 670, 677, 315-319, 671, 678, 568-572, 672, and 679. In certain embodiments of the anti-CD30L provided herein including in Section 2 and this Section 4.1 (such as those of this paragraph), the CDR-L2 comprises the amino acid sequence set forth in any one of SEQ ID NOs: 345-349, 684, 691, 355-359, 685, 692, 593-597, 686, and 693. In certain embodiments of the anti-CD30L provided herein including in Section 2 and this Section 4.1 (such as those of this paragraph), the CDR-L3 comprises the amino acid sequence set forth in any one of SEQ ID NOs: 385-389,698,705, 395-399, 699, 706, 618-622,700, and 707.

Additionally, the anti-CD30L antibody provided herein, including in Section 2 and this Section (Section 4.1), can comprise specific combinations of CDRs of each anti-CD30L clone as listed in Tables 10-16. Accordingly, in one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 635; (b) a CDR-H2 comprising the amino acid sequence set forth in SEQ ID NO: 649; (c) a CDR-H3 comprising the amino acid sequence set forth in SEQ ID NO: 663; (d) a CDR-L1 comprising the amino acid sequence set forth in SEQ ID NO: 677; (e) a CDR-L2 comprising the amino acid sequence set forth SEQ ID NO: 691; and/or (f) a CDR-L3 comprising the amino acid sequence set forth SEQ ID NO: 705. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 107; (b) a CDR-H2 comprising the amino acid sequence set forth in SEQ ID NO: 147; (c) a CDR-H3 comprising the amino acid sequence set forth in SEQ ID NO: 187; (d) a CDR-L1 comprising the amino acid sequence set forth in SEQ ID NO: 307; (e) a CDR-L2 comprising the amino acid sequence set forth SEQ ID NO: 347; and/or (f) a CDR-L3 comprising the amino acid sequence set forth SEQ ID NO: 387. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 105; (b) a CDR-H2 comprising the amino acid sequence set forth in SEQ ID NO: 145; (c) a CDR-H3 comprising the amino acid sequence set forth in SEQ ID NO: 185; (d) a CDR-L1 comprising the amino acid sequence set forth in SEQ ID NO: 305; (e) a CDR-L2 comprising the amino acid sequence set forth SEQ ID NO: 345; and/or (f) a CDR-L3 comprising the amino acid sequence set forth SEQ ID NO: 385. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 106; (b) a CDR-H2 comprising the amino acid sequence set forth in SEQ ID NO: 146; (c) a CDR-H3 comprising the amino acid sequence set forth in SEQ ID NO: 186; (d) a CDR-L1 comprising the amino acid sequence set forth in SEQ ID NO: 306; (e) a CDR-L2 comprising the amino acid sequence set forth SEQ ID NO: 346; and/or (f) a CDR-L3 comprising the amino acid sequence set forth SEQ ID NO: 386. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 108; (b) a CDR-H2 comprising the amino acid sequence set forth in SEQ ID NO: 148; (c) a CDR-H3 comprising the amino acid sequence set forth in SEQ ID NO: 188; (d) a CDR-L1 comprising the amino acid sequence set forth in SEQ ID NO: 308; (e) a CDR-L2 comprising the amino acid sequence set forth SEQ ID NO: 348; and/or (f) a CDR-L3 comprising the amino acid sequence set forth SEQ ID NO: 388. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 109; (b) a CDR-H2 comprising the amino acid sequence set forth in SEQ ID NO: 149; (c) a CDR-H3 comprising the amino acid sequence set forth in SEQ ID NO: 189; (d) a CDR-L1 comprising the amino acid sequence set forth in SEQ ID NO: 309; (e) a CDR-L2 comprising the amino acid sequence set forth SEQ ID NO: 349; and/or (f) a CDR-L3 comprising the amino acid sequence set forth SEQ ID NO: 389. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 628; (b) a CDR-H2 comprising the amino acid sequence set forth in SEQ ID NO: 642; (c) a CDR-H3 comprising the amino acid sequence set forth in SEQ ID NO: 656; (d) a CDR-L1 comprising the amino acid sequence set forth in SEQ ID NO: 670; (e) a CDR-L2 comprising the amino acid sequence set forth SEQ ID NO: 684; and/or (f) a CDR-L3 comprising the amino acid sequence set forth SEQ ID NO: 698.

Similarly, in one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 636; (b) a CDR-H2 comprising the amino acid sequence set forth in SEQ ID NO: 650; (c) a CDR-H3 comprising the amino acid sequence set forth in SEQ ID NO: 664; (d) a CDR-L1 comprising the amino acid sequence set forth in SEQ ID NO: 678; (e) a CDR-L2 comprising the amino acid sequence set forth SEQ ID NO: 692; and/or (f) a CDR-L3 comprising the amino acid sequence set forth SEQ ID NO: 706. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 117; (b) a CDR-H2 comprising the amino acid sequence set forth in SEQ ID NO: 157; (c) a CDR-H3 comprising the amino acid sequence set forth in SEQ ID NO: 197; (d) a CDR-L1 comprising the amino acid sequence set forth in SEQ ID NO: 317; (e) a CDR-L2 comprising the amino acid sequence set forth SEQ ID NO: 357; and/or (f) a CDR-L3 comprising the amino acid sequence set forth SEQ ID NO: 397. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 115; (b) a CDR-H2 comprising the amino acid sequence set forth in SEQ ID NO: 155; (c) a CDR-H3 comprising the amino acid sequence set forth in SEQ ID NO: 195; (d) a CDR-L1 comprising the amino acid sequence set forth in SEQ ID NO: 315; (e) a CDR-L2 comprising the amino acid sequence set forth SEQ ID NO: 355; and/or (f) a CDR-L3 comprising the amino acid sequence set forth SEQ ID NO: 395. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 116; (b) a CDR-H2 comprising the amino acid sequence set forth in SEQ ID NO: 156; (c) a CDR-H3 comprising the amino acid sequence set forth in SEQ ID NO: 196; (d) a CDR-L1 comprising the amino acid sequence set forth in SEQ ID NO: 316; (e) a CDR-L2 comprising the amino acid sequence set forth SEQ ID NO: 356; and/or (f) a CDR-L3 comprising the amino acid sequence set forth SEQ ID NO: 396. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 118; (b) a CDR-H2 comprising the amino acid sequence set forth in SEQ ID NO: 158; (c) a CDR-H3 comprising the amino acid sequence set forth in SEQ ID NO: 198; (d) a CDR-L1 comprising the amino acid sequence set forth in SEQ ID NO: 318; (e) a CDR-L2 comprising the amino acid sequence set forth SEQ ID NO: 358; and/or (f) a CDR-L3 comprising the amino acid sequence set forth SEQ ID NO: 398. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 119; (b) a CDR-H2 comprising the amino acid sequence set forth in SEQ ID NO: 159; (c) a CDR-H3 comprising the amino acid sequence set forth in SEQ ID NO: 199; (d) a CDR-L1 comprising the amino acid sequence set forth in SEQ ID NO: 319; (e) a CDR-L2 comprising the amino acid sequence set forth SEQ ID NO: 359; and/or (f) a CDR-L3 comprising the amino acid sequence set forth SEQ ID NO: 399. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 629; (b) a CDR-H2 comprising the amino acid sequence set forth in SEQ ID NO: 643; (c) a CDR-H3 comprising the amino acid sequence set forth in SEQ ID NO: 657; (d) a CDR-L1 comprising the amino acid sequence set forth in SEQ ID NO: 671; (e) a CDR-L2 comprising the amino acid sequence set forth SEQ ID NO: 685; and/or (f) a CDR-L3 comprising the amino acid sequence set forth SEQ ID NO: 699.

Likewise, in one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 637; (b) a CDR-H2 comprising the amino acid sequence set forth in SEQ ID NO: 651; (c) a CDR-H3 comprising the amino acid sequence set forth in SEQ ID NO: 665; (d) a CDR-L1 comprising the amino acid sequence set forth in SEQ ID NO: 679; (e) a CDR-L2 comprising the amino acid sequence set forth SEQ ID NO: 693; and/or (f) a CDR-L3 comprising the amino acid sequence set forth SEQ ID NO: 707. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 482; (b) a CDR-H2 comprising the amino acid sequence set forth in SEQ ID NO: 520; (c) a CDR-H3 comprising the amino acid sequence set forth in SEQ ID NO: 545; (d) a CDR-L1 comprising the amino acid sequence set forth in SEQ ID NO: 570; (e) a CDR-L2 comprising the amino acid sequence set forth SEQ ID NO: 595; and/or (f) a CDR-L3 comprising the amino acid sequence set forth SEQ ID NO: 620. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 480; (b) a CDR-H2 comprising the amino acid sequence set forth in SEQ ID NO: 518; (c) a CDR-H3 comprising the amino acid sequence set forth in SEQ ID NO: 543; (d) a CDR-L1 comprising the amino acid sequence set forth in SEQ ID NO: 568; (e) a CDR-L2 comprising the amino acid sequence set forth SEQ ID NO: 593; and/or (f) a CDR-L3 comprising the amino acid sequence set forth SEQ ID NO: 618. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 481; (b) a CDR-H2 comprising the amino acid sequence set forth in SEQ ID NO: 519; (c) a CDR-H3 comprising the amino acid sequence set forth in SEQ ID NO: 544; (d) a CDR-L1 comprising the amino acid sequence set forth in SEQ ID NO: 569; (e) a CDR-L2 comprising the amino acid sequence set forth SEQ ID NO: 594; and/or (f) a CDR-L3 comprising the amino acid sequence set forth SEQ ID NO: 619. In another embodiment of the anti-CD30L antibody or antigen binding fragment provided herein, including in Section 2 and this Section (Section 4.1), the antibody or antigen binding fragment thereof comprises: (a)

a CDR-H1 comprising the amino acid sequence set forth in SEQ ID NO: 483; (b) a CDR-H2 comprising the amino acid sequence set forth in SEQ ID NO: 521; (c) a CDR-H3 comprising the amino acid sequence set forth in SEQ ID NO: 546; (d) a CDR-L1 comprising the amino acid sequence set forth in SEQ ID NO: 571; (e) a CDR-L2 comprising the amino acid sequence set forth SEQ ID NO: 596; and/or (f) a CDR-L3 comprising the amino acid sequence set forth SEQ ID NO: 621. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 484; (b) a CDR-H2 comprising the amino acid sequence set forth in SEQ ID NO: 522; (c) a CDR-H3 comprising the amino acid sequence set forth in SEQ ID NO: 547; (d) a CDR-L1 comprising the amino acid sequence set forth in SEQ ID NO: 572; (e) a CDR-L2 comprising the amino acid sequence set forth SEQ ID NO: 597; and/or (f) a CDR-L3 comprising the amino acid sequence set forth SEQ ID NO: 622. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 630; (b) a CDR-H2 comprising the amino acid sequence set forth in SEQ ID NO: 644; (c) a CDR-H3 comprising the amino acid sequence set forth in SEQ ID NO: 658; (d) a CDR-L1 comprising the amino acid sequence set forth in SEQ ID NO: 672; (e) a CDR-L2 comprising the amino acid sequence set forth SEQ ID NO: 686; and/or (f) a CDR-L3 comprising the amino acid sequence set forth SEQ ID NO: 700.

Additionally, in one embodiment of the anti-CD30L antibody or antigen binding fragment provided herein, including in Section 2 and this Section (Section 4.1), the antibody or antigen binding fragment thereof comprises: (i) (a) a CDR-H1 comprising the amino acid sequence set forth in SEQ ID NO: 638; (b) a CDR-H2 comprising the amino acid sequence set forth in SEQ ID NO: 652; (c) a CDR-H3 comprising the amino acid sequence set forth in SEQ ID NO: 666; (d) a CDR-L1 comprising the amino acid sequence set forth in SEQ ID NO: 680; (e) a CDR-L2 comprising the amino acid sequence set forth SEQ ID NO: 694; and/or (f) a CDR-L3 comprising the amino acid sequence set forth SEQ ID NO: 708. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 467; (b) a CDR-H2 comprising the amino acid sequence set forth in SEQ ID NO: 492; (c) a CDR-H3 comprising the amino acid sequence set forth in SEQ ID NO: 530; (d) a CDR-L1 comprising the amino acid sequence set forth in SEQ ID NO: 555; (e) a CDR-L2 comprising the amino acid sequence set forth SEQ ID NO: 580; and/or (f) a CDR-L3 comprising the amino acid sequence set forth SEQ ID NO: 605. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 465; (b) a CDR-H2 comprising the amino acid sequence set forth in SEQ ID NO: 490; (c) a CDR-H3 comprising the amino acid sequence set forth in SEQ ID NO: 528; (d) a CDR-L1 comprising the amino acid sequence set forth in SEQ ID NO: 553; (e) a CDR-L2 comprising the amino acid sequence set forth SEQ ID NO: 578; and/or (f) a CDR-L3 comprising the amino acid sequence set forth SEQ ID NO: 603. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 466; (b) a CDR-H2 comprising the amino acid sequence set forth in SEQ ID NO: 491; (c) a CDR-H3 comprising the amino acid sequence set forth in SEQ ID NO: 529; (d) a CDR-L1 comprising the amino acid sequence set forth in SEQ ID NO: 554; (e) a CDR-L2 comprising the amino acid sequence set forth SEQ ID NO: 579; and/or (f) a CDR-L3 comprising the amino acid sequence set forth SEQ ID NO: 604. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 468; (b) a CDR-H2 comprising the amino acid sequence set forth in SEQ ID NO: 493; (c) a CDR-H3 comprising the amino acid sequence set forth in SEQ ID NO: 531; (d) a CDR-L1 comprising the amino acid sequence set forth in SEQ ID NO: 556; (e) a CDR-L2 comprising the amino acid sequence set forth SEQ ID NO: 581; and/or (f) a CDR-L3 comprising the amino acid sequence set forth SEQ ID NO: 606. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 469; (b) a CDR-H2 comprising the amino acid sequence set forth in SEQ ID NO: 494; (c) a CDR-H3 comprising the amino acid sequence set forth in SEQ ID NO: 532; (d) a CDR-L1 comprising the amino acid sequence set forth in SEQ ID NO: 557; (e) a CDR-L2 comprising the amino acid sequence set forth SEQ ID NO: 582; and/or (f) a CDR-L3 comprising the amino acid sequence set forth SEQ ID NO: 607. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 631; (b) a CDR-H2 comprising the amino acid sequence set forth in SEQ ID NO: 645; (c) a CDR-H3 comprising the amino acid sequence set forth in SEQ ID NO: 659; (d) a CDR-L1 comprising the amino acid sequence set forth in SEQ ID NO: 673; (e) a CDR-L2 comprising the amino acid sequence set forth SEQ ID NO: 687; and/or (f) a CDR-L3 comprising the amino acid sequence set forth SEQ ID NO: 701.

Similarly, in one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 639; (b) a CDR-H2 comprising the amino acid sequence set forth in SEQ ID NO: 653; (c) a CDR-H3 comprising the amino acid sequence set forth in SEQ ID NO: 667; (d) a CDR-L1 comprising the amino acid sequence set forth in SEQ ID NO: 681; (e) a CDR-L2 comprising the amino acid sequence set forth SEQ ID NO: 695; and/or (f) a CDR-L3 comprising the amino acid sequence set forth SEQ ID NO: 709. In another embodiment of the anti-CD30L antibody or antigen binding fragment provided herein, including in Section 2 and this Section (Section 4.1), the antibody or antigen binding fragment thereof comprises: (a)

a CDR-H1 comprising the amino acid sequence set forth in SEQ ID NO: 472; (b) a CDR-H2 comprising the amino acid sequence set forth in SEQ ID NO: 497; (c) a CDR-H3 comprising the amino acid sequence set forth in SEQ ID NO: 535; (d) a CDR-L1 comprising the amino acid sequence set forth in SEQ ID NO: 560; (e) a CDR-L2 comprising the amino acid sequence set forth SEQ ID NO: 585; and/or (f) a CDR-L3 comprising the amino acid sequence set forth SEQ ID NO: 610. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 470; (b) a CDR-H2 comprising the amino acid sequence set forth in SEQ ID NO: 495; (c) a CDR-H3 comprising the amino acid sequence set forth in SEQ ID NO: 533; (d) a CDR-L1 comprising the amino acid sequence set forth in SEQ ID NO: 558; (e) a CDR-L2 comprising the amino acid sequence set forth SEQ ID NO: 583; and/or (f) a CDR-L3 comprising the amino acid sequence set forth SEQ ID NO: 608. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 471; (b) a CDR-H2 comprising the amino acid sequence set forth in SEQ ID NO: 496; (c) a CDR-H3 comprising the amino acid sequence set forth in SEQ ID NO: 534; (d) a CDR-L1 comprising the amino acid sequence set forth in SEQ ID NO: 559; (e) a CDR-L2 comprising the amino acid sequence set forth SEQ ID NO: 584; and/or (f) a CDR-L3 comprising the amino acid sequence set forth SEQ ID NO: 609. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 473; (b) a CDR-H2 comprising the amino acid sequence set forth in SEQ ID NO: 498; (c) a CDR-H3 comprising the amino acid sequence set forth in SEQ ID NO: 536; (d) a CDR-L1 comprising the amino acid sequence set forth in SEQ ID NO: 561; (e) a CDR-L2 comprising the amino acid sequence set forth SEQ ID NO: 586; and/or (f) a CDR-L3 comprising the amino acid sequence set forth SEQ ID NO: 611. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 474; (b) a CDR-H2 comprising the amino acid sequence set forth in SEQ ID NO: 499; (c) a CDR-H3 comprising the amino acid sequence set forth in SEQ ID NO: 537; (d) a CDR-L1 comprising the amino acid sequence set forth in SEQ ID NO: 562; (e) a CDR-L2 comprising the amino acid sequence set forth SEQ ID NO: 587; and/or (f) a CDR-L3 comprising the amino acid sequence set forth SEQ ID NO: 612. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 632; (b) a CDR-H2 comprising the amino acid sequence set forth in SEQ ID NO: 646; (c) a CDR-H3 comprising the amino acid sequence set forth in SEQ ID NO: 660; (d) a CDR-L1 comprising the amino acid sequence set forth in SEQ ID NO: 674; (e) a CDR-L2 comprising the amino acid sequence set forth SEQ ID NO: 688; and/or (f) a CDR-L3 comprising the amino acid sequence set forth SEQ ID NO: 702.

Likewise, in one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 640; (b) a CDR-H2 comprising the amino acid sequence set forth in SEQ ID NO: 654; (c) a CDR-H3 comprising the amino acid sequence set forth in SEQ ID NO: 668; (d) a CDR-L1 comprising the amino acid sequence set forth in SEQ ID NO: 682; (e) a CDR-L2 comprising the amino acid sequence set forth SEQ ID NO: 696; and/or (f) a CDR-L3 comprising the amino acid sequence set forth SEQ ID NO: 710. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 477; (b) a CDR-H2 comprising the amino acid sequence set forth in SEQ ID NO: 515; (c) a CDR-H3 comprising the amino acid sequence set forth in SEQ ID NO: 540; (d) a CDR-L1 comprising the amino acid sequence set forth in SEQ ID NO: 565; (e) a CDR-L2 comprising the amino acid sequence set forth SEQ ID NO: 590; and/or (f) a CDR-L3 comprising the amino acid sequence set forth SEQ ID NO: 615. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 475; (b) a CDR-H2 comprising the amino acid sequence set forth in SEQ ID NO: 513; (c) a CDR-H3 comprising the amino acid sequence set forth in SEQ ID NO: 538; (d) a CDR-L1 comprising the amino acid sequence set forth in SEQ ID NO: 563; (e) a CDR-L2 comprising the amino acid sequence set forth SEQ ID NO: 588; and/or (f) a CDR-L3 comprising the amino acid sequence set forth SEQ ID NO: 613. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 476; (b) a CDR-H2 comprising the amino acid sequence set forth in SEQ ID NO: 514; (c) a CDR-H3 comprising the amino acid sequence set forth in SEQ ID NO: 539; (d) a CDR-L1 comprising the amino acid sequence set forth in SEQ ID NO: 564; (e) a CDR-L2 comprising the amino acid sequence set forth SEQ ID NO: 589; and/or (f) a CDR-L3 comprising the amino acid sequence set forth SEQ ID NO: 614. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 478; (b) a CDR-H2 comprising the amino acid sequence set forth in SEQ ID NO: 516; (c) a CDR-H3 comprising the amino acid sequence set forth in SEQ ID NO: 541; (d) a CDR-L1 comprising the amino acid sequence set forth in SEQ ID NO: 566; (e) a CDR-L2 comprising the amino acid sequence set forth SEQ ID NO: 591; and/or (f) a CDR-L3 comprising the amino acid sequence set forth SEQ ID NO: 616. In yet another embodiment of the anti-CD30L antibody or antigen binding fragment provided herein, including in Section 2 and this Section (Section 4.1), the antibody or antigen binding fragment thereof comprises:

(a) a CDR-H1 comprising the amino acid sequence set forth in SEQ ID NO: 479; (b) a CDR-H2 comprising the amino acid sequence set forth in SEQ ID NO: 517; (c) a CDR-H3 comprising the amino acid sequence set forth in SEQ ID NO: 542; (d) a CDR-L1 comprising the amino acid sequence set forth in SEQ ID NO: 567; (e) a CDR-L2 comprising the amino acid sequence set forth SEQ ID NO: 592; and/or (f) a CDR-L3 comprising the amino acid sequence set forth SEQ ID NO: 617. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 633; (b) a CDR-H2 comprising the amino acid sequence set forth in SEQ ID NO: 647; (c) a CDR-H3 comprising the amino acid sequence set forth in SEQ ID NO: 661; (d) a CDR-L1 comprising the amino acid sequence set forth in SEQ ID NO: 675; (e) a CDR-L2 comprising the amino acid sequence set forth SEQ ID NO: 689; and/or (f) a CDR-L3 comprising the amino acid sequence set forth SEQ ID NO: 703.

Additionally, in one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 641; (b) a CDR-H2 comprising the amino acid sequence set forth in SEQ ID NO: 655; (c) a CDR-H3 comprising the amino acid sequence set forth in SEQ ID NO: 669; (d) a CDR-L1 comprising the amino acid sequence set forth in SEQ ID NO: 683; (e) a CDR-L2 comprising the amino acid sequence set forth SEQ ID NO: 697; and/or (f) a CDR-L3 comprising the amino acid sequence set forth SEQ ID NO: 711. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 487; (b) a CDR-H2 comprising the amino acid sequence set forth in SEQ ID NO: 525; (c) a CDR-H3 comprising the amino acid sequence set forth in SEQ ID NO: 550; (d) a CDR-L1 comprising the amino acid sequence set forth in SEQ ID NO: 575; (e) a CDR-L2 comprising the amino acid sequence set forth SEQ ID NO: 600; and/or (f) a CDR-L3 comprising the amino acid sequence set forth SEQ ID NO: 625. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 485; (b) a CDR-H2 comprising the amino acid sequence set forth in SEQ ID NO: 523; (c) a CDR-H3 comprising the amino acid sequence set forth in SEQ ID NO: 548; (d) a CDR-L1 comprising the amino acid sequence set forth in SEQ ID NO: 573; (e) a CDR-L2 comprising the amino acid sequence set forth SEQ ID NO: 598; and/or (f) a CDR-L3 comprising the amino acid sequence set forth SEQ ID NO: 623. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 486; (b) a CDR-H2 comprising the amino acid sequence set forth in SEQ ID NO: 524; (c) a CDR-H3 comprising the amino acid sequence set forth in SEQ ID NO: 549; (d) a CDR-L1 comprising the amino acid sequence set forth in SEQ ID NO: 574; (e) a CDR-L2 comprising the amino acid sequence set forth SEQ ID NO: 599; and/or (f) a CDR-L3 comprising the amino acid sequence set forth SEQ ID NO: 624. In another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 488; (b) a CDR-H2 comprising the amino acid sequence set forth in SEQ ID NO: 526; (c) a CDR-H3 comprising the amino acid sequence set forth in SEQ ID NO: 551; (d) a CDR-L1 comprising the amino acid sequence set forth in SEQ ID NO: 576; (e) a CDR-L2 comprising the amino acid sequence set forth SEQ ID NO: 601; and/or (f) a CDR-L3 comprising the amino acid sequence set forth SEQ ID NO: 626. In yet another embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 489; (b) a CDR-H2 comprising the amino acid sequence set forth in SEQ ID NO: 527; (c) a CDR-H3 comprising the amino acid sequence set forth in SEQ ID NO: 552; (d) a CDR-L1 comprising the amino acid sequence set forth in SEQ ID NO: 577; (e) a CDR-L2 comprising the amino acid sequence set forth SEQ ID NO: 602; and/or (f) a CDR-L3 comprising the amino acid sequence set forth SEQ ID NO: 627. In one embodiment of the anti-CD30L antibody or antigen binding fragment provided herein, including in Section 2 and this Section (Section 4.1), the antibody or antigen binding fragment thereof comprises: (a) a CDR-H1 comprising the amino acid sequence set forth in SEQ ID NO: 634; (b) a CDR-H2 comprising the amino acid sequence set forth in SEQ ID NO: 648; (c) a CDR-H3 comprising the amino acid sequence set forth in SEQ ID NO: 662; (d) a CDR-L1 comprising the amino acid sequence set forth in SEQ ID NO: 676; (e) a CDR-L2 comprising the amino acid sequence set forth SEQ ID NO: 690; and/or (f) a CDR-L3 comprising the amino acid sequence set forth SEQ ID NO: 704.

The anti-CD30L antibodies can have various CDR sequences as listed in Tables 10-16. Accordingly, in one embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Table 10; (b) a CDR-H2 comprising any CDR-H2 sequence listed in Table 10; (c) a CDR-H3 comprising any CDR-H3 sequence listed in Table 10; (d) a CDR-L1 comprising any CDR-L1 sequence listed in Table 10; (e) a CDR-L2 comprising any CDR-L2 sequence listed in Table 10; and/or (f) a CDR-L3 comprising any CDR-L3 sequence listed in Table 10.

In another embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Table 11; (b) a CDR-H2 comprising any CDR-H2 sequence listed in Table 11; (c) a CDR-H3 comprising any CDR-H3 sequence listed in Table 11; (d) a CDR-L1 comprising any CDR-L1 sequence listed in Table 11; (e) a CDR-L2 comprising any CDR-L2 sequence listed in Table 11; and/or (f) a CDR-L3 comprising any CDR-L3 sequence listed in Table 11.

In a further embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Table 12; (b) a CDR-H2 comprising any CDR-H2 sequence listed in Table 12; (c) a CDR-H3 comprising any CDR-H3 sequence listed in Table 12; (d) a CDR-L1 comprising any CDR-L1 sequence listed in Table 12; (e) a CDR-L2 comprising any CDR-L2 sequence listed in Table 12; and/or (f) a CDR-L3 comprising any CDR-L3 sequence listed in Table 12.

In yet another embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Table 13; (b) a CDR-H2 comprising any CDR-H2 sequence listed in Table 13; (c) a CDR-H3 comprising any CDR-H3 sequence listed in Table 13; (d) a CDR-L1 comprising any CDR-L1 sequence listed in Table 13; (e) a CDR-L2 comprising any CDR-L2 sequence listed in Table 13; and/or (f) a CDR-L3 comprising any CDR-L3 sequence listed in Table 13.

In one embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Table 14; (b) a CDR-H2 comprising any CDR-H2 sequence listed in Table 14; (c) a CDR-H3 comprising any CDR-H3 sequence listed in Table 14; (d) a CDR-L1 comprising any CDR-L1 sequence listed in Table 14; (e) a CDR-L2 comprising any CDR-L2 sequence listed in Table 14; and/or (f) a CDR-L3 comprising any CDR-L3 sequence listed in Table 14.

In another embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Table 15; (b) a CDR-H2 comprising any CDR-H2 sequence listed in Table 15; (c) a CDR-H3 comprising any CDR-H3 sequence listed in Table 15; (d) a CDR-L1 comprising any CDR-L1 sequence listed in Table 15; (e) a CDR-L2 comprising any CDR-L2 sequence listed in Table 15; and/or (f) a CDR-L3 comprising any CDR-L3 sequence listed in Table 15.

In a further embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Table 16; (b) a CDR-H2 comprising any CDR-H2 sequence listed in Table 16; (c) a CDR-H3 comprising any CDR-H3 sequence listed in Table 16; (d) a CDR-L1 comprising any CDR-L1 sequence listed in Table 16; (e) a CDR-L2 comprising any CDR-L2 sequence listed in Table 16; and/or (f) a CDR-L3 comprising any CDR-L3 sequence listed in Table 16.

In yet another embodiment of the anti-CD30L antibody or antigen binding fragment provided herein, including in Section 2 and this Section (Section 4.1), the antibody or antigen binding fragment thereof comprises: (a) a CDR-H1 comprising any CDR-H1 sequence listed in Tables 10-16; (b) a CDR-H2 comprising any CDR-H2 sequence listed in Tables 10-16; (c) a CDR-H3 comprising any CDR-H3 sequence listed in Tables 10-16; (d) a CDR-L1 comprising any CDR-L1 sequence listed in Tables 10-16; (e) a CDR-L2 comprising any CDR-L2 sequence listed in Tables 10-16; and/or (f) a CDR-L3 comprising any CDR-L3 sequence listed in Tables 10-16.

In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Tables 10-16 and 25. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 10. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 11. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 12. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 13. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 14. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 15. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 16. In some embodiments of the anti-CD30L antibody or antigen binding fragment provided herein, including in Section 2 and this Section (Section 4.1), the antibody or antigen binding fragment thereof comprises the CDR-H1, CDR-H2, CDR-H3, CDR-L1, CDR-L2, and CDR-L3 of the corresponding CDR-H1, CDR-H2, CDR-H3, CDR-L1, CDR-L2, and CDR-L3 of any anti-CD30L of the same clone number listed in Table 25.

In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number in Tables 10-16 and 25. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 10. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 11. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 12. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 13. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 14. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 15. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 16. In some embodiments of the anti-CD30L antibody or antigen binding fragment provided herein, including in Section 2 and this Section (Section 4.1), the antibody or antigen binding fragment thereof comprises the VH and VL of the corresponding VH and VL of any anti-CD30L of the same clone number listed in Table 25.

The disclosure also provides that the anti-CD30L antibodies provided herein can comprise various combinations of immunoglobulin heavy chain variable region (VH) and immunoglobulin light chain variable region (VL). In one embodiment of the anti-CD30L antibody or antigen binding fragment provided herein, including in Section 2 and this Section (Section 4.1), the antibody or antigen binding fragment thereof comprises: (a) an immunoglobulin variable region heavy chain (VH) comprising an amino acid sequence having at least about 90, 95, 97, 98, 99, or 100% sequence identity to any one of SEQ ID NOs: 1, 2, 5, 6, 9, 10, 13, 14, 17, 19, 21, 23, 25, 27, 29, and 31; and/or (b) an immunoglobulin variable region light chain (VL) comprising an amino acid sequence having at least about 90, 95, 97, 98, 99, or 100% sequence identity to any one of SEQ ID NOs: 3, 4, 7, 8, 11, 12, 15, 16, 18, 20, 22, 24, 26, 28, and 30. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 1; and/or (b) a VL comprising an amino acid sequence having at least about 90, 95, 97, 98, 99, or 100% sequence identity to SEQ ID NO: 3. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 2; and/or (b) a VL comprising an amino acid sequence having at least about 90, 95, 97, 98, 99, or 100% sequence identity to SEQ ID NO: 4. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 5; and/or (b) a VL comprising an amino acid sequence having at least about 90, 95, 97, 98, 99, or 100% sequence identity to SEQ ID NO: 7. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 6; and/or (b) a VL comprising an amino acid sequence having at least about 90, 95, 97, 98, 99, or 100% sequence identity to SEQ ID NO: 8. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 9; and/or (b) a VL comprising an amino acid sequence having at least about 90, 95, 97, 98, 99, or 100% sequence identity to SEQ ID NO: 11. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 10; and/or (b) a VL comprising an amino acid sequence having at least about 90, 95, 97, 98, 99, or 100% sequence identity to SEQ ID NO: 12. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 13; and/or (b) a VL comprising an amino acid sequence having at least about 90, 95, 97, 98, 99, or 100% sequence identity to SEQ ID NO: 15. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 14; and/or (b) a VL comprising an amino acid sequence having at least about 90, 95, 97, 98, 99, or 100% sequence identity to SEQ ID NO: 16. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 23; and/or (b) a VL comprising an amino acid sequence having at least about 90, 95, 97, 98, 99, or 100% sequence identity to SEQ ID NO: 24. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 25; and/or (b) a VL comprising an amino acid sequence having at least about 90, 95, 97, 98, 99, or 100% sequence identity to SEQ ID NO: 26. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 27; and/or (b) a VL comprising an amino acid sequence having at least about 90, 95, 97, 98, 99, or 100% sequence identity to SEQ ID NO: 28. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 29; and/or (b) a VL comprising an amino acid sequence having at least about 90, 95, 97, 98, 99, or 100% sequence identity to SEQ ID NO: 30. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 90, 95, 97, 98, 99, or 100% sequence identity to SEQ ID NO: 31; and/or (b) a VL comprising an amino acid sequence having at least about 90, 95, 97, 98, 99, or 100% sequence identity to SEQ ID NO: 32.

Additionally, in one embodiment of the anti-CD30L antibody or antigen binding fragment provided herein, including in Section 2 and this Section (Section 4.1), the antibody or antigen binding fragment thereof comprises: (a) an immunoglobulin variable region heavy chain (VH) comprising an amino acid sequence having at least about 80, 81, 82, 83, 84, 85, 86, 87, 88, 89, 90, 91, 92, 93, 94, 95, 96, 97, 98, 99% sequence identity to any one of SEQ ID NOs: 1, 2, 5, 6, 9, 10, 13, 14, 17, 19, 21, 23, 25, 27, 29, and 31; and/or (b) an immunoglobulin variable region light chain (VL) comprising an amino acid sequence having at least about 80, 81, 82, 83, 84, 85, 86, 87, 88, 89, 90, 91, 92, 93, 94, 95, 96, 97, 98, 99% sequence identity to any one of SEQ ID NOs: 3, 4, 7, 8, 11, 12, 15, 16, 18, 20, 22, 24, 26, 28, and 30. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 990% sequence identity to SEQ ID NO: 1; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 3. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 2; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 4. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 5; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 7. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 6; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 8. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 9; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 11. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 10; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 12. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 990% sequence identity to SEQ ID NO: 13; and/or (b) a VL comprising an amino acid sequence having at least about 80, 81, 82, 83, 84, 85, 86, 87, 88, 89, 90, 91, 92, 93, 94, 95, 96, 97, 98, 990% sequence identity to SEQ ID NO: 15. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 14; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 16. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 23; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 24. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 25; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 26. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 27; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 28. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 990% sequence identity to SEQ ID NO: 29; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 30. In one embodiment of the anti-CD30L antibody or antigen binding fragment provided herein, including in Section 2 and this Section (Section 4.1), the antibody or antigen binding fragment thereof comprises: (a) a VH comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 31; and/or (b) a VL comprising an amino acid sequence having at least about 80, 81, 82, 83, 84, 85, 86, 87, 88, 89, 90, 91, 92, 93, 94, 95, 96, 97, 98, 99% sequence identity to SEQ ID NO: 32.

Furthermore, in one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in any one of SEQ ID NOs: 1, 2, 5, 6, 9, 10, 13, 14, 17, 19, 21, 23, 25, 27, 29, and 31; and/or (b) a VL comprising an amino acid sequence set forth in any one of SEQ ID NOs: 3, 4, 7, 8, 11, 12, 15, 16, 18, 20, 22, 24, 26, 28, and 30. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 1; and/or (b) a VL comprising an amino acid sequence set forth in SEQ ID NO: 3. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 2; and/or (b) a VL comprising an amino acid sequence set forth in SEQ ID NO: 4. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 5; and/or (b) a VL comprising an amino acid sequence set forth in SEQ ID NO: 7. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 6; and/or (b) a VL comprising an amino acid sequence set forth in SEQ ID NO: 8. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 9; and/or (b) a VL comprising an amino acid sequence set forth in SEQ ID NO: 11. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 10; and/or (b) a VL comprising an amino acid sequence set forth in SEQ ID NO: 12. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 13; and/or (b) a VL comprising an amino acid sequence set forth in SEQ ID NO: 15. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 14; and/or (b) a VL comprising an amino acid sequence set forth in SEQ ID NO: 16. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 23; and/or (b) a VL comprising an amino acid sequence set forth in SEQ ID NO: 24. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 25; and/or (b) a VL comprising an amino acid sequence set forth in SEQ ID NO: 26. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 27; and/or (b) a VL comprising an amino acid sequence set forth in SEQ ID NO: 28. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 29; and/or (b) a VL comprising an amino acid sequence set forth in SEQ ID NO: 30. In one embodiment of the anti-CD30L antibody or antigen binding fragment provided herein, including in Section 2 and this Section (Section 4.1), the antibody or antigen binding fragment thereof comprises: (a) a VH comprising an amino acid sequence set forth in SEQ ID NO: 31; and/or (b) a VL comprising an amino acid sequence set forth in SEQ ID NO: 32.

The CDRs of the anti-CD30L antibody or antigen binding fragment provided herein are also provided by the CDR definitions as described herein (Kabat, Chothia, AbM, Contact IMGT, and Aho) for the provided VH and VL sequences. Accordingly, in one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 1; and/or (a) the CDR-L1, CDR-L2, and CDR-L3 of the corresponding CDR-L1, CDR-L2, and CDR-L3 of the VL sequence set forth in SEQ ID NO: 3, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 2; and/or (a) the CDR-L1, CDR-L2, and CDR-L3 of the corresponding CDR-L1, CDR-L2, and CDR-L3 of the VL sequence set forth in SEQ ID NO: 4, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 5; and/or (a) the CDR-L1, CDR-L2, and CDR-L3 of the corresponding CDR-L1, CDR-L2, and CDR-L3 of the VL sequence set forth in SEQ ID NO: 7, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 6; and/or (a) the CDR-L1, CDR-L2, and CDR-L3 of the corresponding CDR-L1, CDR-L2, and CDR-L3 of the VL sequence set forth in SEQ ID NO: 8, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 9; and/or (a) the CDR-L1, CDR-L2, and CDR-L3 of the corresponding CDR-L1, CDR-L2, and CDR-L3 of the VL sequence set forth in SEQ ID NO: 11, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 10; and/or (a) the CDR-L1, CDR-L2, and CDR-L3 of the corresponding CDR-L1, CDR-L2, and CDR-L3 of the VL sequence set forth in SEQ ID NO: 12, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 13; and/or (a) the CDR-L1, CDR-L2, and CDR-L3 of the corresponding CDR-L1, CDR-L2, and CDR-L3 of the VL sequence set forth in SEQ ID NO: 15, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 14; and/or (a) the CDR-L1, CDR-L2, and CDR-L3 of the corresponding CDR-L1, CDR-L2, and CDR-L3 of the VL sequence set forth in SEQ ID NO: 16, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 23; and/or (a) the CDR-L1, CDR-L2, and CDR-L3 of the corresponding CDR-L1, CDR-L2, and CDR-L3 of the VL sequence set forth in SEQ ID NO: 24, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 25; and/or (a) the CDR-L1, CDR-L2, and CDR-L3 of the corresponding CDR-L1, CDR-L2, and CDR-L3 of the VL sequence set forth in SEQ ID NO: 26, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 27; and/or (a) the CDR-L1, CDR-L2, and CDR-L3 of the corresponding CDR-L1, CDR-L2, and CDR-L3 of the VL sequence set forth in SEQ ID NO: 28, wherein the CDRs are determined by Kabat, Chothia, AbM, Contact, IMGT, or Aho numbering scheme. In one embodiment of the anti-CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 29; and/or (a) the CDR-L1, CDR-L2, and CDR-L3 of the corresponding CDR-L1, CDR-L2, and CDR-L3 of the VL sequence set forth in SEQ ID NO: 30, wherein the CDRs are determined by Kabat, Chothia, AbM, Contact, IMGT, or Aho numbering scheme. In one embodiment of the anti- CD30L antibody or antigen binding fragment provided herein, including in Section 2 and this Section (Section 4.1), the antibody or antigen binding fragment thereof comprises: (a) the CDR-H1, CDR-H2, and CDR-H3 of the corresponding CDR-H1, CDR-H2, and CDR-H3 of the VH sequence set forth in SEQ ID NO: 31; and/or (a) the CDR-L1, CDR-L2, and CDR-L3 of the corresponding CDR-L1, CDR-L2, and CDR-L3 of the VL sequence set forth in SEQ ID NO: 32, wherein the CDRs are determined by Kabat, Chothia, AbM, Contact, IMGT, or Aho numbering scheme.

As is clear from the descriptions above and below, the anti-CD30L antibodies provided herein can further comprise constant regions. In one embodiment of the anti-CD30L antibody or antigen binding fragment provided herein, including in Section 2 and this Section (Section 4.1), the antibody or antigen binding fragment thereof further comprises an immunoglobulin heavy chain constant region. In one embodiment of the anti-CD30L antibody or antigen binding fragment provided herein, including in Section 2 and this Section (Section 4.1), the antibody or antigen binding fragment thereof further comprises an immunoglobulin light chain constant region. In one embodiment of the anti-CD30L antibody or antigen binding fragment provided herein, including in Section 2 and this Section (Section 4.1), the antibody or antigen binding fragment thereof further comprises an immunoglobulin heavy chain constant region and an immunoglobulin light chain constant region. In one embodiment, the heavy chain constant region is an IgG heavy chain constant region. In one embodiment, the light chain constant region is an IgG light chain constant region. In one embodiment, the light chain constant region is a kappa (κ) chain constant region. In one embodiment, the light chain constant region is a lambda (k) chain constant region. In one embodiment, the heavy chain constant region is a IgG1 heavy chain constant region. In one embodiment, the heavy chain constant region is a IgG2 heavy chain constant region. In one embodiment, the heavy chain constant region is a IgG3 heavy chain constant region. In one embodiment, the heavy chain constant region is a IgG4 heavy chain constant region. In one embodiment, the constant region comprises an amino acid sequence having about 80, 85, 90, 95, 97, 98, 99, or 100% sequence identity to the amino acid sequence set forth by any one of SEQ ID NOs: 500-512. In one embodiment, the constant region comprises an amino acid sequence having about 80, 81, 82, 83, 84, 85, 86, 87, 88, 89, 90, 91, 92, 93, 94, 95, 96, 97, 98, 99% sequence identity to the amino acid sequence set forth by any one of SEQ ID NOs: 500-512. In one embodiment, the constant region comprises the amino acid sequence set forth by any one of SEQ ID NOs: 500-512. In one embodiment, the constant region comprises the amino acid sequence set forth by any one of SEQ ID NO: 500. In one embodiment, the constant region comprises the amino acid sequence set forth by any one of SEQ ID NO: 501. In one embodiment, the constant region comprises the amino acid sequence set forth by any one of SEQ ID NO: 502. In one embodiment, the constant region comprises the amino acid sequence set forth by any one of SEQ ID NO: 503. In one embodiment, the constant region comprises the amino acid sequence set forth by any one of SEQ ID NO: 504. In one embodiment, the constant region comprises the amino acid sequence set forth by any one of SEQ ID NO: 505. In one embodiment, the constant region comprises the amino acid sequence set forth by any one of SEQ ID NO: 506. In one embodiment, the constant region comprises the amino acid sequence set forth by any one of SEQ ID NO: 507. In one embodiment, the constant region comprises the amino acid sequence set forth by any one of SEQ ID NO: 508. In one embodiment, the constant region comprises the amino acid sequence set forth by any one of SEQ ID NO: 509. In one embodiment, the constant region comprises the amino acid sequence set forth by any one of SEQ ID NO: 510. In one embodiment, the constant region comprises the amino acid sequence set forth by any one of SEQ ID NO: 511. In one embodiment, the constant region comprises the amino acid sequence set forth by any one of SEQ ID NO: 512.

The antibody or antigen binding fragment thereof provided herein can have various functional properties as described herein, e.g., in Section 5 (EXAMPLES). Accordingly, in one embodiment of the anti-CD30L antibody or antigen binding fragment provided herein, including in Section 2 and this Section (Section 4.1), the antibody or antigen binding fragment thereof blocks a binding interaction between CD30L and CD30. In one embodiment of the anti-CD30L antibody or antigen binding fragment provided herein, including in Section 2 and this Section (Section 4.1), the antibody or antigen binding fragment thereof inhibits a binding interaction between CD30L and CD30. In one embodiment, the interaction between CD30L and CD30 for assessing the blocking or inhibition is determined in an ELISA assay, a cell binding assay with CD30L expressing cells, a KinExA assay, or a surface plasmon resonance (SPR) assay. In one embodiment, the interaction between CD30L and CD30 for assessing the blocking or inhibition is determined in an ELISA assay. In one embodiment, the interaction between CD30L and CD30 for assessing the blocking or inhibition is determined in a cell binding assay with CD30L expressing cells. In one embodiment, the interaction between CD30L and CD30 for assessing the blocking or inhibition is determined in a KinExA assay. In one embodiment, the interaction between CD30L and CD30 for assessing the blocking or inhibition is determined in an SPR assay.

As shown in Example 8, the anti-CD30L or antigen binding fragment provided herein have high binding specificity for CD30L, binding specifically to CD30L among 6,232 targets tested. Accordingly, in one embodiment of the anti-CD30L antibody or antigen binding fragment provided herein, including in Section 2 and this Section (Section 4.1), the antibody or antigen binding fragment thereof specifically binds to CD30L. In some embodiments, the ELISA, SPR, KinExA, and/or cell binding assay with CD30L expressing cells are as described and demonstrated in Section 5 (EXAMPLES) (e.g. FIGS. 5A, 5F, and 5G).

As further demonstrated herein, e.g. in Section 5 (EXAMPLES), the anti-CD30L antibody provided herein can block or inhibit CD30L-mediated CD30 signaling in cell-based assays. Such cell assays include cytokine release (e.g. IL-8) release dual cell assays. Briefly and using IL-8 release as an example of cytokine release, when co-cultured with CD30L expressing cells (e.g. B16 cells expressing humanCD30L or HEK293 expressing cynoCD30L), K299 CD30+ cells release IL-8 upon ligation with and stimulation by the co-cultured CD30L expressing cells (FIG. 5J). Blocking of the CD30L-CD30 interaction can proportionally reduce the release of IL-8 and thus the amount of IL-8 released can be used as a readout for the effectiveness of antibody mediated blocking of CD30L-CD30 interactions between the co-cultured cells.

Accordingly, in one embodiment of the anti-CD30L antibody or antigen binding fragment provided herein, including in Section 2 and this Section (Section 4.1), the antibody or antigen binding fragment thereof inhibits interleukin-8 secretion in a cell-based assay. In one embodiment of the anti-CD30L antibody or antigen binding fragment provided herein, including in Section 2 and this Section (Section 4.1), the antibody or antigen binding fragment thereof inhibits interleukin-6 secretion in a cell-based assay. In one embodiment of the anti-CD30L antibody or antigen binding fragment provided herein, including in Section 2 and this Section (Section 4.1), the antibody or antigen binding fragment thereof inhibits both interleukin-8 and interleukin-6 secretion in a cell-based assay. In one embodiment of the anti-CD30L antibody or antigen binding fragment provided herein, including in Section 2 and this Section (Section 4.1), the antibody or antigen binding fragment thereof blocks interleukin-8 secretion in a cell-based assay. In one embodiment of the anti-CD30L antibody or antigen binding fragment provided herein, including in Section 2 and this Section (Section 4.1), the antibody or antigen binding fragment thereof blocks interleukin-6 secretion in a cell-based assay. In one embodiment of the anti-CD30L antibody or antigen binding fragment provided herein, including in Section 2 and this Section (Section 4.1), the antibody or antigen binding fragment thereof blocks both interleukin-8 and interleukin-6 secretion in a cell-based assay. In one embodiment of the anti-CD30L antibody or antigen binding fragment provided herein, including in Section 2 and this Section (Section 4.1) such as those of this paragraph, the cell-based assay is a dual cell assay with a cell expressing CD30 and a cell expressing CD30L.

The disclosure demonstrated in Section 5 (EXAMPLES) that the anti-CD30L antibody or antigen binding fragment bind to CD30L with strong binding affinity and blocked CD30L with high effectiveness. Accordingly, in one embodiment of the anti-CD30L antibody or antigen binding fragment provided herein, including in Section 2 and this Section (Section 4.1) such as those of this paragraph, the antibody or antigen binding fragment thereof binds to CD30L with a dissociation equilibrium constant ($K_D$) of no more than 60, no more than 65, no more than 70, no more than 75, no more than 80, no more than 85, no more than 90, no more than 95, no more than 100, no more than 105, no more than 110, no more than 115, no more than 120, no more than 125, no more than 130, no more than 135, no more than 140, no more than 145, no more than 150, no more than 155, no more than 160, no more than 165, no more than 170, no more than 175, no more than 180, no more than 185, no more than 190, no more than 195, no more than 200, no more than 250, no more than 300, no more than 350, no more than 400, no more than 450, no more than 500, no more than 550, no more than 600, no more than 650, no more than 700, no more than 750, no more than 800, no more than 850, no more than 900, no more than 950, or no more than 1000 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a dissociation equilibrium constant ($K_D$) of about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 250, about 300, about 350, about 400, about 450, about 500, about 550, about 600, about 650, about 700, about 750, about 800, about 850, about 900, about 950, or about 1000 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of no more than 90.5 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of no more than 125 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of no more than 65.4 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of no more than 122 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of no more than 51.3 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of no more than 244 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 90.5 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 125 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 64.5 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 122 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 51.3 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 244 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 65 to about 125 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 50 to about 140 pM, about 55 to about 135 pM, about 60 to about 130 pM, about 65 to about 125 pM, about 70 to about 120 pM, about 75 to about 115 pM, about 80 to about 110 pM, about 85 to about 105 pM, about 90 to about 100 pM, or about 95 to about 100 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 51 to about 244 pM. In one embodiment of the anti-CD30L antibody or antigen binding fragment provided herein, including in Section 2 and this Section (Section 4.1) such as those of this paragraph, the antibody or antigen binding fragment thereof binds to CD30L with a $K_D$ of about 50 to about 250 pM, about 51 to about 244 pM, about 55 to about 240 pM, about 60 to about 235 pM, about 65 to about 230 pM, about 70 to about 225 pM, about 75 to about 220 pM, about 80 to about 215 pM, about 80 to about 210 pM, about 85 to about 205 pM, about 90 to about 200 pM, about 95 to about 195 pM, about 100 to about 190 pM, about 105 to about 185 pM, about 110 to about 180 pM, about 115 to about 175 pM, about 120 to about 170 pM, about 125 to about 165 pM, about 130 to about 160 pM, about 135 to about 155 pM, or about 140 to about 150 pM.

Additionally, in one embodiment of the anti-CD30L antibody or antigen binding fragment provided herein, including in Section 2 and this Section (Section 4.1) such as those of this paragraph, the antibody or antigen binding fragment thereof binds to CD30L with an association rate constant ($k_{on}$) of at least $0.1 \times 10^6$, at least $0.2 \times 10^6$, at least $0.3 \times 10^6$, at least $0.4 \times 10^6$, at least $0.5 \times 10^6$, at least $0.6 \times 10^6$, at least $0.7 \times 10^6$, at least $0.8 \times 10^6$, at least $0.9 \times 10^6$, at least $1.0 \times 10^6$, at least $1.1 \times 10^6$, at least $1.2 \times 10^6$, at least $1.3 \times 10^6$, at least $1.4 \times 10^6$, at least $1.5 \times 10^6$, at least $1.55 \times 10^6$, at least $1.56 \times 10^6$, at least $1.57 \times 10^6$, at least $1.58 \times 10^6$, at least $1.59 \times 10^6$, at least $1.60 \times 10^6$, at least $1.61 \times 10^6$, at least $1.62 \times 10^6$, at least $1.63 \times 10^6$, at least $1.64 \times 10^6$, at least $1.65 \times 10^6$, at least $1.66 \times 10^6$, at least $1.67 \times 10^6$, at least $1.68 \times 10^6$, at least $1.69 \times 10^6$, at least $1.7 \times 10^6$, at least $1.8 \times 10^6$, at least $1.9 \times 10^6$, at least $2.0 \times 10^6$, at least $2.1 \times 10^6$, at least $2.2 \times 10^6$, at least $2.3 \times 10^6$, at least $2.4 \times 10^6$, at least $2.5 \times 10^6$, at least $2.6 \times 10^6$, at least $2.7 \times 10^6$, at least $2.8 \times 10^6$, at least $2.9 \times 10^6$, at least $3.0 \times 10^6$, or at least $3.1 \times 10^6 M^{-1}S^{-1}$. In one embodiment of the anti-CD30L antibody or antigen binding fragment provided herein, including in Section 2 and this Section (Section 4.1) such as those of this paragraph, the antibody or antigen binding fragment thereof binds to CD30L with an association rate constant ($k_{on}$) of about $0.1 \times 10^6$, about $0.2 \times 10^6$, about $0.3 \times 10^6$, about $0.4 \times 10^6$, about $0.5 \times 10^6$, about $0.6 \times 10^6$, about $0.7 \times 10^6$, about $0.8 \times 10^6$, about $0.9 \times 10^6$, about $1.0 \times 10^6$, about $1.1 \times 10^6$, about $1.2 \times 10^6$, about $1.3 \times 10^6$, about $1.4 \times 10^6$, about $1.5 \times 10^6$, about $1.55 \times 10^6$, about $1.56 \times 10^6$, about $1.57 \times 10^6$, about $1.58 \times 10^6$, about $1.59 \times 10^6$, about $1.60 \times 10^6$, about $1.61 \times 10^6 M^{-1}S^{-1}$, about $1.62 \times 10^6$, about $1.63 \times 10^6$, about $1.64 \times 10^6$, about $1.65 \times 10^6$, about $1.66 \times 10^6$, about $1.67 \times 10^6$, about $1.68 \times 10^6$, about $1.69 \times 10^6$, about $1.7 \times 10^6$, about $1.8 \times 10^6$, about $1.9 \times 10^6$, about $2.0 \times 10^6$, about $2.1 \times 10^6$, about $2.2 \times 10^6$, about $2.3 \times 10^6$, about $2.4 \times 10^6$, about $2.5 \times 10^6$, about $2.6 \times 10^6$, about $2.7 \times 10^6$, about $2.8 \times 10^6$, about $2.9 \times 10^6$, about $3.0 \times 10^6$, or about $3.1 \times 10^6$. In one embodiment of the anti-CD30L antibody or antigen binding fragment provided herein, including in Section 2 and this Section (Section 4.1) such as those of this paragraph, the antibody or antigen binding fragment thereof binds to CD30L with an association rate constant ($k_{on}$) of about $1.54 \times 10^6$ to about $1.55 \times 10^6$, about $1.53 \times 10^6$ to about $1.56 \times 10^6$, about $1.52 \times 10^6$ to about $1.57 \times 10^6$, about $1.53 \times 10^6$ to about $1.58 \times 10^6$, about $1.52 \times 10^6$ to about $1.59 \times 10^6$, about $1.51 \times 10^6$ to about $1.60 \times 10^6$, or about $1.5 \times 10^6$ to about $1.61 \times 10^6 M^{-1}S^{-1}$. In one embodiment of the anti-CD30L antibody or antigen binding fragment provided herein, including in Section 2 and this Section (Section 4.1) such as those of this paragraph, the antibody or antigen binding fragment thereof binds to CD30L with an association rate constant ($k_{on}$) of about $2.5 \times 10^6$ to about $3.8 \times 10^6$, about $2.4 \times 10^6$ to about $3.9 \times 10^6$, about $2.45 \times 10^6$ to about $3.89 \times 10^6$, about $2.6 \times 10^6$ to about $3.7 \times 10^6$, about $2.7 \times 10^6$ to about $3.6 \times 10^6$, about $2.8 \times 10^6$ to about $3.5 \times 10^6$, about $2.9 \times 10^6$ to about $3.4 \times 10^6$, about $3.0 \times 10^6$ to about $3.3 \times 10^6$, or about $3.1 \times 10^6$ to about $3.2 \times 10^6$, $M^{-1}S^{-1}$.

Furthermore, in one embodiment of the anti-CD30L antibody or antigen binding fragment provided herein, including in Section 2 and this Section (Section 4.1) such as those of this paragraph, the antibody or antigen binding fragment thereof binds to CD30L with a dissociation rate constant ($k_{off}$) of no more than $1.4 \times 10^{-4}$, no more than $1.41 \times 10^{-4}$, no more than $1.5 \times 10^{-4}$, no more than $1.6 \times 10^{-4}$, no more than $1.7 \times 10^{-4}$, no more than $1.8 \times 10^{-4}$, no more than $1.9 \times 10^{-4}$, no more than $2.0 \times 10^{-4}$, no more than $2.1 \times 10^{-4}$, no more than $2.2 \times 10^{-4}$, no more than $2.3 \times 10^{-4}$, no more than $2.4 \times 10^{-4}$, no more than $2.5 \times 10^{-4}$, no more than $2.6 \times 10^{-4}$, no more than $2.7 \times 10^{-4}$, no more than $2.8 \times 10^{-4}$, no more than $2.9 \times 10^{-4}$, no more than $3.0 \times 10^{-4}$, no more than $3.1 \times 10^{-4}$, no more than $3.2 \times 10^{-4}$, no more than $3.3 \times 10^{-4}$, no more than $3.4 \times 10^{-4}$, no more than $3.5 \times 10^{-4}$, no more than $3.6 \times 10^{-4}$, no more than $3.7 \times 10^{-4}$, no more than $3.78 \times 10^{-4}$, or no more than $3.8 \times 10^{-4} S^{-1}$. In one embodiment of the anti-CD30L antibody or antigen binding fragment provided herein, including in Section 2 and this Section (Section 4.1) such as those of this paragraph, the antibody or antigen binding fragment thereof binds to CD30L with a dissociation rate constant ($k_{off}$) of about $1.4 \times 10^{-4}$, about $1.41 \times 10^{-4}$, about $1.5 \times 10^{-4}$, about $1.6 \times 10^{-4}$, about $1.7 \times 10^{-4}$, about $1.8 \times 10^{-4}$, about $1.9 \times 10^{-4}$, about $2.0 \times 10^{-4}$, about $2.1 \times 10^{-4}$, about $2.2 \times 10^{-4}$, about $2.3 \times 10^{-4}$, about $2.4 \times 10^{-4}$, about $2.5 \times 10^{-4}$, about $2.6 \times 10^{-4}$, about $2.7 \times 10^{-4}$, about $2.8 \times 10^{-4}$, about $2.9 \times 10^{-4}$, about $3.0 \times 10^{-4}$, about $3.1 \times 10^{-4}$, about $3.2 \times 10^{-4}$, about $3.3 \times 10^{-4}$, about $3.4 \times 10^{-4}$, about $3.5 \times 10^{-4} S^{-1}$, about $3.6 \times 10^{-4}$, about $3.7 \times 10^{-4}$, about $3.78 \times 10^{-4}$, or about $3.8 \times 10^{-4}$.

The disclosure demonstrates that the anti-CD30L antibody provided herein binds to human CD30L, cyno CD30L, or both human and cyno CD30L. In some embodiments of the anti-CD30L antibody or antigen binding fragment provided herein, including in Section 2 and this Section (Section 4.1), the antibody or antigen binding fragment thereof binds to human CD30L. In some embodiments of the anti-CD30L antibody or antigen binding fragment provided herein, including in Section 2 and this Section (Section 4.1), the antibody or antigen binding fragment thereof binds to cyno CD30L. In some embodiments of the anti-CD30L antibody or antigen binding fragment provided herein, including in Section 2 and this Section (Section 4.1), the antibody or antigen binding fragment thereof binds to both human and cyno CD30L. In some embodiments of the anti-CD30L antibody or antigen binding fragment provided herein, including in Section 2 and this Section (Section 4.1), the antibody or antigen binding fragment thereof specifically binds to human CD30L. In some embodiments of the anti-CD30L antibody or antigen binding fragment provided herein, including in Section 2 and this Section (Section 4.1), the antibody or antigen binding fragment thereof specifically binds to cyno CD30L. In some embodiments of the anti-CD30L antibody or antigen binding fragment provided herein, including in Section 2 and this Section (Section 4.1), the antibody or antigen binding fragment thereof specifically binds to both human and cyno CD30L.

In some embodiments, the antibody or antigen binding fragment thereof that binds CD30L, wherein the antibody or antigen binding fragment thereof: (a) a CDR-H1 comprising the amino acid sequence set forth in any one of SEQ ID NOs: 100-139; (b) a CDR-H2 comprising the amino acid sequence set forth in any one of SEQ ID NOs: 140-179; (c) an immunoglobulin heavy chain CDR3 (CDR-H3) comprising the amino acid sequence set forth in any one of SEQ ID NOs: 180-219; (d) a CDR-L1 comprising the amino acid sequence set forth in any one of SEQ ID NOs: 300-339; (e) a CDR-L2 comprising the amino acid sequence set forth in any one of SEQ ID NOs: 340-379; and/or (f) a CDR-L3 comprising the amino acid sequence set forth in any one of SEQ ID NOs: 380-419.

In some embodiments, the antibody or antigen binding fragment thereof comprises: (a) a CDR-H1 comprising the amino acid sequence set forth in any one of SEQ ID NOs: 100-109; (b) a CDR-H2 comprising the amino acid sequence set forth in any one of SEQ ID NOs: 140-149; (c) an immunoglobulin heavy chain CDR3 (CDR-H3) comprising the amino acid sequence set forth in any one of SEQ ID NOs: 180-189; (d) a CDR-L1 comprising the amino acid sequence set forth in any one of SEQ ID NOs: 300-309; (e) a CDR-L2 comprising the amino acid sequence set forth in any one of SEQ ID NOs: 340-349; and/or (f) a CDR-L3 comprising the amino acid sequence set forth in any one of SEQ ID NOs: 380-389.

In certain embodiments, the antibody or antigen binding fragment thereof comprises: (a) a CDR-H1 comprising the amino acid sequence set forth in any one of SEQ ID NOs: 100-104; (b) a CDR-H2 comprising the amino acid sequence set forth in any one of SEQ ID NOs: 140-144; (c) an immunoglobulin heavy chain CDR3 (CDR-H3) comprising the amino acid sequence set forth in any one of SEQ ID NOs: 180-184; (d) a CDR-L1 comprising the amino acid sequence set forth in any one of SEQ ID NOs: 300-304; (e) a CDR-L2 comprising the amino acid sequence set forth in any one of SEQ ID NOs: 340-344; and/or (f) a CDR-L3 comprising the amino acid sequence set forth in any one of SEQ ID NOs: 380-384.

In certain embodiments, the antibody or antigen binding fragment thereof comprises: (a) a CDR-H1 comprising the amino acid sequence set forth in any one of SEQ ID NOs: 105-109; (b) a CDR-H2 comprising the amino acid sequence set forth in any one of SEQ ID NOs: 145-149; (c) an immunoglobulin heavy chain CDR3 (CDR-H3) comprising the amino acid sequence set forth in any one of SEQ ID NOs: 185-189; (d) a CDR-L1 comprising the amino acid sequence set forth in any one of SEQ ID NOs: 305-309; (e) a CDR-L2 comprising the amino acid sequence set forth in any one of SEQ ID NOs: 345-349; and/or (f) a CDR-L3 comprising the amino acid sequence set forth in any one of SEQ ID NOs: 385-389.

In some embodiments, the antibody or antigen binding fragment thereof comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 1 and 2; and/or (b) the immunoglobulin variable region light chain comprises an amino acid sequence having at least about 90, 95, 97, 98, 99, or 100% sequence identity to any one of SEQ ID NOs: 3 and 4.

In certain embodiments, the immunoglobulin variable region heavy chain comprises an amino acid sequence having about 90% sequence identity to any one of SEQ ID NOs: 1 and 2 to about 100% sequence identity to any one of SEQ ID NOs: 1 and 2. In certain embodiments, the immunoglobulin variable region heavy chain comprises an amino acid sequence having at least about 90% sequence identity to any one of SEQ ID NOs: 1 and 2. In certain embodiments, the immunoglobulin variable region heavy chain comprises an amino acid sequence having at most about 100% sequence identity to any one of SEQ ID NOs: 1 and 2. In certain embodiments, the immunoglobulin variable region heavy chain comprises an amino acid sequence having about 90% sequence identity to any one of SEQ ID NOs: 1 and 2 to about 95% sequence identity to any one of SEQ ID NOs: 1 and 2, about 90% sequence identity to any one of SEQ ID NOs: 1 and 2 to about 97% sequence identity to any one of SEQ ID NOs: 1 and 2, about 90% sequence identity to any one of SEQ ID NOs: 1 and 2 to about 98% sequence identity to any one of SEQ ID NOs: 1 and 2, about 90% sequence identity to any one of SEQ ID NOs: 1 and 2 to about 99% sequence identity to any one of SEQ ID NOs: 1 and 2, about 90% sequence identity to any one of SEQ ID NOs: 1 and 2 to about 100% sequence identity to any one of SEQ ID NOs: 1 and 2, about 950% sequence identity to any one of SEQ ID NOs: 1 and 2 to about 97% sequence identity to any one of SEQ ID NOs: 1 and 2, about 950% sequence identity to any one of SEQ ID NOs: 1 and 2 to about 98% sequence identity to any one of SEQ ID NOs: 1 and 2, about 95% sequence identity to any one of SEQ ID NOs: 1 and 2 to about 99% sequence identity to any one of SEQ ID NOs: 1 and 2, about 950% sequence identity to any one of SEQ ID NOs: 1 and 2 to about 100% sequence identity to any one of SEQ ID NOs: 1 and 2, about 97% sequence identity to any one of SEQ ID NOs: 1 and 2 to about 98% sequence identity to any one of SEQ ID NOs: 1 and 2, about 97% sequence identity to any one of SEQ ID NOs: 1 and 2 to about 99% sequence identity to any one of SEQ ID NOs: 1 and 2, about 97% sequence identity to any one of SEQ ID NOs: 1 and 2 to about 100% sequence identity to any one of SEQ ID NOs: 1 and 2, about 98% sequence identity to any one of SEQ ID NOs: 1 and 2 to about 99% sequence identity to any one of SEQ ID NOs: 1 and 2, about 98% sequence identity to any one of SEQ ID NOs: 1 and 2 to about 100% sequence identity to any one of SEQ ID NOs: 1 and 2, or about 99% sequence identity to any one of SEQ ID NOs: 1 and 2 to about 100% sequence identity to any one of SEQ ID NOs: 1 and 2. In certain embodiments, the immunoglobulin variable region heavy chain comprises an amino acid sequence having about 90% sequence identity to any one of SEQ ID NOs: 1 and 2, about 95% sequence identity to any one of SEQ ID NOs: 1 and 2, about 97% sequence identity to any one of SEQ ID NOs: 1 and 2, about 98% sequence identity to any one of SEQ ID NOs: 1 and 2, about 99% sequence identity to any one of SEQ ID NOs: 1 and 2, or about 100% sequence identity to any one of SEQ ID NOs: 1 and 2.

In certain embodiments, the immunoglobulin variable region light chain comprises an amino acid sequence having about 90% sequence identity to any one of SEQ ID NOs: 3 and 4 to about 100% sequence identity to any one of SEQ ID NOs: 3 and 4. In certain embodiments, the immunoglobulin variable region light chain comprises an amino acid sequence having at least about 90% sequence identity to any one of SEQ ID NOs: 3 and 4. In certain embodiments, the immunoglobulin variable region light chain comprises an amino acid sequence having at most about 100% sequence identity to any one of SEQ ID NOs: 3 and 4. In certain embodiments, the immunoglobulin variable region light chain comprises an amino acid sequence having about 90% sequence identity to any one of SEQ ID NOs: 3 and 4 to about 95% sequence identity to any one of SEQ ID NOs: 3 and 4, about 90% sequence identity to any one of SEQ ID NOs: 3 and 4 to about 97% sequence identity to any one of SEQ ID NOs: 3 and 4, about 90% sequence identity to any one of SEQ ID NOs: 3 and 4 to about 98% sequence identity to any one of SEQ ID NOs: 3 and 4, about 90% sequence identity to any one of SEQ ID NOs: 3 and 4 to about 99% sequence identity to any one of SEQ ID NOs: 3 and 4, about 90% sequence identity to any one of SEQ ID NOs: 3 and 4 to about 100% sequence identity to any one of SEQ ID NOs: 3 and 4, about 950% sequence identity to any one of SEQ ID NOs: 3 and 4 to about 97% sequence identity to any one of SEQ ID NOs: 3 and 4, about 95% sequence identity to any one of SEQ ID NOs: 3 and 4 to about 98% sequence identity to any one of SEQ ID NOs: 3 and 4, about 95% sequence identity to any one of SEQ ID NOs: 3 and 4 to about 99% sequence identity to any one of SEQ ID NOs: 3 and 4, about 95% sequence identity to any one of SEQ ID NOs: 3 and 4 to about 100% sequence identity to any one of SEQ ID NOs: 3 and 4, about 97% sequence identity to any one of SEQ ID NOs: 3 and 4 to about 98% sequence identity to any one of SEQ ID NOs: 3 and 4, about 97% sequence identity to any one of SEQ ID NOs: 3 and 4 to about 99% sequence identity to any one of SEQ ID NOs: 3 and 4, about 97% sequence identity to any one of SEQ ID NOs: 3 and 4 to about 100% sequence identity to any one of SEQ ID NOs: 3 and 4, about 98% sequence identity to any one of SEQ ID NOs: 3 and 4 to about 99% sequence identity to any one of SEQ ID NOs: 3 and 4, about 98% sequence identity to any one of SEQ ID NOs: 3 and 4 to about 100% sequence identity to any one of SEQ ID NOs: 3 and 4, or about 99% sequence identity to any one of SEQ ID NOs: 3 and 4 to about 100% sequence identity to any one of SEQ ID NOs: 3 and 4. In certain embodiments, the immunoglobulin variable region light chain comprises an amino acid sequence having about 90% sequence identity to any one of SEQ ID NOs: 3 and 4, about 95% sequence identity to any one of SEQ ID NOs: 3 and 4, about 97% sequence identity to any one of SEQ ID NOs: 3 and 4, about 98% sequence identity to any one of SEQ ID NOs: 3 and 4, about 99% sequence identity to any one of SEQ ID NOs: 3 and 4, or about 100% sequence identity to any one of SEQ ID NOs: 3 and 4.

In some embodiments, the antibody or antigen binding fragment thereof comprises: (a) a CDR-H1 comprising the amino acid sequence set forth in any one of SEQ ID NOs: 110-119; (b) a CDR-H2 comprising the amino acid sequence set forth in any one of SEQ ID NOs: 150-159; (c) an immunoglobulin heavy chain CDR3 (CDR-H3) comprising the amino acid sequence set forth in any one of SEQ ID NOs: 190-199; (d) a CDR-L1 comprising the amino acid sequence set forth in any one of SEQ ID NOs: 310-319; (e) a CDR-L2 comprising the amino acid sequence set forth in any one of SEQ ID NOs: 350-359; and/or (f) a CDR-L3 comprising the amino acid sequence set forth in any one of SEQ ID NOs: 390-399.

In certain embodiments, the antibody or antigen binding fragment thereof comprises: (a) a CDR-H1 comprising the amino acid sequence set forth in any one of SEQ ID NOs: 110-114; (b) a CDR-H2 comprising the amino acid sequence set forth in any one of SEQ ID NOs: 150-154; (c) an immunoglobulin heavy chain CDR3 (CDR-H3) comprising the amino acid sequence set forth in any one of SEQ ID NOs: 190-194; (d) a CDR-L1 comprising the amino acid sequence set forth in any one of SEQ ID NOs: 310-314; (e) a CDR-L2 comprising the amino acid sequence set forth in any one of SEQ ID NOs: 350-354; and/or (f) a CDR-L3 comprising the amino acid sequence set forth in any one of SEQ ID NOs: 390-394.

In certain embodiments, the antibody or antigen binding fragment thereof comprises: (a) a CDR-H1 comprising the amino acid sequence set forth in any one of SEQ ID NOs: 115-119; (b) a CDR-H2 comprising the amino acid sequence set forth in any one of SEQ ID NOs: 155-159; (c) an immunoglobulin heavy chain CDR3 (CDR-H3) comprising the amino acid sequence set forth in any one of SEQ ID NOs: 195-199; (d) a CDR-L1 comprising the amino acid sequence set forth in any one of SEQ ID NOs: 315-319; (e) a CDR-L2 comprising the amino acid sequence set forth in any one of SEQ ID NOs: 355-359; and/or (f) a CDR-L3 comprising the amino acid sequence set forth in any one of SEQ ID NOs: 395-399.

In some embodiments, the antibody or antigen binding fragment thereof comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 5 and 6; and/or (b) the immunoglobulin variable region light chain comprises an amino acid sequence having at least about 90, 95, 97, 98, 99, or 100% sequence identity to any one of SEQ ID NOs: 7 and 8.

In certain embodiments, the immunoglobulin variable region heavy chain comprises an amino acid sequence having about 90% sequence identity to any one of SEQ ID NOs: 5 and 6 to about 100% sequence identity to any one of SEQ ID NOs: 5 and 6. In certain embodiments, the immunoglobulin variable region heavy chain comprises an amino acid sequence having at least about 90% sequence identity to any one of SEQ ID NOs: 5 and 6. In certain embodiments, the immunoglobulin variable region heavy chain comprises an amino acid sequence having at most about 100% sequence identity to any one of SEQ ID NOs: 5 and 6. In certain embodiments, the immunoglobulin variable region heavy chain comprises an amino acid sequence having about 90% sequence identity to any one of SEQ ID NOs: 5 and 6 to about 95% sequence identity to any one of SEQ ID NOs: 5 and 6, about 90% sequence identity to any one of SEQ ID NOs: 5 and 6 to about 97% sequence identity to any one of SEQ ID NOs: 5 and 6, about 90% sequence identity to any one of SEQ ID NOs: 5 and 6 to about 98% sequence identity to any one of SEQ ID NOs: 5 and 6, about 90% sequence identity to any one of SEQ ID NOs: 5 and 6 to about 99% sequence identity to any one of SEQ ID NOs: 5 and 6, about 90% sequence identity to any one of SEQ ID NOs: 5 and 6 to about 100% sequence identity to any one of SEQ ID NOs: 5 and 6, about 95% sequence identity to any one of SEQ ID NOs: 5 and 6 to about 97% sequence identity to any one of SEQ ID NOs: 5 and 6, about 95% sequence identity to any one of SEQ ID NOs: 5 and 6 to about 98% sequence identity to any one of SEQ ID NOs: 5 and 6, about 95% sequence identity to any one of SEQ ID NOs: 5 and 6 to about 99% sequence identity to any one of SEQ ID NOs: 5 and 6, about 95% sequence identity to any one of SEQ ID NOs: 5 and 6 to about 100% sequence identity to any one of SEQ ID NOs: 5 and 6, about 97% sequence identity to any one of SEQ ID NOs: 5 and 6 to about 98% sequence identity to any one of SEQ ID NOs: 5 and 6, about 97% sequence identity to any one of SEQ ID NOs: 5 and 6 to about 99% sequence identity to any one of SEQ ID NOs: 5 and 6, about 97% sequence identity to any one of SEQ ID NOs: 5 and 6 to about 100% sequence identity to any one of SEQ ID NOs: 5 and 6, about 98% sequence identity to any one of SEQ ID NOs: 5 and 6 to about 99% sequence identity to any one of SEQ ID NOs: 5 and 6, about 98% sequence identity to any one of SEQ ID NOs: 5 and 6 to about 100% sequence identity to any one of SEQ ID NOs: 5 and 6, or about 99% sequence identity to any one of SEQ ID NOs: 5 and 6 to about 100% sequence identity to any one of SEQ ID NOs: 5 and 6. In certain embodiments, the immunoglobulin variable region heavy chain comprises an amino acid sequence having about 90% sequence identity to any one of SEQ ID NOs: 5 and 6, about 95% sequence identity to any one of SEQ ID NOs: 5 and 6, about 97% sequence identity to any one of SEQ ID NOs: 5 and 6, about 98% sequence identity to any one of SEQ ID NOs: 5 and 6, about 99% sequence identity to any one of SEQ ID NOs: 5 and 6, or about 100% sequence identity to any one of SEQ ID NOs: 5 and 6.

In certain embodiments, the immunoglobulin variable region light chain comprises an amino acid sequence having about 90% sequence identity to any one of SEQ ID NOs: 7 and 8 to about 100% sequence identity to any one of SEQ ID NOs: 7 and 8. In certain embodiments, the immunoglobulin variable region light chain comprises an amino acid sequence having at least about 90% sequence identity to any one of SEQ ID NOs: 7 and 8. In certain embodiments, the immunoglobulin variable region light chain comprises an amino acid sequence having at most about 100% sequence identity to any one of SEQ ID NOs: 7 and 8. In certain embodiments, the immunoglobulin variable region light chain comprises an amino acid sequence having about 90% sequence identity to any one of SEQ ID NOs: 7 and 8 to about 95% sequence identity to any one of SEQ ID NOs: 7 and 8, about 90% sequence identity to any one of SEQ ID NOs: 7 and 8 to about 97% sequence identity to any one of SEQ ID NOs: 7 and 8, about 90% sequence identity to any one of SEQ ID NOs: 7 and 8 to about 98% sequence identity to any one of SEQ ID NOs: 7 and 8, about 90% sequence identity to any one of SEQ ID NOs: 7 and 8 to about 99% sequence identity to any one of SEQ ID NOs: 7 and 8, about 90% sequence identity to any one of SEQ ID NOs: 7 and 8 to about 100% sequence identity to any one of SEQ ID NOs: 7 and 8, about 95% sequence identity to any one of SEQ ID NOs: 7 and 8 to about 97% sequence identity to any one of SEQ ID NOs: 7 and 8, about 95% sequence identity to any one of SEQ ID NOs: 7 and 8 to about 98% sequence identity to any one of SEQ ID NOs: 7 and 8, about 95% sequence identity to any one of SEQ ID NOs: 7 and 8 to about 99% sequence identity to any one of SEQ ID NOs: 7 and 8, about 95% sequence identity to any one of SEQ ID NOs: 7 and 8 to about 100% sequence identity to any one of SEQ ID NOs: 7 and 8, about 97% sequence identity to any one of SEQ ID NOs: 7 and 8 to about 98% sequence identity to any one of SEQ ID NOs: 7 and 8, about 97% sequence identity to any one of SEQ ID NOs: 7 and 8 to about 99% sequence identity to any one of SEQ ID NOs: 7 and 8, about 97% sequence identity to any one of SEQ ID NOs: 7 and 8 to about 100% sequence identity to any one of SEQ ID NOs: 7 and 8, about 98% sequence identity to any one of SEQ ID NOs: 7 and 8 to about 99% sequence identity to any one of SEQ ID NOs: 7 and 8, about 98% sequence identity to any one of SEQ ID NOs: 7 and 8 to about 100% sequence identity to any one of SEQ ID NOs: 7 and 8, or about 99% sequence identity to any one of SEQ ID NOs: 7 and 8 to about 100% sequence identity to any one of SEQ ID NOs: 7 and 8. In certain embodiments, the immunoglobulin variable region light chain comprises an amino acid sequence having about 90% sequence identity to any one of SEQ ID NOs: 7 and 8, about 95% sequence identity to any one of SEQ ID NOs: 7 and 8, about 97% sequence identity to any one of SEQ ID NOs: 7 and 8, about 98% sequence identity to any one of SEQ ID NOs: 7 and 8, about 99% sequence identity to any one of SEQ ID NOs: 7 and 8, or about 100% sequence identity to any one of SEQ ID NOs: 7 and 8.

In some embodiments, the antibody or antigen binding fragment thereof comprises: (a) a CDR-H1 comprising the amino acid sequence set forth in any one of SEQ ID NOs: 120-129; (b) a CDR-H2 comprising the amino acid sequence set forth in any one of SEQ ID NOs: 160-169; (c) an immunoglobulin heavy chain CDR3 (CDR-H3) comprising the amino acid sequence set forth in any one of SEQ ID NOs: 200-209; (d) a CDR-L1 comprising the amino acid sequence set forth in any one of SEQ ID NOs: 320-329; (e) a CDR-L2 comprising the amino acid sequence set forth in any one of SEQ ID NOs: 360-369; and/or (f) a CDR-L3 comprising the amino acid sequence set forth in any one of SEQ ID NOs: 400-409.

In certain embodiments, the antibody or antigen binding fragment thereof comprises: (a) a CDR-H1 comprising the amino acid sequence set forth in any one of SEQ ID NOs: 120-124; (b) a CDR-H2 comprising the amino acid sequence set forth in any one of SEQ ID NOs: 160-164; (c) an immunoglobulin heavy chain CDR3 (CDR-H3) comprising the amino acid sequence set forth in any one of SEQ ID NOs: 200-204; (d) a CDR-L1 comprising the amino acid sequence set forth in any one of SEQ ID NOs: 320-324; (e) a CDR-L2 comprising the amino acid sequence set forth in any one of SEQ ID NOs: 360-364; and/or (f) a CDR-L3 comprising the amino acid sequence set forth in any one of SEQ ID NOs: 400-404.

In certain embodiments, the antibody or antigen binding fragment thereof comprises: (a) a CDR-H1 comprising the amino acid sequence set forth in any one of SEQ ID NOs: 125-129; (b) a CDR-H2 comprising the amino acid sequence set forth in any one of SEQ ID NOs: 165-169; (c) an immunoglobulin heavy chain CDR3 (CDR-H3) comprising the amino acid sequence set forth in any one of SEQ ID NOs: 205-209; (d) a CDR-L1 comprising the amino acid sequence set forth in any one of SEQ ID NOs: 325-329; (e) a CDR-L2 comprising the amino acid sequence set forth in any one of SEQ ID NOs: 365-369; and/or (f) a CDR-L3 comprising the amino acid sequence set forth in any one of SEQ ID NO s: 405-409.

In some embodiments, the antibody or antigen binding fragment thereof comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 9 and 10; and/or (b) the immunoglobulin variable region light chain comprises an amino acid sequence having at least about 90, 95, 97, 98, 99, or 100% sequence identity to any one of SEQ ID NOs: 11 and 12.

In certain embodiments, the immunoglobulin variable region heavy chain comprises an amino acid sequence having about 90% sequence identity to any one of SEQ ID NOs: 9 and 10 to about 100% sequence identity to any one of SEQ ID NOs: 9 and 10. In certain embodiments, the immunoglobulin variable region heavy chain comprises an amino acid sequence having at least about 90% sequence identity to any one of SEQ ID NOs: 9 and 10. In certain embodiments, the immunoglobulin variable region heavy chain comprises an amino acid sequence having at most about 100% sequence identity to any one of SEQ ID NOs: 9 and 10. In certain embodiments, the immunoglobulin variable region heavy chain comprises an amino acid sequence having about 90% sequence identity to any one of SEQ ID NOs: 9 and 10 to about 95% sequence identity to any one of SEQ ID NOs: 9 and 10, about 90% sequence identity to any one of SEQ ID NOs: 9 and 10 to about 97% sequence identity to any one of SEQ ID NOs: 9 and 10, about 90% sequence identity to any one of SEQ ID NOs: 9 and 10 to about 98% sequence identity to any one of SEQ ID NOs: 9 and 10, about 90% sequence identity to any one of SEQ ID NOs: 9 and 10 to about 99% sequence identity to any one of SEQ ID NOs: 9 and 10, about 90% sequence identity to any one of SEQ ID NOs: 9 and 10 to about 100% sequence identity to any one of SEQ ID NOs: 9 and 10, about 95% sequence identity to any one of SEQ ID NOs: 9 and 10 to about 97% sequence identity to any one of SEQ ID NOs: 9 and 10, about 95% sequence identity to any one of SEQ ID NOs: 9 and 10 to about 98% sequence identity to any one of SEQ ID NOs: 9 and 10, about 95% sequence identity to any one of SEQ ID NOs: 9 and 10 to about 99% sequence identity to any one of SEQ ID NOs: 9 and 10, about 95% sequence identity to any one of SEQ ID NOs: 9 and 10 to about 100% sequence identity to any one of SEQ ID NOs: 9 and 10, about 97% sequence identity to any one of SEQ ID NOs: 9 and 10 to about 98% sequence identity to any one of SEQ ID NOs: 9 and 10, about 97% sequence identity to any one of SEQ ID NOs: 9 and 10 to about 99% sequence identity to any one of SEQ ID NOs: 9 and 10, about 97% sequence identity to any one of SEQ ID NOs: 9 and 10 to about 100% sequence identity to any one of SEQ ID NOs: 9 and 10, about 98% sequence identity to any one of SEQ ID NOs: 9 and 10 to about 99% sequence identity to any one of SEQ ID NOs: 9 and 10, about 98% sequence identity to any one of SEQ ID NOs: 9 and 10 to about 100% sequence identity to any one of SEQ ID NOs: 9 and 10, or about 99% sequence identity to any one of SEQ ID NOs: 9 and 10 to about 100% sequence identity to any one of SEQ ID NOs: 9 and 10. In certain embodiments, the immunoglobulin variable region heavy chain comprises an amino acid sequence having about 90% sequence identity to any one of SEQ ID NOs: 9 and 10, about 95% sequence identity to any one of SEQ ID NOs: 9 and 10, about 97% sequence identity to any one of SEQ ID NOs: 9 and 10, about 98% sequence identity to any one of SEQ ID NOs: 9 and 10, about 99% sequence identity to any one of SEQ ID NOs: 9 and 10, or about 100% sequence identity to any one of SEQ ID NOs: 9 and 10.

In certain embodiments, the immunoglobulin variable region light chain comprises an amino acid sequence having about 90% sequence identity to any one of SEQ ID NOs: 11 and 12 to about 100% sequence identity to any one of SEQ ID NOs: 11 and 12. In certain embodiments, the immunoglobulin variable region light chain comprises an amino acid sequence having at least about 90% sequence identity to any one of SEQ ID NOs: 11 and 12. In certain embodiments, the immunoglobulin variable region light chain comprises an amino acid sequence having at most about 100% sequence identity to any one of SEQ ID NOs: 11 and 12. In certain embodiments, the immunoglobulin variable region light chain comprises an amino acid sequence having about 90% sequence identity to any one of SEQ ID NOs: 11 and 12 to about 95% sequence identity to any one of SEQ ID NOs: 11 and 12, about 90% sequence identity to any one of SEQ ID NOs: 11 and 12 to about 97% sequence identity to any one of SEQ ID NOs: 11 and 12, about 90% sequence identity to any one of SEQ ID NOs: 11 and 12 to about 98% sequence identity to any one of SEQ ID NOs: 11 and 12, about 90% sequence identity to any one of SEQ ID NOs: 11 and 12 to about 99% sequence identity to any one of SEQ ID NOs: 11 and 12, about 90% sequence identity to any one of SEQ ID NOs: 11 and 12 to about 100% sequence identity to any one of SEQ ID NOs: 11 and 12, about 95% sequence identity to any one of SEQ ID NOs: 11 and 12 to about 97% sequence identity to any one of SEQ ID NOs: 11 and 12, about 95% sequence identity to any one of SEQ ID NOs: 11 and 12 to about 98% sequence identity to any one of SEQ ID NOs: 11 and 12, about 95% sequence identity to any one of SEQ ID NOs: 11 and 12 to about 99% sequence identity to any one of SEQ ID NOs: 11 and 12, about 95% sequence identity to any one of SEQ ID NOs: 11 and 12 to about 100% sequence identity to any one of SEQ ID NOs: 11 and 12, about 97% sequence identity to any one of SEQ ID NOs: 11 and 12 to about 98% sequence identity to any one of SEQ ID NOs: 11 and 12, about 97% sequence identity to any one of SEQ ID NOs: 11 and 12 to about 99% sequence identity to any one of SEQ ID NOs: 11 and 12, about 97% sequence identity to any one of SEQ ID NOs: 11 and 12 to about 100% sequence identity to any one of SEQ ID NOs: 11 and 12, about 98% sequence identity to any one of SEQ ID NOs: 11 and 12 to about 99% sequence identity to any one of SEQ ID NOs: 11 and 12, about 98% sequence identity to any one of SEQ ID NOs: 11 and 12 to about 100% sequence identity to any one of SEQ ID NOs: 11 and 12, or about 99% sequence identity to any one of SEQ ID NOs: 11 and 12 to about 100% sequence identity to any one of SEQ ID NOs: 11 and 12. In certain embodiments, the immunoglobulin variable region light chain comprises an amino acid sequence having about 90% sequence identity to any one of SEQ ID NOs: 11 and 12, about 95% sequence identity to any one of SEQ ID NOs: 11 and 12, about 97% sequence identity to any one of SEQ ID NOs: 11 and 12, about 98% sequence identity to any one of SEQ ID NOs: 11 and 12, about 99% sequence identity to any one of SEQ ID NOs: 11 and 12, or about 100% sequence identity to any one of SEQ ID NOs: 11 and 12.

In some embodiments, the antibody or antigen binding fragment thereof comprises: (a) a CDR-H1 comprising the amino acid sequence set forth in any one of SEQ ID NOs: 130-139; (b) a CDR-H2 comprising the amino acid sequence set forth in any one of SEQ ID NOs: 170-179; (c) an immunoglobulin heavy chain CDR3 (CDR-H3) comprising the amino acid sequence set forth in any one of SEQ ID NOs: 210-219; (d) a CDR-L1 comprising the amino acid sequence set forth in any one of SEQ ID NOs: 330-339; (e) a CDR-L2 comprising the amino acid sequence set forth in any one of SEQ ID NOs: 370-379; and/or (f) a CDR-L3 comprising the amino acid sequence set forth in any one of SEQ ID NOs: 410-419.

In certain embodiments, the antibody or antigen binding fragment thereof comprises: (a) a CDR-H1 comprising the amino acid sequence set forth in any one of SEQ ID NOs: 130-134; (b) a CDR-H2 comprising the amino acid sequence set forth in any one of SEQ ID NOs: 170-174; (c) an immunoglobulin heavy chain CDR3 (CDR-H3) comprising the amino acid sequence set forth in any one of SEQ ID NOs: 210-214; (d) a CDR-L1 comprising the amino acid sequence set forth in any one of SEQ ID NOs: 330-334; (e) a CDR-L2 comprising the amino acid sequence set forth in any one of SEQ ID NOs: 370-374; and/or (f) a CDR-L3 comprising the amino acid sequence set forth in any one of SEQ ID NOs: 410-414.

In certain embodiments, the antibody or antigen binding fragment thereof comprises: (a) a CDR-H1 comprising the amino acid sequence set forth in any one of SEQ ID NOs: 135-139; (b) a CDR-H2 comprising the amino acid sequence set forth in any one of SEQ ID NOs: 175-179; (c) an immunoglobulin heavy chain CDR3 (CDR-H3) comprising the amino acid sequence set forth in any one of SEQ ID NOs: 215-219; (d) a CDR-L1 comprising the amino acid sequence set forth in any one of SEQ ID NOs: 335-339; (e) a CDR-L2 comprising the amino acid sequence set forth in any one of SEQ ID NOs: 375-379; and/or (f) a CDR-L3 comprising the amino acid sequence set forth in any one of SEQ ID NOs: 415-419.

In some embodiments, the antibody or antigen binding fragment thereof comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 13 and 14; and/or (b) the immunoglobulin variable region light chain comprises an amino acid sequence having at least about 90, 95, 97, 98, 99, or 100% sequence identity to any one of SEQ ID NOs: 15 and 16.

In certain embodiments, the immunoglobulin variable region heavy chain comprises an amino acid sequence having about 90% sequence identity to any one of SEQ ID NOs: 13 and 14 to about 100% sequence identity to any one of SEQ ID NOs: 13 and 14. In certain embodiments, the immunoglobulin variable region heavy chain comprises an amino acid sequence having at least about 90% sequence identity to any one of SEQ ID NOs: 13 and 14. In certain embodiments, the immunoglobulin variable region heavy chain comprises an amino acid sequence having at most about 100% sequence identity to any one of SEQ ID NOs: 13 and 14. In certain embodiments, the immunoglobulin variable region heavy chain comprises an amino acid sequence having about 90% sequence identity to any one of SEQ ID NOs: 13 and 14 to about 95% sequence identity to any one of SEQ ID NOs: 13 and 14, about 90% sequence identity to any one of SEQ ID NOs: 13 and 14 to about 97% sequence identity to any one of SEQ ID NOs: 13 and 14, about 90% sequence identity to any one of SEQ ID NOs: 13 and 14 to about 98% sequence identity to any one of SEQ ID NOs: 13 and 14, about 90% sequence identity to any one of SEQ ID NOs: 13 and 14 to about 99% sequence identity to any one of SEQ ID NOs: 13 and 14, about 90% sequence identity to any one of SEQ ID NOs: 13 and 14 to about 100% sequence identity to any one of SEQ ID NOs: 13 and 14, about 95% sequence identity to any one of SEQ ID NOs: 13 and 14 to about 97% sequence identity to any one of SEQ ID NOs: 13 and 14, about 950% sequence identity to any one of SEQ ID NOs: 13 and 14 to about 98% sequence identity to any one of SEQ ID NOs: 13 and 14, about 95% sequence identity to any one of SEQ ID NOs: 13 and 14 to about 99% sequence identity to any one of SEQ ID NOs: 13 and 14, about 950% sequence identity to any one of SEQ ID NOs: 13 and 14 to about 100% sequence identity to any one of SEQ ID NOs: 13 and 14, about 97% sequence identity to any one of SEQ ID NOs: 13 and 14 to about 98% sequence identity to any one of SEQ ID NOs: 13 and 14, about 97% sequence identity to any one of SEQ ID NOs: 13 and 14 to about 99% sequence identity to any one of SEQ ID NOs: 13 and 14, about 97% sequence identity to any one of SEQ ID NOs: 13 and 14 to about 100% sequence identity to any one of SEQ ID NOs: 13 and 14, about 98% sequence identity to any one of SEQ ID NOs: 13 and 14 to about 99% sequence identity to any one of SEQ ID NOs: 13 and 14, about 98% sequence identity to any one of SEQ ID NOs: 13 and 14 to about 100% sequence identity to any one of SEQ ID NOs: 13 and 14, or about 99% sequence identity to any one of SEQ ID NOs: 13 and 14 to about 100% sequence identity to any one of SEQ ID NOs: 13 and 14. In certain embodiments, the immunoglobulin variable region heavy chain comprises an amino acid sequence having about 90% sequence identity to any one of SEQ ID NOs: 13 and 14, about 950% sequence identity to any one of SEQ ID NOs: 13 and 14, about 97% sequence identity to any one of SEQ ID NOs: 13 and 14, about 98% sequence identity to any one of SEQ ID NOs: 13 and 14, about 99% sequence identity to any one of SEQ ID NOs: 13 and 14, or about 100% sequence identity to any one of SEQ ID NOs: 13 and 14.

In certain embodiments, the immunoglobulin variable region light chain comprises an amino acid sequence having about 90% sequence identity to any one of SEQ ID NOs: 15 and 16 to about 100% sequence identity to any one of SEQ ID NOs: 15 and 16. In certain embodiments, the immunoglobulin variable region light chain comprises an amino acid sequence having at least about 90% sequence identity to any one of SEQ ID NOs: 15 and 16. In certain embodiments, the immunoglobulin variable region light chain comprises an amino acid sequence having at most about 100% sequence identity to any one of SEQ ID NOs: 15 and 16. In certain embodiments, the immunoglobulin variable region light chain comprises an amino acid sequence having about 90% sequence identity to any one of SEQ ID NOs: 15 and 16 to about 95% sequence identity to any one of SEQ ID NOs: 15 and 16, about 90% sequence identity to any one of SEQ ID NOs: 15 and 16 to about 97% sequence identity to any one of SEQ ID NOs: 15 and 16, about 90% sequence identity to any one of SEQ ID NOs: 15 and 16 to about 98% sequence identity to any one of SEQ ID NOs: 15 and 16, about 90% sequence identity to any one of SEQ ID NOs: 15 and 16 to about 99% sequence identity to any one of SEQ ID NOs: 15 and 16, about 90% sequence identity to any one of SEQ ID NOs: 15 and 16 to about 100% sequence identity to any one of SEQ ID NOs: 15 and 16, about 95% sequence identity to any one of SEQ ID NOs: 15 and 16 to about 97% sequence identity to any one of SEQ ID NOs: 15 and 16, about 95% sequence identity to any one of SEQ ID NOs: 15 and 16 to about 98% sequence identity to any one of SEQ ID NOs: 15 and 16, about 95% sequence identity to any one of SEQ ID NOs: 15 and 16 to about 99% sequence identity to any one of SEQ ID NOs: 15 and 16, about 95% sequence identity to any one of SEQ ID NOs: 15 and 16 to about 100% sequence identity to any one of SEQ ID NOs: 15 and 16, about 97% sequence identity to any one of SEQ ID NOs: 15 and 16 to about 98% sequence identity to any one of SEQ ID NOs: 15 and 16, about 97% sequence identity to any one of SEQ ID NOs: 15 and 16 to about 99% sequence identity to any one of SEQ ID NOs: 15 and 16, about 97% sequence identity to any one of SEQ ID NOs: 15 and 16 to about 100% sequence identity to any one of SEQ ID NOs: 15 and 16, about 98% sequence identity to any one of SEQ ID NOs: 15 and 16 to about 99% sequence identity to any one of SEQ ID NOs: 15 and 16, about 98% sequence identity to any one of SEQ ID NOs: 15 and 16 to about 100% sequence identity to any one of SEQ ID NOs: 15 and 16, or about 99% sequence identity to any one of SEQ ID NOs: 15 and 16 to about 100% sequence identity to any one of SEQ ID NOs: 15 and 16. In certain embodiments, the immunoglobulin variable region light chain comprises an amino acid sequence having about 90% sequence identity to any one of SEQ ID NOs: 15 and 16, about 95% sequence identity to any one of SEQ ID NOs: 15 and 16, about 97% sequence identity to any one of SEQ ID NOs: 15 and 16, about 98% sequence identity to any one of SEQ ID NOs: 15 and 16, about 99% sequence identity to any one of SEQ ID NOs: 15 and 16, or about 100% sequence identity to any one of SEQ ID NOs: 15 and 16.

In some embodiments of the anti-CD30L antibody or antigen binding fragment provided herein, including in Section 2 and this Section (Section 4.1), the antibody or antigen binding fragment thereof is recombinant antibody or antigen binding fragment thereof.

In certain embodiments of the anti-CD30L antibody or antigen binding fragment provided herein, including in Section 2 and this Section (Section 4.1), the antibody or antigen binding fragment thereof is isolated antibody or antigen binding fragment thereof.

In one additional aspect, provided herein is an antibody or antigen-binding fragment thereof that binds to an epitope of human CD30L recognized by an anti-CD30L antibody or antigen binding fragment provided herein, including in Section 2 and this Section (Section 4.1 such as the preceding paragraphs).

In another aspect, provided herein is an antibody or antigen-binding fragment thereof that competes for the binding to human CD30L with an anti-CD30L antibody or antigen binding fragment provided herein, including in Section 2 and this Section (Section 4.1 such as the preceding paragraphs).

4.2 Germline Reversions

In some instances, germline reversions (for example, mutations of an antibody sequence back to the germline sequence) are useful for improving the safety, pharmacodynamic and/or pharmacokinetic properties of the anti-CD30L antibodies. For example, in certain instances, germline reversion mutations reduce immunogenicity of an anti-CD30L antibody while maintaining the ability to bind CD30L with high affinity and specificity.

Generally, a germline antibody gene or germline antibody gene segment refers to a sequence encoding an immunoglobulin present in the genome of an organism, wherein the genome is not or has not been subjected to mutational processes such a somatic hypermutation (for example, has not experienced a maturation process that leads to genetic rearrangements and mutations that express specific immunoglobulins). Thus, in some instances, the heavy chain germline gene refers to a germline antibody gene or gene fragment encoding an immunoglobulin heavy chain, which includes a V gene (variable), a D gene (diversity), and a J gene (joining), and in certain instances, the C gene (constant). Similarly, in some instances, the light chain germline gene refers to a germline antibody gene or gene fragment encoding an immunoglobulin light chain, which includes a V gene (variable), a J gene (joining), and in some instances, the C gene (constant). In some instances, the amino acid sequence encoded by the germline antibody gene or the germline antibody gene fragment is also referred to as a germline sequence. In certain instances, an amino acids sequence mutation back to a germline amino acid sequence refers to or identifies an amino acid mutation (for example, in a matured antibody amino acid sequence) to the amino acid of the germline amino acid (for example, in the germline antibody sequence). In certain instances, identifying a germline antibody gene or germline antibody gene fragments and their corresponding germline sequences can be obtained or queried from a professional database (for example, IMGT, UNSWIg, NCBI or VBASE2).

Accordingly, in some embodiments, the anti-CD30L comprises one or more amino acid sequence mutations back to a germline amino acid sequence. In certain embodiments, the recombinant antibody or antigen binding fragment thereof comprises a heavy chain variable region and/or light chain variable region comprising about 1 mutation back to a germline sequence to about 20 mutations back to a germline sequence. In certain embodiments, the recombinant antibody or antigen binding fragment thereof comprises a heavy chain variable region and/or light chain variable region comprising at least about 1 mutation back to a germline sequence. In certain embodiments, the recombinant antibody or antigen binding fragment thereof comprises a heavy chain variable region and/or light chain variable region comprising at most about 20 mutations back to a germline sequence. In certain embodiments, the recombinant antibody or antigen binding fragment thereof comprises a heavy chain variable region and/or light chain variable region comprising about 1 mutation back to a germline sequence to about 2 mutations back to a germline sequence, about 1 mutation back to a germline sequence to about 3 mutations back to a germline sequence, about 1 mutation back to a germline sequence to about 4 mutations back to a germline sequence, about 1 mutation back to a germline sequence to about 5 mutations back to a germline sequence, about 1 mutation back to a germline sequence to about 10 mutations back to a germline sequence, about 1 mutation back to a germline sequence to about 15 mutations back to a germline sequence, about 1 mutation back to a germline sequence to about 20 mutations back to a germline sequence, about 2 mutations back to a germline sequence to about 3 mutations back to a germline sequence, about 2 mutations back to a germline sequence to about 4 mutations back to a germline sequence, about 2 mutations back to a germline sequence to about 5 mutations back to a germline sequence, about 2 mutations back to a germline sequence to about 10 mutations back to a germline sequence, about 2 mutations back to a germline sequence to about 15 mutations back to a germline sequence, about 2 mutations back to a germline sequence to about 20 mutations back to a germline sequence, about 3 mutations back to a germline sequence to about 4 mutations back to a germline sequence, about 3 mutations back to a germline sequence to about 5 mutations back to a germline sequence, about 3 mutations back to a germline sequence to about 10 mutations back to a germline sequence, about 3 mutations back to a germline sequence to about 15 mutations back to a germline sequence, about 3 mutations back to a germline sequence to about 20 mutations back to a germline sequence, about 4 mutations back to a germline sequence to about 5 mutations back to a germline sequence, about 4 mutations back to a germline sequence to about 10 mutations back to a germline sequence, about 4 mutations back to a germline sequence to about 15 mutations back to a germline sequence, about 4 mutations back to a germline sequence to about 20 mutations back to a germline sequence, about 5 mutations back to a germline sequence to about 10 mutations back to a germline sequence, about 5 mutations back to a germline sequence to about 15 mutations back to a germline sequence, about 5 mutations back to a germline sequence to about 20 mutations back to a germline sequence, about 10 mutations back to a germline sequence to about 15 mutations back to a germline sequence, about 10 mutations back to a germline sequence to about 20 mutations back to a germline sequence, or about 15 mutations back to a germline sequence to about 20 mutations back to a germline sequence. In certain embodiments, the recombinant antibody or antigen binding fragment thereof comprises a heavy chain variable region and/or light chain variable region comprising about 1 mutation back to a germline sequence, about 2 mutations back to a germline sequence, about 3 mutations back to a germline sequence, about 4 mutations back to a germline sequence, about 5 mutations back to a germline sequence, about 10 mutations back to a germline sequence, about 15 mutations back to a germline sequence, or about 20 mutations back to a germline sequence.

In some embodiments, a recombinant antibody or antigen binding fragment thereof comprising an immunoglobulin variable region heavy chain and an immunoglobulin variable region light chain as set forth in SEQ ID NOs: 1 and 3 comprises one or more amino acid sequence mutations back to a germline amino acid sequence, thereby yielding a germline reverted or germlined anti-CD30L antibody. In certain embodiments, the germline reverted or germlined anti-CD30L antibody comprises the amino acid sequence as set forth in SEQ ID NOs: 2 and 4, or an amino acid sequence at least 90, 95, 95, 96, 97, 98, or 99 percent identical to the amino acid sequence as set forth in SEQ ID NOs: 2 and 4.

In some embodiments, a recombinant antibody or antigen binding fragment thereof comprising an immunoglobulin variable region heavy chain and an immunoglobulin variable region light chain as set forth in SEQ ID NOs: 5 and 7 comprises one or more amino acid sequence mutations back to a germline amino acid sequence, thereby yielding a germline reverted or germlined anti-CD30L antibody. In certain embodiments, the germline reverted or germlined anti-CD30L antibody comprises the amino acid sequence as set forth in SEQ ID NOs: 6 and 8, or an amino acid sequence at least 90, 95, 95, 96, 97, 98, or 99 percent identical to the amino acid sequence as set forth in SEQ ID NOs: 6 and 8.

In some embodiments, a recombinant antibody or antigen binding fragment thereof comprising an immunoglobulin variable region heavy chain and an immunoglobulin variable region light chain as set forth in SEQ ID NOs: 9 and 11 comprises one or more amino acid sequence mutations back to a germline amino acid sequence, thereby yielding a germline reverted or germlined anti-CD30L antibody. In certain embodiments, the germline reverted or germlined anti-CD30L antibody comprises the amino acid sequence as set forth in SEQ ID NOs: 10 and 12, or an amino acid sequence at least 90, 95, 95, 96, 97, 98, or 99 percent identical to the amino acid sequence as set forth in SEQ ID NOs: 10 and 12.

In some embodiments, a recombinant antibody or antigen binding fragment thereof comprising an immunoglobulin variable region heavy chain and an immunoglobulin variable region light chain as set forth in SEQ ID NOs: 13 and 15 comprises one or more amino acid sequence mutations back to a germline amino acid sequence, thereby yielding a germline reverted or germlined anti-CD30L antibody. In certain embodiments, the germline reverted or germlined anti-CD30L antibody comprises the amino acid sequence as set forth in SEQ ID NOs: 14 and 16, or an amino acid sequence at least 90, 95, 95, 96, 97, 98, or 99 percent identical to the amino acid sequence as set forth in SEQ ID NOs: 14 and 16.

4.3 Cysteine Engineering

In some instances, exposed (for example, solvent exposed) thiol moieties (for example, the thiol moiety of a cysteine amino acid residue) contribute to protein aggregation. For example, disulfide linkages between one or more proteins can be formed as a result of thiol oxidation. In certain instances, mutation of solvent exposed cysteine residues (for example, mutation of one or more solvent exposed cysteine residues) are advantageous in reducing protein aggregation, thereby increasing protein solubility.

Generally, solubility references the ability of a protein to remain dispersed within an aqueous solution (for example, the amount of a monomeric protein species in a solution). In certain instances, the solubility of a protein in an aqueous formulation depends upon the proper distribution of amino acid residues and therefore, solubility can, in certain instances, correlate with the production of correctly folded proteins or the production of proteins retaining. Specific function (for example, an antibody binding an antigen). Methods of detecting an increase or decrease in solubility of a protein (for example, an antibody) are known in the art (for example, using routine HPLC techniques, dynamic light scattering techniques, etc.).

Accordingly, in some embodiments, one or more cysteine amino acid residues of the anti-CD30L antibodies are mutated to a non-cysteine amino acid residue (for example, serine). In certain embodiments, the recombinant antibody or antigen binding fragment thereof comprises a heavy chain variable region and/or light chain variable region comprising 1 cysteine residue that is mutated to a non-cysteine residue to 5 cysteine residues that is mutated to a non-cysteine residue. In certain embodiments, the recombinant antibody or antigen binding fragment thereof comprises a heavy chain variable region and/or light chain variable region comprising at least 1 cysteine residue that is mutated to a non-cysteine residue. In certain embodiments, the recombinant antibody or antigen binding fragment thereof comprises a heavy chain variable region and/or light chain variable region comprising at most 5 cysteine residues that is mutated to a non-cysteine residue. In certain embodiments, the recombinant antibody or antigen binding fragment thereof comprises a heavy chain variable region and/or light chain variable region comprising 1 cysteine residue that is mutated to a non-cysteine residue to 2 cysteine residues that is mutated to a non-cysteine residue, 1 cysteine residue that is mutated to a non-cysteine residue to 3 cysteine residues that is mutated to a non-cysteine residue, 1 cysteine residue that is mutated to a non-cysteine residue to 4 cysteine residues that is mutated to a non-cysteine residue, 1 cysteine residue that is mutated to a non-cysteine residue to 5 cysteine residues that is mutated to a non-cysteine residue, 2 cysteine residues that is mutated to a non-cysteine residue to 3 cysteine residues that is mutated to a non-cysteine residue, 2 cysteine residues that is mutated to a non-cysteine residue to 4 cysteine residues that is mutated to a non-cysteine residue, 2 cysteine residues that is mutated to a non-cysteine residue to 5 cysteine residues that is mutated to a non-cysteine residue, 3 cysteine residues that is mutated to a non-cysteine residue to 4 cysteine residues that is mutated to a non-cysteine residue, 3 cysteine residues that is mutated to a non-cysteine residue to 5 cysteine residues that is mutated to a non-cysteine residue, or 4 cysteine residues that is mutated to a non-cysteine residue to 5 cysteine residues that is mutated to a non-cysteine residue. In certain embodiments, the recombinant antibody or antigen binding fragment thereof comprises a heavy chain variable region and/or light chain variable region comprising 1 cysteine residue that is mutated to a non-cysteine residue, 2 cysteine residues that is mutated to a non-cysteine residue, 3 cysteine residues that is mutated to a non-cysteine residue, 4 cysteine residues that is mutated to a non-cysteine residue, or 5 cysteine residues that is mutated to a non-cysteine residue. In some embodiments, one or more cysteine amino acid residues of the anti-CD30L antibody as set forth in SEQ ID NOs: 1-16 are mutated to a non-cysteine amino acid residue.

4.4 Fc Constant Regions

Generally, the fragment crystallizable (Fc) region or domain of an antibody (for example, an anti-CD30L antibody) mediates downstream effector functions via its interaction with Fc-receptors on immune cells (for example, innate immune cells) or with complement protein C1q, the recognition molecule of the complement system. Furthermore, the interaction with Fc-receptors can lead to killing of targeted cells through a variety of immune effector mechanisms, including antibody-dependent cell-mediated cytotoxicity (ADCC) and antibody-dependent cellular phagocytosis (ADCP), and antibody-mediated complement activation may lead to complement-dependent cytotoxicity (CDC). In addition, both Fc-receptor interactions and complement activation can exert a broad range of immunomodulatory functions.

Accordingly, in certain instances, mutations within the Fc region that reduce, inhibit, ablate, and/or abrogate Fc-mediated function (for example, ADCC, ADCP, CDC, etc.) of an anti-CD30L antibodies are advantageous for reducing immune activation resulting from the binding of an anti-CD30L antibody to CD30L. In some embodiments, one or more amino acid modifications may be introduced into the Fc region of an anti-CD30L antibody, thereby generating an Fc region variant. An Fc region may comprise a C-terminal region of an immunoglobulin heavy chain that comprises a hinge region, CH2 domain, CH3 domain, or any combination thereof. As used herein, an Fc region includes native sequence Fc regions and variant Fc regions. The Fc region variant may comprise a human Fc region sequence (e.g., a human IgG1, IgG2, IgG3 or IgG4 Fc region) comprising an amino acid modification (e.g., a substitution, addition, or deletion) at one or more amino acid positions.

In some embodiments, the anti-CD30L antibodies of this disclosure are variants that possess some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity) but retains FcRn binding ability. In some embodiments, antibodies are tested for binding to Fcγ receptors and complement C1q by an ELISA based assay, flow cytometry, SPR, or other methods know to interrogate protein-protein interactions and affinity. In some embodiments, antibodies can be tested for reduced effector functions their ability to activate appropriate cell lines or primary human immune cells in vitro, for example, by assessing their ability to induce expression of activation markers, cytokine/chemokine secretion, proliferation, or cell-killing (e.g. using labeled target cells).

In some embodiments, the anti-CD30L antibodies of this disclosure have a reduced effector function as compared to a human IgG. In general, effector function refers to a biological event resulting from the interaction of an antibody Fc region with an Fc receptor or ligand. In certain instances, non-limiting effector functions include C1q binding, complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (for example, B cell receptor), and B cell activation. In some embodiments, antibody-dependent cell-mediated cytotoxicity (ADCC) refers to a cell-mediated reaction in which nonspecific cytotoxic cells expressing Fc receptors (e.g., natural killer cells, neutrophils, macrophages) recognize bound antibody on a target cell, subsequently causing lysis of the target cell. In some embodiments, complement dependent cytotoxicity (CDC) refers to lysing of a target cells in the presence of complement, where the complement action pathway is initiated by the binding of C1q to antibody bound with the target.

Some Fc regions have a natural lack of effector function, and some Fc regions can comprise mutations that reduce effector functions. For instance, IgG4 has low ADCC and CDC activities and IgG2 has low ADCC activity.

In some embodiments, the anti-CD30L antibodies comprise Fc regions characterized by ADCC that is reduced by at least about 30%, at least about 40%, at least about 50%, at least about 60%, at least about 70% or more as compared to an antibody comprising a non-variant Fc region, such as, an antibody with the same sequence identity but for the substitution(s) that decrease ADCC. The disclosure provides antibodies comprising Fc regions characterized by exhibiting CDC that is reduced by at least about 30%, at least about 40%, at least about 50%, at least about 60%, at least about 70% or more as compared to an antibody comprising a non-variant Fc region, i.e., an antibody with the same sequence identity but for the substitution(s) that decrease CDC. In certain embodiments, the antibodies of this disclosure have reduced effector function as compared with human IgG1.

Non-limiting examples of Fc mutations in IgG1 that may reduce ADCC and/or CDC include substitutions at one or more of positions: 231, 232, 234, 235, 236, 237, 238, 239, 264, 265, 267, 269, 270, 297, 299, 318, 320, 322, 325, 327, 328, 329, 330, and 331 in IgG1, where the numbering system of the constant region is that of the EU index as set forth by Kabat. In certain embodiments, the antibodies of this disclosure have reduced effector function as compared with human IgG1.

In certain embodiments, the recombinant anti-CD30L antibody comprises an IgG1 Fc region comprising an N297A substitution, according to the EU numbering system. In certain embodiments, the recombinant anti-CD30L antibody comprises an IgG1 Fc region comprising an N297Q substitution, according to the EU numbering system. In certain embodiments, the recombinant anti-CD30L antibody comprises an IgG1 Fc region comprising an N297D substitution, according to the EU numbering system. In certain embodiments, the recombinant anti-CD30L antibody comprises an IgG1 Fc region comprising an D265A substitution, according to the EU numbering system. In certain embodiments, the recombinant anti-CD30L antibody comprises an IgG1 Fc region comprising an S228P substitution, according to the EU numbering system. In certain embodiments, the recombinant anti-CD30L antibody comprises an IgG1 Fc region comprising an L235A substitution, according to the EU numbering system. In certain embodiments, the recombinant anti-CD30L antibody comprises an IgG1 Fc region comprising an L237A substitution, according to the EU numbering system. In certain embodiments, the recombinant anti-CD30L antibody comprises an IgG1 Fc region comprising an L234A substitution, according to the EU numbering system. In certain embodiments, the recombinant anti-CD30L antibody comprises an IgG1 Fc region comprising an E233P substitution, according to the EU numbering system. In certain embodiments, the recombinant anti-CD30L antibody comprises an IgG1 Fc region comprising an L234V substitution, according to the EU numbering system. In certain embodiments, the recombinant anti-CD30L antibody comprises an IgG1 Fc region comprising an C236 deletion, according to the EU numbering system. In certain embodiments, the recombinant anti-CD30L antibody comprises an IgG1 Fc region comprising a P238A substitution, according to the EU numbering system. In certain embodiments, the recombinant anti-CD30L antibody comprises an IgG1 Fc region comprising an A327Q substitution, according to the EU numbering system. In certain embodiments, the recombinant anti-CD30L antibody comprises an IgG1 Fc region comprising a P329A substitution, according to the EU numbering system. In certain embodiments, the recombinant anti-CD30L antibody comprises an IgG1 Fc region comprising an P329G substitution, according to the EU numbering system. In certain embodiments, the recombinant anti-CD30L antibody comprises an IgG1 Fc region comprising an L235E substitution, according to the EU numbering system. In certain embodiments, the recombinant anti-CD30L antibody comprises an IgG1 Fc region comprising an P331 S substitution, according to the EU numbering system. In certain embodiments, the recombinant anti-CD30L antibody comprises an IgG1 Fc region comprising an L234F substitution, according to the EU numbering system. In certain embodiments, the recombinant anti-CD30L antibody comprises an IgG1 Fc region comprising a 235G substitution, according to the EU numbering system. In certain embodiments, the recombinant anti-CD30L antibody comprises an IgG1 Fc region comprising an 235Q substitution, according to the EU numbering system. In certain embodiments, the recombinant anti-CD30L antibody comprises an IgG1 Fc region comprising an 235R substitution, according to the EU numbering system. In certain embodiments, the recombinant anti-CD30L antibody comprises an IgG1 Fc region comprising an 235 S substitution, according to the EU numbering system. In certain embodiments, the recombinant anti-CD30L antibody comprises an IgG1 Fc region comprising an 236F substitution, according to the EU numbering system. In certain embodiments, the recombinant anti-CD30L antibody comprises an IgG1 Fc region comprising an 236R substitution, according to the EU numbering system. In certain embodiments, the recombinant anti-CD30L antibody comprises an IgG1 Fc region comprising an 237E substitution, according to the EU numbering system. In certain embodiments, the recombinant anti-CD30L antibody comprises an IgG1 Fc region comprising an 237K substitution, according to the EU numbering system. In certain embodiments, the recombinant anti-CD30L antibody comprises an IgG1 Fc region comprising an 237N substitution, according to the EU numbering system. In certain embodiments, the recombinant anti-CD30L antibody comprises an IgG1 Fc region comprising an 237R substitution, according to the EU numbering system. In certain embodiments, the recombinant anti-CD30L antibody comprises an IgG1 Fc region comprising an 238A substitution, according to the EU numbering system. In certain embodiments, the recombinant anti-CD30L antibody comprises an IgG1 Fc region comprising an 238E substitution, according to the EU numbering system. In certain embodiments, the recombinant anti-CD30L antibody comprises an IgG1 Fc region comprising an 238G substitution, according to the EU numbering system. In certain embodiments, the recombinant anti-CD30L antibody comprises an IgG1 Fc region comprising an 238H substitution, according to the EU numbering system. In certain embodiments, the recombinant anti-CD30L antibody comprises an IgG1 Fc region comprising an 238I substitution, according to the EU numbering system. In certain embodiments, the recombinant anti-CD30L antibody comprises an IgG1 Fc region comprising an 238V substitution, according to the EU numbering system. In certain embodiments, the recombinant anti-CD30L antibody comprises an IgG1 Fc region comprising an 238W substitution, according to the EU numbering system. In certain embodiments, the recombinant anti-CD30L antibody comprises an IgG1 Fc region comprising an 238Y substitution, according to the EU numbering system. In certain embodiments, the recombinant anti-CD30L antibody comprises an IgG1 Fc region comprising an 248A substitution, according to the EU numbering system. In certain embodiments, the recombinant anti-CD30L antibody comprises an IgG1 Fc region comprising an 254D substitution, according to the EU numbering system. In certain embodiments, the recombinant anti-CD30L antibody comprises an IgG1 Fc region comprising an 254E substitution, according to the EU numbering system. In certain embodiments, the recombinant anti-CD30L antibody comprises an IgG1 Fc region comprising an 254G substitution, according to the EU numbering system. In certain embodiments, the recombinant anti-CD30L antibody comprises an IgG1 Fc region comprising an 254H substitution, according to the EU numbering system. In certain embodiments, the recombinant anti-CD30L antibody comprises an IgG1 Fc region comprising an 254I substitution, according to the EU numbering system. In certain embodiments, the recombinant anti-CD30L antibody comprises an IgG1 Fc region comprising an 254N substitution, according to the EU numbering system. In certain embodiments, the recombinant anti-CD30L antibody comprises an IgG1 Fc region comprising an 254P substitution, according to the EU numbering system. In certain embodiments, the recombinant anti-CD30L antibody comprises an IgG1 Fc region comprising an 254Q substitution, according to the EU numbering system. In certain embodiments, the recombinant anti-CD30L antibody comprises an IgG1 Fc region comprising an 254T substitution, according to the EU numbering system. In certain embodiments, the recombinant anti-CD30L antibody comprises an IgG1 Fc region comprising an 254V substitution, according to the EU numbering system. In certain embodiments, the recombinant anti-CD30L antibody comprises an IgG1 Fc region comprising an 255N substitution, according to the EU numbering system. In certain embodiments, the recombinant anti-CD30L antibody comprises an IgG1 Fc region comprising an 256H substitution, according to the EU numbering system. In certain embodiments, the recombinant anti-CD30L antibody comprises an IgG1 Fc region comprising an 256K substitution, according to the EU numbering system. In certain embodiments, the recombinant anti-CD30L antibody comprises an IgG1 Fc region comprising an 256R substitution, according to the EU numbering system. In certain embodiments, the recombinant anti-CD30L antibody comprises an IgG1 Fc region comprising an 256V substitution, according to the EU numbering system. In certain embodiments, the recombinant anti-CD30L antibody comprises an IgG1 Fc region comprising an 264S substitution, according to the EU numbering system. In certain embodiments, the recombinant anti-CD30L antibody comprises an IgG1 Fc region comprising an 265H substitution, according to the EU numbering system. In certain embodiments, the recombinant anti-CD30L antibody comprises an IgG1 Fc region comprising an 265K substitution, according to the EU numbering system. In certain embodiments, the recombinant anti-CD30L antibody comprises an IgG1 Fc region comprising an 265 S sub situation, according to the EU numbering system. In certain embodiments, the recombinant anti-CD30L antibody comprises an IgG1 Fc region comprising an 265Y substitution, according to the EU numbering system. In certain embodiments, the recombinant anti-CD30L antibody comprises an IgG1 Fc region comprising an 267G substitution, according to the EU numbering system. In certain embodiments, the recombinant anti-CD30L antibody comprises an IgG1 Fc region comprising an 267H substitution, according to the EU numbering system. In certain embodiments, the recombinant anti-CD30L antibody comprises an IgG1 Fc region comprising an 267I substitution, according to the EU numbering system. In certain embodiments, the recombinant anti-CD30L antibody comprises an IgG1 Fc region comprising an 267K substitution, according to the EU numbering system. In certain embodiments, the recombinant anti-CD30L antibody comprises an IgG1 Fc region comprising an 268K substitution, according to the EU numbering system. In certain embodiments, the recombinant anti-CD30L antibody comprises an IgG1 Fc region comprising an 269N substitution, according to the EU numbering system. In certain embodiments, the recombinant anti-CD30L antibody comprises an IgG1 Fc region comprising an 269Q substitution, according to the EU numbering system. In certain embodiments, the recombinant anti-CD30L antibody comprises an IgG1 Fc region comprising an 270A substitution, according to the EU numbering system. In certain embodiments, the recombinant anti-CD30L antibody comprises an IgG1 Fc region comprising an 270G substitution, according to the EU numbering system. In certain embodiments, the recombinant anti-CD30L antibody comprises an IgG1 Fc region comprising an 270M substitution, according to the EU numbering system. In certain embodiments, the recombinant anti-CD30L antibody comprises an IgG1 Fc region comprising an 270N substitution, according to the EU numbering system. In certain embodiments, the recombinant anti-CD30L antibody comprises an IgG1 Fc region comprising an 271T substitution, according to the EU numbering system. In certain embodiments, the recombinant anti-CD30L antibody comprises an IgG1 Fc region comprising an 272N substitution, according to the EU numbering system. In certain embodiments, the recombinant anti-CD30L antibody comprises an IgG1 Fc region comprising an 279F substitution, according to the EU numbering system. In certain embodiments, the recombinant anti-CD30L antibody comprises an IgG1 Fc region comprising an 279K substitution, according to the EU numbering system. In certain embodiments, the recombinant anti-CD30L antibody comprises an IgG1 Fc region comprising an 279L substitution, according to the EU numbering system. In certain embodiments, the recombinant anti-CD30L antibody comprises an IgG1 Fc region comprising an 292E substitution, according to the EU numbering system. In certain embodiments, the recombinant anti-CD30L antibody comprises an IgG1 Fc region comprising an 292F substitution, according to the EU numbering system. In certain embodiments, the recombinant anti-CD30L antibody comprises an IgG1 Fc region comprising an 292G substitution, according to the EU numbering system. In certain embodiments, the recombinant anti-CD30L antibody comprises an IgG1 Fc region comprising an 292I substitution, according to the EU numbering system. In certain embodiments, the recombinant anti-CD30L antibody comprises an IgG1 Fc region comprising an 293 S substitution, according to the EU numbering system. In certain embodiments, the recombinant anti-CD30L antibody comprises an IgG1 Fc region comprising an 301W substitution, according to the EU numbering system. In certain embodiments, the recombinant anti-CD30L antibody comprises an IgG1 Fc region comprising an 304E sub situation, according to the EU numbering system. In certain embodiments, the recombinant anti-CD30L antibody comprises an IgG1 Fc region comprising an 311E substitution, according to the EU numbering system. In certain embodiments, the recombinant anti-CD30L antibody comprises an IgG1 Fc region comprising an 311G substitution, according to the EU numbering system. In certain embodiments, the recombinant anti-CD30L antibody comprises an IgG1 Fc region comprising an 311 S substitution, according to the EU numbering system. In certain embodiments, the recombinant anti-CD30L antibody comprises an IgG1 Fc region comprising an 316F substitution, according to the EU numbering system. In certain embodiments, the recombinant anti-CD30L antibody comprises an IgG1 Fc region comprising an 327T substitution, according to the EU numbering system. In certain embodiments, the recombinant anti-CD30L antibody comprises an IgG1 Fc region comprising an 328V substitution, according to the EU numbering system. In certain embodiments, the recombinant anti-CD30L antibody comprises an IgG1 Fc region comprising an 329Y substitution, according to the EU numbering system. In certain embodiments, the recombinant anti-CD30L antibody comprises an IgG1 Fc region comprising an 330R substitution, according to the EU numbering system. In certain embodiments, the recombinant anti-CD30L antibody comprises an IgG1 Fc region comprising an 339E substitution, according to the EU numbering system. In certain embodiments, the recombinant anti-CD30L antibody comprises an IgG1 Fc region comprising an 339L substitution, according to the EU numbering system. In certain embodiments, the recombinant anti-CD30L antibody comprises an IgG1 Fc region comprising an 343I substitution, according to the EU numbering system. In certain embodiments, the recombinant anti-CD30L antibody comprises an IgG1 Fc region comprising an 343V substitution, according to the EU numbering system. In certain embodiments, the recombinant anti-CD30L antibody comprises an IgG1 Fc region comprising an 373A substitution, according to the EU numbering system. In certain embodiments, the recombinant anti-CD30L antibody comprises an IgG1 Fc region comprising an 373G substitution, according to the EU numbering system. In certain embodiments, the recombinant anti-CD30L antibody comprises an IgG1 Fc region comprising an 373 S substitution, according to the EU numbering system. In certain embodiments, the recombinant anti-CD30L antibody comprises an IgG1 Fc region comprising an 376E substitution, according to the EU numbering system. In certain embodiments, the recombinant anti-CD30L antibody comprises an IgG1 Fc region comprising an 376W substitution, according to the EU numbering system. In certain embodiments, the recombinant anti-CD30L antibody comprises an IgG1 Fc region comprising an 376Y substitution, according to the EU numbering system. In certain embodiments, the recombinant anti-CD30L antibody comprises an IgG1 Fc region comprising an 380D substitution, according to the EU numbering system. In certain embodiments, the recombinant anti-CD30L antibody comprises an IgG1 Fc region comprising an 382D substitution, according to the EU numbering system. In certain embodiments, the recombinant anti-CD30L antibody comprises an IgG1 Fc region comprising an 382P substitution, according to the EU numbering system. In certain embodiments, the recombinant anti-CD30L antibody comprises an IgG1 Fc region comprising an 385P substitution, according to the EU numbering system. In certain embodiments, the recombinant anti-CD30L antibody comprises an IgG1 Fc region comprising an 424H substitution, according to the EU numbering system. In certain embodiments, the recombinant anti-CD30L antibody comprises an IgG1 Fc region comprising an 424M substitution, according to the EU numbering system. In certain embodiments, the recombinant anti-CD30L antibody comprises an IgG1 Fc region comprising an 424V substitution, according to the EU numbering system. In certain embodiments, the recombinant anti-CD30L antibody comprises an IgG1 Fc region comprising an 434I substitution, according to the EU numbering system. In certain embodiments, the recombinant anti-CD30L antibody comprises an IgG1 Fc region comprising an 438G substitution, according to the EU numbering system. In certain embodiments, the recombinant anti-CD30L antibody comprises an IgG1 Fc region comprising an 439E substitution, according to the EU numbering system. In certain embodiments, the recombinant anti-CD30L antibody comprises an IgG1 Fc region comprising an 439H substitution, according to the EU numbering system. In certain embodiments, the recombinant anti-CD30L antibody comprises an IgG1 Fc region comprising an 439Q substitution, according to the EU numbering system. In certain embodiments, the recombinant anti-CD30L antibody comprises an IgG1 Fc region comprising an 440A substitution, according to the EU numbering system. In certain embodiments, the recombinant anti-CD30L antibody comprises an IgG1 Fc region comprising an 440D substitution, according to the EU numbering system. In certain embodiments, the recombinant anti-CD30L antibody comprises an IgG1 Fc region comprising an 440E substitution, according to the EU numbering system. In certain embodiments, the recombinant anti-CD30L antibody comprises an IgG1 Fc region comprising an 440F substitution, according to the EU numbering system. In certain embodiments, the recombinant anti-CD30L antibody comprises an IgG1 Fc region comprising an 440M substitution, according to the EU numbering system. In certain embodiments, the recombinant anti-CD30L antibody comprises an IgG1 Fc region comprising an 440T Fc region substitution, according to the EU numbering system. In certain embodiments, the recombinant anti-CD30L antibody comprises an IgG1 Fc region comprising an 440V substitution, according to the EU numbering system.

In certain embodiments, the recombinant anti-CD30L antibody comprises a Fc region selected from the representative sequences disclosed in Table 1.

In certain embodiments, the recombinant anti-CD30L antibody comprises an IgG1 Fc region comprising E233P, according to the EU numbering system. In certain embodiments, the recombinant anti-CD30L antibody comprises an IgG4 Fc region comprising S228P and L235E. In certain embodiments, the recombinant anti-CD30L antibody comprises an IgG1 Fc region comprising L235E, according to the EU numbering system. In certain embodiments, the recombinant anti-CD30L antibody comprises an IgG1 Fc region comprising L234A and L235A, according to the EU numbering system. In certain embodiments, the recombinant anti-CD30L antibody comprises an IgG1 Fc region comprising L234A, L235A, and G237A, according to the EU numbering system. In certain embodiments, the recombinant anti-CD30L antibody comprises an IgG1 Fc region comprising L234A, L235A, P329G, according to the EU numbering system. In certain embodiments, the recombinant anti-CD30L antibody comprises an IgG1 Fc region comprising L234F, L235E, and P331S, according to the EU numbering system. In certain embodiments, the recombinant anti-CD30L antibody comprises an IgG1 Fc region comprising L234A, L235E, and G237A, according to the EU numbering system. In certain embodiments, the recombinant anti-CD30L antibody comprises an IgG1 Fc region comprising L234A, L235E, G237A, and P331 S, according to the EU numbering system. In certain embodiments, the recombinant anti-CD30L antibody comprises an IgG1 Fc region comprising L234A, L235A, G237A, P238S, H268A, A330S, and P331S (IgG1), according to the EU numbering

TABLE 1

Mutations Abrogating Effector Function

| Mutation(s) | Effect |
|---|---|
| E233P | Decreases binding to FcγRI, II, III |
| S228P, L235E SPLE in IgG4 | Decreases binding to FcγRI |
| L235E | Decreases binding to FcγRs |
| L234A, L235A | Decreases binding to FcγRI, II, III |
| L234A, L235A, G237A | Decreases binding to FcγRI, II, III, C1q |
| L234A, L235A, P329G | Decreases binding to FcγRI, II, III, C1q |
| L234F, L235E, P331S | Decreases binding to FcγRI, II, III, C1q |
| L234A, L235E, G237A | Decreases binding to FcγRI, II, III, C1q |
| L234A, L235E, G237A, P331S | Decreases binding to FcγRI, II, III, C1q |
| L234A, L235A, G237A, P238S, H268A, A330S, P331S (IgG1σ) | Decreases binding to FcγRI, IIa, IIb, IIIa |
| L234A, L235A, P329A | Decreases binding to FcγRI, II, III, C1q |
| G236R, L328R | Decreases binding to FcγRI, II, III |
| G237A | Decreases binding to FcγRII |
| F241A | Decreases binding to C1q |
| V264A | Decreases binding to C1q |
| D265A | Decreases binding to FcγRI, II, III |
| D265A, N297A | Decreases binding to FcγRI, II, III, C1q |
| D265A, N297G | Decreases binding to FcγRI, II, III, C1q |
| D270A | Decreases binding to C1q |
| N297A, G, D, Q | Elimination of N-linked glycosylation |
| | Decreases binding to FcγRI, II, III, C1q |
| P329A, G, R | Decreases binding to C1q |
| A330L | Decreases binding to C1q |
| P331A, S | Diminished C1q binding |
| IgG2 | Decreases binding to FcγRs |
| IgG4 | Decreases binding to FcγRs; Does not activate complement system |
| S228P | Prevent IgG4 Fab arm exchange |
| S228P, F234A, L235A (IgG4) | Decreases binding to FcγRI, IIa, IIIa |
| IgG2-IgG4 cross-subclass (IgG2/G4) | Decreases binding to FcγRI, II, III, C1q |
| IgG2-IgG3 cross-subclass | Decreases binding to FcγRs; Decreases binding to C1q |
| H268Q, V309L, A330S, P331S (IgG2m4) | Decreases binding to FcγRI, II, III, C1q |
| V234A, G237A, P238S, H268A, V309L, A330S, P331S (IgG2σ) | Decreases binding to FcγRI, IIa, IIb, IIIa, C1q |
| High mannose glycosylation | Decreases binding to C1q | system. In certain embodiments, the recombinant anti-CD30L antibody comprises an IgG1 Fc region comprising L234A, L235A, and P329A, according to the EU numbering system. In certain embodiments, the recombinant anti-CD30L antibody comprises an IgG1 Fc region comprising G236R and L328R, according to the EU numbering system. In certain embodiments, the recombinant anti-CD30L antibody comprises an IgG1 Fc region comprising G237A, according to the EU numbering system. In certain embodiments, the recombinant anti-CD30L antibody comprises an IgG1 Fc region comprising F241A, according to the EU numbering system. In certain embodiments, the recombinant anti-CD30L antibody comprises an IgG1 Fc region comprising V264A, according to the EU numbering system. In certain embodiments, the recombinant anti-CD30L antibody comprises an IgG1 Fc region comprising D265A, according to the EU numbering system. In certain embodiments, the recombinant anti-CD30L antibody comprises an IgG1 Fc region comprising D265A and N297A, according to the EU numbering system. In certain embodiments, the recombinant anti-CD30L antibody comprises an IgG1 Fc region comprising D265A and N297G, according to the EU numbering system. In certain embodiments, the recombinant anti-CD30L antibody comprises an IgG1 Fc region comprising D270A, according to the EU numbering system. In certain embodiments, the recombinant anti-CD30L antibody comprises an IgG1 Fc region comprising N297A, according to the EU numbering system. In certain embodiments, the recombinant anti-CD30L antibody comprises an IgG1 Fc region comprising N297G, according to the EU numbering system. In certain embodiments, the recombinant anti-CD30L antibody comprises an IgG1 Fc region comprising N297D, according to the EU numbering system. In certain embodiments, the recombinant anti-CD30L antibody comprises an IgG1 Fc region comprising N297Q, according to the EU numbering system. In certain embodiments, the recombinant anti-CD30L antibody comprises an IgG1 Fc region comprising P329A, according to the EU numbering system. In certain embodiments, the recombinant anti-CD30L antibody comprises an IgG1 Fc region comprising P329G, according to the EU numbering system. In certain embodiments, the recombinant anti-CD30L antibody comprises an IgG1 Fc region comprising P329R, according to the EU numbering system. In certain embodiments, the recombinant anti-CD30L antibody comprises an IgG1 Fc region comprising A330L, according to the EU numbering system. In certain embodiments, the recombinant anti-CD30L antibody comprises an IgG1 Fc region comprising P331A, according to the EU numbering system. In certain embodiments, the recombinant anti-CD30L antibody comprises an IgG1 Fc region comprising P331S, according to the EU numbering system. In certain embodiments, the recombinant anti-CD30L antibody comprises an IgG2 Fc region. In certain embodiments, the recombinant anti-CD30L antibody comprises an IgG4 Fc region. In certain embodiments, the recombinant anti-CD30L antibody comprises an IgG4 Fc region comprising S228P, according to the EU numbering system. In certain embodiments, the recombinant anti-CD30L antibody comprises an IgG4 Fc region comprising S228P, F234A, and L235A, according to the EU numbering system. In certain embodiments, the recombinant anti-CD30L antibody comprises an IgG2-IgG4 cross-subclass (IgG2/G4) Fc region. In certain embodiments, the recombinant anti-CD30L antibody comprises an IgG2-IgG3 cross-subclass Fc region. In certain embodiments, the recombinant anti-CD30L antibody comprises an IgG2 Fc region comprising H268Q, V309L, A330S, and P331S, according to the EU numbering system. In certain embodiments, the recombinant anti-CD30L antibody comprises an IgG2 Fc region comprising V234A, G237A, P238S, H268A, V309L, A330S, and P331S, according to the EU numbering system. In certain embodiments, the recombinant anti-CD30L antibody comprises a Fc region comprising high mannose glycosylation.

In certain embodiments, the recombinant anti-CD30L antibody comprises an IgG4 Fc region comprising a S228P substitution, according to the EU numbering system. In certain embodiments, the recombinant anti-CD30L antibody comprises an IgG4 Fc region comprising an A330S substitution, according to the EU numbering system. In certain embodiments, the recombinant anti-CD30L antibody comprises an IgG4 Fc region comprising a P331S substitution, according to the EU numbering system.

In certain embodiments, the recombinant anti-CD30L antibody comprises an IgG2 Fc region comprising an A330S substitution, according to the EU numbering system. In certain embodiments, the recombinant anti-CD30L antibody comprises an IgG2 Fc region comprising an P331S substitution, according to the EU numbering system. In certain embodiments, the recombinant anti-CD30L antibody comprises an IgG2 Fc region comprising an 234A substitution, according to the EU numbering system. In certain embodiments, the recombinant anti-CD30L antibody comprises an IgG2 Fc region comprising an 237A substitution, according to the EU numbering system.

In some embodiments, assessment of ADCC activity of an anti-CD30L antibody comprises adding the antibody to target cells in combination with immune effector cells, which may be activated by the antigen-antibody complexes resulting in cytolysis of the target cell. Cytolysis may be detected by the release of label (for example, radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp Med 166:1351-1361; Wilkinson et al., 2001, J Immunol Methods 258:183-191; Patel et al., 1995 J Immunol Methods 184:29-38. Alternatively, or additionally, ADCC activity of the antibody of interest may be assessed in vivo, e.g., in an animal model such as that disclosed in Clynes et al., 1998, PNAS USA 95:652-656.

In some embodiments, antibodies comprising a Fc region herein exhibit decreased ADCC activities as compared to an unmodified antibody (e.g., an antibody with human IgG1). In some embodiments, the antibodies herein exhibit ADCC activities that are at least 2-fold, or at least 3-fold, or at least 5-fold or at least 10-fold or at least 50-fold or at least 100-fold less than that of an unmodified antibody. In some embodiments, antibodies herein exhibit ADCC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody. In certain embodiments, antibodies herein have no detectable ADCC activity. In certain embodiments, the reduction and/or ablatement of ADCC activity may be attributed to the reduced affinity antibodies of the invention exhibit for Fc ligands and/or receptors.

In some embodiments, an assessment of complement activation, a CDC assay, may be performed as described in Gazzano-Santoro et al., 1996, J. Immunol. Methods, 202: 163. In some embodiments, antibodies comprising Fc regions described herein exhibit decreased affinities to C1q relative to an unmodified antibody (e.g., human IgG1). In some embodiments, antibodies herein exhibit affinities for C1q receptor that are at least 2 fold, or at least 3 fold, or at least 5 fold, or at least 7 fold, or at least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than an unmodified antibody. In some embodiments, antibodies herein exhibit affinities for C1q that are at least 90%, at least 80%, at least 70%, at least 60%, at least 50%, at least 40%, at least 30%, at least 20%, at least 10%, or at least 5% less than an unmodified antibody.

In some embodiments, antibodies comprising Fc regions described herein exhibit decreased CDC activities as compared to an unmodified antibody (e.g., human IgG1). In some embodiments, antibodies herein exhibit CDC activities that are at least 2-fold, or at least 3-fold, or at least 5-fold or at least 10-fold or at least 50-fold or at least 100-fold less than that of an unmodified antibody. In some embodiments, antibodies herein exhibit CDC activities that are reduced by at least 10%, or at least 20%, or by at least 300%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody. In certain embodiments, antibodies herein exhibit no detectable CDC activities. In some embodiments, the reduction and/or ablatement of CDC activity may be attributed to the reduced affinity antibodies of the invention exhibit for Fc ligands and/or receptors.

Accordingly, further provided and described herein are anti-CD30L antibodies comprising a variant Fc region (for example, harboring mutations) that reduce the cytotoxic response (for example, ADCC or CDC) elicited by an anti-CD30L antibody. In some embodiments, an anti-CD30L antibody described herein comprises a Fc region comprising SEQ ID NO: 500 or a sequence at least about 90%, 91%, 92%, 93%, 94%, 95%, 96%, 97%, 98%, or 99% identical to SEQ ID NO: 501. In some embodiments, an anti-CD30L antibody described herein comprises a Fc region comprising SEQ ID NO: 501 or a sequence at least about 90%, 91%, 92%, 93%, 94%, 95%, 96%, 97%, 98%, or 99% identical to SEQ ID NO: 501. In some embodiments, an anti-CD30L antibody described herein comprises a Fc region comprising SEQ ID NO: 502 or a sequence at least about 90%, 91%, 92%, 93%, 94%, 95%, 96%, 97%, 98%, or 99% identical to SEQ ID NO: 502. In some embodiments, an anti-CD30L antibody described herein comprises a Fc region comprising SEQ ID NO: 503 or a sequence at least about 90%, 91%, 92%, 93%, 94%, 95%, 96%, 97%, 98%, or 99% identical to SEQ ID NO: 503. In some embodiments, an anti-CD30L antibody described herein comprises a Fc region comprising SEQ ID NO: 504 or a sequence at least about 90%, 91%, 92%, 93%, 94%, 95%, 96%, 97%, 98%, or 99% identical to SEQ ID NO: 504. In some embodiments, an anti-CD30L antibody described herein comprises a Fc region comprising SEQ ID NO: 505 or a sequence at least about 90%, 91%, 92%, 93%, 94%, 95%, 96%, 97%, 98%, or 99% identical to SEQ ID NO: 505. In some embodiments, an anti-CD30L antibody described herein comprises a Fc region comprising SEQ ID NO: 506 or a sequence at least about 90%, 91%, 92%, 93%, 94%, 95%, 96%, 97%, 98%, or 99% identical to SEQ ID NO: 506. In some embodiments, an anti-CD30L antibody described herein comprises a Fc region comprising SEQ ID NO: 507 ora sequence at least about 90%, 91%, 92%, 93%, 94%, 95%, 96%, 97%, 98%, or 99% identical to SEQ ID NO: 507. In some embodiments, an anti-CD30L antibody described herein comprises a Fc region comprising SEQ ID NO: 508 or a sequence at least about 90%, 91%, 92%, 93%, 94%, 95%, 96%, 97%, 98%, or 99% identical to SEQ ID NO: 508. In some embodiments, an anti-CD30L antibody described herein comprises a Fc region comprising SEQ ID NO: 509 or a sequence at least about 90%, 91%, 92%, 93%, 94%, 95%, 96%, 97%, 98%, or 99% identical to SEQ ID NO: 509. In some embodiments, an anti-CD30L antibody described herein comprises a Fc region comprising SEQ ID NO: 510 or a sequence at least about 90%, 91%, 92%, 93%, 94%, 95%, 96%, 97%, 98%, or 99% identical to SEQ ID NO: 510. In some embodiments, an anti-CD30L antibody described herein comprises a Fc region comprising SEQ ID NO: 511 or a sequence at least about 90%, 91%, 92%, 93%, 94%, 95%, 96%, 97%, 98%, or 99% identical to SEQ ID NO: 511. In some embodiments, an anti-CD30L antibody described herein comprises a Fc region comprising SEQ ID NO: 512 or a sequence at least about 90%, 91%, 92%, 93%, 94%, 95%, 96%, 97%, 98%, or 99% identical to SEQ ID NO: 512.

In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises (a) a CDR-H1 comprising the amino acid sequence set forth in any one of SEQ ID NOs: 100-109; (b) a CDR-H2 comprising the amino acid sequence set forth in any one of SEQ ID NOs: 140-149; (c) an immunoglobulin heavy chain CDR3 (CDR-H3) comprising the amino acid sequence set forth in any one of SEQ ID NOs: 180-189; (d) a CDR-L1 comprising the amino acid sequence set forth in any one of SEQ ID NOs: 300-309; (e) a CDR-L2 comprising the amino acid sequence set forth in any one of SEQ ID NOs: 340-349; and/or (f) a CDR-L3 comprising the amino acid sequence set forth in any one of SEQ ID NOs: 380-389. In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 1 and 2; and/or (b) the immunoglobulin variable region light chain comprises an amino acid sequence having at least about 90, 95, 97, 98, 99, or 100% sequence identity to any one of SEQ ID NOs: 3 and 4. In certain embodiments, the anti-CD30L antibody comprises a Fc region comprising the amino acid sequence as set forth in any one of SEQ ID NOs: 500-512 or a sequence at least about 90, 91, 92, 93, 94, 95, 96, 97, 98, or 99% identical to SEQ ID NOs: 500-512. In certain embodiments, the anti-CD30L antibody comprises a Fc region comprising one or more of the mutations as set forth in Table 1.

In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises (a) a CDR-H1 comprising the amino acid sequence set forth in any one of SEQ ID NOs: 110-119; (b)

a CDR-H2 comprising the amino acid sequence set forth in any one of SEQ ID NOs: 150-159; (c) an immunoglobulin heavy chain CDR3 (CDR-H3) comprising the amino acid sequence set forth in any one of SEQ ID NOs: 190-199; (d) a CDR-L1 comprising the amino acid sequence set forth in any one of SEQ ID NOs: 310-319; (e) a CDR-L2 comprising the amino acid sequence set forth in any one of SEQ ID NOs: 350-359; and/or (f) a CDR-L3 comprising the amino acid sequence set forth in any one of SEQ ID NOs: 390-399. In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 5 and 6; and/or (b) the immunoglobulin variable region light chain comprises an amino acid sequence having at least about 90, 95, 97, 98, 99, or 100% sequence identity to any one of SEQ ID NOs: 7 and 8. In certain embodiments, the anti-CD30L antibody comprises a Fc region comprising the amino acid sequence as set forth in any one of SEQ ID NOs: 500-512 or a sequence at least about 90, 91, 92, 93, 94, 95, 96, 97, 98, or 99% identical to SEQ ID NOs: 500-512. In certain embodiments, the anti-CD30L antibody comprises a Fc region comprising one or more of the mutations as set forth in Table 1.

In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises (a) a CDR-H1 comprising the amino acid sequence set forth in any one of SEQ ID NOs: 120-129; (b) a CDR-H2 comprising the amino acid sequence set forth in any one of SEQ ID NOs: 160-169; (c) an immunoglobulin heavy chain CDR3 (CDR-H3) comprising the amino acid sequence set forth in any one of SEQ ID NOs: 200-209; (d) a CDR-L1 comprising the amino acid sequence set forth in any one of SEQ ID NOs: 320-329; (e) a CDR-L2 comprising the amino acid sequence set forth in any one of SEQ ID NOs: 360-369; and/or (f) a CDR-L3 comprising the amino acid sequence set forth in any one of SEQ ID NOs: 400-409. In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 9 and 10; and/or (b) the immunoglobulin variable region light chain comprises an amino acid sequence having at least about 90, 95, 97, 98, 99, or 100% sequence identity to any one of SEQ ID NOs: 11 and 12. In certain embodiments, the anti-CD30L antibody comprises a Fc region comprising the amino acid sequence as set forth in any one of SEQ ID NOs: 500-512 or a sequence at least about 90, 91, 92, 93, 94, 95, 96, 97, 98, or 99% identical to SEQ ID NOs: 500-512. In certain embodiments, the anti-CD30L antibody comprises a Fc region comprising one or more of the mutations as set forth in Table 1.

In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises (a) a CDR-H1 comprising the amino acid sequence set forth in any one of SEQ ID NOs: 130-139; (b) a CDR-H2 comprising the amino acid sequence set forth in any one of SEQ ID NOs: 170-179; (c) an immunoglobulin heavy chain CDR3 (CDR-H3) comprising the amino acid sequence set forth in any one of SEQ ID NOs: 210-219; (d) a CDR-L1 comprising the amino acid sequence set forth in any one of SEQ ID NOs: 330-339; (e) a CDR-L2 comprising the amino acid sequence set forth in any one of SEQ ID NOs: 370-379; and/or (f) a CDR-L3 comprising the amino acid sequence set forth in any one of SEQ ID NOs: 410-419. In certain embodiments, the recombinant antibody or antigen binding fragment thereof comprises a variant Fc region (for example, harboring mutations) that reduce the cytotoxic response (for example, ADCC or CDC) elicited by an anti-CD30L antibody and wherein the anti-CD30L antibody comprises an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 13 and 14; and/or (b) the immunoglobulin variable region light chain comprises an amino acid sequence having at least about 90, 95, 97, 98, 99, or 100% sequence identity to any one of SEQ ID NOs: 15 and 16. In certain embodiments, the anti-CD30L antibody comprises a Fc region comprising the amino acid sequence as set forth in any one of SEQ ID NOs: 500-512 or a sequence at least about 90, 91, 92, 93, 94, 95, 96, 97, 98, or 99% identical to SEQ ID NOs: 500-512. In certain embodiments, the anti-CD30L antibody comprises a Fc region comprising one or more of the mutations as set forth in Table 1.

4.5 Pharmaceutical Compositions

Compositions comprising the anti-CD30L recombinant antibodies or antigen binding fragments thereof of the current disclosure are included in a pharmaceutical composition comprising one or more pharmaceutically acceptable excipients, carriers, and diluents. As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. In certain embodiments, the antibodies of the current disclosure are administered suspended in a sterile solution. In certain embodiments, the solution comprises about 0.9% NaCl. In certain embodiments, the solution comprises about 5.0% dextrose. In certain embodiments, the solution further comprises one or more of: buffers, for example, acetate, citrate, histidine, succinate, phosphate, bicarbonate and hydroxymethylaminomethane (Tris); surfactants, for example, polysorbate 80 (Tween 80), polysorbate 20 (Tween 20), and poloxamer 188; polyol/disaccharide/polysaccharides, for example, glucose, dextrose, mannose, mannitol, sorbitol, sucrose, trehalose, and dextran 40; amino acids, for example, glycine or arginine; antioxidants, for example, ascorbic acid, methionine; or chelating agents, for example, EDTA or EGTA.

In certain embodiments, the anti-CD30L antibodies of the current disclosure are shipped/stored lyophilized and reconstituted before administration. In certain embodiments, lyophilized antibody formulations comprise a bulking agent such as, mannitol, sorbitol, sucrose, trehalose, dextran 40, or combinations thereof. The lyophilized formulation can be contained in a vial comprised of glass or other suitable non-reactive material. The antibodies when formulated, whether reconstituted or not, can be buffered at a certain pH, generally less than 8.0. In certain embodiments, the pH can be between 4.5 and 7.5, 4.5 and 6.0, 4.5 and 5.5, 7.5 and 5.0, or 5.0 and 8.0.

Also described herein are kits comprising one or more of the anti-CD30L antibodies described herein in a suitable container and one or more additional components selected from: instructions for use; a diluent, an excipient, a carrier, and a device for administration.

4.6 Methods of Treatment

The recombinant anti-CD30L antibodies or antigen binding fragments thereof described herein are useful in various embodiments for treating or ameliorating an autoimmune disorder in an individual. For example, in some embodiments, the recombinant anti-CD30L antibodies or antigen binding fragments thereof are useful in methods of treating an autoimmune disorder in an individual, wherein the method comprises administering the recombinant anti-CD30L antibodies or antigen binding fragments thereof to the individual. Accordingly, provided methods of treating an autoimmune disorder in an individual, wherein the method comprises administering the recombinant anti-CD30L antibodies or antigen binding fragments thereof to the individual, thereby treating or meliorating the immune disorder. In certain embodiments, the autoimmune disorder is inflammatory bowel disease (IBD). In certain embodiments, the inflammatory bowel disease (IBD) is Crohn's disease (CD), ulcerative colitis (UC), and/or fibrosis. In certain instances, Inflammatory bowel disease (IBD) refers to a chronic disorder characterized by inflammation of the gastrointestinal tract. IBD encompasses and/or includes ulcerative colitis, which affects the large intestine and/or rectum, and Crohn's disease, which can affect the entire gastrointestinal system or be localized to the small intestine (ileum) and regions of the large intestine.

The terms "patient" "individual" or "subject" are used interchangeably and refer to any animal, including, but not limited to, humans, non-human primates, rodents, and domestic and game animals, which is to be the recipient of a particular treatment. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In various embodiments, a subject can be one who has been previously diagnosed with or identified as suffering from or having a condition in need of treatment. In certain embodiments, the subject is a human. In various other embodiments, the subject previously diagnosed with or identified as suffering from or having a condition may or may not have undergone treatment for a condition. In yet other embodiments, a subject can also be one who has not been previously diagnosed as having a condition (i.e., a subject who exhibits one or more risk factors for a condition). An "individual in need" of treatment for a particular condition can be a subject having that condition, diagnosed as having that condition, or at risk of developing that condition. In some embodiments, the individual is a "patient," that has been diagnosed with a disease or condition described herein.

In certain embodiments, administering the recombinant anti-CD30L antibodies or antigen binding fragments thereof comprises administering a therapeutically effective amount of the recombinant anti-CD30L antibodies or antigen binding fragments thereof. In certain instances, the term "therapeutically effective amount" refers to an amount of an antibody, polypeptide, polynucleotide, small organic molecule, or other drug effective to "treat" a disease or disorder in a subject or mammal. In certain instances, therapeutically effective amount of the drug reduces the severity of symptoms of the disease or disorder. In some embodiments, the disease or disorder comprises inflammatory bowel disease (IBD), Crohn's disease (CD), or ulcerative colitis (UC). In certain embodiments, the IBD, CD, and/or UC are severe or medically refractory forms of the IBD, CD, and/or UC. Non-limiting examples of symptoms of IBD, CD, and/or UC include, but are not limited to, diarrhea, fever, fatigue, abdominal pain, abdominal cramping, inflammation, ulceration, nausea, vomiting, bleeding, blood in stool, reduced appetite, and weight loss.

In certain instances, the terms, "treat" or "treating" as used herein refer to both therapeutic treatment and prophylactic or preventative measures (e.g., disease progression), wherein the object is to prevent or slow down (lessen) the targeted pathologic condition. In some embodiments provided herein, individuals in need of treatment include those already with a disease or condition, as well as those susceptible to develop the disease or condition. In additional embodiments, the disease or condition comprises an inflammatory disease or autoimmune condition.

The recombinant anti-CD30L antibodies or antigen binding fragments thereof described herein are further useful in various embodiments for inhibiting, reducing, and/or preventing an inflammatory immune response or immune activation in an individual, wherein the method comprises administering the recombinant anti-CD30L antibodies or antigen binding fragments thereof. In certain instances, the inflammatory immune response or immune activation comprises the expression, release, and/or activation of cytokine molecules and signaling pathways. In certain instances, cytokines is a generic term for proteins released by one cell population which act on another cell as intercellular mediators. Examples of such cytokines are lymphokines, monokines, and traditional polypeptide hormones. Included among the cytokines are transforming growth factors (TGFs) such as TGF-$\alpha$ and TGF-$\beta$; insulin-like growth factor-I and —II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-10, IL-11, IL-12, IL-13, IL-17, IL-21, IL-22, IL-26; a tumor necrosis factor such as TNF-$\alpha$ or TNF-$\beta$; and other polypeptide factors including LIF and kit ligand (KL). The anti-CD30L antibodies are useful for reducing the expression/secretion of pro-inflammatory cytokines such as, for example, IL-1, IL-1$\alpha$, IL-2, IL-6, IL-7, IL-8, IL-12, IL-23, interferon-$\alpha$, -$\beta$, and -$\gamma$, and GM-CSF. Without being bound by theory, pro-inflammatory cytokines are released by inflammatory T cell subsets such as $T_h1$ or $T_h17$ cells, which play a role in many immune mediated pathologies including inflammatory bowel disease, ulcerative colitis, and Crohn's disease. Thus, effective reduction or blockade of these pro-inflammatory cytokines or interleukins addresses a key etiology of many autoimmune and inflammatory disorders. In another instance, the inflammatory immune response or immune activation comprises apoptosis of cells affected by an autoimmune disorder. In another instance, the inflammatory immune response or immune activation comprises the presence or activation of immune cells (e.g. macrophages, T cells, T helper cells, natural killer cells, etc.) in a tissue affected by an autoimmune disorder. In certain embodiments, immune cells encompass any cell derived from a hematopoietic stem cell that plays a role in the immune response. Immune cells include, without limitation, lymphocytes, such as T cells and B cells, antigen-presenting cells (APC), dendritic cells, monocytes, macrophages, natural killer (NK) cells, mast cells, basophils, eosinophils, or neutrophils, as well as any progenitors of such cells. In certain embodiments, the immune cell is a T cell. In certain embodiments, T cells include all cells within the T cell lineage, including thymocytes, immature T cells, mature T cells and the like. Thus, T cells include CD4$^+$ T cells, CD8$^+$ T cells, T helper ($T_h$) cells (for example, $T_h1$, $T_h2$ and $T_h17$ cells) and T regulatory ($T_{reg}$) cells.

Accordingly, provided herein are methods if inhibiting, reducing, and/or preventing an inflammatory immune response or immune activation in an individual. In some embodiments, the inflammatory immune response or immune activation is characterized by the presence or activation of cytokine signaling molecules, the presence or activation of cellular apoptosis, and/or the presence or activation of immune cells. In certain embodiments, the presence or activation of cytokine signaling molecules, the presence or activation of cellular apoptosis, and/or the presence or activation of immune cells is the result of an autoimmune disorder. In certain embodiments, the presence or activation of cytokine signaling molecules, the presence or activation of cellular apoptosis, and/or the presence or activation of immune cells is localized to a specific tissue affected by the autoimmune disorder. In certain embodiments, the autoimmune disease or disorder comprises inflammatory bowel disease (IBD), Crohn's disease (CD), or ulcerative colitis (UC). In certain embodiments, the IBD, CD, and/or UC are severe or medically refractory forms of the IBD, CD, and/or UC.

Furthermore, the recombinant anti-CD30L antibodies or antigen binding fragments thereof described herein are useful for inhibiting and/or reducing binding of a CD30L molecule to a CD30 molecule. In some embodiments, the recombinant anti-CD30L antibodies or antigen binding fragments thereof described herein are useful for preventing an interaction inhibiting and/or reducing binding of a CD30L molecule to a CD30 molecule in an individual. In some embodiments, inhibiting and/or reducing binding of a CD30L molecule to a CD30 molecule prevents, reduces, or inhibits an inflammatory immune response and/or the activation of immune cells, as described herein. Accordingly, provided are method of inhibiting and/or reducing binding of a CD30L molecule to a CD30 molecule, wherein the method comprises administering the recombinant anti-CD30L antibodies or antigen binding fragments thereof described herein to the individual. In certain embodiments, the individual comprises an autoimmune disorder. In certain embodiments, the autoimmune disorder comprises inflammatory bowel disease (IBD), Crohn's disease (CD), or ulcerative colitis (UC). In certain embodiments, the IBD, CD, and/or UC are severe or medically refractory forms of the IBD, CD, and/or UC.

4.7 Exemplary Embodiments

As described herein, provided are recombinant antibodies and/or antigen binding fragments thereof that binds CD30L, wherein the antibody or antigen binding fragment thereof comprises: (a) a CDR-H1 comprising the amino acid sequence set forth in any one of SEQ ID NOs: 100-139 or 220-234; (b) a CDR-H2 comprising the amino acid sequence set forth in any one of SEQ ID NOs: 140-179 or 235-249; (c) an immunoglobulin heavy chain CDR3 (CDR-H3) comprising the amino acid sequence set forth in any one of SEQ ID NOs: 180-219 or 250-264; (d) a CDR-L1 comprising the amino acid sequence set forth in any one of SEQ ID NOs: 300-339 or 420-434; (e) a CDR-L2 comprising the amino acid sequence set forth in any one of SEQ ID NOs: 340-379 or 435-449; and/or (f) a CDR-L3 comprising the amino acid sequence set forth in any one of SEQ ID NOs: 380-419 or 450-464.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 100-109; (b) a CDR-H2 comprising the amino acid sequence set forth in any one of SEQ ID NOs: 140-149; (c) an immunoglobulin heavy chain CDR3 (CDR-H3) comprising the amino acid sequence set forth in any one of SEQ ID NOs: 180-189; (d) a CDR-L1 comprising the amino acid sequence set forth in any one of SEQ ID NOs: 300-309; (e) a CDR-L2 comprising the amino acid sequence set forth in any one of SEQ ID NOs: 340-349; and/or (f) a CDR-L3 comprising the amino acid sequence set forth in any one of SEQ ID NOs: 380-389.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 100-104; (b) a CDR-H2 comprising the amino acid sequence set forth in any one of SEQ ID NOs: 140-144; (c) an immunoglobulin heavy chain CDR3 (CDR-H3) comprising the amino acid sequence set forth in any one of SEQ ID NOs: 180-184; (d) a CDR-L1 comprising the amino acid sequence set forth in any one of SEQ ID NOs: 300-304; (e) a CDR-L2 comprising the amino acid sequence set forth in any one of SEQ ID NOs: 340-344; and/or (f) a CDR-L3 comprising the amino acid sequence set forth in any one of SEQ ID NOs: 380-384.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 105-109; (b) a CDR-H2 comprising the amino acid sequence set forth in any one of SEQ ID NOs: 145-149; (c) an immunoglobulin heavy chain CDR3 (CDR-H3) comprising the amino acid sequence set forth in any one of SEQ ID NOs: 185-189; (d) a CDR-L1 comprising the amino acid sequence set forth in any one of SEQ ID NOs: 305-309; (e) a CDR-L2 comprising the amino acid sequence set forth in any one of SEQ ID NOs: 345-349; and/or (f) a CDR-L3 comprising the amino acid sequence set forth in any one of SEQ ID NOs: 385-389.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 1 and 2; and/or (b) the immunoglobulin variable region light chain comprises an amino acid sequence having at least about 90, 95, 97, 98, 99, or 100% sequence identity to any one of SEQ ID NOs: 3 and 4.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 110-119; (b) a CDR-H2 comprising the amino acid sequence set forth in any one of SEQ ID NOs: 150-159; (c) an immunoglobulin heavy chain CDR3 (CDR-H3) comprising the amino acid sequence set forth in any one of SEQ ID NOs: 190-199; (d) a CDR-L1 comprising the amino acid sequence set forth in any one of SEQ ID NOs: 310-319; (e) a CDR-L2 comprising the amino acid sequence set forth in any one of SEQ ID NOs: 350-359; and/or (e) a CDR-L3 comprising the amino acid sequence set forth in any one of SEQ ID NOs: 390-399.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 110-114; (b) a CDR-H2 comprising the amino acid sequence set forth in any one of SEQ ID NOs: 150-154; (c) an immunoglobulin heavy chain CDR3 (CDR-H3) comprising the amino acid sequence set forth in any one of SEQ ID NOs: 190-194; (d) a CDR-L1 comprising the amino acid sequence set forth in any one of SEQ ID NOs: 310-314; (e) a CDR-L2 comprising the amino acid sequence set forth in any one of SEQ ID NOs: 350-354; and/or (e) a CDR-L3 comprising the amino acid sequence set forth in any one of SEQ ID NOs: 390-394.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 115-119; (b) a CDR-H2 comprising the amino acid sequence set forth in any one of SEQ ID NOs: 155-159; (c) an immunoglobulin heavy chain CDR3 (CDR-H3) comprising the amino acid sequence set forth in any one of SEQ ID NOs: 195-199; (d) a CDR-L1 comprising the amino acid sequence set forth in any one of SEQ ID NOs: 315-319; (e) a CDR-L2 comprising the amino acid sequence set forth in any one of SEQ ID NOs: 355-359; and/or (f) a CDR-L3 comprising the amino acid sequence set forth in any one of SEQ ID NOs: 395-399.

In some embodiments, provided is an antibody or antigen binding fragment thereof of any of the preceding embodiments, comprising an immunoglobulin variable region heavy chain and an immunoglobulin variable region light chain, wherein (a) the immunoglobulin variable region heavy chain comprises an amino acid sequence having at least about 90, 95, 97, 98, 99, or 100% sequence identity to any one of SEQ ID NOs: 5 and 6; and/or (b) the immunoglobulin variable region light chain comprises an amino acid sequence having at least about 90, 95, 97, 98, 99, or 100% sequence identity to any one of SEQ ID NOs: 7 and 8.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 120-129; (b) a CDR-H2 comprising the amino acid sequence set forth in any one of SEQ ID NOs: 160-169; (c) an immunoglobulin heavy chain CDR3 (CDR-H3) comprising the amino acid sequence set forth in any one of SEQ ID NOs: 200-209; (d) a CDR-L1 comprising the amino acid sequence set forth in any one of SEQ ID NOs: 320-329; (e) a CDR-L2 comprising the amino acid sequence set forth in any one of SEQ ID NOs: 360-369; and/or (f) a CDR-L3 comprising the amino acid sequence set forth in any one of SEQ ID NOs: 400-409.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 120-124; (b) a CDR-H2 comprising the amino acid sequence set forth in any one of SEQ ID NOs: 160-164; (c) an immunoglobulin heavy chain CDR3 (CDR-H3) comprising the amino acid sequence set forth in any one of SEQ ID NOs: 200-204; (d) a CDR-L1 comprising the amino acid sequence set forth in any one of SEQ ID NOs: 320-324; (e) a CDR-L2 comprising the amino acid sequence set forth in any one of SEQ ID NOs: 360-364; and/or (f) a CDR-L3 comprising the amino acid sequence set forth in any one of SEQ ID NOs: 400-404.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 125-129; (b) a CDR-H2 comprising the amino acid sequence set forth in any one of SEQ ID NOs: 165-169; (c) an immunoglobulin heavy chain CDR3 (CDR-H3) comprising the amino acid sequence set forth in any one of SEQ ID NOs: 205-209; (d) a CDR-L1 comprising the amino acid sequence set forth in any one of SEQ ID NOs: 325-329; (e) a CDR-L2 comprising the amino acid sequence set forth in any one of SEQ ID NOs: 365-369; and/or (f) a CDR-L3 comprising the amino acid sequence set forth in any one of SEQ ID NOs: 405-409.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 9 and 10; and/or (b) the immunoglobulin variable region light chain comprises an amino acid sequence having at least about 90, 95, 97, 98, 99, or 100% sequence identity to any one of SEQ ID NOs: 11 and 12.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 130-139; (b) a CDR-H2 comprising the amino acid sequence set forth in any one of SEQ ID NOs: 170-179; (c) an immunoglobulin heavy chain CDR3 (CDR-H3) comprising the amino acid sequence set forth in any one of SEQ ID NOs: 210-219; (d) a CDR-L1 comprising the amino acid sequence set forth in any one of SEQ ID NOs: 330-339; (e) a CDR-L2 comprising the amino acid sequence set forth in any one of SEQ ID NOs: 370-379; and/or (f) a CDR-L3 comprising the amino acid sequence set forth in any one of SEQ ID NOs: 410-419.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 130-134; (b) a CDR-H2 comprising the amino acid sequence set forth in any one of SEQ ID NOs: 170-174; (c) an immunoglobulin heavy chain CDR3 (CDR-H3) comprising the amino acid sequence set forth in any one of SEQ ID NOs: 210-214; (d) a CDR-L1 comprising the amino acid sequence set forth in any one of SEQ ID NOs: 330-334; (e) a CDR-L2 comprising the amino acid sequence set forth in any one of SEQ ID NOs: 370-374; and/or (f) a CDR-L3 comprising the amino acid sequence set forth in any one of SEQ ID NOs: 410-414.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 135-139; (b) a CDR-H2 comprising the amino acid sequence set forth in any one of SEQ ID NOs: 175-179; (c) an immunoglobulin heavy chain CDR3 (CDR-H3) comprising the amino acid sequence set forth in any one of SEQ ID NOs: 215-219; (d) a CDR-L1 comprising the amino acid sequence set forth in any one of SEQ ID NOs: 335-339; (e) a CDR-L2 comprising the amino acid sequence set forth in any one of SEQ ID NOs: 375-379; and/or (f) a CDR-L3 comprising the amino acid sequence set forth in any one of SEQ ID NOs: 415-419.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NOs: 13 and 14; and/or (b) the immunoglobulin variable region light chain comprises an amino acid sequence having at least about 90, 95, 97, 98, 99, or 100% sequence identity to any one of SEQ ID NOs: 15 and 16.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 220-224; (b) a CDR-H2 comprising the amino acid sequence set forth in any one of SEQ ID NOs: 235-239; (c) an immunoglobulin heavy chain CDR3 (CDR-H3) comprising the amino acid sequence set forth in any one of SEQ ID NOs: 250-254; (d) a CDR-L1 comprising the amino acid sequence set forth in any one of SEQ ID NOs: 420-424; (e) a CDR-L2 comprising the amino acid sequence set forth in any one of SEQ ID NOs: 435-439; and/or (f) a CDR-L3 comprising the amino acid sequence set forth in any one of SEQ ID NOs: 450-454.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NO: 17; and/or (b) the immunoglobulin variable region light chain comprises an amino acid sequence having at least about 90, 95, 97, 98, 99, or 100% sequence identity to any one of SEQ ID NO: 15 and 18.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 225-229; (b) a CDR-H2 comprising the amino acid sequence set forth in any one of SEQ ID NOs: 240-244; (c) an immunoglobulin heavy chain CDR3 (CDR-H3) comprising the amino acid sequence set forth in any one of SEQ ID NOs: 255-259; (d) a CDR-L1 comprising the amino acid sequence set forth in any one of SEQ ID NOs: 425-429; (e) a CDR-L2 comprising the amino acid sequence set forth in any one of SEQ ID NOs: 440-444; and/or (f) a CDR-L3 comprising the amino acid sequence set forth in any one of SEQ ID NOs: 455-459.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NO: 19; and/or (b) the immunoglobulin variable region light chain comprises an amino acid sequence having at least about 90, 95, 97, 98, 99, or 100% sequence identity to any one of SEQ ID NO: 15 and 20.

In some embodiments, provided is an antibody or antigen binding fragment thereof of any of the preceding embodiments, wherein the antibody or antigen binding fragment thereof comprises: (a) a CDR-H1 comprising the amino acid sequence set forth in any one of SEQ ID NOs: 230-234; (b) a CDR-H2 comprising the amino acid sequence set forth in any one of SEQ ID NOs: 245-249; (c) an immunoglobulin heavy chain CDR3 (CDR-H3) comprising the amino acid sequence set forth in any one of SEQ ID NOs: 260-264; (d) a CDR-L1 comprising the amino acid sequence set forth in any one of SEQ ID NOs: 430-434; (e) a CDR-L2 comprising the amino acid sequence set forth in any one of SEQ ID NOs: 445-449; and/or (f) a CDR-L3 comprising the amino acid sequence set forth in any one of SEQ ID NOs: 460-464.

In some embodiments, provided is an antibody or antigen binding fragment thereof of any of the preceding embodiments, comprising an immunoglobulin variable region heavy chain and an immunoglobulin variable region light chain, wherein: (a) the immunoglobulin variable region heavy chain comprises an amino acid sequence having at least about 90, 95, 97, 98, 99, or 100% sequence identity to any one of SEQ ID NO: 21; and/or (b) the immunoglobulin variable region light chain comprises an amino acid sequence having at least about 90, 95, 97, 98, 99, or 100% sequence identity to any one of SEQ ID NO: 15 and 22.

In some embodiments, provided is an antibody or antigen binding fragment thereof of any of the preceding embodiments, comprising a constant region (e.g. a fragment crystallizable (Fc) region) having reduced antibody-dependent cell-mediated cytotoxicity (ADCC) function as compared to human IgG1 and/or reduced complement-dependent cytotoxicity (CDC) as compared to human IgG1. In some embodiments, provided is an antibody or antigen binding fragment thereof of any of the preceding embodiments, wherein the Constant region comprises an amino acid sequence having 80, 85, 90, 95, 97, 98, 99, or 100% sequence identity to the amino acid sequence set forth by any one of SEQ ID NOs: 500-512. In some embodiments, provided is an antibody or antigen binding fragment thereof of any of the preceding embodiments, wherein the Constant region comprises the amino acid sequence set forth by any one of SEQ ID NOs: 500-512.

In some embodiments, provided is an antibody or antigen binding fragment thereof of any of the preceding embodiments, comprising a constant region having an amino acid sequence variant corresponding to (a) 297A, 297Q, 297G, or 297D, (b) 279F, 279K, or 279L, (c) 228P, (d) 235A, 235E, 235G, 235Q, 235R, or 235S, (e) 237A, 237E, 237K, 237N, or 237R, (f) 234A, 234V, or 234F, (g) 233P, (h) 328A, (i) 327Q or 327T, (j) 329A, 329G, 329Y, or 329R (k) 331 S, (l) 236F or 236R, (m) 238A, 238E, 238G, 238H, 238I, 238V, 238W, or 238Y, (n) 248A, (o) 254D, 254E, 254G, 254H, 254I, 254N, 254P, 254Q, 254T, or 254V, (p) 255N, (q) 256H, 256K, 256R, or 256V, (r) 264S, (s) 265H, 265K, 265S, 265Y, or 265A, (t) 267G, 267H, 267I, or 267K, (u) 268K, (v) 269N or 269Q, (w) 270A, 270G, 270M, or 270N, (x) 271T, (y) 272N, (z) 292E, 292F, 292G, or 292I, (aa) 293S, (bb) 301W, (cc) 304E, (dd) 311E, 311G, or 311S, (ee) 316F, (ff) 328V, (gg) 330R, (hh) 339E or 339L, (ii) 343I or 343V, (jj) 373A, 373G, or 373S, (kk) 376E, 376W, or 376Y, (11) 380D, (mm) 382D or 382P, (nn) 385P, (oo) 424H, 424M, or 424V, (pp) 434I, (qq) 438G, (rr) 439E, 439H, or 439Q, (ss) 440A, 440D, 440E, 440F, 440M, 440T, or 440V, (tt) E233P, (uu) L235E, (vv) L234A and L235A, (ww) L234A, L235A, and G237A, (xx) L234A, L235A, and P329G, (yy) L234F, L235E, and P331 S, (zz) L234A, L235E, and G237A, (aaa) L234A, L235E, G237A, and P331 S (bbb) L234A, L235A, G237A, P238S, H268A, A330S, and P331 S, (ccc) L234A, L235A, and P329A, (ddd) G236R and L328R, (eee) G237A, (fff) F241A, (ggg) V264A, (hhh) D265A, (iii) D265A and N297A, (jjj) D265A and N297G, (kkk) D270A, (111) A330L, (mmm) P331A or P331 S, or (nnn) any combination of (a)-(mmm), per EU numbering.

In some embodiments, provided is an antibody or antigen binding fragment thereof of any of the preceding embodiments, wherein the recombinant antibody or antigen binding fragment thereof is an IgG antibody. In some embodiments, provided is an antibody or antigen binding fragment thereof of any of the preceding embodiments, wherein the IgG antibody is IgG1, IgG2, IgG3, or IgG4. In some embodiments, provided is an antibody or antigen binding fragment thereof of any of the preceding embodiments, wherein the recombinant antibody or antigen binding fragment thereof is human, chimeric, or humanized.

In some embodiments, provided is an antibody or antigen binding fragment thereof of any of the preceding embodiments, wherein the recombinant antibody or antigen binding fragment thereof is a Fab, F(ab)'₂, a single-domain antibody, or a single chain variable fragment (scFv). In some embodiments, provided is an antibody or antigen binding fragment thereof of any of the preceding embodiments, wherein the recombinant antibody or antigen binding fragment thereof is a bispecific or multispecific antibody.

In some embodiments, provided is an antibody or antigen binding fragment thereof of any of the preceding embodiments, wherein the recombinant antibody or antigen binding fragment thereof inhibits a binding interaction between CD30L and CD30.

In an aspect, further provided are nucleic acids encoding the recombinant antibody or antigen binding fragment thereof of any of the preceding embodiments. Also provided are cells comprising the recombinant antibody or antigen binding fragment thereof of any of the preceding embodiments. In some embodiments, the cell is a eukaryotic cell. In some embodiments, the cell is a prokaryotic cell.

In an aspect, provided are recombinant antibodies or antigen binding fragments thereof of any the preceding embodiments for use in a method of inhibiting binding of CD30L to CD30. Further provided are recombinant antibodies or antigen binding fragments thereof of any the preceding embodiments for use in a method of inhibiting activation of CD30 signaling in a cell. Also provided are recombinant antibodies or antigen binding fragments thereof of any the preceding embodiments for use in a method of inhibiting activation, expression, and/or secretion of a pro-inflammatory cytokine protein.

In an aspect, provided are recombinant antibodies or antigen binding fragments thereof of any the preceding embodiments for use in treating an autoimmune disease in an individual in need thereof. In some embodiments, the autoimmune disease is irritable bowel disease. In some embodiments, the irritable bowel disease comprises ulcerative colitis (UC) or Crohn's Disease (CD).

In an aspect, provided are methods of treating or ameliorating an autoimmune disease in an individual in need thereof, the method comprising administering to the individual the recombinant antibody or antigen binding fragment thereof of any of the preceding embodiments, thereby treating or ameliorating the autoimmune disease. Also provided are methods for inhibiting and/or reducing binding of CD30L to CD30 in an individual with an inflammatory or autoimmune disorder, the method comprising administering to an individual afflicted with the inflammatory or autoimmune disorder the recombinant antibody or antigen binding fragment thereof of the preceding embodiments, thereby inhibiting and/or reducing the binding of CD30L to CD30. Further provided are methods of reducing and/or inhibiting inflammation in an individual, the method comprising administering to the individual the recombinant antibody or antigen binding fragment thereof of any of the preceding embodiments, thereby reducing and/or inhibiting inflammation.

In some embodiments, the provided are methods of any of the preceding embodiments, wherein the individual has an autoimmune disease. In some embodiments, the provided are methods of any of the preceding embodiments, wherein the autoimmune disease is irritable bowel disease. In some embodiments, the provided are methods of any of the preceding embodiments, wherein the irritable bowel disease comprises ulcerative colitis (UC) or Crohn's Disease (CD).

In some embodiments, the provided are methods of any of the preceding embodiments, wherein reducing and/or inhibiting inflammation comprises reducing an amount of pro-inflammatory cytokine expression or secretion in the individual or a tissue of the individual. In some embodiments, the provided are methods of any of the preceding embodiments, wherein the pro-inflammatory cytokine comprises interleukin 8 and/or interleukin 6. In some embodiments, the provided are methods of any of the preceding embodiments, wherein the individual has an autoimmune disease. In some embodiments, the provided are methods of any of the preceding embodiments, wherein the autoimmune disease is irritable bowel disease. In some embodiments, the provided are methods of any of the preceding embodiments, wherein the irritable bowel disease comprises ulcerative colitis (UC) or Crohn's Disease (CD).

5. EXAMPLES

The following examples are illustrative of the embodiments described herein and are not to be interpreted as limiting the scope of this disclosure. To the extent that specific materials are mentioned, it is merely for purposes of illustration and is not intended to be limiting. One skilled in the art may develop equivalent means or reactants without the exercise of inventive capacity and without departing from the scope of this disclosure.

Example 1: Generation and Identification of Anti-CD30L Antibodies

Mice with humanized immunoglobulin locus were used for antibody generation. Mice were inoculated with human CD30L expressing cells (B16 cell line transfected to express human CD30L), DNA encoding human CD30L, and recombinant human CD30L protein. At certain time points following the start of the immunizations, the serum of the mice was screened for reactivity to human CD30L and cynomolgus CD30L and plasma cells from mice with high titers were fused to generate hybridomas.

The hybridomas were then expanded, screened and selected based on their flow cytometry binding to cells expressing human and cyno CD30L, CD30:CD30L blocking activity when CD30L is expressed on cells by flow cytometry, ELISA binding to recombinant human CD30L protein, ELISA binding to recombinant cynomolgus CD30L protein, and CD30:CD30L blocking ability in an ELISA binding assay. Table 2, Table 3, and Table 4 show data from hybridoma screening assays. The anti-CD30L antibodies shown in Table 2 and Table 3 effectively bind recombinant CD30L, cells expressing CD30L, and inhibit binding of CD30L to CD30. Clone 1 comprises the CDRs as set forth in SEQ ID NOs: 100-104, 140-144, 180-184, 300-304, 340-344, and 380-384; Clone 2 comprises the CDRs as set forth in SEQ ID NOs: 110-114, 150-154, 190-194, 310-314, 350-354, and 390-394; Clone 3 comprises the CDRs as set forth in SEQ ID NOs: 120-124, 160-164, 200-204, 320-324, 360-364, and 400-404; and Clone 4 comprises the CDRs as set forth in SEQ ID NOs: 130-134, 170-174, 210-214, 330-334, 370-374, and 410$^{-414}$; Clone 59 comprises the CDRs as set forth in SEQ ID NOs: 220-224, 235-239, 250-254, 420-424, 435-439, and 450-454; Clone 60 comprises the CDRs as set forth in SEQ ID NOs: 225-229, 240-244, 255-259, 425-429, 440-444, and 455-459; and Clone 61 comprises the CDRs as set forth in SEQ ID NOs: 230-234, 245-249, 260-264, 430-434, 445-449, and 460-464.

TABLE 2

Cell binding and ELISA screening against CD30L

| | Cell Binding (MFI) | | Elisa Binding (OD) | | |
|---|---|---|---|---|---|
| Clone ID | huCD30L (1/50 dil) | cyCD30L (1/50 dil) | huCD30L (1/50 dil) | huCD30L (1/500 dil) | huCD30L (1/5000 dil) |
| 1 | 208 | 77.3 | 3.586 | 3.025 | 1.283 |
| 2 | 280 | 57.6 | 2.147 | 1.712 | 0.565 |
| 3 | 153 | 72.4 | 3.495 | 2.54 | 0.662 |
| 4 | 151 | 67.8 | 3.075 | 2.652 | 0.68 |
| 5 | 205 | 79.6 | 3.166 | 2.849 | 1.111 |
| 6 | 200 | 61.9 | 2.374 | 1.377 | 0.503 |
| 7 | 234 | 77.6 | 2.17 | 1.404 | 0.395 |
| 8 | 186 | 69.9 | 2.255 | 1.074 | 0.255 |
| 9 | 234 | 62.8 | 1.829 | 1.202 | 0.358 |
| 10 | 192 | 74.6 | 2.14 | 1.233 | 0.313 |
| 11 | 176 | 68.4 | 2.294 | 1.274 | 0.324 |
| 12 | 186 | 76.7 | 3.067 | 2.679 | 0.822 |
| 13 | 168 | 69.6 | 3.244 | 2.797 | 0.825 |
| 14 | 168 | 70.3 | 2.045 | 1.129 | 0.27 |
| 15 | 176 | 67.1 | 2.951 | 2.6 | 0.754 |
| 16 | 176 | 76 | 2.014 | 1.133 | 0.284 |

TABLE 2-continued

Cell binding and ELISA screening against CD30L

| | Cell Binding (MFI) | | Elisa Binding (OD) | | |
|---|---|---|---|---|---|
| Clone ID | huCD30L (1/50 dil) | cyCD30L (1/50 dil) | huCD30L (1/50 dil) | huCD30L (1/500 dil) | huCD30L (1/5000 dil) |
| 17 | 166 | 68.3 | 3.184 | 2.448 | 0.719 |
| 18 | 171 | 70.1 | 3.183 | 2.571 | 0.774 |
| 19 | 137 | 57.5 | 1.87 | 0.93 | 0.221 |
| 20 | 197 | 79.8 | 2.085 | 1.345 | 0.3 |
| 21 | 160 | 66.2 | 2.302 | 1.239 | 0.295 |
| 22 | 156 | 74.6 | 3.128 | 2.673 | 0.82 |
| 23 | 170 | 64.2 | 3.482 | 2.494 | 0.701 |
| 24 | 170 | 68.7 | 3.176 | 2.618 | 0.697 |
| 25 | 155 | 64.2 | 3.104 | 2.411 | 0.621 |
| 26 | 167 | 66 | 2.919 | 2.48 | 0.658 |
| 27 | 149 | 68.8 | 3.206 | 2.395 | 0.605 |
| 28 | 144 | 68 | 3.046 | 2.342 | 0.569 |
| 29 | 139 | 65.9 | 3.158 | 2.306 | 0.588 |
| 30 | 154 | 62.9 | 3.137 | 2.389 | 0.645 |
| 31 | 141 | 68.2 | 3.043 | 2.316 | 0.589 |
| 32 | 149 | 68.2 | 3.012 | 2.397 | 0.608 |
| 33 | 132 | 68.5 | 3.059 | 2.224 | 0.536 |
| 34 | 115 | 57 | 1.923 | 0.784 | 0.177 |
| 35 | 148 | 57.4 | 3.18 | 2.429 | 0.572 |
| 36 | 146 | 57.7 | 3.288 | 2.308 | 0.582 |
| 37 | 127 | 57.2 | 1.826 | 0.834 | 0.193 |
| 38 | 146 | 63.1 | 2.864 | 2.31 | 0.628 |
| 39 | 135 | 52.4 | 2.004 | 0.846 | 0.178 |
| 40 | 123 | 50.4 | 1.198 | 0.791 | 0.191 |
| 41 | 120 | 51.9 | 0.502 | 0.349 | 0.081 |
| 42 | 104 | 53.1 | 3.109 | 1.928 | 0.408 |
| 43 | 104 | 51.7 | 1.772 | 0.643 | 0.142 |
| 44 | 76.2 | 46.4 | 1.545 | 0.52 | 0.114 |
| 45 | 0.54 | 0.54 | 0.314 | 0.085 | 0.047 |
| 46 | 0.74 | 0.77 | 0.454 | 0.111 | 0.054 |
| 47 | 0.59 | 0.76 | 0.61 | 0.138 | 0.053 |
| 48 | 0.86 | 0.63 | 0.418 | 0.108 | 0.043 |
| 49 | 2.83 | 2.86 | 0.143 | 0.054 | 0.043 |
| 50 | 0.23 | 0.16 | 0.047 | 0.046 | 0.047 |
| 51 | 0.23 | 0.16 | 0.052 | 0.048 | 0.042 |
| 52 | 0.61 | 0.77 | 0.499 | 0.137 | 0.053 |
| 53 | 18.8 | 11.4 | 0.887 | 0.18 | 0.059 |
| 54 | 0.58 | 0.75 | 0.471 | 0.128 | 0.05 |
| 55 | 0.47 | 0.57 | 0.331 | 0.086 | 0.047 |
| 56 | 0.25 | 0.17 | 0.043 | 0.042 | 0.043 |
| 57 | 0.26 | 0.18 | 0.041 | 0.041 | 0.04 |
| 58 | 0.53 | 0.23 | 0.033 | 0.043 | 0.039 |

TABLE 3

Cell binding and ELISA screening against CD30L

| Clone ID | Cell Binding HuCD30L Flow (MFI) | ELISA Binding HuCD30L ELISA (OD) |
|---|---|---|
| 59 | 9785.31 | 0.06 |
| 60 | 1090.51 | 0.23 |
| 61 | 361.75 | 1.42 |

TABLE 4

ELISA screening against CD30L and CD30:CD30L blocking data

| | Elisa Binding (OD) | | | Elisa CD30 Neutralization (% inhibition) | | | |
|---|---|---|---|---|---|---|---|
| | cyCD30L | | | | | | |
| Clone ID | (1/50 dil) | cyCD30L (1/500 dil) | (1/5000 dil) | huCD30L (undil) | huCD30L (1/10 dil) | huCD30L (1/100 dil) | huCD30L (1/1000 dil) |
| 1 | 2.833 | 2.866 | 1.155 | 98% | 98% | 34% | 0% |
| 2 | 3.762 | 3.177 | 1.226 | 98% | 98% | 45% | 1% |

TABLE 4-continued

ELISA screening against CD30L and CD30:CD30L blocking data

| | Elisa Binding (OD) | | | Elisa CD30 Neutralization | | | |
| --- | --- | --- | --- | --- | --- | --- | --- |
| | cyCD30L | | cyCD30L | (% inhibition) | | | |
| Clone ID | (1/50 dil) | cyCD30L (1/500 dil) | (1/5000 dil) | huCD30L (undil) | huCD30L (1/10 dil) | huCD30L (1/100 dil) | huCD30L (1/1000 dil) |
| 3 | 3.199 | 2.348 | 0.552 | 98% | 95% | 17% | 3% |
| 4 | 2.575 | 2.378 | 0.583 | 98% | 96% | 10% | 0% |
| 5 | 2.899 | 2.774 | 0.974 | 98% | 98% | 36% | 7% |
| 6 | 3.482 | 2.574 | 0.793 | 98% | 98% | 25% | 0% |
| 7 | 3.665 | 2.742 | 0.837 | 98% | 98% | 21% | 0% |
| 8 | 3.443 | 2.266 | 0.616 | 98% | 98% | 25% | 0% |
| 9 | 3.432 | 2.539 | 0.794 | 98% | 98% | 29% | 0% |
| 10 | 3.356 | 2.254 | 0.655 | 98% | 98% | 28% | 0% |
| 11 | 2.99 | 2.507 | 0.675 | 98% | 97% | 28% | 0% |
| 12 | 2.442 | 2.636 | 0.69 | 98% | 97% | 16% | 0% |
| 13 | 2.787 | 2.522 | 0.699 | 98% | 97% | 17% | 3% |
| 14 | 3.228 | 2.08 | 0.557 | 98% | 97% | 17% | 0% |
| 15 | 2.644 | 2.48 | 0.656 | 98% | 97% | 22% | 7% |
| 16 | 3.227 | 2.006 | 0.582 | 98% | 97% | 23% | 6% |
| 17 | 2.689 | 2.636 | 0.69 | 98% | 97% | 17% | 0% |
| 18 | 2.567 | 2.559 | 0.637 | 98% | 96% | 20% | 4% |
| 19 | 3.328 | 1.905 | 0.453 | 98% | 96% | 8% | 0% |
| 20 | 3.349 | 2.583 | 0.679 | 98% | 98% | 24% | 6% |
| 21 | 3.372 | 2.008 | 0.511 | 98% | 96% | 16% | 1% |
| 22 | 2.752 | 2.441 | 0.631 | 98% | 96% | 24% | 10% |
| 23 | 2.845 | 2.474 | 0.625 | 98% | 96% | 17% | 3% |
| 24 | 2.583 | 2.416 | 0.617 | 98% | 96% | 17% | 6% |
| 25 | 2.537 | 2.283 | 0.534 | 98% | 95% | 9% | 0% |
| 26 | 2.303 | 2.267 | 0.574 | 98% | 95% | 18% | 5% |
| 27 | 2.693 | 2.293 | 0.503 | 98% | 94% | 16% | 4% |
| 28 | 2.589 | 2.244 | 0.516 | 98% | 96% | 15% | 2% |
| 29 | 2.85 | 2.287 | 0.522 | 98% | 92% | 18% | 8% |
| 30 | 2.694 | 2.314 | 0.578 | 98% | 96% | 12% | 0% |
| 31 | 2.473 | 2.269 | 0.493 | 98% | 88% | 9% | 1% |
| 32 | 2.461 | 2.37 | 0.507 | 98% | 89% | 16% | 1% |
| 33 | 2.727 | 2.154 | 0.473 | 98% | 91% | 9% | 4% |
| 34 | 3.249 | 1.683 | 0.366 | 98% | 93% | 12% | 2% |
| 35 | 2.703 | 2.218 | 0.484 | 98% | 92% | 19% | 5% |
| 36 | 2.428 | 2.288 | 0.525 | 98% | 94% | 10% | 0% |
| 37 | 3.065 | 1.631 | 0.353 | 99% | 86% | 10% | 4% |
| 38 | 2.694 | 2.352 | 0.568 | 98% | 92% | 16% | 5% |
| 39 | 3.336 | 1.72 | 0.358 | 98% | 93% | 13% | 1% |
| 40 | 1.192 | 0.682 | 0.198 | 0% | 0% | 0% | 0% |
| 41 | 2.063 | 1.382 | 0.409 | 64% | 52% | 13% | 18% |
| 42 | 2.633 | 1.893 | 0.36 | 98% | 76% | 11% | 6% |
| 43 | 3.064 | 1.385 | 0.278 | 98% | 76% | 8% | 0% |
| 44 | 2.911 | 1.185 | 0.223 | 98% | 66% | 5% | 0% |
| 45 | 1.138 | 0.248 | 0.067 | 1% | 0% | 0% | 0% |
| 46 | 1.388 | 0.338 | 0.079 | 67% | 57% | 26% | 5% |
| 47 | 1.785 | 0.447 | 0.094 | 0% | 0% | 28% | 0% |
| 48 | 1.163 | 0.279 | 0.071 | 9% | 5% | 0% | 0% |
| 49 | 0.064 | 0.058 | 0.045 | 0% | 0% | 0% | 2% |
| 50 | 0.046 | 0.048 | 0.063 | 3% | 4% | 2% | 0% |
| 51 | 0.052 | 0.049 | 0.043 | 1% | 0% | 4% | 1% |
| 52 | 1.713 | 0.463 | 0.092 | 5% | 0% | 0% | 0% |
| 53 | 1.84 | 0.397 | 0.089 | 83% | 7% | 0% | 3% |
| 54 | 1.716 | 0.426 | 0.102 | 0% | 22% | 0% | 0% |
| 55 | 1.253 | 0.262 | 0.069 | 7% | 3% | 9% | 14% |
| 56 | 0.057 | 0.045 | 0.049 | 0% | 0% | 0% | 0% |
| 57 | 0.046 | 0.043 | 0.046 | 0% | 0% | 0% | 1% |
| 58 | 0.052 | 0.043 | 0.043 | 0% | 0% | 0% | 0% |

Example 2: Functional Activity of CD30L Antibodies

When engaged by CD30L, expressed at the cell surface or in a recombinant soluble form, CD30+ Karpas 299 (K299) (cells from Dr Abraham Karpas at the University of Cambridge) cells release IL-8 in the supernatant. Interleukin 8 is a chemokine produced by macrophages and other cell types such as epithelial cells, and functions in activating an inflammatory and/or immune response. A monoclonal antibody binding to CD30L in such a way to neutralize CD30-CD30L interaction can therefore be identified using this functional assay by detecting inhibition of IL-8 release. A dual cell, IL-8 release assay was developed with the K299 cells expressing human CD30 and B16-huCD30L or HEK-cyCD30L. Clones 1-2 effectively reduced, inhibited, and/or prevented IL-8 release. In this assay, the anti-CD30L antibody test articles showed marked improvements (e.g. lower IC50) over the control test article anti-CD30L Reference 1 antibody (Ref1, comprising heavy chain of SEQ ID NO: 768 and light chain of SEQ ID NO: 769), an antibody that binds CD30L and blocks its interaction with CD30. Table 5 shows the results of the assay.

TABLE 5

IL-8 release, dual cell assay

| Clone | Inhibition of IL-8 release in a dual cell assay (B16-huCD30L cells + K299 cells) IC$_{50}$ (nM) | | Inhibition of IL-8 release in a dual cell assay (HEK293-cyCD30L cells + K299 cells) IC$_{50}$ (nM) | |
|---|---|---|---|---|
| | Mouse IgG | Human IgG1 | Mouse IgG | Human IgG1 |
| Ref1 | | 1.74 | | 0.68 |
| 1 | 1.99 | 1.1 | 0.55 | 0.22 |
| 2 | 1.20 | 0.6 | 0.46 | 0.24 |

Example 3: Anti-CD30L Antibody Binding to Cell-Expressed CD30L

Anti-CD30L antibody binding to a CD30L target was determined by flow cytometry, using B16 cells transfected to express human CD30L (compared to non-transfected B16), and using HEK293 cells transfected to express cynomolgus CD30L (compared to non-transfected HEK293). In brief, the cell lines were detached with a non-enzymatic EDTA-based reagent, incubated on ice with increasing concentrations of anti-CD30L antibodies (from 0.002 nM to 33.5 nM) in flow cytometry buffer, and washed to remove unbound molecules. Cell surface bound antibodies were detected using a fluorescently labeled anti-human-IgG or anti-mouse IgG, depending on the Fc portion of the antibodies. After incubation with the secondary antibody, the cells were washed, fixed in a paraformaldehyde solution, and analyzed by flow cytometry to detect antibody binding. The results from this assay are shown in Table 6.

TABLE 6

Summary of cell-based binding and blocking assays

| Clone | Binding of antibodies to B16-huCD30L cells EC$_{50}$ (nM) | | Antibody mediated blocking of huCD30 binding to B16-huCD30L cells IC$_{50}$ (nM) | |
|---|---|---|---|---|
| | Mouse IgG | Human IgG1 | Mouse IgG | Human IgG1 |
| Ref1 | | 1.74 | | 2.77 |
| 1 | 1.95 | 1.41 | 3.06 | 1.35 |
| 2 | 1.21 | 0.81 | 1.84 | 0.86 |

To assess the potency of the disclosed anti-CD30L antibodies to inhibit binding between CD30 and CD30L, a flow cytometry-based assay was developed using cells expressing human CD30L (B16-huCD30L) and cells expressing cyno CD30L (HEK-cyCD30L). In this assay, the binding of soluble fluorescently-labeled CD30-Fc to CD30 was detected at the surface of the cells by flow cytometry. The pre-incubation of these cells with increasing concentrations of blocking anti-CD30L antibodies inhibited the binding of fluorescent CD30-Fc to the cell surface in a dose dependent manner. The results from this assay are shown in Table 6. In both assays (binding and blocking), the anti-CD30L antibody test articles show improvements (e.g. lower EC50 and lower IC50 values) over the control test article anti-CD30L Reference 1 antibody (Ref1, comprising heavy chain of SEQ ID NO: 768 and light chain of SEQ ID NO: 769), an antibody that binds CD30L and blocks its interaction with CD30.

Example 4: Anti-CD30L Antibody Binding to Human Primary Cells

Peripheral blood mononuclear cells (PBMCs) were isolated from freshly collected whole blood from Ulcerative Colitis (UC) and Crohn's Disease (CD) patients, by conventional density gradient centrifugation. To induce CD30L expression on primary lymphocytes, the isolated cells were stimulated overnight with Phorbol 12-myristate 13-acetate (PMA) and ionomycin. The next day, the stimulated cells, along with non-stimulated cells kept as control, were collected, washed and incubated on ice with increasing concentrations of fluorescently labeled anti-CD30L antibodies or isotype control (from 0.001 nM to 60 nM). After washing to remove unbound antibodies, the cells were fixed in a paraformaldehyde solution and analyzed by flow cytometry to quantify cell surface antibody binding. Typical results from this assay are shown in Table 7.

TABLE 7

Binding to primary lymphocytes from UC and CD patients stimulated with PMA/ionomycin.

| Antibody Clone | Patient 1 (CD, #04-021) Binding $EC_{50}$ (nM) | Patient 2 (UC, #03-041) Binding $EC_{50}$ (nM) | Patient 3 (UC, #02-180) Binding $EC_{50}$ (nM) | Patient 4 (CD, #01-051) Binding $EC_{50}$ (nM) |
|---|---|---|---|---|
| Ref1 (HC of SEQ ID NO: 768 & LC of SEQ ID NO: 769) | 3.63 | 3.12 | 3.07 | 2.82 |
| 1 | 7.45 | 5.43 | 5.57 | 4.53 |
| 2 | 2.40 | 1.55 | 1.71 | 1.72 |

Example 5: Generation and Identification of Additional Anti-CD30L Antibodies

To identify additional antibody sequences, including additional CDR sequences, that can specifically bind to CD30L, block CD30-CD30L interaction, and block CD30L-mediated CD30 signaling, multiple additional antibody campaigns were independently performed. Three different and independently constructed and humanized mouse strains (#1, #2, or #3) were used for antibody generation. Two of the mouse strains (#2 or #3) were designed to maximize antibody diversity. All mice were inoculated with human CD30L expressing cells (B16 cell line transfected to express human CD30L), DNA encoding human CD30L, and recombinant human CD30L protein. At certain time points following the start of the immunizations, the serum of the mice was screened for reactivity to human CD30L, cynomolgus CD30L and mouse CD30L. B cells from mice with strong titers were imported to a BEACON instrument for single B cell screening. The BEACON screening aimed to identify CD30L blocking antibodies that exhibited human and cynomolgus species cross reactivity and on-cell target binding.

B cells from the BEACON screening were exported to multi-well plates for VH and VL sequencing and production of recombinant antibodies. Purified recombinant antibodies were tested for binding to recombinant human CD30L, cynomolgus CD30L and mouse CD30L and to cells expressing human and cynomolgus CD30L (Table 8). In addition, the ability of each antibody to block CD30L binding to CD30 was tested. Briefly, individual anti-human biosensors were loaded with purified IgG (normalized to 10 µg/mL) and a baseline was measured for each biosensor. Biosensors were saturated with biotin and with polyclonal huIgG and a baseline was measured. Loaded biosensors were then allowed to bind CD30L and the association rate was measured for the binding. Biosensors were moved to buffer wells to measure the dissociation rate. Biosensors were reloaded with CD30L and moved to wells with CD30. Association of CD30 results in an increase in relative units over background (0.15) and is indicative of a non-blocking antibody clone.

TABLE 8

Purified recombinant antibodies bind CD30L and compete with CD30

| Clone ID | Mouse Strain | rhCD30L (+) ELISA | rcyCD30L (+) ELISA | rmCD30L (+) ELISA | hCD30L B16 (+) FLOW | Parental (−) FLOW | rhCD30L: rhCD30 Blocking |
|---|---|---|---|---|---|---|---|
| 62 | #1 | 0.555 | 0.332 | 0.047 | 4826784 | 11596 | 0.0557 |
| 86 | #1 | 1.435 | 0.748 | 0.045 | 4493586 | 11572 | 0.0631 |
| 87 | #1 | 0.051 | 0.057 | 0.045 | 10958 | 10992 | No binding |
| 88 | #1 | 0.283 | 0.109 | 0.045 | 1052602 | 10999 | 0.0547 |
| 89 | #1 | 0.449 | 0.146 | 0.058 | 1984901 | 11095 | 0.0532 |
| 90 | #1 | 1.641 | 0.798 | 0.046 | 5997151 | 11468 | 0.068 |
| 63 | #1 | 1.871 | 0.724 | 0.046 | 6070933 | 11113 | 0.0592 |
| 91 | #1 | 0.268 | 0.104 | 0.044 | 1051940 | 10786 | 0.0547 |
| 92 | #1 | 0.251 | 0.057 | 0.045 | 47034 | 10869 | 0.0642 |
| 93 | #1 | 0.144 | 0.066 | 0.045 | 234134 | 11002 | No binding |
| 94 | #1 | 0.982 | 0.245 | 0.059 | 4535943 | 11254 | 0.0551 |
| 95 | #1 | 0.866 | 0.262 | 0.045 | 1503954 | 11012 | 0.053 |
| 96 | #1 | 0.048 | 0.057 | 0.046 | 12183 | 11785 | No binding |
| 97 | #1 | 0.05 | 0.055 | 0.055 | 13077 | 11219 | No binding |
| 64 | #1 | 2.041 | 0.951 | 0.049 | 5667300 | 11683 | 0.0633 |
| 98 | #1 | 0.049 | 0.056 | 0.048 | 35192 | 11365 | No binding |
| 99 | #1 | 0.048 | 0.055 | 0.049 | 11119 | 11472 | No binding |
| 65 | #1 | 1.966 | 1.378 | 0.047 | 6913949 | 11367 | 0.0522 |
| 100 | #1 | 0.049 | 0.055 | 0.048 | 10750 | 11549 | No binding |
| 66 | #1 | 2.047 | 0.056 | 0.045 | 19034 | 11297 | 0.2575 |

TABLE 8-continued

Purified recombinant antibodies bind CD30L and compete with CD30

| Clone ID | Mouse Strain | rhCD30L (+) ELISA | rcyCD30L (+) ELISA | rmCD30L (+) ELISA | hCD30L B16 (+) FLOW | Parental (−) FLOW | rhCD30L: rhCD30 Blocking |
|---|---|---|---|---|---|---|---|
| 101 | #1 | 0.052 | 0.055 | 0.046 | 10757 | 11622 | No binding |
| 67 | #1 | 2.352 | 0.089 | 0.046 | 197523 | 11267 | 0.2053 |
| 68 | #2 or #3 | 1.707 | 0.867 | 0.044 | 5578433 | 10925 | 0.055 |
| 102 | #2 or #3 | 0.412 | 0.231 | 0.045 | 2417049 | 11384 | 0.0697 |
| 69 | #2 or #3 | 0.353 | 0.138 | 0.047 | 4929180 | 11328 | 0.2273 |
| 103 | #2 or #3 | 0.05 | 0.058 | 0.049 | 11442 | 10952 | No binding |
| 70 | #2 or #3 | 1.514 | 0.709 | 0.046 | 6946359 | 12003 | 0.0687 |
| 104 | #2 or #3 | 0.238 | 0.065 | 0.047 | 774533 | 11524 | 0.0394 |
| 71 | #2 or #3 | 1.733 | 0.855 | 0.046 | 5382299 | 11676 | 0.0529 |
| 72 | #2 or #3 | 0.813 | 0.262 | 0.046 | 5242171 | 11521 | 0.0696 |
| 73 | #2 or #3 | 0.634 | 0.169 | 0.045 | 4377595 | 11469 | 0.0646 |
| 74 | #2 or #3 | 1.561 | 0.634 | 0.047 | 6843276 | 12458 | 0.0807 |
| 105 | #2 or #3 | 0.048 | 0.058 | 0.048 | 10970 | 11632 | No binding |
| 106 | #2 or #3 | 0.051 | 0.056 | 0.046 | 11924 | 11608 | No binding |
| 107 | #2 or #3 | 0.049 | 0.057 | 0.05 | 10499 | 11162 | No binding |
| 108 | #2 or #3 | 0.048 | 0.081 | 0.051 | 13882 | 15347 | No binding |
| 75 | #2 or #3 | 1.177 | 0.349 | 0.044 | 5907158 | 11251 | 0.0739 |
| 76 | #1 | 1.665 | 0.494 | 0.045 | 5656499 | 11271 | 0.0684 |
| 77 | #1 | 1.74 | 0.96 | 0.05 | 5186725 | 11680 | 0.0926 |
| 78 | #1 | 1.545 | 0.972 | 0.049 | 6565681 | 11228 | 0.0959 |
| 79 | #1 | 1.464 | 0.538 | 0.05 | 6388847 | 11415 | 0.0718 |
| 109 | #1 | 1.762 | 0.703 | 0.055 | 6506456 | 10919 | 0.0749 |
| 80 | #1 | 0.941 | 0.475 | 0.048 | 8301813 | 12058 | 0.0635 |
| 110 | #1 | 1.952 | 0.999 | 0.051 | 6507107 | 11209 | 0.1115 |
| 81 | #1 | 1.596 | 1.412 | 0.052 | 7156876 | 11429 | 0.2136 |
| 82 | #1 | 1.408 | 0.982 | 0.048 | 8422953 | 11194 | 0.071 |
| 83 | #1 | 1.855 | 1.214 | 0.049 | 6828103 | 11641 | 0.0855 |
| 84 | #1 | 1.643 | 0.732 | 0.052 | 6810066 | 12542 | 0.0638 |
| 85 | #1 | 1.03 | 0.283 | 0.067 | 5284859 | 12331 | 0.08 |

A subset of antibody clones (clones 62-85) with robust CD30L binding and CD30 blocking activity were selected for larger scale production based on the binding and blocking data, as well as VH and VL sequence considerations. Affinities to human CD30L were determined using a Carterra instrument (Table 9). Recombinant blocking activity of the clones were also evaluated in an ELISA format, in which CD30L was added to the plate, followed by CD30 and a dose response of the antibody clones. The IC50 of the clones determined in such ELISA assay was shown in Table 9. Clones were also tested in a functional assay. Briefly, when engaged by CD30L, expressed at the cell surface or in a recombinant soluble form, CD30+ Karpas 299 (K299) cells release IL-8 in the supernatant. Interleukin 8 is a chemokine produced by macrophages and other cell types such as epithelial cells, and functions in activating an inflammatory and/or immune response. A monoclonal antibody binding to CD30L in such a way to neutralize CD30-CD30L interaction can therefore be identified using this functional assay by detecting inhibition of IL-8 release. A dual cell, IL-8 release assay was developed with the K299 cells endogenously expressing human CD30 and B16-huCD30L ("dual cell assay"). The ability of each tested clone to inhibit or block CD30L-mediated CD30 signaling was shown in in Table 9, in which "++" indicates complete blocking of IL-8 release in the dual cell assay, "+" indicates inhibition of IL-8 release in the dual cell assay, and "−" indicates no inhibition of IL-8 release in the dual cell assay despite of inhibiting or blocking recombinant CD30-CD30L binding. FIG. 1A-1E shows a dose response of CD30L antibodies in dual cell IL-8 release assay, huCD30L B16 flow assay and binding/blocking ELISA which were the basis for Table 9.

TABLE 9

Characterization of select anti-CD30L antibodies

| Clone ID | KD (Carterra) | Recombinant blocking ELISA (IC50 nM) | Dual cell assay |
|---|---|---|---|
| 62 | 8.77E−09 | 5.936 | − |
| 63 | 1.85E−09 | 3.178 | + |
| 64 | 1.57E−09 | 3.174 | + |
| 65 | 1.52E−09 | 3.66 | + |
| 66 | 4.23E−10 | 12.25 | − |
| 67 | 1.15E−09 | 12.02 | − |
| 68 | 1.59E−08 | 3.658 | − |
| 69 | 4.83E−09 | 3.195 | NA |
| 70 | 2.83E−10 | 4.192 | − |
| 71 | 2.07E−08 | 3.576 | − |
| 72 | 4.72E−09 | 4.045 | − |
| 73 | 7.41E−09 | 4.791 | − |
| 74 | 3.58E−10 | 3.712 | − |
| 75 | 3.19E−09 | 3.394 | − |
| 76 | 5.57E−10 | 1.669 | − |
| 77 | 4.16E−10 | 2.716 | − |
| 78 | 3.13E−10 | 11.76 | − |
| 79 | 8.57E−10 | 2.023 | NA |
| 80 | 3.54E−09 | 2.739 | ++ |
| 81 | 1.37E−07 | 2.763 | NA |
| 82 | 5.59E−10 | 3.508 | + |
| 83 | 1.94E−10 | 3.742 | − |

TABLE 9-continued

Characterization of select anti-CD30L antibodies

| Clone ID | KD (Carterra) | Recombinant blocking ELISA (IC50 nM) | Dual cell assay |
|---|---|---|---|
| 84 | 3.23E−10 | 4.604 | − |
| 85 | 1.22E−08 | 6.375 | − |

Taking the above Examples (Examples 1-5) together, at leastthree differenthumanized mouse strains have been immunized, multiple independent antibody campaigns have been conducted at different time points, and at least 110 antibodies have been generated and tested. Of the 110 anti-CD30L antibody clones tested, the vast majority of the 110 clones bound to CD30L and the vast majority of the 110 clones blocked CD30-CD30L recombinant protein binding (see Tables 2-9). Among the 110 clones, seven clones (clones 1, 2, 63-65, 80 and 82) blocked or inhibited CD30L-mediated CD30 signaling, e.g. CD30L-mediated IL-8 release (see Tables 5, 6, and 9).

Example 6: Structural Determinants of Binding to CD30L and Blocking/Inhibiting CD30L-Mediated CD30 Signaling As shown above, 110 clones across multiple antibody campaigns with at least three different mouse strains were generated, with the vast majority of which demonstrating robust binding to recombinant CD30L and cell surface CD30L and blocking/inhibiting recombinant CD30-CD30L binding. Despite such large number of clones from diverse campaigns and background, 7 anti-CD30L (clones 1, 2, 63-65, 80 and 82) blocked/inhibited both CD30-CD30L recombination protein interaction and functionally blocked/inhibited CD30L-mediated CD30 signaling in a dual cell assay. Therefore, the structural (including the primary structure, e.g. amino acid sequence) features of the 7 clones that confer them the binding and functional blocking capability were determined. The clones were sequenced and the CDR sequences of the 7 clones were identified according to Kabat, Chothia, AbM, Contact, IMGT, and Aho numbering scheme. Each of the 6 CDRs (CDR-H1, CDR-H2, CDR-H3, CDR-L1, CDR-L2, and CDR-L3) was aligned to determine the sequence and sequence features common to all of them, which can be the determinants of their common capacity to both block/inhibit CD30-CD30L recombination protein interaction and functionally block/inhibit CD30L-mediated CD30 signaling in a dual cell assay. As shown in Tables 10-16, despite coming from different mice and different antibody campaign, the corresponding CDR sequences of the 7 clones aligned well with identical residues at certain positions and conserved variations at others, suggesting that these conserved sequence features confer their common capacity to both block/inhibit CD30-CD30L recombination protein interaction and functionally block/inhibit CD30L-mediated CD30 signaling in a dual cell assay.

Accordingly, consensus sequences for each of the 6 CDRs (CDR-H1, CDR-H2, CDR-H3, CDR-L1, CDR-L2, and CDR-L3) was established based on the clones as shown in Tables 10-16 to capture the common sequence features, which can be the determinants of their common capacity to both block/inhibit CD30-CD30L recombination protein interaction and functionally block/inhibit CD30L-mediated CD30 signaling in a dual cell assay. In each of Tables 10-16, the consensus_1 sequence shows the common sequence features of clones 1, 2, and 80, which completely blocked both CD30-CD30L recombination protein interaction and CD30L-mediated CD30 signaling in a dual cell assay; the consensus_2 sequence shows the common sequence features of clones 1, 2, 63-65, 80 and 82, which both block/inhibit CD30-CD30L recombination protein interaction and functionally block/inhibit CD30L-mediated CD30 signaling in a dual cell assay.

TABLE 10

Alignment and Consensus Sequences of Clones 1, 2, 63-65, 80 and 82 based on Kabat numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| 1 (germlined) | GYYWS (SEQ ID NO: 107) | YIFYSGYTKYNPSLKS (SEQ ID NO: 147) | DRWDFDY (SEQ ID NO: 187) | RASQGIRNNLG (SEQ ID NO: 307) | AESSLQS (SEQ ID NO: 347) | LQDFNYPYT (SEQ ID NO: 387) | ++ |
| 2 (germlined) | DYAMH (SEQ ID NO: 117) | GISWRSGNIGYADSVKG (SEQ ID NO: 157) | DKGIGFMNYEGFDY (SEQ ID NO: 197) | RASQGISNHLA (SEQ ID NO: 317) | AASSLQS (SEQ ID NO: 357) | QQYVTYPLT (SEQ ID NO: 397) | ++ |
| 80 | SYDMH (SEQ ID NO: 482) | SIGIGGDTYYPGSVKG (SEQ ID NO: 520) | GEWDLLWYFMDV (SEQ ID NO: 545) | RASQGISSWLA (SEQ ID NO: 570) | AASSLQS (SEQ ID NO: 595) | QQANSFPLT (SEQ ID NO: 620) | ++ |
| 63 | SYSMN (SEQ ID NO: 467) | YISSSSSTIYDADSVKG (SEQ ID NO: 492) | EAVPGYYNYNMDV (SEQ ID NO: 530) | RASQSISSRLA (SEQ ID NO: 555) | KASNLES (SEQ ID NO: 580) | QQYNSYSRT (SEQ ID NO: 605) | + |
| 64 | NYAMT (SEQ ID NO: 472) | AISGFGGSTYYADSVKG (SEQ ID NO: 497) | DHDYYAFDY (SEQ ID NO: 535) | RASQSISYLN (SEQ ID NO: 560) | AVSSLQS (SEQ ID NO: 585) | QQSYSTPYT (SEQ ID NO: 610) | + |
| 65 | NYAMT (SEQ ID NO: 477) | AISGVGGSTYYAASVKG (SEQ ID NO: 515) | DHDYYAFDY (SEQ ID NO: 540) | RASQSINSYLN (SEQ ID NO: 565) | SASSLQS (SEQ ID NO: 590) | QQSYSTPYT (SEQ ID NO: 615) | + |
| 82 | NAWMS (SEQ ID NO: 487) | RIKSKTYGGTTDYAAPVKG (SEQ ID NO: 525) | DPWNYVNYNYFMDV (SEQ ID NO: 550) | RASQDIRNYLA (SEQ ID NO: 575) | AASTLQS (SEQ ID NO: 600) | QNYFSVPLT (SEQ ID NO: 625) | + |
| Consensus_1 based on Kabat | X1-Y-X2-X3-X4, wherein X1 is G, D, or S; X2 is Y, A, or D; X3 is W or M; and X4 is S or H (SEQ ID NO: 712) | X1-I-X2-X3-X4-X5-G-X6-X7-X8-X9-X10-S-X11-K-X12, wherein X1 is Y, G, or S; X2 is S, G, or none; X3 is F, W, or I; X4 is Y, R, or S; X5 is G, or S; X6 is Y, N, or D; X7 is T or I; X8 is K, G, or Y; X9 is N, A, or P; and X10 is P, D, or G; X11 is L or V; and X12 is S or G (SEQ ID NO: 724) | X1-X2-X3-X4-X5-X6-X7-W-X8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, Y, or none; X8 is Y, or none; X10 is D, E, or none; X11 is G or none; X12 is M or none; and X13 is Y or V (SEQ ID NO: 736) | R-A-S-Q-G-I-X1-X2-X3-L-X4, wherein X1 is R or S; X2 is N, H or W; and X4 is G or A (SEQ ID NO: 744) | A-X1-S-S-L-Q-S, wherein X1 is A or E (SEQ ID NO: 752) | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | |
| Consensus_2 based on Kabat | X1-X2-X3-X4-X5, wherein X1 is G, D, N, or S; X2 is Y or A; X3 is Y, A, S, W, or D; X4 is W or G, or none | X1-I-X2-X3-X4-X5-X6-X7-X8-X9-X10-X11-X12-X13-X14-K-X15, wherein X1 is Y, G, S, A or R; X2 is S, A or R; X3 is F, or none; | X1-X2-X3-X4-X5-X6-X7-X8-X9-X10-X11-X12-X13-X14-D-X15, wherein X1 is D or none; X2 is R, K, G, P, or none; X3 is G, | R-A-S-Q-X1-I-X2-X3-X4-L-X5, wherein X1 is G, S, or D; X2 is R, S, or N; X3 is N or S; X4 is N, H, W, R, or Y; X4 is N, T, or | X1-X2-S-X3-L-X4-X5-X6-X7-T, wherein S, A, K, orS; X2 is A, E, or V; X3 is S, N, or T; and X4 is Q or | X1-Q-X2-X3-X4-X5-X6-X7-T, wherein X1 is L or Q; X2 is D, Y, A, or S; X3 is F, V, N, or Y; X4 is N, T, or | |

TABLE 10-continued

Alignment and Consensus Sequences of Clones 1, 2, 63-65, 80 and 82 based on Kabat numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
|  | M; and X5 is N, T, S or H (SEQ ID NO: 713) | W, I, S, G or T; X4 is Y, R, S, F, or none; X5 is G or S; X6 is G or S; X7 is Y, N, D, T or S; X8 is T or I; X9 is K, G, Y, or D; X10 is Y or D; X11 is N, A, or P; and X12 is P, D, G, or A; X13 is S or P; X14 is L or V; and X15 is S or G (SEQ ID NO: 725) | E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or none; X11 is D, E, N, or none; X12 is G or none; X13 is F or Y; X14 is M or none; and X15 is Y or V (SEQ ID NO: 737) | Y; and X5 is G, A, or N (SEQ ID NO: 745) | E (SEQ ID NO: 753) | S; X5 is Y, F, T, or V; X6 is P or S; X7 is Y, L or R (SEQ ID NO: 761) |  |

TABLE 11

Alignment and Consensus Sequences of Clones 1,2, 63-65, 80 and 82 based on Chothia numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| 1 (germlined) | GGSISGY (SEQ ID NO: 105) | FYSGY (SEQ ID NO: 145) | DRWDFDY (SEQ ID NO: 185) | RASQGIRNNLG (SEQ ID NO: 305) | AESSLQS (SEQ ID NO: 345) | LQDFNPYT (SEQ ID NO: 385) | ++ |
| 2 (germlined) | GFNPDDY (SEQ ID NO: 115) | SWRSGN (SEQ ID NO: 155) | DKGIGFNWNYEGFDY (SEQ ID NO: 195) | RASQGISNHLA (SEQ ID NO: 315) | AASSLQS (SEQ ID NO: 355) | QQVTYPLT (SEQ ID NO: 395) | ++ |
| 80 | GFTFSSY (SEQ ID NO: 480) | GIGGD (SEQ ID NO: 518) | GEWDLLWYFMDV (SEQ ID NO: 543) | RASQGISSWLA (SEQ ID NO: 568) | AASSLQS (SEQ ID NO: 593) | QQANSFPLT (SEQ ID NO: 618) | ++ |
| 63 | GFMFSSY (SEQ ID NO: 465) | SSSSST (SEQ ID NO: 490) | EAVPGYYNYMDV (SEQ ID NO: 528) | RASQSISSRLA (SEQ ID NO: 553) | KASNLES (SEQ ID NO: 578) | QQYNSYSRT (SEQ ID NO: 603) | + |
| 64 | GFTFSNY (SEQ ID NO: 470) | SGFGGS (SEQ ID NO: 495) | DHDYYAPDY (SEQ ID NO: 533) | RASQSISSYLN (SEQ ID NO: 558) | AVSSLQS (SEQ ID NO: 583) | QQSYSTPYT (SEQ ID NO: 608) | + |
| 65 | GFTFSNY (SEQ ID NO: 475) | SGYGGS (SEQ ID NO: 513) | DHDYYAFDY (SEQ ID NO: 538) | RASQSINSYLN (SEQ ID NO: 563) | SASSLQS (SEQ ID NO: 588) | QQSYSTPYT (SEQ ID NO: 613) | + |
| 82 | GITFSNA (SEQ ID NO: 485) | KSKTYGGT (SEQ ID NO: 523) | DPWNYVNYNYFMDV (SEQ ID NO: 548) | RASQDIRNVLA (SEQ ID NO: 573) | AASTLQS (SEQ ID NO: 598) | QNYFSVPLT (SEQ ID NO: 623) | + |
| Consensus_1 based on Chothia | G-X1-X2-X3-X4-X5-Y, wherein X1 is G or F; X2 is S, N, or T; X3 is I or F; X4 is S or D; and X5 is G, D, or S (SEQ ID NO: 714) | X1-X2-X3-X4-G-X5, wherein X1 is S, G, or none; X2 is F, W, or I; X3 is Y, R, or none; X4 is S or G; and X5 is Y, N, or D (SEQ ID NO: 726) | X1-X2-X3-X4-X5-X6-X7-W8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E, or none; X11 is G or none; X12 is M or none; and X13 is Y or V (SEQ ID NO: 736) | R-A-S-Q-G-I-X1-X2-X3-L-X4, wherein X1 is R or Q; X2 is N or S; X3 is N, H or W; and X4 is G or A (SEQ ID NO: 744) | A-X1-S-S-L-Q-S, wherein X1 is A or E (SEQ ID NO: 752) | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | |
| Consensus_2 based on Chothia | G-X1-X2-X3-X4-X5-X6, wherein X1 is G, F or is S, G, or none | X1-X2-X3-X4-X5-X6, wherein X1 X7-X8-X9-X10-X11-X12-X13-X14-D-X15, | X1-X2-X3-X4-X5-X6-X7-X8-X9-X10-X11-X12-X13-X14-D-X15, | R-A-S-Q-X1-I-X2-X3-X4-L-X5, wherein X1 is G, S, or D; X2 is R, S, | X1-X2-S-X3-L-X4-S, wherein X1 is A, K, orS; X2 is A, | X1-Q-X2-X3-X4-X5-X6-X7-T, wherein X1 is L or Q; X2 is D, | |

TABLE 11-continued

Alignment and Consensus Sequences of Clones 1,2, 63-65, 80 and 82 based on Chothia numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| | I; X2 is S, N, T, or M; X3 is I or F; X4 is S or D; X5 is G, D, S, or N; and X6 is Y or A (SEQ ID NO: 715) | X2 isF, W, G, S, I, or T; X3 is Y, R, S, F, or none; X4 is S or G; X5 is G or S; and X6 is Y, N, D, T, or S (SEQ ID NO: 727) | wherein X1 is D or none; X2 is R, K, G, P, or none; X3 is G, E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or none; X11 is D, E, N, or none; X12 is G or none; X13 is F or Y; X14 is M or none; and X15 is Y or V (SEQ ID NO: 737) | or N; X3 is N or S; X4 is N, H, W, R, or Y; and X5 is G, A, or N (SEQ ID NO: 745) | E, or V; X3 is S, N, or T; and X4 is Q or E (SEQ ID NO: 753) | Y, A, or S; X3 is F, V, N, or Y; X4 is N, T, or S; X5 is Y, F, T, or V; X6 is P or S; X7 is Y, L or R (SEQ ID NO: 761) | |

TABLE 12

Alignment and Consensus Sequences of Clones 1, 2, 63-65, 80 and 82 based on AbM numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| 1 (germlined) | GGSISGYYWS (SEQ ID NO: 106) | YIFYSGYTK (SEQ ID NO: 146) | DRWDFDY (SEQ ID NO: 186) | RASQGIRNNLG (SEQ ID NO: 306) | AESSLQS (SEQ ID NO: 346) | LQDFNYPYT (SEQ ID NO: 386) | ++ |
| 2 (germlined) | GFNFDDYAMH (SEQ ID NO: 116) | GISWRSGNIG (SEQ ID NO: 156) | DKGIGFNWNYEGFDY (SEQ ID NO: 196) | RASQGISNHLA (SEQ ID NO: 316) | AASSLQS (SEQ ID NO: 356) | QQVTYPLT (SEQ ID NO: 396) | ++ |
| 80 | GFTFSSYDMH (SEQ ID NO: 481) | SIGIGGDTY (SEQ ID NO: 519) | GEWDLLWYFMDV (SEQ ID NO: 544) | RASQGISSWLA (SEQ ID NO: 569) | AASSLQS (SEQ ID NO: 594) | QQANSFPLT (SEQ ID NO: 619) | ++ |
| 63 | GFMFSSYSMN (SEQ ID NO: 466) | YISSSSSTIY (SEQ ID NO: 491) | EAYPGYYYNYMDV (SEQ ID NO: 529) | RASQSISSRLA (SEQ ID NO: 554) | KASNLES (SEQ ID NO: 579) | QQYNSYSRT (SEQ ID NO: 604) | + |
| 64 | GFTFSNYAMT (SEQ ID NO: 471) | AISGFGGSTY (SEQ ID NO: 496) | DHDYYAFDY (SEQ ID NO: 534) | RASQSISSYLN (SEQ ID NO: 559) | AVSSLQS (SEQ ID NO: 584) | QQSYSTPYT (SEQ ID NO: 609) | + |
| 65 | GFTFSNYAMT (SEQ ID NO: 476) | AISGYGGSTY (SEQ ID NO: 514) | DHDYYAFDY (SEQ ID NO: 539) | RASQSINSYLN (SEQ ID NO: 564) | SASSLQS (SEQ ID NO: 589) | QQSYSTPYT (SEQ ID NO: 614) | + |
| 82 | GITFSNAWMS (SEQ ID NO: 486) | RIKSKTYGGTTD (SEQ ID NO: 524) | DPWNYVNYNYFMDV (SEQ ID NO: 549) | RASQDIRNYLA (SEQ ID NO: 574) | AASTLQS (SEQ ID NO: 599) | QNYFSVPLT (SEQ ID NO: 624) | + |
| Consensus_1 based on AbM | G-X1-X2-X3-X4-X5-Y-X6-X7-X8, wherein X1 is G or F; X2 is S, N, or T; X3 is I or F; X4 is S or D; X5 is G, D, or S; X6 is Y, A, or D; X7 is W or M; and X8 is S or H (SEQ ID NO: 716) | X1-I-X2-X3-X4-X5-G-X6-X7-X8, wherein X1 is Y, G, or S; X2 is S, G, or none; X3 is F, W, or I; X4 is Y, R, or none; X5 is G or S; X6 is Y, N, or D; X7 is T or I; X8 is K, G, or Y (SEQ ID NO: 728) | X1-X2-X3-X4-X5-X6-X7-W-X8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, Y, or none; X8 is Y, or none; X9 is D, E, or none; X10 is G or none; X11 is M or none; X12 is Y or V (SEQ ID NO: 736) | R-A-S-Q-G-I-X1-X2-X3-L-X4, wherein X1 is R or S; X2 is N, H or W; X3 is N, H or W; and X4 is G or A (SEQ ID NO: 744) | A-X1-S-S-L-Q-S, wherein X1 is A or E (SEQ ID NO: 752) | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | |
| Consensus_2 based on AbM | G-X1-X2-X3-X4-X5-X6-X7-X8-X9, wherein X1 is G, F or I; X2 is S, N, T, or M; X3 | X1-X2-X3-X4-X5-X6-X7-X8-X9, wherein X1 is Y, G, S, A or R; X2 is S, G, or none; X3 is F, W, I, | X1-X2-X3-X4-X5-X6-X7-X8-X9-X10-X11-X12-X13-X14-D-X15, wherein X1 is D or none; X2 is R, K, G, | R-A-S-Q-X1-I-X2-X3-X4-L-X5, wherein X1 is G, S, or D; X2 is R, S, or N; X3 | X1-X2-S-L-X4-S, wherein X1 is A, K, or S; X2 is A, E, or V; X3 is S, N, or T; X4 | X1-Q-X2-X3-X4-X5-X6-X7-T, wherein X1 is L or Q; X2 is D, Y, A, or S; X3 is F, V, N, or | |

TABLE 12-continued

Alignment and Consensus Sequences of Clones 1, 2, 63-65, 80 and 82 based on AbM numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| | is I or F; X4 is S or D; X5 is G, D, S, or N; X6 is Y or A; X7 is Y, A, D, S or W; X8 is W or M; and X9 is S, H, N, or T (SEQ ID NO: 717) | S, G or T; X4 is Y, R, S, F, or none; X5 is G or S; X6 is G or S; X7 is Y, N, D, T or S; X8 is T or I; X9 is K,G, Y, or D (SEQ ID NO: 729) | P, or none; X3 is G, E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or none; X11 is D, E, N, or none; X12 is G or none; X13 is F or Y; X14 is M or none; and X15 is Y or V (SEQ ID NO: 737) | is N, H, W, R, or Y; and X5 is G, A, or N (SEQ ID NO: 745) | and X4 is Q or E (SEQID NO: 753) | Y; X4 is N, T, or S; X5 is Y, F, T, or V; X6 is P or S; X7 is Y, L or R (SEQ ID NO: 761) | |

TABLE 13

Alignment and Consensus Sequences of Clones 1, 2, 63-65, 80 and 82 based on Contact numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| 1 (germlined) | SGYYWS (SEQ ID NO: 108) | WIGYIFYSGYTK (SEQ ID NO: 148) | ARDRWDFD (SEQ ID NO: 188) | RNNLGWY (SEQ ID NO: 308) | LLIYAESSLQ (SEQ ID NO: 348) | LQDFNYPY (SEQ ID NO: 388) | ++ |
| 2 (germlined) | DDYAMH (SEQ ID NO: 118) | WVSGISWRSGNIG (SEQ ID NO: 158) | AKDKGIGPNWNYEGFD (SEQ ID NO: 198) | SNHLAWF (SEQ ID NO: 318) | SLIYAASSLQ (SEQ ID NO: 358) | QQYVTYPL (SEQ ID NO: 398) | ++ |
| 80 | SSYDMH (SEQ ID NO: 483) | WVSSIGIGGDTY (SEQ ID NO: 521) | AR GEWDLLWY FMD (SEQ ID NO: 546) | SSWLAWY (SEQ ID NO: 571) | LLIYAASSLQ (SEQ ID NO: 596) | QQANSFPL (SEQ ID NO: 621) | ++ |
| 63 | SSYSMN (SEQ ID NO: 468) | WVSYISSSSSTIY (SEQ ID NO: 493) | TR EAYPGYYYN YMD (SEQ ID NO: 531) | SSRLAWY (SEQ ID NO: 556) | LLIYKASNLE (SEQ ID NO: 581) | QQYNSYSR (SEQ ID NO: 606) | + |
| 64 | SNYAMT (SEQ ID NO: 473) | WVSAISGFGGSTY (SEQ ID NO: 498) | AKDHDYYAFD (SEQ ID NO: 536) | SSYLNWY (SEQ ID NO: 561) | LLIYAVSSLQ (SEQ ID NO: 586) | QQSYSTPY (SEQ ID NO: 611) | + |
| 65 | SNYAMT (SEQ ID NO: 478) | WVSAISGYGGSTY (SEQ ID NO: 516) | AKDHDYYAFD (SEQ ID NO: 541) | NSYLNWY (SEQ ID NO: 566) | LLIYSASSLQ (SEQ ID NO: 591) | QQSYSTPY (SEQ ID NO: 616) | + |
| 82 | SNAWMS (SEQ ID NO: 488) | WVGRIKSKTYGGTTD (SEQ ID NO: 526) | TTDPWNYVNYNYFMD (SEQ ID NO: 551) | RNYLAWY (SEQ ID NO: 576) | LLVYAASTLQ (SEQ ID NO: 601) | QNYFSVPL (SEQ ID NO: 626) | + |
| Consensus_1 based on Contact | X1-X2-Y-X3-X4-X5, wherein X1 is S or D; X2 is G, D, or S; X3 is Y, A, or D; X4 is W or M; and X5 is S or H (SEQ ID NO: 718) | W-X1-X2-X3-I-X4-X5-X6-X7-G-X8-X9-X10, wherein X1 is 1 or V; X2 is G or S; X3 is Y, G, or S; X4 is S, G, or none; X5 is F, W, or I; X6 is F, W, or none; X7 is G or S; X8 is Y, N, or D; X9 is T or I; X10 is K, G, or Y (SEQ ID NO: 730) | A-X1-X2-X3-X4-X5-X6-X7-X8-W-X9-X10-X11-X12-F-X13-D, wherein X1 is K or R; X2 is D or none; X3 is R, K, or G; X4 is G, E, or none; X5 is I, W, or none; X6 is G, D, or none; X7 is F, L, or none; X8 is N, L, or none; X9 is N, Y, or none; X10 is Y, or none; X11 is D, E, or none; X12 is G or none; and X13 is M or none (SEQ ID NO: 738) | X1-X2-X3-L-X4-W-X5, wherein X1 is R or Q; X2 is N or S; X3 is N, H or W; X4 is G or A; and X5 is Y or F (SEQ ID NO: 746) | X1-L-I-Y-A-X2-S-S-L-Q, wherein X1 is L or S; and X2 is A or E (SEQ ID NO: 754) | X1-Q-X2-X3-X4-X5-P-X6, wherein X1 is L or Q; X2 is D, Y, or A; X3 is F, V, or N; X4 is N, T, or S; X5 is Y or F; X6 is Y or L (SEQ ID NO: 762) | |
| Consensus_2 based on Contact | X1-X2-X3-X4-X5-X6, wherein X1 is S or D; X2 is G, D, N, or S; X3 is Y or A; X4 | W-X1-X2-X3-I-X4-X5-X6-X7-X8-X9-X10-X11-X12-X13-X14-X15-X16-D, wherein X1 is A or T; X2 is K, R, | X1-X2-X3-X4-X5-X6-X7-X8-X9-X10-X11-X12-X13-X14-X15-X16-D, wherein X1 is A or T; X2 is K, R, | X1-X2-X3-L-X4-W-X5, wherein X1 is R, S, or N; X2 is N, H, or S; X3 is N, W, R, or Y; X4 is | X1-L-X2-Y-X3-X4-S-L-X6, wherein X1 is L or S; X2 is I or V; X3 is A, K, or S; X4 is | X1-Q-X2-X3-X4-X5-X6-X7, wherein X1 is L or Q; X2 is D, Y, A, or S; X3 is F, V, N, or Y; X4 | |

TABLE 13-continued

Alignment and Consensus Sequences of Clones 1, 2, 63-65, 80 and 82 based on Contact numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| | is Y, A, S, W, or D; X5 is W or M; and X6 is N, T, S or H (SEQ ID NO: 719) | X4 is S, G, or none; X5 is F, W, I, S, G or T; X6 is Y, R, S, F, or none; X7 is G or S; X8 is G or S; X9 is Y, N, D, T or S; X10 is T or I; X10 is K, G, Y, or D (SEQ ID NO: 731) | or T; X3 is D or none; X4 is R, K, G, P, or none; X5 is G, E, W, or none; X6 is I, W, A, N, or none; X7 is G, D, Y, or none; X8 is F, L, P, H, V, or none; X9 is N, L, G, D, or none; X10 is W or Y; X11 is N, Y, or none; X12 is Y, A, or none; X13 is D, E, N, or none; X14 is G or none; X15 is F or Y; and X16 is M or none (SEQ ID NO: 739) | G, A, or N; Y or F (SEQ ID NO: 747) | A, E, or V; X5 is S, N, or T; and X6 is Q or E (SEQ ID NO: 755) | is N, T, or S; X5 is Y, F, T, or V; X6 is P or S; X7 is Y, L or R (SEQ ID NO: 763) | |

TABLE 14

Alignment and Consensus Sequences of Clones 1, 2, 63-65, 80 and 82 based on IMGT numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| 1 (germlined) | GGSISGYY (SEQ ID NO: 109) | IFYSGYT (SEQ ID NO: 149) | ARDRWDFDY (SEQ ID NO: 189) | QGIRNN (SEQ ID NO: 309) | AE (SEQ ID NO: 349) | LQDFNYPYT (SEQ ID NO: 389) | ++ |
| 2 (germlined) | GFNFDDYA (SEQ ID NO: 119) | ISWRSGNI (SEQ ID NO: 159) | AKDKGIGFNWNYEGFDY (SEQ ID NO: 199) | QGISNH (SEQ ID NO: 319) | AA (SEQ ID NO: 359) | QQYVTVPLT (SEQ ID NO: 399) | ++ |
| 80 | GFTFSSYD (SEQ ID NO: 484) | IGIGGDT (SEQ ID NO: 522) | ARGEWDLLWYFMDV (SEQ ID NO: 547) | QGISSW (SEQ ID NO: 572) | AA (SEQ ID NO: 597) | QQANSFPLT (SEQ ID NO: 622) | ++ |
| 63 | GFMFSSYS (SEQ ID NO: 469) | ISSSSSTI (SEQ ID NO: 494) | TR EAYPGYYYNYMDV (SEQ ID NO: 532) | QSISSR (SEQ ID NO: 557) | KA (SEQ ID NO: 582) | QQYNSYSRT (SEQ ID NO: 607) | + |
| 64 | GFTFSNYA (SEQ ID NO: 474) | ISGFGGST (SEQ ID NO: 499) | AKDHDYYAFDY (SEQ ID NO: 537) | QSISSY (SEQ ID NO: 562) | AV (SEQ ID NO: 587) | QQSYSTPYT (SEQ ID NO: 612) | + |
| 65 | GFTFSNYA (SEQ ID NO: 479) | ISGYGGST (SEQ ID NO: 517) | AKDHDYYAFDY (SEQ ID NO: 542) | QSINSY (SEQ ID NO: 567) | SA (SEQ ID NO: 592) | QQSYSTPYT (SEQ ID NO: 617) | + |
| 82 | GITFSNAW (SEQ ID NO: 489) | IKSKTYGGTT (SEQ ID NO: 527) | TTDPWNYVNYYFMDV (SEQ ID NO: 552) | QDIRNY (SEQ ID NO: 577) | AA (SEQ ID NO: 602) | QNYFSVPLT (SEQ ID NO: 627) | + |
| Consensus_1 based on IMGT | G-X1-X2-X3-X4-X5-Y-X6, wherein X1 is G or F; X2 is S, N, or T; X3 is I or F; X4 is S, D, or S; X5 is Y, A, or D (SEQ ID NO: 720) | I-X1-X2-X3-X4-G-X5-X6, wherein X1 is S, G, or none; X2 is F, W, or I; X3 is Y, R, or none; X4 is G or S; X5 is Y, N, or D; and X6 is T or I (SEQ ID NO: 732) | A-X1-X2-X3-X4-X5-X6-X7-X8-W-X9-X10-X11-X12-F-X13-D-X14, wherein X1 is K or R; X2 is D or none; X3 is R, K, or G; X4 is G, E, or none; X5 is I, W, or none; X6 is G, D, or none; X7 is F, L, or none; X8 is N, L, or none; X9 is N, Y, or none; X10 is Y, or none; X11 is D, E, or none; X12 is G or none; X13 is M or none; and X14 is Y or V (SEQ ID NO: 740) | Q-G-I-X1-X2-X3, wherein X1 is R or S; X2 is N or S; and X3 is N, H or W (SEQ ID NO: 748) | A-X1, wherein X1 is A or E (SEQ ID NO: 756) | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | |
| Consensus_2 based on IMGT | G-X1-X2-X3-X4-X5-X6-X7, wherein X1 is G, F or I; X2 is S, N, T, or M; X3 is I or F; X4 | I-X1-X2-X3-X4-X5-X6-X7, wherein X1 is S, G, or none; X2 is F, W, I, S, G or T; X3 is Y, R, S, F, or | X1-X2-X3-X4-X5-X6-X7-X8-X9-X10-X11-X12-X13-X14-X15-X16-D-X17, wherein X1 is A or T; X2 is K, R, or T; X3 | Q-X1-I-X2-X3-X4, wherein X1 is G, S, or D; X2 is R, S, or N; X3 is N or S; and | | X1-Q-X2-X3-X4-X5-X6-X7-T, wherein X1 is L or Q; X2 is D, Y, A, or S; X3 is F, V, N, or Y; X4 is N, |

TABLE 14-continued

Alignment and Consensus Sequences of Clones 1, 2, 63-65, 80 and 82 based on IMGT numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| | is S or D; X5 is G, D, S, or N; X6 is Y or A; and X7 is Y, A, D, S, or W (SEQ ID NO: 721) | none; X4 is G or S; X5 is G or S; X6 is Y, N, D,T or S; and X7 is T or I (SEQ ID NO: 733) | is D or none; X4 is R, K, G, P, or none; X5 is G, E, W, or none; X6 is I, W, A, N, or none; X7 is G, D, Y, or none; X8 is F, L, P, H, V, or none; X9 is N, L, G, D, or none; X10 is W or Y; X11 is N, Y, or none; X12 is Y, A, or none; X13 is D, E, N, or none; X14 is G or none; X15 is F or Y; X16 is M or none; and X17 is Y or V (SEQ ID NO: 741) | X4 is N, H, W, R, or Y (SEQ ID NO: 749) | or V (SEQ ID NO: 757) | T, or S; X5 is Y, F, T, or V; X6 is P or S; X7 is Y, L or R (SEQ ID NO: 761) | |

TABLE 15

Alignment and Consensus Sequences of Clones 1, 2, 63-65, 80 and 82 based on Aho numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| 1 (germlined) | VSGGSISGYY (SEQ ID NO: 628) | IFYSGYTKYNPSLKSR (SEQ ID NO: 642) | DRWDFD (SEQ ID NO: 656) | ASQGIRNN (SEQ ID NO: 670) | AESSLQSGVPSR (SEQ ID NO: 684) | DFNYPY (SEQ ID NO: 698) | ++ |
| 2 (germlined) | ASGFNFDDYA (SEQ ID NO: 629) | ISWRSGNIGYADSVKGR (SEQ ID NO: 643) | DKGIGFNWNYEGFD (SEQ ID NO: 657) | ASQGISNH (SEQ ID NO: 671) | AASSLQSGVPSR (SEQ ID NO: 685) | YVTYPL (SEQ ID NO: 699) | ++ |
| 80 | VSGFTFSSYD (SEQ ID NO: 630) | IGIGGDTYYPGSVKGR (SEQ ID NO: 644) | GEWDLLWYFMD (SEQ ID NO: 658) | ASQGISSW (SEQ ID NO: 672) | AASSLQSGVPSR (SEQ ID NO: 686) | ANSFPL (SEQ ID NO: 700) | ++ |
| 63 | ASGFMFSSYS (SEQ ID NO: 631) | ISSSSSTIYDADSVKGR (SEQ ID NO: 645) | EAYPGYYYNYMD (SEQ ID NO: 659) | ASQSISSR (SEQ ID NO: 673) | KASNLESGVPSR (SEQ ID NO: 687) | YNSYSR (SEQ ID NO: 701) | + |
| 64 | ASGFTFSNYA (SEQ ID NO: 632) | ISGFGGSTYYADSVKGR (SEQ ID NO: 646) | DHDYYAFD (SEQ ID NO: 660) | ASQSISSY (SEQ ID NO: 674) | AVSSLQSGVPSR (SEQ ID NO: 688) | SYSTPY (SEQ ID NO: 702) | + |
| 65 | ASGFTFSNYA (SEQ ID NO: 633) | ISGYGGSTYYAASVKGR (SEQ ID NO: 647) | DHDYYAFD (SEQ ID NO: 661) | ASQSINSY (SEQ ID NO: 675) | SASSLQSGVPSR (SEQ ID NO: 689) | SYSTPY (SEQ ID NO: 703) | + |
| 82 | VSGITFSNAW (SEQ ID NO: 634) | IKSKTYGGTTDYAAPVKGR (SEQ ID NO: 648) | DPWNYVNYNYFMD (SEQ ID NO: 662) | ASQDIRNY (SEQ ID NO: 676) | AASTLQSGVPSR (SEQ ID NO: 690) | YFSVPL (SEQ ID NO: 704) | + |
| Consensus_1 based on Aho | X1-S-G-X2-X3-X4-X5-X6-Y-X7, wherein X1 is V or A; X2 is G or F; X3 is S, N, or T; X4 is I or F; X5 is S or D; X6 is G, D, or S; and X7 is Y, A, or D (SEQ ID NO: 722) | I-X1-X2-X3-X4-G-X5-X6-X7-Y-X8-X9-S-X10-K-X11-R, wherein X1 is S, G, or none; X2 is F, W, or I; X3 is Y, R, or none; X4 is G or S; X5 is Y, N, or D; X6 is T or I; X7 is K, G, or Y; X8 is N, A, or P; X9 is P, D or G; X10 is L or V; and X11 is G or S (SEQ ID NO: 734) | I-X1-X2-X3-X4-X5-X6-X7-W-X8-X9-X10-X11-F-X12-D, wherein X1 is D or none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E, or none; X11 is G or none; and X12 is M or none (SEQ ID NO: 742) | A-S-Q-G-I-X1-X2-X3, wherein X1 is R or S; X2 is N or S; and X3 is N, H or W or E (SEQ ID NO: 750) | A-X1-S-S-L-Q-S-G-V-P-S-R, wherein X1 is A or E (SEQ ID NO: 758) | X1-X2-X3-X4-P-X5, wherein X1 is D, Y, or A; X2 is F, V, or N; X3 is N, T, or S; X4 is Y or F; X5 is Y or L (SEQ ID NO: 764) | |
| Consensus_2 based on Aho | X1-S-G-X2-X3-X4-X5-X6-X7-X8, wherein X1 is V or A; X2 is G, F or I; X3 is S, N, T, | I-X1-X2-X3-X4-X5-X6-X7-X8-X9-X10-X11-X12-X13-K-X14-R, wherein X1 is S, G, or none; X2 is F, W, I, S, G or | X1-X2-X3-X4-X5-X6-X7-X8-X9-X10-X11-X12-X13-X14-D, wherein X1 is D or none; X2 is R, K, G, | A-S-Q-X1-I-X2-X3-X4, wherein X1 is G, S, or D; X2 is R, S, or N; X3 is N or S; and X4 is | X1-X2-S-G-V-P-S-R, wherein X1 is A, K, or S; X2 is E, or V; X3 is | X1-X2-X3-X4-X5-X6, wherein X1 is D, Y, A, or S; X2 is F, V, N, or Y; X3 is | |

TABLE 15-continued

Alignment and Consensus Sequences of Clones 1, 2, 63-65, 80 and 82 based on Aho numbering (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| | or M; X4 is I or F; X5 is S or D; X6 is G, D, S, or N; X7 is Y or A; and X8 is Y, A, D, S or W (SEQ ID NO: 723) | T; X3 is Y, R, S, F, or none; X4 is G or S; X5 is G or S; X6 is Y, N, D, T or S; X7 is T or I; X8 is K, G, Y, or D; X9 is Y or D; X10 is N, A, or P; X11 is P, D, G, or A; X12 is S or P; X13 is L or V; and X14 is G or S (SEQ ID NO: 735) | P, or none; X3 is G, E, W, or none; X4 is I, W, A, N, or none; X5 is G, D, Y, or none; X6 is F, L, P, H, V, or none; X7 is N, L, G, D, or none; X8 is W or V; X9 is N, Y, or none; X10 is D, E, N, or none; X11 is G or none; X12 is G or none; X13 is F or Y; and X14 is M or none (SEQ ID NO: 743) | N, H, W, R, or Y (SEQ ID NO: 751) | S, N, or T; and X4 is Q or E (SEQ ID NO: 759) | N, T, or S; X4 is Y, F, T, or V; X5 is P or S; X6 is Y, L or R (SEQ ID NO: 765) | |

TABLE 16

Alignment and Consensus Sequences of Clones 1, 2, 63-65, 80 and 82 based on cross-linking studies described in Example 7 and Kabat and Contact numbering scheme (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| 1 (germlined) | GYYWS (SEQ ID NO: 635) | WIGYIFYSGYTK (SEQ ID NO: 649) | DRWDFDY (SEQ ID NO: 663) | RASQGIRNNLG (SEQ ID NO: 677) | AESSLQS (SEQ ID NO: 691) | LQDFNYPYT (SEQ ID NO: 705) | ++ |
| 2 (germlined) | DYAMH (SEQ ID NO: 636) | WVSGISWRSGNIG (SEQ ID NO: 650) | DKGIGFNWNYEGFDY (SEQ ID NO: 664) | RASQGISNHLA (SEQ ID NO: 678) | AASSLQS (SEQ ID NO: 692) | QQYVTPLT (SEQ ID NO: 706) | ++ |
| 80 | SYDMH (SEQ ID NO: 637) | WVSSIGIGGDTY (SEQ ID NO: 651) | GEWDLLWYFMDV (SEQ ID NO: 665) | RASQGISSWLA (SEQ ID NO: 679) | AASSLQS (SEQ ID NO: 693) | QQANSFPLT (SEQ ID NO: 707) | ++ |
| 63 | SYSMN (SEQ ID NO: 638) | WVSYISSSSTIY (SEQ ID NO: 652) | EAYPGYYYNYMDV (SEQ ID NO: 666) | RASQSISSRLA (SEQ ID NO: 680) | KASNLES (SEQ ID NO: 694) | QQYNSYSRT (SEQ ID NO: 708) | + |
| 64 | NYAMT (SEQ ID NO: 639) | WVSAISGFGGSTY (SEQ ID NO: 653) | DHDYYAFDY (SEQ ID NO: 667) | RASQSISSYLN (SEQ ID NO: 681) | AVSSLQS (SEQ ID NO: 695) | QQSYSTPYT (SEQ ID NO: 709) | + |
| 65 | NYAMT (SEQ ID NO: 640) | WVSAISGYGGSTY (SEQ ID NO: 654) | DHDYYAFDY (SEQ ID NO: 668) | RASQSINSYLN (SEQ ID NO: 682) | SASSLQS (SEQ ID NO: 696) | QQSYSTPYT (SEQ ID NO: 710) | + |
| 82 | NAWMS (SEQ ID NO: 641) | WVGRIKSKTYGGTTD (SEQ ID NO: 655) | DPWNYVNYNYFMDV (SEQ ID NO: 669) | RASQDIRNYLA (SEQ ID NO: 683) | AASTLQS (SEQ ID NO: 697) | QNYFSVPLT (SEQ ID NO: 711) | + |
| Consensus_1 based on Cross-linking | X1-Y-X2-X3-X4, wherein X1 is G, D, or S; X2 is Y, A, or D; X3 is W or M; and X4 is S or H (SEQ ID NO: 712) | W-X1-X2-X3-I-X4-X5-X6-X7-G-X8-X9-X10, wherein X1 is I or V; X2 is G or S; X3 is Y, G, or S; X4 is S, G, or none; X5 is F, W, or I; X6 is Y, R, or none; X7 is G or S; X8 is Y, N, or D; X9 is T or I; X10 is K, G, or Y (SEQ ID NO: 730) | X1-X2-X3-X4-X5-X6-X7-W-X8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E, or none; X11 is G or none; X12 is M or none; and X13 is Y or V (SEQ ID NO: 736) | R-A-S-Q-G-I-X1-X2-X3-L-X4, wherein X1 is R or S; X2 is N or S; X3 is N, H or W; and X4 is G or A (SEQ ID NO: 744) | A-X1-S-S-L-Q-S, wherein X1 is A or E (SEQ ID NO: 752) | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | |
| Consensus_2 based on Cross-linking | X1-X2-X3-X4-X5, wherein X1 is G, D, N, or S; X2 is Y or A; X3 is | W-X1-X2-X3-I-X4-X5-X6-X7-X8-X9-X10-X11-X12-X13-X14-D-X15, wherein X1 is I or V; X2 is G or S; X3 | X1-X2-X3-X4-X5-X6-X7-X8-X9-X10-X11-X12-X13-X14-X15, wherein X1 is D or | R-A-S-Q-X1-I-X2-X3-X4-L-X5, wherein X1 is G, S, or D; X2 is R, S, or N; X3 | X1-X2-S-X3-L-X4-S, wherein X1 is A, K, or S; X2 is A, E, or V; | X1-Q-X2-X3-X4-X5-X6-X7-T, wherein X1 is L or Q; X2 is D, Y, A, or | |

TABLE 16-continued

Alignment and Consensus Sequences of Clones 1,2, 63-65, 80 and 82 based on cross-linking studies described in Example 7 and Kabat and Contact numbering scheme (where applicable, space was inserted into the CDR sequences to demonstrate the alignment; in the table "++" indicates complete blocking of IL-8 release in the dual cell assay, "+" indicates inhibition of IL-8 release in the dual cell assay as shown in FIG. 1)

| Clone ID/ Consensus | CDR-H1 | CDR-H2 | CDR-H3 | CDR-L1 | CDR-L2 | CDR-L3 | Functional blocking |
|---|---|---|---|---|---|---|---|
| | Y, A, S, W, or D; X4 is W or M; and X5 is N, T, S or H (SEQ ID NO: 713) | is Y, G, S, A or R; X4 is S, G, or none; X5 is F, W, I, S, G or T; X6 is Y, R, S, F, or none; X7 is G or S; X8 is G or S; X9 is Y, N, D, T or S; X10 is T or I; X10 is K, G, Y, or D (SEQ ID NO: 731) | none; X2 is R, K, G, P, or none; X3 is G, E, W, or none; X4 is I, W, A, N, or none; X5 is G, D, Y, or none; X6 is F, L, P, H, V, or none; X7 is N, L, G, D, or none; X8 is W orY; X9 is N, Y, or none; X10 is Y, A, or none; X11 is D, E, N, or none; X12 is G or none; X13 is F or Y; X14 is M or none; and X15 is Y or V (SEQ ID NO: 737) | is N or S; X4 is N, H, W, R, or Y; and X5 is G, A, or N (SEQ ID NO: 745) | X3 is S, N, or T; and X4 is Q or E (SEQ ID NO: 753) | S; X3 is F, V, N, or Y; X4 is N, T, or S; X5 is Y, F, T, or V; X6 is P or S; X7 is Y, L or R (SEQ ID NO: 761) | |

Example 7: Mapping Binding Epitope on CD30L of the Anti-CD30L Antibodies and the Sequence and Structural Determinants for Such Binding Epitope To map the binding epitope on CD30L of the clones that both block/inhibit CD30-CD30L recombination protein interaction and functionally block/inhibit CD30L-mediated CD30 signaling in a dual cell assay, cross-linking, enzyme digestion and peptide mass spectrometry studies on the antibody-CD30L complex were performed. Since the 7 clones demonstrated sequence similarity and common primary structure (sequence) features, a representative clone, germlined clone 2 comprising VH set forth in SEQ ID NO: 6, VL set forth in SEQ ID NO:8 and IgG1 constant region set forth in SEQ ID NO: 504 was used in the study. The CD30L extracellular domain ("ECD") comprising SEQ ID NO: 34 was used. Before starting the epitope mapping, a high-mass MALDI analysis has been performed to verify the integrity and aggregation level for each sample, including germlined clone 2 and the CD30L extracellular domain comprising SEQ ID NO: 34 used for the complex formation (data not shown).

The germlined clone 2 anti-CD30L antibody and the ECD were mixed and incubated to allow the complex formation, and then cross-linked to convert the non-covalent interactions into covalent bond for detection. The cross-linking study thus allows the direct analysis of non-covalent interaction by High-Mass MALDI mass spectrometry. By mixing a protein sample containing non-covalent interactions with a specially developed cross-linking mixture (Bich, C et al. Anal. Chem., 2010, 82 (1), pp 172-179), non-covalent complex can be specifically detected with high-sensitivity. The covalent binding generated allows the interacting species to survive the sample preparation process and the MALDI ionization. A special High-Mass detection system allows characterizing the interaction in the High-Mass range.

Each mixture prepared for the control (antibody alone or CD30L ECD alone) and for the antibody-CD30L complex (germlined clone 2 and CD30L ECD complex) was submitted to cross-linking using DSS MALDI MS analysis kit. The protein solutions (9 µl) were mixed with 1 µl of DSS Stabilizer reagent (2 mg/ml) and incubated at room temperature. After the incubation time (180 minutes) the samples were prepared for MALDI analysis for all the samples. The samples were analysed by High-Mass MALDI MS immediately after crystallization with sinapinic acid matrix (10 mg/ml) in acetonitrile/water (1:1, v/v), TFA 0.1% (DSS MALDI Kit). In control samples, MALDI TOF peaks corresponding to theoretically calculated values for antibody only or CD30L ECD only were detected (data not shown). After cross-linking, MALDI TOF peaks corresponding to the antibody-CD30L complex (germlined clone 2 and CD30L ECD complex) were detected, demonstrating the proper formation of the antibody-CD30L complex (data not shown).

Before the epitope mapping studies, peptide mass fingerprint of CD30L ECD was determined. To characterize CD30L ECD, the sample was subjected to trypsin, chymotrypsin, Asp-N, elastase and thermolysin proteolysis followed by nLC-Q-Exactive™ MS/MS analysis. Briefly, two tubes of 10 µL of CD30L ECD (15.34 µM) were prepared. One of the two was mixed with 1 µL of DSS d0/d12 (2 mg/mL; DMF) before 180 minutes incubation time at room temperature. The other tube was not mixed with the cross-linking regent (control). Both tubes were kept 180 minutes at room temperature. After incubation, the cross-linking reaction was stopped by adding 1 µL of Ammonium Bicarbonate (20 mM final concentration) before additional 60 minutes incubation at room temperature. Then, both tubes were dried using speedvac before 8M urea resuspension (10 L). After mixing, DTT (1 µl, 500 mM) was added to both tubes. The mixture was then incubated 60 minutes at 37° C. After incubation, iodoacetamide (1 µl, 1M) was added to each tube before additional 60 minutes incubation at room temperature, in a dark room. After incubation, 100 of the proteolytic buffer were added to both tubes. Trypsin buffer contains 50 mM Ambic pH 8.5, 5% acetonitrile; chymotrypsin buffer contains Tris HCl 100 mM, CaCL2 10 mM pH 7.8; the ASP-N buffer contains Phosphate buffer 50 mM pH 7.8; elastase buffer contains Tris HCl 50 mM pH 8.0 and thermolysin buffer contains Tris HCl 50 mM, CaCL2 0.5 mM pH 9.0. For trypsin proteolysis, 100 µl of the reduced/alkyled CD30L ECD were mixed with 1 µl of trypsin (Promega™) with the ratio 1/100. The proteolytic mixture was incubated overnight at 37° C. For chymotrypsin proteolysis, 100 µl of the reduced/alkyled CD30L ECD were mixed with 0.5 µl of chymotrypsin (Promega™) with the ratio 1/200. The proteolytic mixture was incubated overnight at 25° C. For ASP-N proteolysis, 100 µl of the reduced/alkyled CD30L ECD were mixed with 0.5 µl of ASP-N (Promega™) with the ratio 1/200. The proteolytic mixture was incubated overnight at 37° C. For elastase proteolysis, 100 µl of the reduced/alkyled CD30L ECD were mixed with 1 µl of elastase (Promega™) with the ratio 1/100. The proteolytic mixture was incubated overnight at 37° C. For thermolysin proteolysis, 100 µl of the reduced/alkyled TNFSF8 were mixed with 2 µl of thermolysin (Promega™) with a ratio 1/50. The proteolytic mixture was incubated overnight at 70° C. After digestion formic acid 1% final was added to the solution.

Figures 1D, 1E:
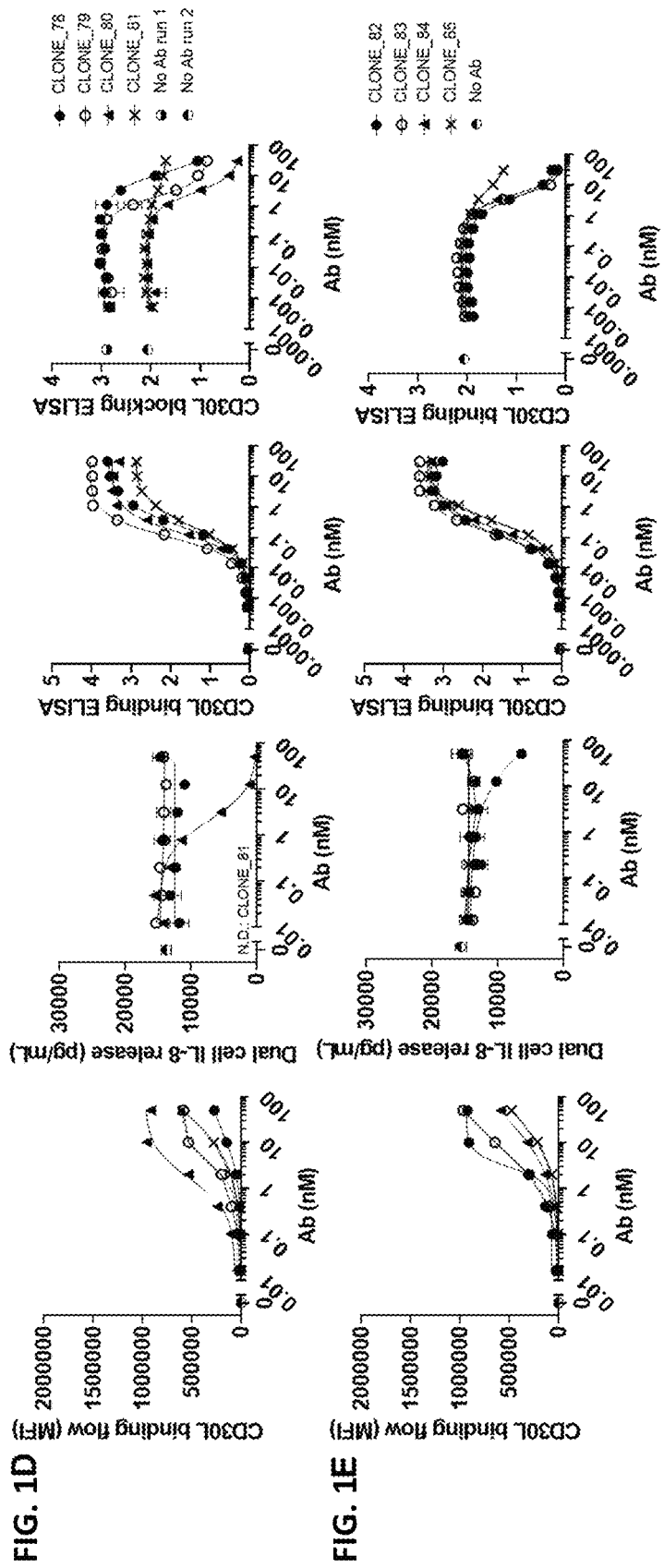
Figure 2:
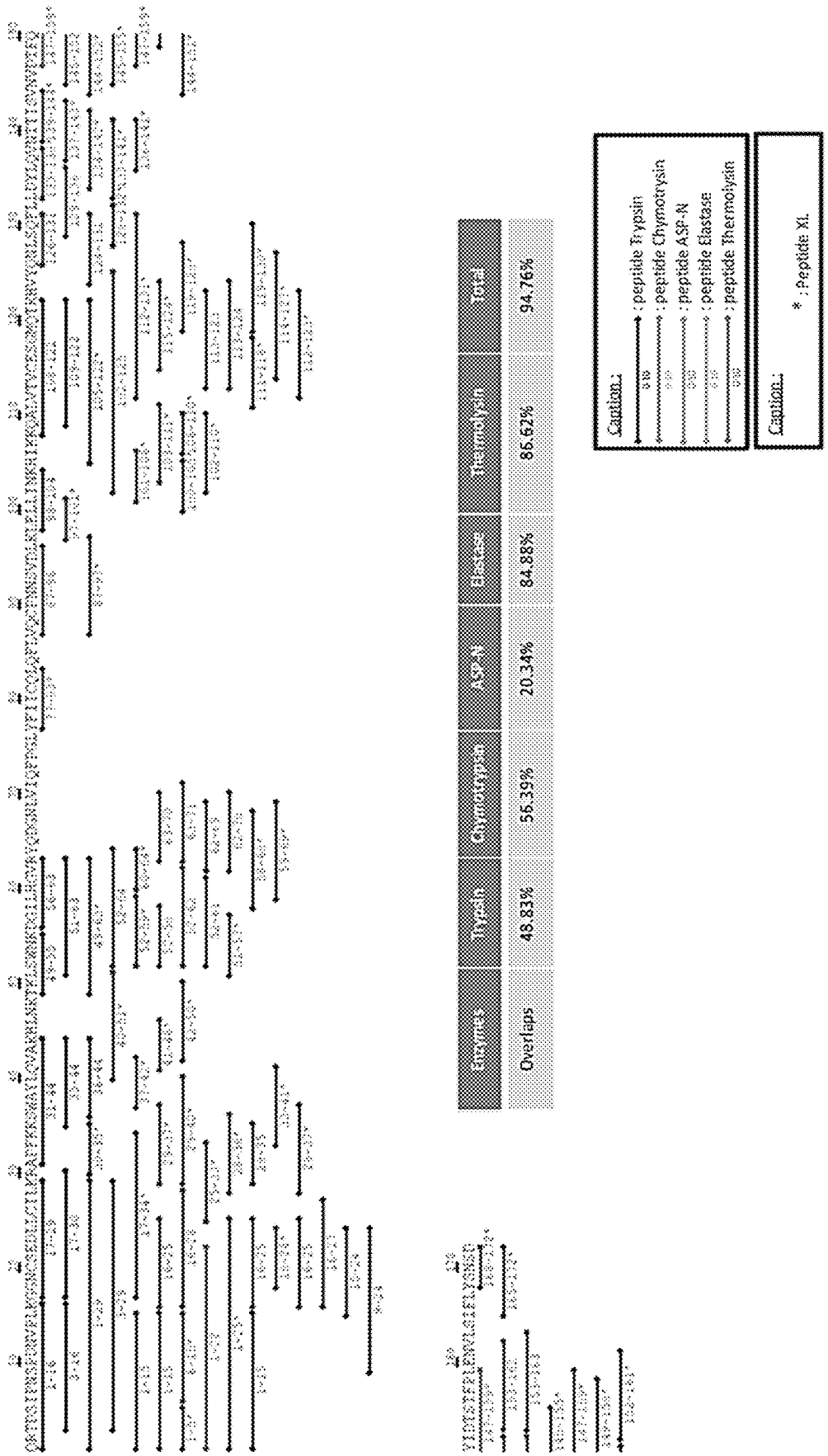
FIG. 2 depicts the overlap mapping of the peptides generated from trypsin, chymotrypsin, ASP-N, elastase, and/or thermolysin proteolysis, demonstrating that the peptide signature covers 94.76% of the CD30L ECD sequence (SEQ ID NO:34).

After proteolysis, 1 µl of the peptide solution generated by proteolysis was loaded onto a nano-liquid chromatography system (Ultimate 3000-RSLC) and the Q-Exactive™ MS analysis was then performed. Based on the results obtained from such MS analyses, overlap mapping of the peptides generated from trypsin, chymotrypsin, ASP-N, elastase, and/or thermolysin proteolysis as determined and shown in FIG. 2. Combining the peptides of Trypsin, Chymotrypsin, ASP-N, Elastase and Thermolysin proteolysis, 94.76% of the CD30L ECD sequence (SEQ ID NO: 34) is covered.

To determine the epitope on CD30L by anti-CD30L binding with high resolution, the protein complexes of CD30L ECD (SEQ ID NO: 34) and anti-CD30L (clone 2 germlined) were incubated with deuterated cross-linkers and subjected to multi-enzymatic cleavage with the enzymes and procedures as described above for determining peptide mass fingerprint of CD30L ECD. After enrichment of the cross-linked peptides, the samples were analyzed by high resolution mass spectrometry (nLC-Q-Exactive™ MS) and the data generated were analyzed using XQuest 2.0 and Stavrox 3.6 software.

After trypsin, chymotrypsin, ASP-N, elastase, and thermolysin proteolysis of the complex between CD30L ECD and anti-CD30L with deuterated d0d12, the nLC-orbitrap MS/MS analysis detected nine cross-linked peptides between CD30L ECD (SEQ ID NO: 34) and anti-CD30L (clone 2 germlined). The sequences and positions of cross-links are presented in the Table 17.

TABLE 17

Cross-linked peptides detected between CD30L ECD (SEQ ID NO: 34) and anti-CD30L (clone 2 germlined)

| Sequence | Enzyme | Sequence on anti-CD30L | Sequence on CD30L ECD (SEQ ID NO: 34) | XLType | Cross-linking position on anti-CD30L | Cross-linking position on CD30L ECD (SEQ ID NO: 34) | Identified on StavroX |
|---|---|---|---|---|---|---|---|
| ATYYCQQYVTYP (SEQ ID NO: 772)-QRTDSIPNSPDNVPLKGGNCSEDL (SEQ ID NO: 773)-a10-b16 | Thermolysin | 84-95 (SEQ ID NO: 8) | 1-24 | inter-protein xl | 93 (SEQ IDN O: 8) | 16 | Yes |
| GLEWVSGISWR (SEQ ID NO: 774)-GGNCSEDLLCILK (SEQ ID NO: 775)-a6-b5 | Trypsin | 44-54 (SEQ ID NO: 6) | 17-29 | inter-protein xl | 49 (SEQ IDN O: 6) | 21 | Yes |
| SLIYAASSLQSGVPSR (SEQ ID NO: 776)-GGNCSEDLLCILK (SEQ ID NO: 775)-a7-b5 | Trypsin | 46-61 (SEQ ID NO: 8) | 17-29 | inter-protein xl | 52 (SEQ ID NO: 8) | 21 | Yes |
| IGFNWNYEG (SEQ ID NO: 777)-LKGGNCSEDLLC (SEQ ID NO: 778)-a7-b7 | Thermolysin | 102-110 (SEQ ID NO: 6) | 15-26 | inter-protein xl | 108 (SEQ ID NO: 6) | 21 | Yes |
| SLRLSCAASGFNFDDYAMHWVR (SEQ ID NO: 779)-RAPFK (SEQ ID NO: 780)-a19-b1 | Trypsin | 17-38 (SEQ ID NO: 6) | 30-34 | inter-protein xl | 35 (SEQ ID NO: 6) | 30 | Yes |
| FDYWG (SEQ ID NO: 781)-KHLNKTKLS (SEQ ID NO: 782)-a3-b5 (SEQ ID NO: 608) | Elastase | 111-115 (SEQ ID NO: 6) | 44-52 | inter-protein xl | 113 (SEQ ID NO: 6) | 48 | Yes |
| LQSGVPSR (SEQ ID NO: 783)-AKHLNKTK (SEQ ID NO: 784)-a3-b6 | Thermolysin | 54-61 (SEQ ID NO: 8) | 43-50 | inter-protein xl | 56 (SEQ ID NO: 8) | 48 | Yes |
| ISWRSGNIGYADS (SEQ ID NO: 785)-VRYQDGNLV (SEQ ID NO: 786)-a5-b2 | Thermolysin | 51-63 (SEQ ID NO: 6) | 62-70 | inter-protein xl | 55 (SEQ ID NO: 6) | 63 | Yes |
| ISWRSGNIGYADS (SEQ ID NO: 785)-VRYQDGNLV (SEQ ID NO: 786)-a5-b3 | Thermolysin | 51-63 (SEQ ID NO: 6) | 62-70 | inter-protein xl | 55 (SEQ ID NO: 6) | 64 | Yes |

Therefore, the studies with chemical cross-linking, high-mass MALDI mass spectrometry and nLC-Orbitrap mass spectrometry characterized the molecular interface between CD30L and a representative anti-CD30L that blocked/inhibited both CD30-CD30L recombination protein interaction and functionally blocked/inhibited CD30L-mediated CD30 signaling in a dual cell assay. The analyses demonstrate that the epitope on CD30L for such representative anti-CD30L (clone 2 germlined) include the amino acids the amino acids K16, 521, R30, K48, R63, and/or Y64 of SEQ ID NO: 34, as shown in Table 17 above and Table 18 below.

TABLE 18

Epitope on CD30L and the corresponding contact residues in CDR of the representative anti-CD30L

| | |
|---|---|
| VH H35 (CDRH1) | R30 (R92) |
| VH S49 (FR-CDRH2) | S21 (S83) |
| VH S55 (CDRH2) | R63, Y64 (R125, Y126) |
| VH Y108 (CDRH3) | S21 (S83) |
| VH Y113 (CDRH3) | K48 (K110) |
| VL S52 (CDRL2) | S21 (S83) |

TABLE 18-continued

Epitope on CD30L and the corresponding contact residues in CDR of the representative anti-CD30L

| | |
|---|---|
| VL S56 (CDRL2) | K48 (K110) |
| VL T93 (CDRL3) | K16 (K78) |

Figure 3:
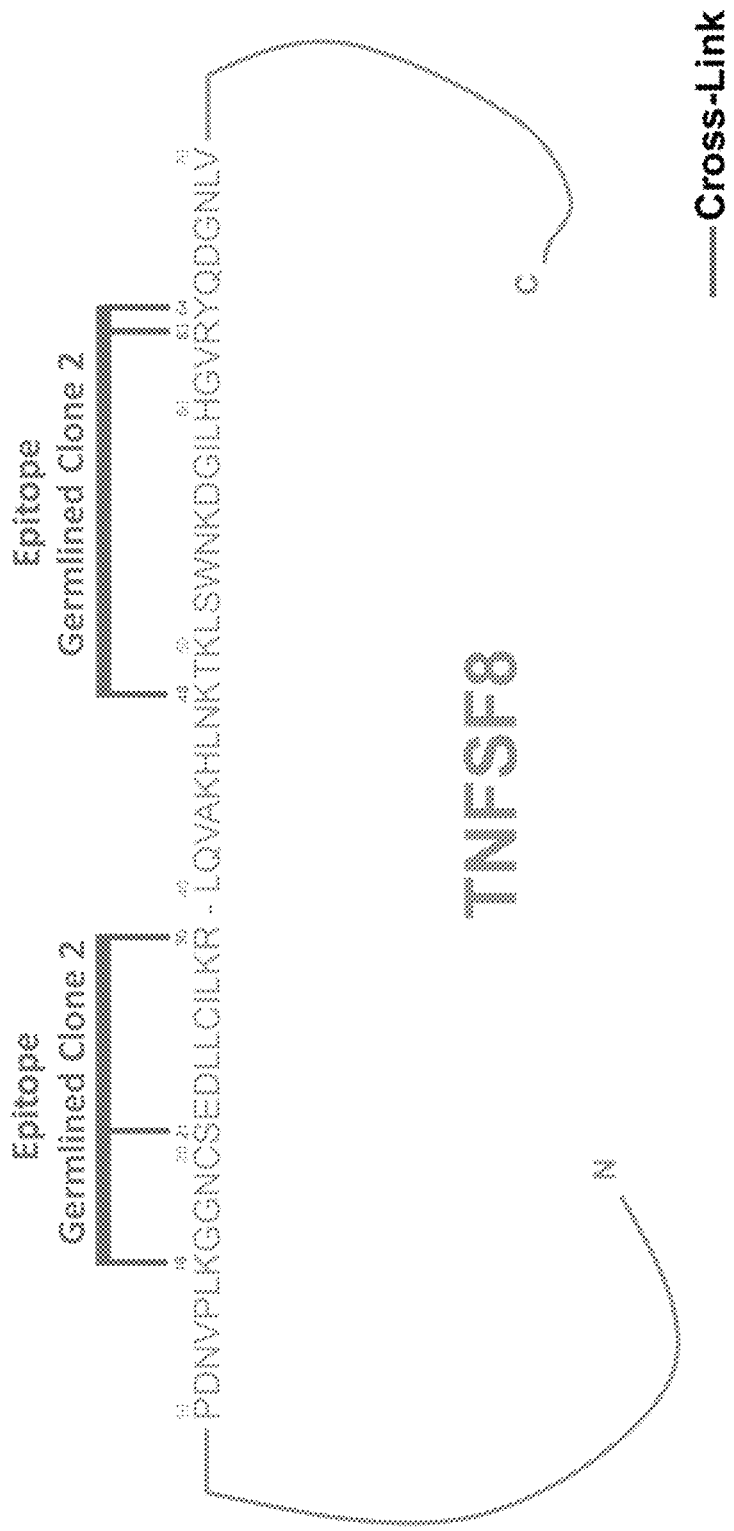
FIG. 3 depicts the epitope determined from cross-linking and mass spectrometry studies in the context of parts of the CD30L ECD sequence (amino acids 10-30 and 40-70 of SEQ ID NO: 34).
Figure 4E:
Figure 4J:
Figure 4D:
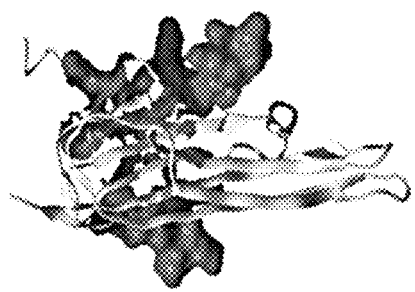
Figure 4I:
Figure 4C:
Figure 4H:
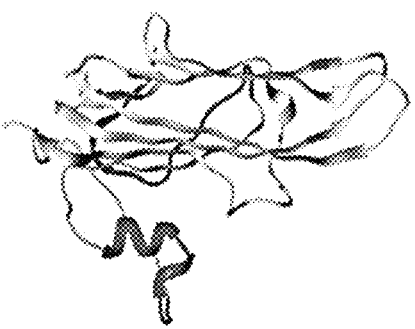
Figure 4B:
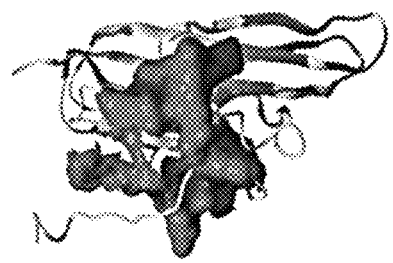
Figure 4G:
Figure 4A:
Figure 4F:

Having established the epitope on CD30L for a representative anti-CD30L (germlined clone 2) that blocked/inhibited both CD30-CD30L recombination protein interaction and functionally blocked/inhibited CD30L-mediated CD30 signaling in a dual cell assay, the corresponding structural and sequence features conferring the functional property for such representative anti-CD30L were analyzed. As shown in Table 17 and Table 18, eight amino acid residues from 5 of the 6 CDRs of the germlined clone 2 came into significant stable contact with the epitope on CD30L, as demonstrated by the crosslinking of the residues in close proximity in the complex between CD30 and anti-CD30L. The corresponding epitope-interacting residues and the corresponding interactions were mapped by identifying the crosslinked peptides in Table 17 and the interaction pairs were listed in each row of Table 18. FIG. 3 further summarized the cross-linked epitope in the context of the CD30L ECD sequence (SEQ ID NO: 34). FIG. 4A-4J provided the 3 dimensional structure of the epitope on CD30L as identified.

Based on the detected CD30L-interacting residues from the anti-CD30L CDR sequences, the CDRs from the representative anti-CD30L antibody (germlined clone 2) that confer the CD30L binding and blocking functionality were further determined by combining CDRs from Kabat numbering scheme and the Contact numbering scheme, as shown in Table 16 (referred to as based on cross-linking studies or cross-linking based). Such cross-linking based CDRs encompasses all the CD30L-interacting residues detected in the cross-linking studies. The cross-linking based CDRs, the identified CD30L-interacting residues, and the consensus CDR sequences provided herein (e.g. Table 16), when combined with the fact that the CDRs demonstrated robust alignment and significant similarity across the 7 out of the 110 clones from multiple independent antibody campaigns, provides the sequence and structural features for antibodies binding to the epitope and/or for antibodies having the CD30L binding and blocking functionality provided herein.

Example 8: Specificity of the Anti-CD30L Antibodies

Before the binding of the anti-CD30L antibodies to targets other than CD30L (off-target binding) can be assessed, an assay system was established and validated to investigate such off-target binding. Briefly, 4 representative antibodies were tested, including anti-CD30L antibody clone 1, clone 1 germlined, clone 2, and clone 2 germlined, all of which further comprising IgG1 constant regions (SEQ ID NO: 502). All 4 antibodies showed low to medium levels of background binding to untransfected HEK293 cells when tested at 2, 5 and 20 µg/mL, whilst germlined clone 2 showed low levels of background binding to untransfected HEK293 cells when tested at 2, 5 and 20 µg/mL. Binding to over-expressed TNFSF8 (CD30L), the primary target, was observed with equal intensity at all 3 concentrations (2, 5 and 20 µg/mL) tested. Based upon these data, further off-target binding was assessed at the concentration of g/mL to minimize the background.

Having established and validated the assay, all 4 antibodies (clone 1, clone 1 germlined, clone 2, and clone 2 germlined) at 5 µg/mL were screened for binding against fixed human HEK293 cells, individually expressing 5,861 full-length human plasma membrane proteins and cell surface-tethered human secreted proteins plus a further 371 human heterodimers. For the off-target screening, 5,861 expression vectors, encoding both ZsGreen1 and a full-length human plasma membrane protein or a cell surface-tethered human secreted protein, were individually arrayed in duplicate across 18 microarray slides ('slide-sets'). In addition, vectors encoding a further 371 human heterodimers were co-arrayed across a further microarray slide. This study with a library of 6,232 (5, 861+371) targets other than CD30L revealed no specific binding to 6,213 µlibrary targets, and only 19 preliminary library hits altogether for further investigation, among which is CD30L (hit #3 of the 19 hits).

To confirm the preliminary findings, each library hit was re-expressed, along with 2 control receptors, and re-tested with 5 µg/mL of each test antibody individually or control treatments. Briefly, vectors encoding each of the 19 hits identified in the library screen, plus vectors encoding CD20 and EGFR, were arrayed and expressed in HEK293 cells on new slides. This conformation study was performed both on fixed and live cells. The procedure and analyses were carried out as for described for the initial screen except that identical slides were treated, either after cell fixation or in the absence of cell fixation, with 5 µg/mL of each test antibody individually, 1 µg/mL Rituximab biosimilar (positive control), or no test molecule (AF647 anti-hIgG Fc secondary only) (n=2 slides per treatment for fixed cell screen and n=1 slide per treatment for live cell screen). Binding to target-expressing cells and untransfected cells was again assessed by fluorescence imaging.

In the confirmation screen, all 19 µlibrary hits (one of which is CD30L) and 2 control receptors (CD20 and EGFR) were over-expressed in HEK293 cells. As expected, the Rituximab biosimilar showed a med/strong intensity interaction with over-expressed CD20, validating the incubation conditions and detection system.

The binding of each of the tested anti-CD30L antibodies to CDH13 (hit #16 of the 19 hits) was very weak (very low confidence) in the library screen. Lack of reproducibility into the confirmation screen indicates that this was not a real interaction.

Twelve of the 19 µlibrary hits (#4 to #15 fo the 19 hits, which are IGHG3, SLC22A23, CXCL12, IGF2, EDN2, IGF1, PAPPA, IGHG4, IGHG1, IGHG2, FCGR3A+FCER1G and FCGR3A+CD247, respectively) were bound by at least 1 of the control treatments (Rituximab biosimilar and/or no primary test molecule). These are therefore classed as non-specific, and included Fc gamma receptors (hit #s 14 and 15, FCGR3A+FCER1G and FCGR3A+CD247 respectively) which are presumably Fc-domain mediated and IGHG3 (hit #4) which is known to be bound directly by the secondary detection antibody. Hit #3 is TNFSF8 (CD30L), the primary target of the antibodies tested.

The signal intensities for the further 5 of the 19 µlibrary hits (hit #s 1, 2, 19, 20 and 21, which are FCGR1A, SLC38A4, GPR87, EPHA7, CACNA2D4) in the confirmation screen were classed as very weak (with the exception that clone 1 and clone 1 germlined binding to EPHA7 in live 293 cells was classified as weak) and, in 1 instance, only observed on 1 of the 2 replicate slides. For such hits, signals are so close to background levels that there is little to no confidence that they are real and/or specific. Thus no significance were attributed to such hits.

In contrast, the 4 representative anti-CD30L antibodies tested in this Example, including anti-CD30L antibody clone 1, clone 1 germlined, clone 2, and clone 2 germlined, all showed specific, strong intensity, interactions with TNFSF8 (CD30L), their primary target, on both fixed and live cell microarrays.

These data demonstrate high specificity of the 4 representative anti-CD30L antibodies tested in this Example, including anti-CD30L antibody clone 1, clone 1 germlined, clone 2, and clone 2 germlined for their primary target, TNFSF8 (CD30L).

Example 9: Additional Binding Studies and Comparison with Reference Anti-CD30L Antibodies Representative anti-CD30L clone antibodies (clone 1, clone 1 germlined, clone 2, and clone 2 germlined) were also characterized for binding affinity to cynomolgus and human CD30L and for their ability to neutralize the interaction of CD30L to CD30. Binding of the representative anti-CD30L clones to recombinant cynomolgus (cyno) and human CD30L has been demonstrated by ELISA binding assays with purified human or cyno CD30L and by binding to CD30L expressing B16 or HEK293 cells in flow cytometry, with human or cyno CD30L expressed on HEK293 or B16 cells. In the B16 or HEK293 cell binding assays (cell binding assays as shown in FIG. 5A), the representative anti-CD30L clones were all shown to bind strongly to CD30L with nanomolar or sub-nanomolar affinity (Table 19). The representative binding and blocking curves for germlined clone 2 from such cell binding assays were shown in FIGS. 5B to 5E. In the ELISA binding assays with purified human or cyno CD30L (ELISA configuration shown in FIGS. 5F and 5G), the representative anti-CD30L clones were all shown to bind strongly to CD30L with picomolar affinity for recombinant human CD30L and nanomolar affinity for cyno CD30L (Table 20). The representative binding and blocking curves from the ELISA for germlined clone 2 were shown in FIGS. 5H and 5I. When directly compared with the reference 1 (ref1) anti-CD30L (comprising HC of SEQ ID NO: 768 and LC of SEQ ID NO: 769), all 4 representative anti-CD clones had better $IC_{50}$, up to 2.74 fold better $IC_{50}$ (clone 2 germlined) against humanCD30L and up to 2.13 fold better $IC_{50}$ (clone 2 germlined) against cyno CD30L, at which the representative anti-CD30L clones blocked the binding of recombinant CD30-Fc to human or cyno CD30L expressed on HEK293 or B16 cells, (Table 19). In addition, these 4 representative anti-CD30L clones were tested in an IL-8 release dual cell assay, for cynoCD30L involving the K299 $CD30^+$ cell line co-cultured with HEK293-cynoCD30L and for human CD30L involving K299 $CD30^+$ cell line co-cultured with B16-humanCD30L cells. In such IL-8 release dual cell assay, K299 $CD30^+$ release IL-8 upon ligation with and stimulation by the co-cultured CD30L expressing cells (FIG. 5J). Blocking of the CD30L-CD30 interaction can proportionally reduce the release of IL-8 and thus the amount of IL-8 released can be used as a readout for the effectiveness of antibody mediated blocking of CD30L-CD30 interactions between the co-cultured cells (FIG. 5J). All 4 representative anti-CD30L clones potently and effectively neutralized the cell-cell interaction mediated by CD30 and CD30L ligation and blocked IL-8 release, with $IC_{50}$ in the sub-subnanomolar (clone 2 and clone 2 germlined) or nanomolar (clone 1 and clone 1 germlined) range (Table 21). The representative IL-8 release curves from the dual cell assay for germlined clone 2 were shown in FIGS. 5K and 5L. When directly compared with the reference 1 (ref1) anti-CD30L (comprising HC of SEQ ID NO: 768 and LC of SEQ ID NO: 769), all 4 representative anti-CD30L clones had better $IC_{50}$, up to 2.0 fold better $IC_{50}$ (clone 2) against humanCD30L and up to 2.6 fold better $IC_{50}$ (clone 2) against cyno CD30L, at which the representative anti-CD30L clones functionally blocked IL-8 release in the dual cell assay (Table 21).

TABLE 19

Summary of (1) the binding $EC_{50}$ of the representative anti-CD30L clones to human or cyno CD30L expressed on HEK293 or B16 cells as indicated and (2) the $IC_{50}$ at which the representative anti-CD30L clones blocked the binding of recombinant CD30-Fc to human or cyno CD30L expressed on HEK293 or B16 cells as indicated.

| Clones | Human CD30L | | Cyno CD30L | |
| --- | --- | --- | --- | --- |
| | Binding to B16-rhCD30L $EC_{50}$ (nM) | Ab-mediated blocking of CD30-Fc to B16-huCD30L cells $IC_{50}$ (nM) | Binding to HEK293-cyCD30L $EC_{50}$ (nM) | Ab-mediated blocking of CD30-Fc to HEK293-cyCD30L cells $IC_{50}$ (nM) |
| Ref1 | 1.12 | 1.84 | 0.56 | 0.73 |
| CLONE_1 | 1.11 | 1.06 | 0.67 | 0.51 |
| CLONE_1_germlined | 1.12 | 1.05 | 0.58 | 0.54 |
| CLONE_2 | 0.74 | 0.79 | 0.30 | 0.34 |
| CLONE_2_germlined | 0.64 | 0.67 | 0.33 | 0.34 |

TABLE 20

Summary of (1) the binding $EC_{50}$ of the representative anti-CD30L clones to purified human or cyno CD30L in an ELISA assay and (2) the $IC_{50}$ at which the representative anti-CD30L clones blocked the binding of recombinant CD30-Fc to purified human or cyno CD30L in an ELISA assay.

| Clones | Human CD30L | | Cyno CD30L | |
| --- | --- | --- | --- | --- |
| | Binding to rhCD30L $EC_{50}$ (nM) | Ab-mediated blocking of CD30-Fc to huCD30L $IC_{50}$ (nM) | Binding to rcyCD30L $EC_{50}$ (nM) | Ab-mediated blocking of CD30-Fc to rcyCD30L $IC_{50}$ (nM) |
| CLONE_1 | 0.05 | 2.14 | 0.07 | 1.58 |
| CLONE_1_germlined | 0.05 | 1.85 | 0.07 | 1.71 |
| CLONE_2 | 0.04 | 1.35 | 0.05 | 1.28 |
| CLONE_2_germlined | 0.03 | 1.92 | 0.05 | 1.53 |

TABLE 21

Summary of the IC$_{50}$ at which the representative anti-CD30L clones blocked the IL-8 release in a dual cell assay.

| Clones | Inhibition of IL-8 release in a dual cell assay (B16-huCD30L cells + K299 cells) IC$_{50}$ (nM) | Inhibition of IL-8 release in a dual cell assay (HEK293-cyCD30L cells + K299 cells) IC$_{50}$ (nM) |
|---|---|---|
| Ref1 | 1.61 | 0.79 |
| CLONE_1 | 1.43 | 0.39 |
| CLONE_1_germlined | 1.29 | 0.43 |
| CLONE_2 | 0.81 | 0.31 |
| CLONE_2_germlined | 0.89 | 0.41 |

To more precisely define and compare the binding affinities (dissociation equilibrium constant, $K_D$), the association rate constant (on rate, $k_{on}$), and the dissociation rate constant (off rate, $k_{off}$), the kinetic exclusion assay (KinExA) was performed. KinExA measures the equilibrium binding affinity and kinetics between unmodified binding molecules in solution. For affinity analysis, the equilibrium dissociation constant, $K_D$, is experimentally determined and reflects the strength of the binding interaction. The rate of association, $k_{on}$, is also experimentally determined, while the rate of dissociation, $k_{off}$, is calculated based on the equation: $k_{off}=K_d \times k_{on}$.

A $K_D$ analysis requires immobilization of one interaction partner to a solid phase which is then used as a probe to capture the other interaction partner, the constant binding partner (Fab). For each experiment, CD30L antigen is titrated in a background of the Fab and allowed to reach equilibrium. The solutions are then briefly exposed to the solid phase and a portion of free Fab is captured. The captured Fab is then labeled with a fluorescent secondary molecule. The short contact time with the solid phase is less than the time needed for dissociation of the pre-formed complex in solution, thus competition between the solution and the solid phase titrated binding partner is kinetically excluded.

The signals generated from the captured Fab, which are directly proportional to the concentration of free Fab in the equilibrated samples, are used to determine the $K_D$ value. The KinExA Pro software performs a least squares analysis on the measured data to fit optimal solution for the $K_D$ and the activity of the Fab to a curve representative of a 1:1 reversible bi-molecular interaction.

Using a KinExA 3200 instrument, the affinity and kinetics were measured for the Fab of a representative anti-CD30L, clone 2 germlined, to human CD30L. The $K_D$, $k_{on}$, and $k_{off}$ were shown in Table 22.

TABLE 22

Binding of Fab of clone 2 germlined to human CD30L.

| | |
|---|---|
| $K_D$ | 90.5 pM |
| 95% Confidence Interval | 65.4 to 125 pM |
| On Rate ($k_{on}$) (M$^{-1}$s$^{-1}$) | 1.55 × 10$^6$ |
| 95% Confidence Interval (M$^{-1}$s$^{-1}$) | 1.50 × 10$^6$ to 1.61 × 10$^6$ |
| Off Rate ($k_{off}$) (s$^{-1}$) | 1.41 × 10$^{-4}$ |

Using a KinExA 3200 instrument, the affinity and kinetics were measured for the Fab of a representative anti-CD30L, clone 2 germlined, to cyno CD30L. The $K_D$, $k_{on}$, and $k_{off}$ were shown in Table 23.

TABLE 23

Binding of the Fab of clone 2 germlined to cyno CD30L.

| | |
|---|---|
| $K_D$ | 122 pM |
| 95% Confidence Interval | 51.3 to 244 pM |
| On Rate ($k_{on}$) (M$^{-1}$s$^{-1}$) | 3.1 × 10$^6$ |
| 95% Confidence Interval (M$^{-1}$s$^{-1}$) | 2.45 × 10$^6$ to 3.89 × 10$^6$ |
| Off Rate ($k_{off}$) (s$^{-1}$) | 3.78 × 10$^{-4}$ |

As a direct comparison, using a KinExA 3200 instrument, the affinity and kinetics were measured for the Fab of the reference 1 (ref1) anti-CD30L (comprising VH of SEQ ID NO:766 and VL of SEQ ID NO: 767), to human CD30L. The $K_D$, $k_{on}$, and $k_{off}$ for this reference 1 anti-CD30L were shown in Table 24.

TABLE 24

Binding of Fab of the reference 1 anti-CD30L to human CD30L.

| | |
|---|---|
| $K_D$ | 377 pM |
| 95% Confidence Interval | 289 to 489 pM |
| On Rate ($k_{on}$) (M$^{-1}$s$^{-1}$) | 9.37 × 105 |
| 95% Confidence Interval (M$^{-1}$s$^{-1}$) | 7.56 × 10$^5$ to 1.09 × 10$^6$ |
| Off Rate ($k_{off}$) (s$^{-1}$) | 3.53 × 10$^{-4}$ |

Therefore, the representative anti-CD30L provided herein, clone 2 germlined, has picomolar affinity for both human and cyno CD30L and has 4.2 fold higher $K_D$ than the reference 1 anti-CD30L in a head-to-head comparison with the reference 1 anti-CD30L.

Example 10. Study of the Effect of Anti-CD30L in Cynomolgus T Cell-Dependent Antibody Responses In Vivo This disclosure provides studies on the effect of anti-CD30L in T cell-dependent antibody responses in a non-human primate model of humoral immunity.

Briefly, keyhole limpet hemocyanin (KLH) is a model antigen that is commonly used in mechanistic studies of cellular and humoral immunity. The robust availability of well-characterized tools and reagents to study murine and non-human primate KLH-specific antibody responses makes it a key model in preclinical drug characterization, target validation, and immune mechanism of action studies. 18 naïve male cynomolgus monkeys (*Macaca fascicularis*) between 3-6 years old and between 3.5-6.0 kg body weight were allocated to treatment groups according to Table 24. Monkeys were immunized intramuscularly (I.M.) with 10 mg of KLH in PBS in 1 mL, with half the volume injected into each quadricep on day 0. Group 2 tested the CTLA4-Ig treatment, a published positive control for preventing T cell dependent antibody responses (TDAR) compared to vehicle (PBS) treated animals in Group 1. Groups 3 and 4 tested the effect of CD30L blockade during the primary anti-KLH response with 0.3 and 3 mg/kg a representative anti-CD30L, clone 2 germlined comprising VH of SEQ ID NO: 6, VL of SEQ ID NO: 8, and IgG1 constant region set forth in SEQ ID NO:504.

TABLE 24

Study design for the Effect of Anti-CD30L in cynomolgus T cell-dependent antibody responses in vivo

| Group | KLH injection | Test article | N | Route | Conc. mg/ml | Dosage mg/kg | mL/kg | Regimen |
|---|---|---|---|---|---|---|---|---|
| 1 | Y | Vehicle | 3 | I.V. slow bolus | N/A | N/A | 2 | −2 days before primary immunization q.w. starting day 7 for 3 weeks (4 total doses, D −2, D 7, D 14, D 21) |
| 2 | Y | CTLA4-Ig | 3 | S.C. | 5 | 10 | 2 | −2 days before primary immunization 2× per week 3 weeks (8 total doses, D −2, D 1, D 4, D 7, D 11, D 14, D 18, D 21) |
| 3 | Y | Clone 2 germlined (anti-CD30L) | 3 | I.V. slow bolus | 1.5 | 3 | 2 | −2 days before primary immunization q.w. starting day 7 for 3 weeks (4 total doses, D −2, D 7, D 14, D 21) |
| 4 | Y | Clone 2 germlined (anti-CD30L) | 3 | I.V. slow bolus | 0.15 | 0.3 | 2 | −2 days before primary immunization q.w. starting day 7 for 3 weeks (4 total doses, D −2, D 7, D 14, D 21) |

Serum samples were isolated from blood collected from the cephalic or femoral vein on days-7, 4, 9, 14, and 28. Blood was kept at room temperature for 30 minutes and centrifuged to isolate serum prior to storage at −80° C. until use. Serum was analyzed for KLH-specific IgM and IgG.

KLH-specific IgM levels in the serum of Vehicle treated animals peaked at day 9 and then quickly diminished through day 28 post-immunization (FIG. 6A). CTLA4-Ig treatment delayed the peak of anti-KLH IgM, but had a variable effect on the magnitude of the peak, with a trend toward decreasing overall anti-KLH IgM levels (measured by the area under the curve (AUC), FIG. 6B). CD30L blockade by anti-CD30L germlined clone 2 did not alter the timing of the peak anti-KLH IgM levels, but reduced the magnitude of the peak in 3/3 0.3 mg/kg treated animals and to a greater degree in 2/3 3 mg/kg treated animals (FIG. 6B). The overall anti-KLH IgM levels measured by AUC showed a comparable trend toward reduction in anti-CD30L treated monkey when compared to CTLA-Ig treated monkey, which as described above is a published positive control for preventing T cell dependent antibody responses (TDAR) (FIG. 6B).

KLH-specific IgG levels in the serum of Vehicle treated animals peaked at day 14 and were maintained through day 28 post-immunization (FIG. 6C). Similar to its effect on anti-KLH IgM, CTLA4-Ig treatment delayed the peak of anti-KLH IgG, and reduced the magnitude of the peak, resulting in a reduction of overall anti-KLH IgG levels measured by AUC (FIG. 6D). CD30L blockade by anti-CD30L germlined clone 2 had some effect on the timing of primary anti-KLH IgG response at 0.3 mg/kg or 3 mg/kg, and appeared to reduce both the peak and the overall (AUC) anti-KLH IgG levels in 2 of the 3 animals treated with 3 mg/kg (FIGS. 6C and 6D).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

6. SEQUENCE LISTING

TABLE 25

Sequence Listing

| SEQ ID | SEQUENCE | Description 1 | Description 2 | Description 3 |
|---|---|---|---|---|
| 1 | QVQLQESGPGLVKPSETLSLTCTVS GGSISGYYWSWIRQPPVKGLEWIGY IFYSGYTKYNPSLKSRVTISVDTSK NQFSLKLSSVTAADTAVYYCARDRW DFDYWGQGALVTVSS | CLONE_1_VH_ parental | | |
| 2 | QVQLQESGPGLVKPSETLSLTCTVS GGSTSGYYWSWTRQPPGKGLEWTGY TFYSGYTKYNPSLKSRVTTSVDTSK NQFSLKLSSVTAADTAVYYCARDRW DFDYWGQGTLVTVSS | CLONE_1_VH_ germlined | | |
| 3 | ATQMTQSPSYLSASVGDRVTTACRA SQGTRNNLGWYQQKPGKAPKLLTYA ESSLQSGVPSRFSGSGSGTDFTLTT SSLQPEDFATYYCLQDFNYPYTFGQ GTKLETK | CLONE_1_VL_ parental | | |

TABLE 25-continued

Sequence Listing

| SEQ ID | SEQUENCE | Description 1 | Description 2 | Description 3 |
|---|---|---|---|---|
| 4 | AIQMTQSPSSLSASVGDRVTITCRA SQGIRNNLGWYQQKPGKAPKLLIYA ESSLQSGVPSRFSGSGSGTDFTLTI SSLQPEDFATYYCLQDFNYPYTFGQ GTKLETK | CLONE_1_VL_ germlined | | |
| 5 | EVQLVESGGGLVQPGRSLRLSCAAS GFNFDDYAMHWVRQAPGKGLEWVSG TSWRSGNTGYAGSVKGRFTTSRDNA KNSLYLQMNSLRPEDSALYYCAKDK GTGFNWNYEGFDYWGQGTLVTVSS | CLONE_2_VH_ parental | | |
| 6 | EVQLVESGGGLVQPGRSLRLSCAAS GFNFDDYAMHWVRQAPGKGLEWVSG TSWRSGNTGYADSVKGRFTTSRDNA KNSLYLQMNSLRAEDTALYYCAKDK GTGFNWNYEGFDYWGQGTLVTVSS | CLONE_2_VH_ germlined | | |
| 7 | DIQMTQSPSSLSASVGDRVTITCRA SQGISNHLAWFQQKPGKAPKSLIYA ASSLQSGVPSKFSGSGSGTDFTLTI SSLQPEDFATYYCQQYVTYPLTFGG GTKVEIK | CLONE_2_VL_ parental | | |
| 8 | DIQMTQSPSSLSASVGDRVTITCRA SQGISNHLAWFQQKPGKAPKSLIYA ASSLQSGVPSRFSGSGSGTDFTLTI SSLQPEDFATYYCQQYVTYPLTFGG GTKVEIK | CLONE_2_VL_ germlined | | |
| 9 | QVQLQESGPGLVKPSETLSLTCTVS GGSISGYYWSWIRQPPVKGLEWIGY IFYSGYTKYNPSLKSRVTISVDTSK NQFSLKLSSVTAADTAVYYCARDRW DFDYWGQGALVTVSS | CLONE_3_VH_ parental | | |
| 10 | QVQLQESGPGLVKPSETLSLTCTVS GGSTSGYYWSWTRQPPGKGLEWTGY TFYSGYTKYNPSLKSRVTTSVDTSK NQFSLKLSSVTAADTAVYYCARDRW DFDYWGQGTLVTVSS | CLONE_3_VH_ germlined | | |
| 11 | DIVMTQSPLSLPVTPGEPASFSCRS SQSLLHSNGYNYLDWYLQKPGQSPQ LLIYLGSNRASGVPDRFSGSGSGTD FTLKISRVEAADVGVYYCMQALQTP RTFGQGTKVEIK | CLONE_3_VL_ parental | | |
| 12 | DIVMTQSPLSLPVTPGEPASISCRS SQSLLHSNGYNYLDWYLQKPGQSPQ LLIYLGSNRASGVPDRFSGSGSGTD FTLKISRVEAEDVGVYYCMQALQTP RTFGQGTKVEIK | CLONE_3_VL_ germlined | | |
| 13 | QVQLVESGGGVVQPGRSLRLSCAAS GFPFSSYGMHWVRQAPGKGLEWVTF IWFDGNNKDYADSVKGRFSVSRDNS KNTLYLQMNSLRADDTAVYYCARNG VYYGSGAYVDYWGQGTLVTVSS | CLONE_4_VH_ parental | | |
| 14 | QVQLVESGGGVVQPGRSLRLSCAAS GFPFSSYGMHWVRQAPGKGLEWVTF IWFDGNNKDYADSVKGRFTTSRDNS KNTLYLQMNSLRAEDTAVYYCARNG VYYGSGAYVDYWGQGTLVTVSS | CLONE_4_VH_ germlined | | |
| 15 | DIVMTQSPLSLPVTPGEPASFSCRS SQSLLHSNGYNYLDWYLQKPGQSPQ LLIYLGSNRASGVPDRFSGSGSGTD FTLKISRVEAADVGVYYCMQALQTP RTFGQGTKVEIK | CLONE_4_VL_ parental | | |
| 16 | DIVMTQSPLSLPVTPGEPASISCRS SQSLLHSNGYNYLDWYLQKPGQSPQ LLIYLGSNRASGVPDRFSGSGSGTD | CLONE_4_VL_ germlined | | |

TABLE 25-continued

Sequence Listing

| SEQ ID | SEQUENCE | Description 1 | Description 2 | Description 3 |
|---|---|---|---|---|
| | FTLKISRVEAEDVGVYYCMQALQTP RTFGQGTKVEIK | | | |
| 17 | QVQLVESGGGVVQPGRSLRLSCAAS GFTFSIYGMHWVRQAPGKGLEWVAV IWYDGSNKYYVDSVKGRFTISRDNS KNSLYLQMNSLRAEDTAVYYCAREG NLFDYWGQGTLVTVSS | CLONE_59_ VH | | |
| 18 | DIQMTQSPSTLSASVGDRVTITCRA SQSISSWLAWYQQKPGKAPKLLIYK ASSLESGVPSRFSGSGSGTEFTLTI SSLKPDDFATYYCQQYKSYYTFGQG TKLEIK | CLONE_59_ VL | | |
| 19 | QVHLVESGGGVVQPGRSLRLSCAAS GFAFNIYGMHWVRQAPGKGLEWVAV ISYDGSNKVYADSVKGRFSISRDNS KNTLYLQMNSLRAEDTAVYYCAKSG GITMVRGVFDYWGQGTLVTVSS | CLONE_60_ VH | | |
| 20 | DIQMTQSPSSLPASVGDRVTITCRA SQGIRNDLGWYQQKPGKAPKRLIHA ASSLHSGVPSRFSGSGSGTEFTLTI SSLQPEDFATYYCLQHNRYPITFGQ GTRLEIK | CLONE_60_ VL | | |
| 21 | QITLKESGPTLVKPTQTLTLTCTFS GFSLSTSGVGVGWIRQPPGKALEWL ALIYWNDDKRYSPSLKSRLTITKDT SKNQVVLTMTNMDPVDTATYYCAHR RTTTVTIYYYMDVWGKGTTVTVSS | CLONE_61_ VH | | |
| 22 | EIVMTQSPATLSVSPGERATLSCRA SQSVSSNLAWYQQKPGQAPRLLIYG ASTRATGIPARFSGSGSGTEFTLTI SSLQSEDFAVYYCQQYNNWPFTFGP GTKVDIK | CLONE_61_ VL | | |
| 23 | EVQLVESGGGLVQPGGSLRLSCAAS GFMFSSYSMNWVRQAPGKGLEWVSY ISSSSSTIYDADSVKGRFTISRDDA KNSLYLQMNSLRDEDTAVYYCTREA YPGYYYNYMDVWGKGTTVTVSS | CLONE_63_ VH | | |
| 24 | DIQMTQSPSSLSASVGDRVTITCRA SQSISSRLAWYQQKPGKAPNLLIYK ASNLESGVPSRFSGSGSGTEFTLTI SSLQPDDFATYYCQQYNSYSRTFGQ GTKVEIK | CLONE_63_ VL | | |
| 25 | EVQLVESGGGLVQPGGSLRLSCAAS GFTFSNYAMTWVRQAPGKGLEWVSA ISGFGGSTYYADSVKGRFTISRDNS KNTLYLQMNSLRAEDTAVYYCAKDH DYYAFDYWGQGTLVTVSS | CLONE_64_ VH | | |
| 26 | DIQMTQSPSSLSASVGDRVTITCRA SQSISSYLNWYQQKPGKAPKLLIYA VSSLQSGVPSRFSGSGSGTDFTLTI SSLQPEDFATYYCQQSYSTPYTFGQ GTKLEIK | CLONE_64_ VL | | |
| 27 | EVQLVESGGGLVQPGGSLRLSCAAS GFTFSNYAMTWVRQAPGKGLEWVSA ISGYGGSTYYAASVKGRFTISRDNS KNTLFLQMNSLRAEDTAVYYCAKDH DYYAFDYWGQGTLVPVSS | CLONE_65_ VH | | |
| 28 | DIQMTQSPSSLSASVGDRVTITCRA SQSINSYLNWYQQKPGKAPKLLIYS ASSLQSGVPSRFSGSGSGTDFTLTI SSLQPEDFATYYCQQSYSTPYTFGQ GTKLEIK | CLONE_65_ VL | | |

TABLE 25-continued

Sequence Listing

| SEQ ID | SEQUENCE | Description 1 | Description 2 | Description 3 |
|---|---|---|---|---|
| 29 | EVQLVESGGGLVQPGGSLRLSCEVS GFTFSSYDMHWVRQVTGTGLEWVSS IGIGGDTYYPGSVKGRFTISRENAK NSLYLQMNSLRGGDTGVYYCARGEW DLLWYFMDVWGKGTTVTVSS | CLONE_80_ VH | | |
| 30 | DIQMTQSPSSLSASIGDRVTITCRA SQGISSWLAWYQQKPGKAPKLLIYA ASSLQSGVPSRFSGSGSGTDFTLTI SSLQPEDFATYYCQQANSFPLTFGG GTKVEIK | CLONE_80_ VL | | |
| 31 | EVQLVESGGGLVQPGGSLRLSCAVS GITFSNAWMSWVRQAPGKGLEWVGR IKSKTYGGTTDYAAPVKGRFIISRD DSKDTLYLQMNSLKTEDTAIYYCTT DPWNYVNYNYFMDVWGKGTTVTVSS | CLONE_82_ VH | | |
| 32 | DIQMTQSPSSLSASVGDRVTITCRA SQDIRNYLAWYQQKPGKITHLLVYA ASTLQSGVPSRFSGSGSGTDFTLTI NSLQPEDVATYYCQNYFSVPLTFGG GTKVEIK | CLONE_82_ VL | | |
| 33 | MDPGLQQALNGMAPPGDTAMHVPAG SVASHLGTTSRSYFYLTTATLALCL VFTVATIMVLVVQRTDSIPNSPDNV PLKGGNCSEDLLCILKRAPFKKSWA YLQVAKHLNKTKLSWNKDGILHGVR YQDGNLVIQFPGLYFIICQLQFLVQ CPNNSVDLKLELLINKHIKKQALVT VCESGMQTKHVYQNLSQFLLDYLQV NTTISVNVDTFQYIDTSTFPLENVL SIFLYSNSD | CD30L full length sequence | | |
| 34 | QRTDSIPNSPDNVPLKGGNCSEDLL CILKRAPFKKSWAYLQVAKHLNKTK LSWNKDGILHGVRYQDGNLVIQFPG LYFIICQLQFLVQCPNNSVDLKLEL LINKHIKKQALVTVCESGMQTKHVY QNLSQFLLDYLQVNTTISVNVDTFQ YIDTSTFPLENVLSIFLYSNSD | CD30L extracellular domain sequence | | |
| 766 | QVQLQESGPGLVKPSETLSLTCTVS GGSISSYIWSWIRQPAGKGLEWIGR IYASGNTNYNPSLKSRVTISVDTSK NQFSLKLSSMTAADTAVYYCARDYR VAGTYYYYGLDVWGQGTTVTVSS | Reference- 1(Ref1)_VH | | |
| 767 | QSALTQPASVSGSPGQSITISCTGT SSDVGVYDYVSWYQQHPGKAPKLMI YEVSNRPSGVSNRFSGSKSGNTASL TISGLQTEDEADYYCSSYTSRSTWV FGGGTKLTVL | Reference- 1(Ref1)_VL | | |
| 768 | QVQLQESGPGLVKPSETLSLTCTVS GGSISSYIWSWIRQPAGKGLEWIGR IYASGNTNYNPSLKSRVTISVDTSK NQFSLKLSSMTAADTAVYYCARDYR VAGTYYYYGLDVWGQGTTVTVSSA STKGPSVFPLAPSSKSTSGGTAALG CLVKDYFPEPVTVSWNSGALTSGVH TFPAVLQSSGLYSLSSVVTVPSSSL GTQTYICNVNHKPSNTKVDKKVEPK SCDKTHTCPPCPAPEAAGAPSVFLF PPKPKDTLMISRTPEVTCVVVDVSH EDPEVKFNWYVDGVEVHNAKTKPRE EQYNSTYRVVSVLTVLHQDWLNGKE YKCKVSNKALPAPIEKTISKAKGQP REPQVYTLPPSRDELTKNQVSLTCL VKGFYPSDIAVEWESNGQPENNYKT TPPVLDSDGSFFLYSRLTVDRSRWQ QGNVFSCSVMHEALHNHYTQKSLSL SPGK | Reference- 1(Ref1)_ Heavy Chain (HC) | | |

TABLE 25-continued

| Sequence Listing | | | | |
|---|---|---|---|---|
| SEQ ID | SEQUENCE | Description 1 | Description 2 | Description 3 |
| 769 | QSALTQPASVSGSPGQSITISCTGT SSDVGVYDYVSWYQQHPGKAPKLMI YEVSNRPSGVSNRFSGSKSGNTASL TISGLQTEDEADYYCSSYTSRSTWV FGGGTKLTVLGQPKAAPSVTLFPPS SEELQANRATLVCLISDFYPGAVTV AWKADSSPVKAGVETTTPSKQSNNK YAASSYLSLTPEQWKSHKSYSCQVT HEGSTVEKTVAPTECS | Reference-1(Ref1)_Light Chain (LC) | | |
| 100 | GGSISGY | CLONE_1 | Chothia | CDR-H1 |
| 101 | GGSISGYYWS | | AbM | |
| 102 | GYYWS | | Kabat | |
| 103 | SGYYWS | | Contact | |
| 104 | GGSISGYY | | IMGT | |
| 105 | GGSISGY | CLONE_1_germlined | Chothia | CDR-H1 |
| 106 | GGSISGYYWS | | AbM | |
| 107 | GYYWS | | Kabat | |
| 108 | SGYYWS | | Contact | |
| 109 | GGSISGYY | | IMGT | |
| 110 | GFNFDDY | CLONE_2 | Chothia | CDR-H1 |
| 111 | GFNFDDYAMH | | AbM | |
| 112 | DYAMH | | Kabat | |
| 113 | DDYAMH | | Contact | |
| 114 | GFNFDDYA | | IMGT | |
| 115 | GFNFDDY | CLONE_2_germlined | Chothia | CDR-H1 |
| 116 | GFNFDDYAMH | | AbM | |
| 117 | DYAMH | | Kabat | |
| 118 | DDYAMH | | Contact | |
| 119 | GFNFDDYA | | IMGT | |
| 120 | GGSISGY | CLONE_3 | Chothia | CDR-H1 |
| 121 | GGSISGYYWS | | AbM | |
| 122 | GYYWS | | Kabat | |
| 123 | SGYYWS | | Contact | |
| 124 | GGSISGYY | | IMGT | |
| 125 | GGSISGY | CLONE_3_germlined | Chothia | CDR-H1 |
| 126 | GGSISGYYWS | | AbM | |
| 127 | GYYWS | | Kabat | |
| 128 | SGYYWS | | Contact | |
| 129 | GGSISGYY | | IMGT | |
| 130 | GFPFSSY | CLONE_4 | Chothia | CDR-H1 |

TABLE 25-continued

Sequence Listing

| SEQ ID | SEQUENCE | Description 1 | Description 2 | Description 3 |
|---|---|---|---|---|
| 131 | GFPFSSYGMH | | AbM | |
| 132 | SYGMH | | Kabat | |
| 133 | SSYGMH | | Contact | |
| 134 | GFPFSSYG | | IMGT | |
| 135 | GFPFSSY | CLONE_4_germlined | Chothia | CDR-H1 |
| 136 | GFPFSSYGMH | | AbM | |
| 137 | SYGMH | | Kabat | |
| 138 | SSYGMH | | Contact | |
| 139 | GFPFSSYG | | IMGT | |
| 140 | FYSGY | CLONE_1 | Chothia | CDR-H2 |
| 141 | YIFYSGYTK | | AbM | |
| 142 | YIFYSGYTKYNPSLKS | | Kabat | |
| 143 | WIGYIFYSGYTK | | Contact | |
| 144 | IFYSGYT | | IMGT | |
| 145 | FYSGY | CLONE_1_germlined | Chothia | CDR-H2 |
| 146 | YIFYSGYTK | | AbM | |
| 147 | YIFYSGYTKYNPSLKS | | Kabat | |
| 148 | WIGYIFYSGYTK | | Contact | |
| 149 | IFYSGYT | | IMGT | |
| 150 | SWRSGN | CLONE_2 | Chothia | CDR-H2 |
| 151 | GISWRSGNIG | | AbM | |
| 152 | GISWRSGNIGYAGSVKG | | Kabat | |
| 153 | WVSGISWRSGNIG | | Contact | |
| 154 | ISWRSGNI | | IMGT | |
| 155 | SWRSGN | CLONE_2_germlined | Chothia | CDR-H2 |
| 156 | GISWRSGNIG | | AbM | |
| 157 | GISWRSGNIGYADSVKG | | Kabat | |
| 158 | WVSGISWRSGNIG | | Contact | |
| 159 | ISWRSGNI | | IMGT | |
| 160 | FYSGY | CLONE_3 | Chothia | CDR-H2 |
| 161 | YIFYSGYTK | | AbM | |
| 162 | YIFYSGYTKYNPSLKS | | Kabat | |
| 163 | WIGYIFYSGYTK | | Contact | |
| 164 | IFYSGYT | | IMGT | |
| 165 | FYSGY | CLONE_3_germlined | Chothia | CDR-H2 |
| 166 | YIFYSGYTK | | AbM | |

TABLE 25-continued

Sequence Listing

| SEQ ID | SEQUENCE | Description 1 | Description 2 | Description 3 |
|---|---|---|---|---|
| 167 | YIFYSGYTKYNPSLKS | | Kabat | |
| 168 | WIGYIFYSGYTK | | Contact | |
| 169 | IFYSGYT | | IMGT | |
| 170 | WFDGNN | CLONE_4 | Chothia | CDR-H2 |
| 171 | FIWFDGNNKD | | AbM | |
| 172 | FIWFDGNNKDYADSVKG | | Kabat | |
| 173 | WVTFIWFDGNNKD | | Contact | |
| 174 | IWFDGNNK | | IMGT | |
| 175 | WFDGNN | CLONE_4_germlined | Chothia | CDR-H2 |
| 176 | FIWFDGNNKD | | AbM | |
| 177 | FIWFDGNNKDYADSVKG | | Kabat | |
| 178 | WVTFIWFDGNNKD | | Contact | |
| 179 | IWFDGNNK | | IMGT | |
| 180 | DRWDFDY | CLONE_1 | Chothia | CDR-H3 |
| 181 | DRWDFDY | | AbM | |
| 182 | DRWDFDY | | Kabat | |
| 183 | ARDRWDFD | | Contact | |
| 184 | ARDRWDFDY | | IMGT | |
| 185 | DRWDFDY | CLONE_1_germlined | Chothia | CDR-H3 |
| 186 | DRWDFDY | | AbM | |
| 187 | DRWDFDY | | Kabat | |
| 188 | ARDRWDFD | | Contact | |
| 189 | ARDRWDFDY | | IMGT | |
| 190 | DKGIGFNWNYEGFDY | CLONE_2 | Chothia | CDR-H3 |
| 191 | DKGIGFNWNYEGFDY | | AbM | |
| 192 | DKGIGFNWNYEGFDY | | Kabat | |
| 193 | AKDKGIGFNWNYEGFD | | Contact | |
| 194 | AKDKGIGFNWNYEGFDY | | IMGT | |
| 195 | DKGIGFNWNYEGFDY | CLONE_2_germlined | Chothia | CDR-H3 |
| 196 | DKGIGFNWNYEGFDY | | AbM | |
| 197 | DKGIGFNWNYEGFDY | | Kabat | |
| 198 | AKDKGIGFNWNYEGFD | | Contact | |
| 199 | AKDKGIGFNWNYEGFDY | | IMGT | |
| 200 | DRWDFDY | CLONE_3 | Chothia | CDR-H3 |
| 201 | DRWDFDY | | AbM | |
| 202 | DRWDFDY | | Kabat | |

TABLE 25-continued

Sequence Listing

| SEQ ID | SEQUENCE | Description 1 | Description 2 | Description 3 |
|---|---|---|---|---|
| 203 | ARDRWDFD | | Contact | |
| 204 | ARDRWDFDY | | IMGT | |
| 205 | DRWDFDY | CLONE_3_germlined | Chothia | CDR-H3 |
| 206 | DRWDFDY | | AbM | |
| 207 | DRWDFDY | | Kabat | |
| 208 | ARDRWDFD | | Contact | |
| 209 | ARDRWDFDY | | IMGT | |
| 210 | NGVYYGSGAYVDY | CLONE_4 | Chothia | CDR-H3 |
| 211 | NGVYYGSGAYVDY | | AbM | |
| 212 | NGVYYGSGAYVDY | | Kabat | |
| 213 | ARNGVYYGSGAYVD | | Contact | |
| 214 | ARNGVYYGSGAYVDY | | IMGT | |
| 215 | NGVYYGSGAYVDY | CLONE_4_germlined | Chothia | CDR-H3 |
| 216 | NGVYYGSGAYVDY | | AbM | |
| 217 | NGVYYGSGAYVDY | | Kabat | |
| 218 | ARNGVYYGSGAYVD | | Contact | |
| 219 | ARNGVYYGSGAYVDY | | IMGT | |
| 220 | GFTFSIY | CLONE_59 | Chothia | CDR-H1 |
| 221 | GFTFSIYGMH | | AbM | |
| 222 | IYGMH | | Kabat | |
| 223 | SIYGMH | | Contact | |
| 224 | GFTFSIYG | | IMGT | |
| 225 | GFAFNIY | CLONE_60 | Chothia | CDR-H1 |
| 226 | GFAFNIYGMH | | AbM | |
| 227 | IYGMH | | Kabat | |
| 228 | NIYGMH | | Contact | |
| 229 | GFAFNIYG | | IMGT | |
| 230 | GFSLSTSGV | CLONE_61 | Chothia | CDR-H1 |
| 231 | GFSLSTSGVGVG | | AbM | |
| 232 | TSGVGVG | | Kabat | |
| 233 | STSGVGVG | | Contact | |
| 234 | GFSLSTSGVG | | IMGT | |
| 235 | WYDGSN | CLONE_59 | Chothia | CDR-H2 |
| 236 | VIWYDGSNKY | | AbM | |
| 237 | VIWYDGSNKYYVSVKG | | Kabat | |
| 238 | WVAVIWYDGSNKY | | Contact | |

TABLE 25-continued

Sequence Listing

| SEQ ID | SEQUENCE | Description 1 | Description 2 | Description 3 |
|---|---|---|---|---|
| 239 | IWYDGSNK | | IMGT | |
| 240 | SYDGSN | CLONE_60 | Chothia | CDR-H2 |
| 241 | VISYDGSNKV | | AbM | |
| 242 | VISYDGSNKVYADSVKG | | Kabat | |
| 243 | WVAVISYDGSNKV | | Contact | |
| 244 | ISYDGSNK | | IMGT | |
| 245 | YWNDD | CLONE_61 | Chothia | CDR-H2 |
| 246 | LIYWNDDKR | | AbM | |
| 247 | LIYWNDDKRYSPSLKS | | Kabat | |
| 248 | WLALIYWNDDKR | | Contact | |
| 249 | IYWNDDK | | IMGT | |
| 250 | EGNLFDY | CLONE_59 | Chothia | CDR-H3 |
| 251 | EGNLHDY | | AbM | |
| 252 | EGNLFDY | | Kabat | |
| 253 | AREGNLFD | | Contact | |
| 254 | AREGNLFDY | | IMGT | |
| 255 | SGGITMVRGVFDY | CLONE_60 | Chothia | CDR-H3 |
| 256 | SGGITMVRGVFDY | | AbM | |
| 257 | SGGITMVRGVFDY | | Kabat | |
| 258 | AKSGGITMVRGVFD | | Contact | |
| 259 | AKSGGITMVRGVEDY | | IMGT | |
| 260 | RRTTTVTIYYYYMDV | CLONE_61 | Chothia | CDR-H3 |
| 261 | RRTTTVTIYYYYMDV | | AbM | |
| 262 | RRTTTVTIYYYYMDV | | Kabat | |
| 263 | AHRRTTTVTIYYYYMD | | Contact | |
| 264 | AHRRTTTVTYYYYMDV | | IMGT | |
| 300 | RASQGIRNNLG | CLONE_1 | Chothia | CDR-L1 |
| 301 | RASQGIRNNLG | | AbM | |
| 302 | RASQGIRNNLG | | Kabat | |
| 303 | RNNLGWY | | Contact | |
| 304 | QGIRNN | | IMGT | |
| 305 | RASQGIRNNLG | CLONE_1_germlined | Chothia | CDR-L1 |
| 306 | RASQGIRNNLG | | AbM | |
| 307 | RASQGIRNNLG | | Kabat | |
| 308 | RNNLGWY | | Contact | |
| 309 | QGIRNN | | IMGT | |
| 310 | RASQGISNHLA | CLONE_2 | Chothia | CDR-L1 |

TABLE 25-continued

Sequence Listing

| SEQ ID | SEQUENCE | Description 1 | Description 2 | Description 3 |
|---|---|---|---|---|
| 311 | RASQGISNHLA | | AbM | |
| 312 | RASQGISNHLA | | Kabat | |
| 313 | SNHLAWF | | Contact | |
| 314 | QGISNH | | IMGT | |
| 315 | RASQGISNHLA | CLONE_2_germlined | Chothia | CDR-L1 |
| 316 | RASQGISNHLA | | AbM | |
| 317 | RASQGISNHLA | | Kabat | |
| 318 | SNHLAWF | | Contact | |
| 319 | QGISNH | | IMGT | |
| 320 | RSSQSLLHSNGYNYLD | CLONE_3 | Chothia | CDR-L1 |
| 321 | RSSQSLLHSNGYNYLD | | AbM | |
| 322 | RSSQSLLHSNGYNYLD | | Kabat | |
| 323 | LHSNGYNYLDWY | | Contact | |
| 324 | QSLLHSNGYNY | | IMGT | |
| 325 | RSSQSLLHSNGYNYLD | CLONE_3_germlined | Chothia | CDR-L1 |
| 326 | RSSQSLLHSNGYNYLD | | AbM | |
| 327 | RSSQSLLHSNGYNYLD | | Kabat | |
| 328 | LHSNGYNYLDWY | | Contact | |
| 329 | QSLLHSNGYNY | | IMGT | |
| 330 | RSSQSLLHSNGYNYLD | CLONE_4 | Chothia | CDR-L1 |
| 331 | RSSQSLLHSNGYNYLD | | AbM | |
| 332 | RSSQSLLHSNGYNYLD | | Kabat | |
| 333 | LHSNGYNYLDWY | | Contact | |
| 334 | QSLLHSNGYNY | | IMGT | |
| 335 | RSSQSLLHSNGYNYLD | CLONE_4_germlined | Chothia | CDR-L1 |
| 336 | RSSQSLLHSNGYNYLD | | AbM | |
| 337 | RSSQSLLHSNGYNYLD | | Kabat | |
| 338 | LHSNGYNYLDWY | | Contact | |
| 339 | QSLLHSNGYNY | | IMGT | |
| 340 | AESSLQS | CLONE_1 | Chothia | CDR-L2 |
| 341 | AESSLQS | | AbM | |
| 342 | AESSLQS | | Kabat | |
| 343 | LLIYAESSLQ | | Contact | |
| 344 | AE | | IMGT | |
| 345 | AESSLQS | CLONE_1_germlined | Chothia | CDR-L2 |
| 346 | AESSLQS | | AbM | |

TABLE 25-continued

Sequence Listing

| SEQ ID | SEQUENCE | Description 1 | Description 2 | Description 3 |
|---|---|---|---|---|
| 347 | AESSLQS | | Kabat | |
| 348 | LLIYAESSLQ | | Contact | |
| 349 | AE | | IMGT | |
| 350 | AASSLQS | CLONE_2 | Chothia | CDR-L2 |
| 351 | AASSLQS | | AbM | |
| 352 | AASSLQS | | Kabat | |
| 353 | SLIYAASSLQ | | Contact | |
| 354 | AA | | IMGT | |
| 355 | AASSLQS | CLONE_2_germlined | Chothia | CDR-L2 |
| 356 | AASSLQS | | AbM | |
| 357 | AASSLQS | | Kabat | |
| 358 | SLIYAASSLQ | | Contact | |
| 359 | AA | | IMGT | |
| 360 | LGSNRAS | CLONE_3 | Chothia | CDR-L2 |
| 361 | LGSNRAS | | AbM | |
| 362 | LGSNRAS | | Kabat | |
| 363 | LLIYLGSNRA | | Contact | |
| 364 | LG | | IMGT | |
| 365 | LGSNRAS | CLONE_3_germlined | Chothia | CDR-L2 |
| 366 | LGSNRAS | | AbM | |
| 367 | LGSNRAS | | Kabat | |
| 368 | LLIYLGSNRA | | Contact | |
| 369 | LG | | IMGT | |
| 370 | LGSNRAS | CLONE_4 | Chothia | CDR-L2 |
| 371 | LGSNRAS | | AbM | |
| 372 | LGSNRAS | | Kabat | |
| 373 | LLIYLGSNRA | | Contact | |
| 374 | LG | | IMGT | |
| 375 | LGSNRAS | CLONE_4_germlined | Chothia | CDR-L2 |
| 376 | LGSNRAS | | AbM | |
| 377 | LGSNRAS | | Kabat | |
| 378 | LLIYLGSNRA | | Contact | |
| 379 | LG | | IMGT | |
| 380 | LQDFNYPYT | CLONE_1 | Chothia | CDR-L3 |
| 381 | LQDFNYPYT | | AbM | |

TABLE 25-continued

Sequence Listing

| SEQ ID | SEQUENCE | Description 1 | Description 2 | Description 3 |
|---|---|---|---|---|
| 382 | LQDFNYPYT | | Kabat | |
| 383 | LQDFNYPY | | Contact | |
| 384 | LQDFNYPYT | | IMGT | |
| 385 | LQDFNYPYT | CLONE_1_germlined | Chothia | CDR-L3 |
| 386 | LQDFNYPYT | | AbM | |
| 387 | LQDFNYPYT | | Kabat | |
| 388 | LQDFNYPY | | Contact | |
| 389 | LQDFNYPYT | | IMGT | |
| 390 | QQYVTYPLT | CLONE_2 | Chothia | CDR-L3 |
| 391 | QQYVTYPLT | | AbM | |
| 392 | QQYVTYPLT | | Kabat | |
| 393 | QQYVTYPL | | Contact | |
| 394 | QQYVTYPLT | | IMGT | |
| 395 | QQYVTYPLT | CLONE_2_germlined | Chothia | CDR-L3 |
| 396 | QQYVTYPLT | | AbM | |
| 397 | QQYVTYPLT | | Kabat | |
| 398 | QQYVTYPL | | Contact | |
| 399 | QQYVTYPLT | | IMGT | |
| 400 | MQALQTPRT | CLONE_3 | Chothia | CDR-L3 |
| 401 | MQALQTPRT | | AbM | |
| 402 | MQALQTPRT | | Kabat | |
| 403 | MQALQTPR | | Contact | |
| 404 | MQALQTPRT | | IMGT | |
| 405 | MQALQTPRT | CLONE_3_germlined | Chothia | CDR-L3 |
| 406 | MQALQTPRT | | AbM | |
| 407 | MQALQTPRT | | Kabat | |
| 408 | MQALQTPR | | Contact | |
| 409 | MQALQTPRT | | IMGT | |
| 410 | MQALQTPRT | CLONE_4 | Chothia | CDR-L3 |
| 411 | MQALQTPRT | | AbM | |
| 412 | MQALQTPRT | | Kabat | |
| 413 | MQALQTPR | | Contact | |
| 414 | MQALQTPRT | | IMGT | |
| 415 | MQALQTPRT | CLONE_4_germlined | Chothia | CDR-L3 |
| 416 | MQALQTPRT | | AbM | |
| 417 | MQALQTPRT | | Kabat | |

TABLE 25-continued

| Sequence Listing | | | | |
|---|---|---|---|---|
| SEQ ID | SEQUENCE | Description 1 | Description 2 | Description 3 |
| 418 | MQALQTPR | | Contact | |
| 419 | MQALQTPRT | | IMGT | |
| 420 | RASQSISSWLA | CLONE_59 | Chothia | CDR-L1 |
| 421 | RASQSISSWLA | | AbM | |
| 422 | RASQSISSWLA | | Kabat | |
| 423 | SSWLAWY | | Contact | |
| 424 | QSISSW | | IMGT | |
| 425 | RASQGIRNDLG | CLONE_60 | Chothia | CDR-L1 |
| 426 | RASQGIRNDLG | | AbM | |
| 427 | RASQGIRNDLG | | Kabat | |
| 428 | RNDLGWY | | Contact | |
| 429 | QGIRND | | IMGT | |
| 430 | RASQSVSSNLA | CLONE_61 | Chothia | CDR-L1 |
| 431 | RASQSVSSNLA | | AbM | |
| 432 | RASQSVSSNLA | | Kabat | |
| 433 | SSNLAWY | | Contact | |
| 434 | QSVSSN | | IMGT | |
| 435 | KASSLES | CLONE_59 | Chothia | CDR-L2 |
| 436 | KASSEES | | AbM | |
| 437 | KASSLES | | Kabat | |
| 438 | LLIYKASSLE | | Contact | |
| 439 | KA | | IMGT | |
| 440 | AASSLHS | CLONE_60 | Chothia | CDR-L2 |
| 441 | AASSLHS | | AbM | |
| 442 | AASSLHS | | Kabat | |
| 443 | RLIHAASSLH | | Contact | |
| 444 | AA | | IMGT | |
| 445 | GASTRAT | CLONE_61 | Chothia | CDR-L2 |
| 446 | GASTRAT | | AbM | |
| 447 | GASTRAT | | Kabat | |
| 448 | LLIYGASTRA | | Contact | |
| 449 | GA | | IMGT | |
| 450 | QQYKSYYT | CLONE_59 | Chothia | CDR-L3 |
| 451 | QQYKSYYT | | AbM | |
| 452 | QQYKSYYT | | Kabat | |
| 453 | QQYKSYY | | Contact | |
| 454 | QQYKSYYT | | IMGT | |

TABLE 25-continued

Sequence Listing

| SEQ ID | SEQUENCE | Description 1 | Description 2 | Description 3 |
|---|---|---|---|---|
| 455 | LQHNRYPIT | CLONE_60 | Chothia | CDR-L3 |
| 456 | LQHNRYPIT | | AbM | |
| 457 | LQHNRYPIT | | Kabat | |
| 458 | LQHNRYPI | | Contact | |
| 459 | LQHNRYPIT | | IMGT | |
| 460 | QQYNNWPFT | CLONE_61 | Chothia | CDR-L3 |
| 461 | QQYNNWPFT | | AbM | |
| 462 | QQYNNWPFT | | Kabat | |
| 463 | QQYNNWPF | | Contact | |
| 464 | QQYNNWPFT | | IMGT | |
| 465 | GEMFSSY | CLONE_63 | Chothia | CDR-H1 |
| 466 | GFMFSSYSMN | | AbM | |
| 467 | SYSMN | | Kabat | |
| 468 | SSYSMN | | Contact | |
| 469 | GFMFSSYS | | IMGT | |
| 470 | GFTFSNY | CLONE_64 | Chothia | CDR-H1 |
| 471 | GFTFSNYAMT | | AbM | |
| 472 | NYAMT | | Kabat | |
| 473 | SNYAMT | | Contact | |
| 474 | GFTFSNYA | | IMGT | |
| 475 | GFTFSNY | CLONE_65 | Chothia | CDR-H1 |
| 476 | GFTFSNYAMT | | AbM | |
| 477 | NYAMT | | Kabat | |
| 478 | SNYAMT | | Contact | |
| 479 | GFTFSNYA | | IMGT | |
| 480 | GFTPSSY | CLONE_80 | Chothia | CDR-H1 |
| 481 | GFTFSSYDMH | | AbM | |
| 482 | SYDMH | | Kabat | |
| 483 | SSYDMH | | Contact | |
| 484 | GFTPSSYD | | IMGT | |
| 485 | GITFSNA | CLONE_82 | Chothia | CDR-H1 |
| 486 | GITFSNAWMS | | AbM | |
| 487 | NAWMS | | Kabat | |
| 488 | SNAWMS | | Contact | |
| 489 | GITFSNAW | | IMGT | |
| 490 | SSSSST | CLONE_63 | Chothia | CDR-H2 |
| 491 | YISSSSSTIY | | AbM | |
| 492 | YISSSSSTIYDADSVKG | | Kabat | |

TABLE 25-continued

Sequence Listing

| SEQ ID | SEQUENCE | Description 1 | Description 2 | Description 3 |
|---|---|---|---|---|
| 493 | WVSYISSSSSTIY | | Contact | |
| 494 | ISSSSSTI | | IMGT | |
| 495 | SGFGGS | CLONE_64 | Chothia | CDR-H2 |
| 496 | AISGFGGSTY | | AbM | |
| 497 | AISGFGGSTYYADSVKG | | Kabat | |
| 498 | WVSAISGFGGSTY | | Contact | |
| 499 | ISGFGGST | | IMGT | |
| 513 | SGYGGS | CLONE_65 | Chothia | CDR-H2 |
| 514 | AISGYGGSTY | | AbM | |
| 515 | AISGYGGSTYYAASVKG | | Kabat | |
| 516 | WVSAISGYGGSTY | | Contact | |
| 517 | ISGYGGST | | IMGT | |
| 518 | GIGGD | CLONE_80 | Chothia | CDR-H2 |
| 519 | SIGIGGDTY | | AbM | |
| 520 | SIGIGGDTYYPGSVKG | | Kabat | |
| 521 | WVSSIGIGGDTY | | Contact | |
| 522 | IGIGGDT | | IMGT | |
| 523 | KSKTYGGT | CLONE_82 | Chothia | CDR-H2 |
| 524 | RIKSKTYGGTTD | | AbM | |
| 525 | RIKSKTYGGTTDYAAPVKG | | Kabat | |
| 526 | WVGRIKSKTYGGTTD | | Contact | |
| 527 | IKSKTYGGTT | | IMGT | |
| 528 | EAYPGYYYNYMDV | CLONE_63 | Chothia | CDR-H3 |
| 529 | EAYPGYYYNYMDV | | AbM | |
| 530 | EAYPGYYYNYMDV | | Kabat | |
| 531 | TREAYPGYYYNYMD | | Contact | |
| 532 | TREATPGYYYNYMDV | | IMGT | |
| 533 | DHDYYAFDY | CLONE_64 | Chothia | CDR-H3 |
| 534 | DHDYYAFDY | | AbM | |
| 535 | DHDYYAFDY | | Kabat | |
| 536 | AKDHDYYAFD | | Contact | |
| 537 | AKDHDYYAFDY | | IMGT | |
| 538 | DHDYYAFDY | CLONE_65 | Chothia | CDR-H3 |
| 539 | DHDYYAFDY | | AbM | |
| 540 | DHDYYAFDY | | Kabat | |
| 541 | AKDHDYYAFD | | Contact | |
| 542 | AKDHDYYAFDY | | IMGT | |

TABLE 25-continued

Sequence Listing

| SEQ ID | SEQUENCE | Description 1 | Description 2 | Description 3 |
| --- | --- | --- | --- | --- |
| 543 | GEWDLLWYFMDV | CLONE_80 | Chothia | CDR-H3 |
| 544 | GEWDLLWYFMDV | | AbM | |
| 545 | GEWDLLWYFMDV | | Kabat | |
| 546 | ARGEWDLLWYFMD | | Contact | |
| 547 | ARGEWDLLWYFMDV | | IMGT | |
| 548 | DPWNYVNYNYFMDV | CLONE_82 | Chothia | CDR-H3 |
| 549 | DPWNYVNYNYEMDV | | AbM | |
| 550 | DPWNYVNYNYFMDV | | Kabat | |
| 551 | TTDPWNYVNYNYFMD | | Contact | |
| 552 | TTDPWNYVNYNYFMDV | | IMGT | |
| 553 | RASQSISSRLA | CLONE_63 | Chothia | CDR-L1 |
| 554 | RASQSISSRLA | | AbM | |
| 555 | RASQSISSRLA | | Kabat | |
| 556 | SSRLAWY | | Contact | |
| 557 | QSISSR | | IMGT | |
| 558 | RASQSISSYLN | CLONE_64 | Chothia | CDR-L1 |
| 559 | RASQSTSSYTN | | AbM | |
| 560 | RASQSISSYLN | | Kabat | |
| 561 | SSYLNWY | | Contact | |
| 562 | QSISSY | | IMGT | |
| 563 | RASQSINSYLN | CLONE_65 | Chothia | CDR-L1 |
| 564 | RASQSINSYLN | | AbM | |
| 565 | RASQSINSYLN | | Kabat | |
| 566 | NSYLNWY | | Contact | |
| 567 | QSINSY | | IMGT | |
| 568 | RASQCISSWLA | CLONE_80 | Chothia | CDR-L1 |
| 569 | RASQGISSWLA | | AbM | |
| 570 | RASQGISSWLA | | Kabat | |
| 571 | SSALARY | | Contact | |
| 572 | QGISSW | | IMGT | |
| 573 | RASQDIRNYLA | CLONE_82 | Chothia | CDR-L1 |
| 574 | RASQDIRNYLA | | AbM | |
| 575 | RASQDIRNYLA | | Kabat | |
| 576 | RNYLAWY | | Contact | |
| 577 | QDIRNY | | IMGT | |
| 578 | KASNLES | CLONE_63 | Chothia | CDR-L2 |
| 579 | KASNLES | | AbM | |
| 580 | KASNLES | | Kabat | |

TABLE 25-continued

Sequence Listing

| SEQ ID | SEQUENCE | Description 1 | Description 2 | Description 3 |
|---|---|---|---|---|
| 581 | LLIYKASNLE | | Contact | |
| 582 | KA | | IMGT | |
| 583 | AVSSLQS | CLONE_64 | Chothia | CDR-L2 |
| 584 | AVSSLQS | | AbM | |
| 585 | AVSSLQS | | Kabat | |
| 586 | LLIYAVSSLQ | | Contact | |
| 587 | AV | | IMGT | |
| 588 | SASSLQS | CLONE_65 | Chothia | CDR-L2 |
| 589 | SASSLQS | | AbM | |
| 590 | SASSLQS | | Kabat | |
| 591 | LLIYAASSLQ | | Contact | |
| 592 | AA | | IMGT | |
| 593 | AASSLOS | CLONE_80 | Chothia | CDR-L2 |
| 594 | AASLQS | | AbM | |
| 595 | AASSLQS | | Kabat | |
| 596 | LLIYAASSLQ | | Contact | |
| 597 | AA | | IMGT | |
| 598 | AASTLQS | CLONE_82 | Chothia | CDR-L2 |
| 599 | AASTLQS | | AbM | |
| 600 | AASTLOS | | Kabat | |
| 601 | LLVYAASTLQ | | Contact | |
| 602 | AA | | IMGT | |
| 603 | QQYNSYSRT | CLONE_63 | Chothia | CDR-L3 |
| 604 | QQYNSYSRT | | AbM | |
| 605 | QQYNSYSRT | | Kabat | |
| 606 | QQYNSYSR | | Contact | |
| 607 | QQYNSYSRT | | IMGT | |
| 608 | QQSYSTPYT | CLONE_64 | Chothia | CDR-L3 |
| 609 | QQSYSTPYT | | AbM | |
| 610 | QQSYSTPYT | | Kabat | |
| 611 | QOSYSTPY | | Contact | |
| 612 | QQSYSTPYT | | IMGT | |
| 613 | QQSYSTPYT | CLONE_65 | Chothia | CDR-L3 |
| 614 | QQSYSTPYT | | AbM | |
| 615 | QQSYSTPYT | | Kabat | |
| 616 | QQSYSTPY | | Contact | |
| 617 | QQSYSTPYT | | IMGT | |

TABLE 25-continued

Sequence Listing

| SEQ ID | SEQUENCE | Description 1 | Description 2 | Description 3 |
|---|---|---|---|---|
| 618 | QQANSFPLT | CLONE_80 | Chothia | CDR-L3 |
| 619 | QQANSFPLT | | AbM | |
| 620 | QQANSFPLT | | Kabat | |
| 621 | QQANSFPL | | Contact | |
| 622 | QQANSFPLT | | IMGT | |
| 623 | QNYFSVPLT | CLONE_82 | Chothia | CDR-L3 |
| 624 | QNYFSVPLT | | AbM | |
| 625 | QNYFSVPLT | | Kabat | |
| 626 | QNYFSVPL | | Contact | |
| 627 | QNYFSVPLT | | IMGT | |
| 628 | VSGGSISGYY | CLONE_1_germlined | Aho | CDR-H1 |
| 629 | ASGFNFDDYA | CLONE_2_germlined | Aho | CDR-H1 |
| 630 | VSGFTFSSYD | CLONE_80 | Aho | CDR-H1 |
| 631 | ASGFMFSSYS | CLONE_63 | Aho | CDR-H1 |
| 632 | ASGFTFSNYA | CLONE_64 | Aho | CDR-H1 |
| 633 | ASGfTFSNYA | CLONE_65 | Aho | CDR-H1 |
| 634 | VSGITFSNAW | CLONE_82 | Aho | CDR-H1 |
| 635 | GYYWS (SEQ ID NO: 107) | CLONE_1_germlined | Cross-linking | CDR-H1 |
| 636 | DYAMH (SEQ ID NO: 117) | CLONE_2_germlined | Cross-linking | CDR-H1 |
| 637 | SYDMH (SEQ ID NO: 482) | CLONE_80 | Cross-linking | CDR-H1 |
| 638 | SYSMN (SEQ ID NO: 467) | CLONE_63 | Cross-linking | CDR-H1 |
| 639 | NYAMT (SEQ ID NO: 472) | CLONE_64 | Cross-linking | CDR-H1 |
| 640 | NYAMT (SEO ID NO: 477) | CLONE_65 | Cross-linking | CDR-H1 |
| 641 | NAWMS (SEQ ID NO: 487) | CLONE_82 | Cross-linking | CDR-H1 |
| 642 | IFYSGYTKYNPSLKSR | CLONE_1_germlined | Aho | CDR-H2 |
| 643 | ISWRSGNIGYADSVKGR | CLONE_2_germlined | Aho | CDR-H2 |
| 644 | IGIGGDTYYPGSVKGR | CLONE_80 | Aho | CDR-H2 |
| 645 | ISSSSSTIYDADSVKGR | CLONE_63 | Aho | CDR-H2 |
| 646 | ISGFGGSTYYADSVKGR | CLONE_64 | Aho | CDR-H2 |
| 647 | ISGYGGSTYYAASVKGR | CLONE_65 | Aho | CDR-H2 |
| 648 | IKSKTYGGTTDYAAPVKGR | CLONE_82 | Aho | CDR-H2 |
| 649 | WIGYIFYSGYTK (SEQ ID NO: 148) | CLONE_1_germlined | Cross-linking | CDR-H2 |

TABLE 25-continued

Sequence Listing

| SEQ ID | SEQUENCE | Description 1 | Description 2 | Description 3 |
|---|---|---|---|---|
| 650 | WVSGISWRSGNIG (SEQ ID NO: 158) | CLONE_2_germlined | Cross-linking | CDR-H2 |
| 651 | WVSSIGIGGDTY (SEQ ID NO: 521) | CLONE_80 | Cross-linking | CDR-H2 |
| 652 | WVSYISSSSSTIY (SEQ ID NO: 493) | CLONE_63 | Cross-linking | CDR-H2 |
| 653 | WVSAISGFGGSTY (SEQ ID NO: 498) | CLONE_64 | Cross-linking | CDR-H2 |
| 654 | WVSAISGYGGSTY (SEQ ID NO: 516) | CLONE_65 | Cross-linking | CDR-H2 |
| 655 | WVGRIKSKTYGGTTD (SEQ ID NO: 526) | CLONE_82 | Cross-linking | CDR-H2 |
| 656 | DEEDED | CLONE_1_germlined | Aho | CDR-H3 |
| 657 | DKGIGFNWNYEGFD | CLONE_2_germlined | Aho | CDR-H3 |
| 658 | GEWDLLWYFMD | CLONE_80 | Aho | CDR-H3 |
| 659 | EAYPGYYYNYMD | CLONE_63 | Aho | CDR-H3 |
| 660 | DHDYYAFD | CLONE_64 | Aho | CDR-H3 |
| 661 | DHDYYAFD | CLONE_65 | Aho | CDR-H3 |
| 662 | DPWNYVNYNYFMD | CLONE_82 | Aho | CDR-H3 |
| 663 | DRWDFDY (SEQ ID NO: 187) | CLONE_1_germlined | Cross-linking | CDR-H3 |
| 664 | DKGIGFNWNYEGFDY (SEQ ID NO: 197) | CLONE_2_germlined | Cross-linking | CDR-H3 |
| 660 | GEWDLLWYFMDV (SEQ ID NO: 545) | CLONE_80 | Cross-linking | CDR-H3 |
| 666 | EAYPGYYYNYMDV (SEQ ID NO: 530) | CLONE_63 | Cross-linking | CDR-H3 |
| 667 | DHDYYAFDY (SEQ ID NO: 535) | CLONE_64 | Cross-linking | CDR-H3 |
| 668 | DHDYYAFDY (SEQ ID NO: 540) | CLONE_65 | Cross-linking | CDK-H3 |
| 669 | DPWNYVNYNYFMDV(SEQID NO: 550) | CLONE_82 | Cross-linking | CDR-H3 |
| 670 | ASQGIRNN | CLONE_1_germlined | Aho | CDR-L1 |
| 671 | ASQGISNH | CLONE_2_germlined | Aho | CDR-L1 |
| 672 | ASQGISSW | CLONE_80 | Aho | CDR-L1 |
| 673 | ASQSISSR | CLONE_63 | Aho | CDR-L1 |
| 674 | ASQSISSY | CLONE_64 | Aho | CDR-L1 |
| 675 | ASQSINSY | CLONE_65 | Aho | CDR-L1 |
| 676 | ASQDIRNY | CLONE_82 | Aho | CDR-L1 |
| 677 | RASQGIRNNLG (SEQ ID NO: 307) | CLONE_1_germlined | Cross-linking | CDR-L1 |

TABLE 25-continued

Sequence Listing

| SEQ ID | SEQUENCE | Description 1 | Description 2 | Description 3 |
| --- | --- | --- | --- | --- |
| 678 | RASQGISNHLA (SEQ ID NO: 317) | CLONE_2_germlined | Cross-linking | CDR-L1 |
| 679 | RASQCISSWLA (SEQ ID NO 570) | CLONE_80 | Cross-linking | CDR-L1 |
| 680 | RASQSISSRLA (SEQ ID NO: 555) | CLONE_63 | Cross-linking | CDR-L1 |
| 681 | RASQSISSYLN (SEQ ID NO: 560) | CLONE_64 | Cross-linking | CDR-L1 |
| 682 | RASQSINSYLN (SEQ ID NO: 565) | CLONE_65 | Cross-linking | CDR-L1 |
| 683 | RASQDIRNYLA (SEQ ID NO: 575) | CLONE_82 | Cross-linking | CDR-L1 |
| 684 | AESSLQSGVPSR | CLONE_1_germlined | Aho | CDR-L2 |
| 685 | AASSLQSGVPSR | CLONE_2_germlined | Aho | CDR-L2 |
| 686 | AASSLQSGVPSR | CLONE_80 | Aho | CDR-L2 |
| 687 | KASNLESGVPSR | CLONE_63 | Aho | CDR-L2 |
| 688 | AVSSLQSGVPSR | CLONE_64 | Aho | CDR-L2 |
| 689 | SASSLQSGVPSR | CLONE_65 | Aho | CDR-L2 |
| 690 | AASTLQSGVPSR | CLONE_82 | Aho | CDR-L2 |
| 691 | AESSLQS (SEQ ID NO: 347) | CLONE_1_germlined | Cross-linking | CDR-L2 |
| 692 | AASSLQS (SEQ ID NO: 357) | CLONE_2_germlined | Cross-linking | CDR-L2 |
| 693 | AASSLQS (SEQ ID NO: 595) | CLONE_80 | Cross-linking | CDR-L2 |
| 694 | KASNLES (SEQ ID NO: 580) | CLONE_63 | Cross-linking | CDR-L2 |
| 695 | AVSSLQS (SEQ ID NO: 585) | CLONE_64 | Cross-linking | CDR-L2 |
| 696 | SASSLQS (SEQ ID NO: 590) | CLONE_65 | Cross-linking | CDR-L2 |
| 697 | AASTLQS (SEQ ID NO: 600) | CLONE_82 | Cross-linking | CDR-L2 |
| 698 | DFNYPY | CLONE_1_germlined | Aho | CDR-L3 |
| 699 | YVTYPL | CLONE_2_germlined | Aho | CDR-L3 |
| 700 | ANSFPL | CLONE_80 | Aho | CDR-L3 |
| 701 | YNSYSR | CLONE_63 | Aho | CDR-L3 |
| 702 | SYSTPY | CLONE_64 | Aho | CDR-L3 |
| 703 | SYSTPY | CLONE_65 | Aho | CDR-L3 |
| 704 | YFSVPL | CLONE_82 | Aho | CDR-L3 |
| 705 | LQDFNYPYT (SEQ ID NO: 387) | CLONE_1_germlined | Cross-linking | CDR-L3 |

TABLE 25-continued

Sequence Listing

| SEQ ID | SEQUENCE | Description 1 | Description 2 | Description 3 |
|---|---|---|---|---|
| 706 | QQYVTYPLT (SEQ ID NO: 397) | CLONE_2_ germlined | Cross-linking | CDR-L3 |
| 707 | QQANSFPLT (SEQ ID NO: 620) | CLONE_80 | Cross-linking | CDR-L3 |
| 708 | QQYNSYSRT (SEQ ID NO: 605) | CLONE_63 | Cross-linking | CDR-L3 |
| 709 | QQSYSTPYT (SEQ ID NO: 610) | CLONE_64 | Cross-linking | CDR-L3 |
| 710 | QQSYSTPYT (SEQ ID NO: 615) | CLONE_65 | Cross-linking | CDR-L3 |
| 711 | QNYFSVPLT (SEQ ID NO: 625) | CLONE_82 | Cross-linking | CDR-L3 |
| 712 | X1-Y-X2-X3-X4, wheerin X1 is G, D, or S; X2 is Y, A, or D; X3 is W or M; and X4 is S or H (SEQ ID NO: 712) | Consensus_1 | based on Kabat | CDR-H1 |
| 713 | X1-X2-X3-X4-X5, wherein X1 is G, D, N, or S; X2 is Y or A; X3 is Y, A, S, W, or D; X4 is W or M; and X5 is N, T, S or H (SEQ ID NO: 713) | Consensus_2 | based on Cross-linking | CDR-H1 |
| 714 | G-X1-X2-X3-X4-X5-Y, wherein X1 is G or F; X2 is S, N, or T; X3 is I or F; X4 is S or D; and X5 is G, D, or S (SEQ ID NO: 714) | Consensus | based on Chothia | CDR-H1 |
| 715 | G-X1-X2-X3-X4-X5-X6, wherein X1 is G, F or I; X2 is S, N, T, or M; X3 is I or F; X4 is S or D; X5 is G, D, S, or N; and X6 is Y or A (SEQ ID NO: 715) | Consensus_2 | based on Chothia | CDR-H1 |
| 716 | G-X1-X2-X3-X4-X5-Y-X6-X7-A8, wherein X1 is G or F; X2 is S, N, or T; X3 is I or F; X4 is S or D; X5 is G, D, or S; X6 is Y, A, or D; X7 is W or M; and X8 is S or H (SEQ ID NO: 716) | Consensus_1 | based on AbM | CDR-H1 |
| 717 | G-X1-X2-X3-X4-X5-X6-X7-X8, X9, wherein X1 is G, F or I; X2 is S, N, T, or M; X3 is I or F; X4 is S or D; X5 is G, D, S, or Y, A, D, S or W; X8 is W or M; and X9 is S, H, N, or T (SEQ ID NO: 717) | Consensus_2 | based on AbM | CDR-H1 |
| 718 | X1-X2-Y-X3-X4-X5, wherein X1 is S or D; X2 is G, D, or S; X3 is Y, A, or D; X4 is W or M; and X5 is S or H (SEQ ID NO: 718) | Consensus_1 | based on. Contact | CDR-H1 |

TABLE 25-continued

Sequence Listing

| SEQ ID | SEQUENCE | Description 1 | Description 2 | Description 3 |
|---|---|---|---|---|
| 719 | X1-X2-X3-X4-X5-X6, wherein X1 is S or D; X2 or A; X4 is Y, A, S2, W, or D; X5 is W or M; and X6 is N, T, S or H (SEQ ID NO: 719) | Consensus_ | based on Contact | CDR-H1 |
| 720 | G-X1-X2-X3-X4-X5-Y-X6, wherein X1 is G or F; X2 is S, N, or T; X3 is I or F, X4 is S or D; X5 is G, D, or S; and X6 is Y, A, or D (SEQ ID NO: 720) | Consensus_1 | based on IMGT | CDR-H1 |
| 721 | G-X1-X2-X3-X4-X5-X6-X7, wherein X1 is G, F or I; X2 is S, N, T, or M; X3 is I or F; X4 is S or: D; X5 is G, D, S, or N; X6 is Y or A; and X7 is Y, A, D, S, or W (SEQ ID NO: 721) | Consensus_2 | based on IMGT | CDR-H1 |
| 722 | X1-S-G-X2-X3-X4-X5-X6-Y-X7, wherein X1 is V or A; X2 is G or F; X3 is S, N, or T; X4 is I or F; X5 is S or D; X6 is G, d, or S; and X7 is X, A, or D (SEQ ID NO: 722) | Consensus_1 | based on Aho | CDR-H1 |
| 723 | X1-S-G-X2-X3-X4-X5-X6-X7-X8, wherein X1 is V or A; X2 is G, F or I; X3 is S, N, T, or M; X4 is I or F; X5 is S or D; X6 is G, D, S, or N; X7 is X or A; and X8 is Y, A, D, S or W (SEQ ID NO: 723) | Consensus_2 | based on Aho | CDR-H1 |
| 712 | X1-Y-X2-X3-X4, wherein X1 is G, D, or S; X2 is Y, A, or D; X3 is X or M; and X4 is S or H (SEQ ID NO: 712) | Consensus_1 | based on Cross-linking | CDR-H1 |
| 713 | X1-X2-X3-X4-X5, wherein X1 is G, D, N, or S; X2 W, or D; X4 is W or M; and X5 is N, T, S or H (SEQ ID NO: 713) | Consensus_2 | based on Cross-linking | CDR-H1 |
| 724 | X1-I-X2-X3-X4-X5-G-X6-X7-X8-Y-X9-X10-S-X11-K-X12, wherein X1 is X, G, or S, X2 is S, G, or none; X3 is F, W, or I; X4 is Y, R, or none; X5 is G or S; X6 is Y, N, or D; X7 is T or I; X8 is K, G, or Y; X9 is N, A, or P; X10 is P, D, or G; X11 is I or V; and X12 is S or G (SEQ ID NO: 724) | Consensus_1 | based on Kabat | CDR-H2 |
| 725 | X1-I-X2-X3-X4-X5-46-X7-X8-29-X10-X1 1-x12-x13-X14-K-X15, wherein XI is G, or none; X3 is F, W, I, S, G or T; X4 is Y, R, S, F, or none; X5 i.s G or S; X6 i.s G or S; X7 i.s Y, N, D, T or S; X 8 is T o r 1; X9 is K, G, Y, or D; | Consensus_2 | based on Kabat | CDR-H2 |

TABLE 25-continued

Sequence Listing

| SEQ ID | SEQUENCE | Description 1 | Description 2 | Description 3 |
|---|---|---|---|---|
| | XI0 is Y or D; XII is N, A, or P; and X12 is P, D, X14 is L or V; and X15 is S or G (SEQ ID NO: 725) | | | |
| 726 | X1-X2-X3-X4-G-X5, wherein X1 is S, G, or none; X2 is F, W, or I; X3 is Y, R, or none; X4 is S or G; and X5 is Y, N, or D (SEQ ID NO: 726) | Consensus_1 | based on Chothia | CDR-H2 |
| 727 | X1-X2-X3-X4-X5-X6, wherein X1 is S, G, or none; X2 is F, W, G, S, I, or T; X3 is Y, R, S, F, or none; X4 is S or G; X5 is G or S; and X6 is Y, N, D, T, or S (SEQ ID NO: 727) | Consensus_2 | based on Chothia | CDR-H2 |
| 728 | X1-I-X2-X3-X4-X5-G-X6-X7-X8, wherein X1 is Y, G, or S; X2 is S, G, or none; X3 is F, W, or I; X4 is Y, R, or none; X5 is G or S; X6 is Y, N, or D; X7 is T or I; X8 is K, G, or Y (SEQ ID NO: 728) | Consensus_1 | based on AbM | CDR-H2 |
| 729 | X1-1-X2-X3-X4-X5-X6-X7-X8-X9, wherein X1 is Y, G, S, A or R; X2 is S, G, or none; X3 is F, W, I, S, G or T; X4 is Y, R, S, F, or none; X5 is G or S; X6 is G or S; X7 is Y, N, D, T or S; X8 is T or I; X9 is K, G, Y, or D (SEQ ID NO: 729) | Consensus_2 | based on AbM | CDR-H2 |
| 730 | W-X1-X2-X3-I-X4-X5-X6-X7-G-X8-X9-X10, wherein X1 is I or V; X2 is G or S; X3 is Y or G, or S; X4 is S, G, or none; X5 is F, W, or I; X6 is Y, R, or none; X7 is G or S; X8 is Y, N, or D; X9 is T or I; X10 is K, G, or Y (SEQ ID NO: 730) | Consensus_1 | based on Contact | CDR-H2 |
| 731 | W-X1-X2-X3-I-X4-X5-X6-X7-X8-X9-X10-X11, wherein X1 is I or V; X2 is G or S; X3 is Y, G, S, A or R, X4 is S, G, or none; X5 is F, W, I, S, G or T; X6 is Y, R, S, F, or none; X7 is G or S; X8 is G or S; X9 is Y, N, D, T or S; X10 is T or I; X10 is K, G, Y, or D (SEQ ID NO: 731) | Consensus_2 | based on Cross-linking | CDR-H2 |
| 732 | I-X1-X2-S3-S4-G-X5-X6, wherein XI is S, G, or none; X2 is F, W, or I; X3 is Y, R, or none; X4 is G or S; X5 is Y, N, or D; and X6 is T or I (SEQ ID NO: 732) | Consensus_1 | based on IMGT | CDR-H2 |
| 733 | I-XI-X2-X3-X4-X5-X6-X7, wherein X1 is S, G, or | Consensus_2 | based on IMGT | CDR-H2 |

TABLE 25-continued

Sequence Listing

| SEQ ID | SEQUENCE | Description 1 | Description 2 | Description 3 |
|---|---|---|---|---|
| | none; X2 is F, W, I, S, G or T; X3 is Y, R, S, F, or none; X4 is G or S; X5 is G or S; X6 is Y, N, D, T or S; and X7 is T or I (SEQ ID NO: 733) | | | |
| 734 | I-X1-X2-X3-X4-G-X5-X6-X7-Y-X8-X9-S-X10-K-X11-R, wherein X1 is S, G, or none; X2 is F, W, or I; X3 is Y, R, or none; X4 is G or S; X5 is Y, N, or D; X6 is T or I; X7 is K, G, or Y; X8 is N, A, or P; X9 is p, D or G; X10 is L or V; and X11 is G or S (SEQ ID NO: 734) | Consensus_1 | based on Aho | CDR-H2 |
| 735 | I-X1-X2-X3-X4-X5-X6-X7-X8-X9-X10-X11-X12-X13-K-X14-R, wherein X1 is S,, G, or none; X2 is F, W, I, S, G or T; X3 is Y, R, S, F, or none; X4 is G or S; X5 is G or S; X6 is Y, N, D, T or S; X7 is T or I; X8 is K, G, Y, or D; X9 is Y or D; X10 is N, or A; X12 is S or P; X13 is L or V; and X14 is G or S (SEQ ID NO: 735) | Consensus_2 | based on Aho | CDR-H2 |
| 730 | W-X1-X2-X3-I-X4-X5-X6-X7-G-X8-X9-X10, wherein X1 is I or V; X2 is G or S; X3 is Y or G, or S; X4 is S, G, or none; X5 is F, W, or I; X6 is Y, R, or none; X7 is G or S; X8 is Y, N, or D; X9 is T or I; X10 is K, G, or Y (SEQ ID NO: 730) | Consensus_1 | based on Cross-linking | CDR-H2 |
| 731 | W-X1-X2-X3-I-X4-X5-X6-X7-X8-X9-X10-X11, wherein X1 is I or V; X2 is G or S; X3 is Y, G, S, A or R, X4 is S, G, or none; X5 is F, W, I, S, G or T; X6 is Y, R, S, F, or none; X7 is G or S; X8 is G or S; X9 is Y, N, D, T or S; X10 is T or I; X10 is K, G, Y, or D (SEQ ID NO: 731) | Consensus_2 | based on Cross-linking | CDR-H2 |
| 736 | X1-X2-X3-X4-X5-X6-X7-W-X8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E , or none; X11 is G or none; X12 is M or none; and X13 is Y or V (SEQ ID NO: 736) | Consensus_1 | based on Chothia | CDR-H3 |
| 737 | X1-X2-X3-X4-X5-X6-X7-X8-X9-X10-X11-X12-X13-X14-D-X15, wherein X1 is D or | Consensus_2 | based on AbM | CDR-H3 |

TABLE 25-continued

Sequence Listing

| SEQ ID | SEQUENCE | Description 1 | Description 2 | Description 3 |
|---|---|---|---|---|
| | none; X2 is R, K, G, P, or none; X3 is G, E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or none; X11 is D, E, N, or none; X12 is G or none; X13 is F or Y; X14 is M or none; and X15 iS Y or V (SEQ ID NO: 737) | | | |
| 736 | X1-X2-X3-X4-X5-X6-X7-W-X8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E, or none; X11 is G or none; X12 is M or none; and X13 is Y or V (SEQ ID NO: 736) | Consensus_1 | based on Chothia | CDR-H3 |
| 737 | X1-X2-X3-X4-X5-X6-X7-X8-X9-X10-X11-X12-X13-X14-D-X15, wherein X1 is D or none; X2 is R, K, G, P, or none; X3 is G, E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or none; X11 is D, E, N, or none; X12 is G or none; X13 is F or Y; X14 is M or none; and X15 iS Y or V (SEQ ID NO: 737) | Consensus_2 | based on Chothia | CDR-H3 |
| 736 | X1-X2-X3-X4-X5-X6-X7-W-X8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E, or none; X11 is G or none; X12 is M or none; and X13 is Y or V (SEQ ID NO: 736) | Consensus_1 | based on AbM | CDR-H3 |
| 737 | X1-X2-X3-X4-X5-X6-X7-X8-X9-X10-X11-X12-X13-X14-D-X15, wherein X1 is D or none; X2 is R, K, G, P, or none; X3 is G, E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or | Consensus_2 | based on AbM | CDR-H3 |

TABLE 25-continued

Sequence Listing

| SEQ ID | SEQUENCE | Description 1 | Description 2 | Description 3 |
|---|---|---|---|---|
| | none; X11 is D, E, N, or none; X12 is G or none; X13 is F or Y; X14 is M or none; and X15 iS Y or V (SEQ ID NO: 737) | | | |
| 738 | A-X1-X2-X3-X4-X5-X6-X7-X8-W-X9-X10-X11-X12-F-X13-D, wherein X1 is K or R; X2 is D or none; X3 is R, K, or G; X4 is G, E, or none; X5 is I, W, or none; X6 is G, D, or none; X7 is F, L, or none; X8 is N, L, or none; X9 is N, Y, or none; X10 is Y, or none; X11 is D, E, or none; X12 is G or none; and X13 is M or none (SEQ ID NO: 738) | Consensus_1 | based on Contact | CDR-H3 |
| 739 | X1-X2-X3-X4-X5-X6-X7-X88-X9-X10-X11-X12-X13-X14-X15-X16-D, wherein X1 is A or T; X2 is K, R, or T; X3 is D or none; X4is R, K, G, P, or none; X5 is G, E, W, or none; X6 is I, W, A, N, or none; X7 is G, D, Y, or none; X8 is F, L, P, H, V, or none; X9 is N, L, G, D, or none; X10 is X or Y; X11 is N, Y, or none; X12 is Y, A, or none; X13 is D, E, N, or none; X14 is G or none; X15 is F or Y; and X16 is M or none (SEQ ID NO: 739) | Consensus_2 | based on Contact | CDR-H3 |
| 740 | A-X1-X2-X3-X4-X5-X6-X7-X8-W-X9-X10-X11-X12-F-X13-D-X14, wherein X1 is K or R, X2 is D or none; X3 is R, K, or G, X4 is G, E, or none, X5 is I, W, or none; X6 is G, D, or none; X7 is F, L, or none, X8 is N, L, or none; X9 is N, Y, or none; X10 is Y, or none; X11 is D, E, or none, X12 is G or none, X13 is M or none; and X14 is Y or V (SEQ ID NO: 740) | Consensus_1 | based on IMGT | CDR-H3 |
| 741 | X1-X2-X3-X4-X5-X6-X7-X8-X9-X10-X11-X12-X13-X14-X15-X16-D-X17, wherein X1 is A or T, X2 is K, R, or T; X3 is D or none; X4 is R, K, G, P, or none; X5 is G, E, W, or none; X6 is I, W, A, N, or none; X7 ix G, D, Y, or none; X8 is F, L, P, H, V, or none; X9 is N, L, G, D, or none; X10 is W or Y; X11 is N, Y, or none; X12 is Y, A, or none; X13 is D, E, N, or none; X14 is | Consensus_2 | based on IMGT | CDR-H3 |

TABLE 25-continued

Sequence Listing

| SEQ ID | SEQUENCE | Description 1 | Description 2 | Description 3 |
|---|---|---|---|---|
| | G or none; X15 is F or Y; X16 is M or none; and X17 is Y or V (SEQ ID NO: 741) | | | |
| 742 | X1-X2-X3-X4-X5-X6-X7-W-X8-X9-10-X11-F-X12-D, wherein X1 is D or: none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E, or none; X11 is G or none; and X12 is M or none (SEQ ID NO: 742) | Consensus_1 | based on Aho | CDR-H3 |
| 743 | X1-X2-X3-X4-X5-X6-X7-X8-X9-X10-X11-X12-X13-X14-D, wherein X1 is D or none; X2 is R, K, G, P, or none; X3 is G, E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or none; X11 is D, E, N, or none; X12 is G or: none; X13 is F or Y; and X14 is M or none (SEQ ID NO: 743 | Consensus_2 | based on Aho | CDR-H3 |
| 736 | X1-X2-X3-X4-X5-X6-X7-W-X8-X9-X10-X11-F-X12-D-X13, wherein X1 is D or none; X2 is R, K, or G; X3 is G, E, or none; X4 is I, W, or none; X5 is G, D, or none; X6 is F, L, or none; X7 is N, L, or none; X8 is N, Y, or none; X9 is Y, or none; X10 is D, E, or none; X11 is G or none; X12 is M or none; and X13 is Y or V (SEQ ID NO: 736) | Consensus_1 | based on Cross-linking | CDR-H3 |
| 737 | X1-X2-X3-X4-X5-X6-X7-X8-X9-X10-X11-X12-X13-X14-D-X15, wherein X1 is D or none; X2 is R, K, G, P, or none; X3 is G, E, W, or none; X4 is I, W, A, N, or none; X5 is G, D, Y, or none; X6 is F, L, P, H, V, or none; X7 is N, L, G, D, or none; X8 is W or Y; X9 is N, Y, or none; X10 is Y, A, or none; X11 is D, E, N, or none; X12 is G or none; X13 is F or Y; X14 is M or none; and X15 iS Y or V (SEQ ID NO: 737) | Consensus_2 | based on Cross-linking | CDR-H3 |

TABLE 25-continued

Sequence Listing

| SEQ ID | SEQUENCE | Description 1 | Description 2 | Description 3 |
|---|---|---|---|---|
| 744 | R-A-S-Q-G-I-X1-X2-X3-L-X4, wherein X1 is R or S; X2 is N or S; X3 is N, H or W; and X4 is G or A (SEQ ID NO: 744) | Consensus_1 | based on Kabat | CDR-L1 |
| 745 | R-A-S-Q-X1-I-X2-X3-X4-L-X5, wherein X1 is G, S, or D; X2 is; R, S, or N; X3 is N or S; X4 is N, H, W, R, or Y; and X5 is G, A, or N (SEQ ID NO: 745) | Consensus_2 | based on Kabat | CDR-L1 |
| 744 | R-A-S-Q-G-I-X1-X2-X3-L-X4, wherein X1 is R or S; X2 is N or S; X3 is N, H or W; and X4 is G or A (SEQ ID NO: 744) | Consensus_1 | based on Chothia | CDR-L1 |
| 745 | R-A-S-Q-X1-I-X2-X3-X4-L-X5, wherein X1 is G, S, or D; X2 is; R, S, or N; X3 is N or S; X4 is N, H, W, R, or Y; and X5 is G, A, or N (SEQ ID NO: 745) | Consensus_2 | based on Chothia | CDR-L1 |
| 744 | R-A-S-Q-G-I-X1-X2-X3-L-X4, wherein X1 is R or S; X2 is N or S; X3 is N, H or W; and X4 is G or A (SEQ ID NO: 744) | Consensus_1 | based on AbM | CDR-L1 |
| 745 | R-A-S-Q-X1-I-X2-X3-X4-L-X5, wherein X1 is G, S, or D; X2 is; R, S, or N; X3 is N or S; X4 is N, H, W, R, or Y; and X5 is G, A, or N (SEQ ID NO: 745) | Consensus_2 | based on AbM | CDR-L1 |
| 746 | X1-X2-X3-L-X4-W-X5, wherein X1 is R or S; X2 is N or S; X3 is N, H or W; X4 is G or A; and X5 is Y or F (SEQ ID NO: 746) | Consensus_1 | based on Contact | CDR-L1 |
| 747 | X1-X2-X3-L-X4-W-X5, wherein X1 is R, S, or N; X2 is N or S; X3 is N, H, W, R, or Y; X4 is G, A, or N; and X5 Y or F (SEQ ID NO: 747) | Consensus_2 | based on Contact | CDR-L1 |
| 748 | Q-G-I-X1-X2-X3, wherein X1 is R or S; X2 is N or S; and X3 is N, H or W (SEQ ID NO: 748) | Consensus_1 | based on IMGT | CDR-L1 |
| 749 | Q-X1-I-X2-X3-X4, wherein X1 is G, S, or D; X2 is R, S, or N; X3 is N or S; and X4 is N, H, W, R, or Y (SEQ ID NO: 749) | Consensus_2 | based on IMGT | CDR-L1 |
| 750 | A-S-Q-G-I-X1-X2-X3, wherein X1 is R or S; X2 is N or S; and X3 is N, H or W (SEQ ID NO: 750) | Consensus_1 | based on Aho | CDR-L1 |
| 751 | A-S-Q-X1-I-X2-X3-X4, wherein X1 is G, S, or D; X2 is R, S, or N; X3 is N or S; and X4 is N, H, W, R, or Y (SEQ ID NO: 751) | Consensus_2 | based on Aho | CDR-L1 |

TABLE 25-continued

Sequence Listing

| SEQ ID | SEQUENCE | Description 1 | Description 2 | Description 3 |
|---|---|---|---|---|
| 744 | R-A-S-Q-G-I-X1-X2-X3-L-X4, wherein X1 is R or S; X2 is N or S; X3 is N, H or W; and X4 is G or A (SEQ ID NO: 744) | Consensus_1 | based on Cross-linking | CDR-L1 |
| 745 | R-A-S-Q-X1-I-X2-X3-X4-L-X5, wherein X1 is G, S, or D; X2 is R, S, or N; X3 is N or S; X4 is N, H, W, R, or Y; and X5 is G, A, or N (SEQ ID NO: 745) | Consensus_2 | based on Cross-linking | CDR-L1 |
| 752 | A-X1-S-S-L-Q-S, wherein XK is A or E (SEQ ID NO: 752) | Consensus_1 | based on Kabat | CDR-L2 |
| 753 | X1-X2-S-X3-L-X4-S, wherein X1 is A, K, or S; X2 is A, E, or V; X3 is S, N, or T; and X4 is Q or E (SEQ ID NO: 753) | Consensus_2 | based on Kabat | CDR-L2 |
| 752 | A-X1-S-S-L-Q-S, wherein XK is A or E (SEQ ID NO: 752) | Consensus_1 | based on Chothia | CDR-L2 |
| 753 | X1-X2-S-X3-L-X4-S, wherein X1 is A, K, or S; X2 is A, E, or V; X3 is S, N, or T; and X4 is Q or E (SEQ ID NO: 753) | Consensus_2 | based on Chothia | CDR-L2 |
| 752 | A-X1-S-S-L-Q-S, wherein XK is A or E (SEQ ID NO: 752) | Consensus_1 | based on AbM | CDR-L2 |
| 753 | X1-X2-S-X3-L-X4-S, wherein X1 is A, K, or S; X2 is A, E, or V; X3 is S, N, or T; and X4 is Q or E (SEQ ID NO: 753) | Consensus_2 | based on AbM | CDR-L2 |
| 754 | X1-L-I-Y-A-X2-S-S-L-Q, wherein X1 is L, or S; and X2 A or E (SEQ ID NO: 754) | Consensus_1 | based on Contact | CDR-L2 |
| 755 | X1-L-X2-Y-X3-X4-S-X5-L-X6, wherein X1 is L or S; X2 is I or V; X3 is A, K, or S, X4 is A, E, or V; X5 is S, N, or T; and X6 is Q or E (SEQ ID NO: 755) | Consensus_2 | based on Contact | CDR-L2 |
| 756 | A-X1, wherein X1 is A or E (SEQ ID NO: 756) | Consensus_1 | based on IMGT | CDR-L2 |
| 757 | X1-X2, wherein X1 is A, K, or S; and X2 is A, E, or V (SEQ ID NO: 757) | Consensus_2 | based on IMGT | CDR-L2 |
| 758 | A-X1-S-S-L-Q-S-G-V-P-S-R, wherein X1 is A or E (SEQ ID NO: 758) | Consensus_1 | based on Aho | CDR-L2 |
| 759 | X1-X2-S-X3-L-X4-S-G-V-P-S-R, wherein X1 is A, K, or S; X2 is A, E, or V; X3 is S, N, or T; and, X4 is Q or E (SEQ ID NO: 759) | Consensus_2 | based on Aho | CDR-L2 |

TABLE 25-continued

Sequence Listing

| SEQ ID | SEQUENCE | Description 1 | Description 2 | Description 3 |
|---|---|---|---|---|
| 752 | A-X1-S-S-L-Q-S, wherein XK is A or E (SEQ ID NO: 752) | Consensus_1 | based on Cross-linking | CDR-L2 |
| 753 | X1-X2-S-X3-L-X4-S, wherein X1 is A, K, or S; X2 is A, E, or V; X3 is S, N, or T; and X4 is Q or E (SEQ ID NO: 753) | Consensus_2 | based on Cross-linking | CDR-L2 |
| 760 | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | Consensus_1 | based on Kabat | CDR-L3 |
| 761 | X1-Q-X2-X3-X4-X5-X6-X7-T, where in X1 is L or Q; X2 D, Y A, or S; X3 is F, V, N, or Y; X4 is N, T, or S; X5 is Y, F, T, or V; X6 is P or S; X7 is Y, L or R (SEQ ID NO: 761) | Consensus_2 | based on Kabat | CDR-L3 |
| 760 | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | Consensus_1 | based on Chothia | CDR-L3 |
| 761 | X1-Q-X2-X3-X4-X5-X6-X7-T, where in X1 is L or Q; X2 D, Y A, or S; X3 is F, V, N, or Y; X4 is N, T, or S; X5 is Y, F, T, or V; X6 is P or S; X7 is Y, L or R (SEQ ID NO: 761) | Consensus_2 | based on Chothia | CDR-L3 |
| 760 | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | Consensus_1 | based on AbM | CDR-L3 |
| 761 | X1-Q-X2-X3-X4-X5-X6-X7-T, where in X1 is L or Q; X2 D, Y A, or S; X3 is F, V, N, or Y; X4 is N, T, or S; X5 is Y, F, T, or V; X6 is P or S; X7 is Y, L or R (SEQ ID NO: 761) | Consensus_2 | based on AbM | CDR-L3 |
| 762 | X1-Q-X2-X3-X4-X5-P-X6, wherein X1 is L or Q; X2 is D, Y, or A; X3 is F, V, or N; X4 is N, T, or S; X5 is X or F; X6 is Y or L (SEQ ID NO: 762) | Consensus_1 | based on Contact | CDR-L3 |
| 763 | X1-Q-X2-X3-X4-X5-X6-X7, wherein X1 is L or Q; X2 D, Y, A, or S; X3 is F, V, N, or Y; X4 is N, T, or S; X5 is Y, F, T, or v; X6 is P or S; X7 is Y, L or R (SEQ ID NO: 763) | Consensus_2 | based on Contact | CDR-L3 |

TABLE 25-continued

Sequence Listing

| SEQ ID | SEQUENCE | Description 1 | Description 2 | Description 3 |
|---|---|---|---|---|
| 760 | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | Consensus_1 | based on IMGT | CDR-L3 |
| 761 | X1-Q-X2-X3-X4-X5-X6-X7-T, where in X1 is L or Q; X2 D, Y A, or S; X3 is F, V, N, or Y; X4 is N, T, or S; X5 is Y, F, T, or V; X6 is P or S; X7 is Y, L or R (SEQ ID NO: 761) | Consensus_2 | based on IMGT | CDR-L3 |
| 764 | X1-X2-X3-X4-P-X5, wherein X1 is D, Y, or A; X2 is F, V, or N; X3 is N, T, or S; X4 is Y or F; X5 is Y or L (SEQ ID NO: 764) | Consensus_1 | based on Aho | CDR-L3 |
| 765 | X1-X2-X3-X4-X5-X6, wherein X1 is D, Y, A, or S; X2 is F, V, N, or Y; X3 is N, T, or S; X4 is Y, F, T, or V; X5 is P or S; X6 is Y, L or R (SEQ ID NO: 765) | Consensus_2 | based on Aho | CDR-L3 |
| 760 | X1-Q-X2-X3-X4-X5-P-X6-T, wherein X1 is L or Q; X2 is D, Y, or A; X3 is F, V, or N; X4 is N, T, or S; X5 is Y or F; X6 is Y or L (SEQ ID NO: 760) | Consensus_1 | based on Cross-linking | CDR-L3 |
| 761 | X1-Q-X2-X3-X4-X5-X6-X7-T, where in X1 is L or Q; X2 D, Y A, or S; X3 is F, V, N, or Y; X4 is N, T, or S; X5 is Y, F, T, or V; X6 is P or S; X7 is Y, L or R (SEQ ID NO: 761) | Consensus_2 | based on Cross-linking | CDR-L3 |
| 500 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPEAAGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ L234A_L235A | | |
| 501 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELEGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ L235E | | |

TABLE 25-continued

Sequence Listing

| SEQ ID | SEQUENCE | Description 1 | Description 2 | Description 3 |
|---|---|---|---|---|
| 502 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPEAAGAPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ L234A_L235A_ G237A | | |
| 503 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPEAEGAPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ L234A_L235E_ G237A | | |
| 504 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPEAAGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALAAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ L234A_L235A_ P329A | | |
| 505 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPEAAGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALAAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ L234A_L235A_ P329G | | |
| 506 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPEAAGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALAAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ P329A | | |

TABLE 25-continued

Sequence Listing

| SEQ ID | SEQUENCE | Description 1 | Description 2 | Description 3 |
|---|---|---|---|---|
| 507 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPEEFGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPASIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ L234E_L235F_ P331S | | |
| 508 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELLGGPSVFL FPPKPKDTLMISRTPEVTCVVVAVS HEDPEVKFNWYVDGVEVHNAKTKPR EEQYGSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_ D265A_N297G | | |
| 509 | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELLGGPSVFL FPPKPKDTLMISRTPEVTCVVVDVS HEDPEVKFNWYVDGVEVHNAKTKPR EEQYGSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK | CONSTANT_N 297G | | |
| 510 | ASTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPPCPAPEFLGGPSVFLFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL GK | CONSTANT_ S228P | | |
| 511 | ASTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPPCPAPEFEGGPSVFLFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL GK | CONSTANT_ S228P_L235E | | |

TABLE 25-continued

Sequence Listing

| SEQ ID | SEQUENCE | Description 1 | Description 2 | Description 3 |
|---|---|---|---|---|
| 512 | ASTKGPSVFPLAPCSRSTSESTAAL GCLVKDYFPEPVTVSWNSGALTSGV HTFPAVLQSSGLYSLSSVVTVPSSS LGTKTYTCNVDHKPSNTKVDKRVES KYGPPCPPCPAPEAAGGPSVFLFPP KPKDTLMISRTPEVTCVVVDVSQED PEVQFNWYVDGVEVHNAKTKPREEQ FNSTYRVVSVLTVLHQDWLNGKEYK CKVSNKGLPSSIEKTISKAKGQPRE PQVYTLPPSQEEMTKNQVSLTCLVK GFYPSDIAVEWESNGQPENNYKTTP PVLDSDGSFFLYSRLTVDKSRWQEG NVFSCSVMHEALHNHYTQKSLSLSL GK | CONSTANT_ S228P_F234A_ L235A | | |

```
                         SEQUENCE LISTING

Sequence total quantity: 786
SEQ ID NO: 1             moltype = AA   length = 115
FEATURE                  Location/Qualifiers
REGION                   1..115
                         note = Description of Artificial Sequence:
                         Syntheticpolypeptide
source                   1..115
                         mol_type = protein
                         organism = synthetic construct
SEQUENCE: 1
QVQLQESGPG LVKPSETLSL TCTVSGGSIS GYYWSWIRQP PVKGLEWIGY IFYSGYTKYN   60
PSLKSRVTIS VDTSKNQFSL KLSSVTAADT AVYYCARDRW DFDYWGQGAL VTVSS       115

SEQ ID NO: 2             moltype = AA   length = 115
FEATURE                  Location/Qualifiers
REGION                   1..115
                         note = Description of Artificial Sequence:
                         Syntheticpolypeptide
source                   1..115
                         mol_type = protein
                         organism = synthetic construct
SEQUENCE: 2
QVQLQESGPG LVKPSETLSL TCTVSGGSIS GYYWSWIRQP PGKGLEWIGY IFYSGYTKYN   60
PSLKSRVTIS VDTSKNQFSL KLSSVTAADT AVYYCARDRW DFDYWGQGTL VTVSS       115

SEQ ID NO: 3             moltype = AA   length = 107
FEATURE                  Location/Qualifiers
REGION                   1..107
                         note = Description of Artificial Sequence:
                         Syntheticpolypeptide
source                   1..107
                         mol_type = protein
                         organism = synthetic construct
SEQUENCE: 3
AIQMTQSPSY LSASVGDRVT IACRASQGIR NNLGWYQQKP GKAPKLLIYA ESSLQSGVPS   60
RFSGSGSGTD FTLTISSLQP EDFATYYCLQ DFNYPYTFGQ GTKLEIK                107

SEQ ID NO: 4             moltype = AA   length = 107
FEATURE                  Location/Qualifiers
REGION                   1..107
                         note = Description of Artificial Sequence:
                         Syntheticpolypeptide
source                   1..107
                         mol_type = protein
                         organism = synthetic construct
SEQUENCE: 4
AIQMTQSPSS LSASVGDRVT ITCRASQGIR NNLGWYQQKP GKAPKLLIYA ESSLQSGVPS   60
RFSGSGSGTD FTLTISSLQP EDFATYYCLQ DFNYPYTFGQ GTKLEIK                107

SEQ ID NO: 5             moltype = AA   length = 124
FEATURE                  Location/Qualifiers
REGION                   1..124
```

```
                      note = Description of Artificial Sequence:
                        Syntheticpolypeptide
source                1..124
                      mol_type = protein
                      organism = synthetic construct
SEQUENCE: 5
EVQLVESGGG LVQPGRSLRL SCAASGFNFD DYAMHWVRQA PGKGLEWVSG ISWRSGNIGY    60
AGSVKGRFTI SRDNAKNSLY LQMNSLRPED SALYYCAKDK GIGFNWNYEG FDYWGQGTLV   120
TVSS                                                                124

SEQ ID NO: 6          moltype = AA  length = 124
FEATURE               Location/Qualifiers
REGION                1..124
                      note = Description of Artificial Sequence:
                        Syntheticpolypeptide
source                1..124
                      mol_type = protein
                      organism = synthetic construct
SEQUENCE: 6
EVQLVESGGG LVQPGRSLRL SCAASGFNFD DYAMHWVRQA PGKGLEWVSG ISWRSGNIGY    60
ADSVKGRFTI SRDNAKNSLY LQMNSLRAED TALYYCAKDK GIGFNWNYEG FDYWGQGTLV   120
TVSS                                                                124

SEQ ID NO: 7          moltype = AA  length = 107
FEATURE               Location/Qualifiers
REGION                1..107
                      note = Description of Artificial Sequence:
                        Syntheticpolypeptide
source                1..107
                      mol_type = protein
                      organism = synthetic construct
SEQUENCE: 7
DIQMTQSPSS LSASVGDRVT ITCRASQGIS NHLAWFQQKP GKAPKSLIYA ASSLQSGVPS    60
KFSGSGSGTD FTLTISSLQP EDFATYYCQQ YVTYPLTFGG GTKVEIK                 107

SEQ ID NO: 8          moltype = AA  length = 107
FEATURE               Location/Qualifiers
REGION                1..107
                      note = Description of Artificial Sequence:
                        Syntheticpolypeptide
source                1..107
                      mol_type = protein
                      organism = synthetic construct
SEQUENCE: 8
DIQMTQSPSS LSASVGDRVT ITCRASQGIS NHLAWFQQKP GKAPKSLIYA ASSLQSGVPS    60
RFSGSGSGTD FTLTISSLQP EDFATYYCQQ YVTYPLTFGG GTKVEIK                 107

SEQ ID NO: 9          moltype = AA  length = 115
FEATURE               Location/Qualifiers
REGION                1..115
                      note = Description of Artificial Sequence:
                        Syntheticpolypeptide
source                1..115
                      mol_type = protein
                      organism = synthetic construct
SEQUENCE: 9
QVQLQESGPG LVKPSETLSL TCTVSGGSIS GYYWSWIRQP PVKGLEWIGY IFYSGYTKYN    60
PSLKSRVTIS VDTSKNQFSL KLSSVTAADT AVYYCARDRW DFDYWGQGAL VTVSS        115

SEQ ID NO: 10         moltype = AA  length = 115
FEATURE               Location/Qualifiers
REGION                1..115
                      note = Description of Artificial Sequence:
                        Syntheticpolypeptide
source                1..115
                      mol_type = protein
                      organism = synthetic construct
SEQUENCE: 10
QVQLQESGPG LVKPSETLSL TCTVSGGSIS GYYWSWIRQP PGKGLEWIGY IFYSGYTKYN    60
PSLKSRVTIS VDTSKNQFSL KLSSVTAADT AVYYCARDRW DFDYWGQGTL VTVSS        115

SEQ ID NO: 11         moltype = AA  length = 112
FEATURE               Location/Qualifiers
REGION                1..112
                      note = Description of Artificial Sequence:
                        Syntheticpolypeptide
source                1..112
                      mol_type = protein
                      organism = synthetic construct
```

```
SEQUENCE: 11
DIVMTQSPLS LPVTPGEPAS FSCRSSQSLL HSNGYNYLDW YLQKPGQSPQ LLIYLGSNRA    60
SGVPDRFSGS GSGTDFTLKI SRVEAADVGV YYCMQALQTP RTFGQGTKVE IK           112

SEQ ID NO: 12              moltype = AA  length = 112
FEATURE                    Location/Qualifiers
REGION                     1..112
                           note = Description of Artificial Sequence:
                           Syntheticpolypeptide
source                     1..112
                           mol_type = protein
                           organism = synthetic construct
SEQUENCE: 12
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQALQTP RTFGQGTKVE IK           112

SEQ ID NO: 13              moltype = AA  length = 122
FEATURE                    Location/Qualifiers
REGION                     1..122
                           note = Description of Artificial Sequence:
                           Syntheticpolypeptide
source                     1..122
                           mol_type = protein
                           organism = synthetic construct
SEQUENCE: 13
QVQLVESGGG VVQPGRSLRL SCAASGFPFS SYGMHWVRQA PGKGLEWVTF IWFDGNNKDY    60
ADSVKGRFSV SRDNSKNTLY LQMNSLRADD TAVYYCARNG VYYGSAYVD YWGQGTLVTV    120
SS                                                                  122

SEQ ID NO: 14              moltype = AA  length = 122
FEATURE                    Location/Qualifiers
REGION                     1..122
                           note = Description of Artificial Sequence:
                           Syntheticpolypeptide
source                     1..122
                           mol_type = protein
                           organism = synthetic construct
SEQUENCE: 14
QVQLVESGGG VVQPGRSLRL SCAASGFPFS SYGMHWVRQA PGKGLEWVTF IWFDGNNKDY    60
ADSVKGRFTI SRDNSKNTLY LQMNSLRAED TAVYYCARNG VYYGSAYVD YWGQGTLVTV    120
SS                                                                  122

SEQ ID NO: 15              moltype = AA  length = 112
FEATURE                    Location/Qualifiers
REGION                     1..112
                           note = Description of Artificial Sequence:
                           Syntheticpolypeptide
source                     1..112
                           mol_type = protein
                           organism = synthetic construct
SEQUENCE: 15
DIVMTQSPLS LPVTPGEPAS FSCRSSQSLL HSNGYNYLDW YLQKPGQSPQ LLIYLGSNRA    60
SGVPDRFSGS GSGTDFTLKI SRVEAADVGV YYCMQALQTP RTFGQGTKVE IK           112

SEQ ID NO: 16              moltype = AA  length = 112
FEATURE                    Location/Qualifiers
REGION                     1..112
                           note = Description of Artificial Sequence:
                           Syntheticpolypeptide
source                     1..112
                           mol_type = protein
                           organism = synthetic construct
SEQUENCE: 16
DIVMTQSPLS LPVTPGEPAS ISCRSSQSLL HSNGYNYLDW YLQKPGQSPQ LLIYLGSNRA    60
SGVPDRFSGS GSGTDFTLKI SRVEAEDVGV YYCMQALQTP RTFGQGTKVE IK           112

SEQ ID NO: 17              moltype = AA  length = 116
FEATURE                    Location/Qualifiers
REGION                     1..116
                           note = Description of Artificial Sequence:
                           Syntheticpolypeptide
source                     1..116
                           mol_type = protein
                           organism = synthetic construct
SEQUENCE: 17
QVQLVESGGG VVQPGRSLRL SCAASGFTFS IYGMHWVRQA PGKGLEWVAV IWYDGSNKYY    60
VDSVKGRFTI SRDNSKNSLY LQMNSLRAED TAVYYCAREG NLFDYWGQGT LVTVSS       116

SEQ ID NO: 18              moltype = AA  length = 106
```

```
FEATURE                 Location/Qualifiers
REGION                  1..106
                        note = Description of Artificial Sequence:
                          Syntheticpolypeptide
source                  1..106
                        mol_type = protein
                        organism = synthetic construct
SEQUENCE: 18
DIQMTQSPST LSASVGDRVT ITCRASQSIS SWLAWYQQKP GKAPKLLIYK ASSLESGVPS    60
RFSGSGSGTE FTLTISSLKP DDFATYYCQQ YKSYYTFGQG TKLEIK                 106

SEQ ID NO: 19           moltype = AA  length = 122
FEATURE                 Location/Qualifiers
REGION                  1..122
                        note = Description of Artificial Sequence:
                          Syntheticpolypeptide
source                  1..122
                        mol_type = protein
                        organism = synthetic construct
SEQUENCE: 19
QVHLVESGGG VVQPGRSLRL SCAASGFAFN IYGMHWVRQA PGKGLEWVAV ISYDGSNKVY    60
ADSVKGRFSI SRDNSKNTLY LQMNSLRAED TAVYYCAKSG GITMVRGVFD YWGQGTLVTV   120
SS                                                                 122

SEQ ID NO: 20           moltype = AA  length = 107
FEATURE                 Location/Qualifiers
REGION                  1..107
                        note = Description of Artificial Sequence:
                          Syntheticpolypeptide
source                  1..107
                        mol_type = protein
                        organism = synthetic construct
SEQUENCE: 20
DIQMTQSPSS LPASVGDRVT ITCRASQGIR NDLGWYQQKP GKAPKRLIHA ASSLHSGVPS    60
RFSGSGSGTE FTLTISSLQP EDFATYYCLQ HNRYPITFGQ GTRLEIK                107

SEQ ID NO: 21           moltype = AA  length = 125
FEATURE                 Location/Qualifiers
REGION                  1..125
                        note = Description of Artificial Sequence:
                          Syntheticpolypeptide
source                  1..125
                        mol_type = protein
                        organism = synthetic construct
SEQUENCE: 21
QITLKESGPT LVKPTQTLTL TCTFSGFSLS TSGVGVGWIR QPPGKALEWL ALIYWNDDKR    60
YSPSLKSRLT ITKDTSKNQV VLTMTNMDPV DTATYYCAHR RTTTVTIYYY YMDVWGKGTT   120
VTVSS                                                              125

SEQ ID NO: 22           moltype = AA  length = 107
FEATURE                 Location/Qualifiers
REGION                  1..107
                        note = Description of Artificial Sequence:
                          Syntheticpolypeptide
source                  1..107
                        mol_type = protein
                        organism = synthetic construct
SEQUENCE: 22
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPFTFGP GTKVDIK                107

SEQ ID NO: 23           moltype = AA  length = 122
FEATURE                 Location/Qualifiers
REGION                  1..122
                        note = Description of Artificial Sequence:
                          Syntheticpolypeptide
source                  1..122
                        mol_type = protein
                        organism = synthetic construct
SEQUENCE: 23
EVQLVESGGG LVQPGGSLRL SCAASGFMFS SYSMNWVRQA PGKGLEWVSY ISSSSSTIYD    60
ADSVKGRFTI SRDDAKNSLY LQMNSLRDED TAVYYCTREA YPGYYYNYMD VWGKGTTVTV   120
SS                                                                 122

SEQ ID NO: 24           moltype = AA  length = 107
FEATURE                 Location/Qualifiers
REGION                  1..107
                        note = Description of Artificial Sequence:
                          Syntheticpolypeptide
```

```
source                  1..107
                        mol_type = protein
                        organism = synthetic construct
SEQUENCE: 24
DIQMTQSPSS LSASVGDRVT ITCRASQSIS SRLAWYQQKP GKAPNLLIYK ASNLESGVPS   60
RFSGSGSGTE FTLTISSLQP DDFATYYCQQ YNSYSRTFGQ GTKVEIK                107

SEQ ID NO: 25           moltype = AA  length = 118
FEATURE                 Location/Qualifiers
REGION                  1..118
                        note = Description of Artificial Sequence:
                        Syntheticpolypeptide
source                  1..118
                        mol_type = protein
                        organism = synthetic construct
SEQUENCE: 25
EVQLVESGGG LVQPGGSLRL SCAASGFTFS NYAMTWVRQA PGKGLEWVSA ISGFGGSTYY   60
ADSVKGRFTI SRDNSKNTLY LQMNSLRAED TAVYYCAKDH DYYAFDYWGQ GTLVTVSS   118

SEQ ID NO: 26           moltype = AA  length = 107
FEATURE                 Location/Qualifiers
REGION                  1..107
                        note = Description of Artificial Sequence:
                        Syntheticpolypeptide
source                  1..107
                        mol_type = protein
                        organism = synthetic construct
SEQUENCE: 26
DIQMTQSPSS LSASVGDRVT ITCRASQSIS SYLNWYQQKP GKAPKLLIYA VSSLQSGVPS   60
RFSGSGSGTD FTLTISSLQP EDFATYYCQQ SYSTPYTFGQ GTKLEIK                107

SEQ ID NO: 27           moltype = AA  length = 118
FEATURE                 Location/Qualifiers
REGION                  1..118
                        note = Description of Artificial Sequence:
                        Syntheticpolypeptide
source                  1..118
                        mol_type = protein
                        organism = synthetic construct
SEQUENCE: 27
EVQLVESGGG LVQPGGSLKL SCAASGFTFS NYAMTWVRQA PGKGLEWVSA ISGYGGSTYY   60
AASVKGRFTI SRDNSKNTLF LQMNSLRAED TAVYYCAKDH DYYAFDYWGQ GTLVPVSS   118

SEQ ID NO: 28           moltype = AA  length = 107
FEATURE                 Location/Qualifiers
REGION                  1..107
                        note = Description of Artificial Sequence:
                        Syntheticpolypeptide
source                  1..107
                        mol_type = protein
                        organism = synthetic construct
SEQUENCE: 28
DIQMTQSPSS LSASVGDRVT ITCRASQSIN SYLNWYQQKP GKAPKLLIYS ASSLQSGVPS   60
RFSGSGSGTD FTLTISSLQP EDFATYYCQQ SYSTPYTFGQ GTKLEIK                107

SEQ ID NO: 29           moltype = AA  length = 120
FEATURE                 Location/Qualifiers
REGION                  1..120
                        note = Description of Artificial Sequence:
                        Syntheticpolypeptide
source                  1..120
                        mol_type = protein
                        organism = synthetic construct
SEQUENCE: 29
EVQLVESGGG LVQPGGSLRL SCEVSGFTFS SYDMHWVRQV TGTGLEWVSS IGIGGDTYYP   60
GSVKGRFTIS RENAKNSLYL QMNSLRGGDT GVYYCARGEW DLLWYFMDVW GKGTTVTVSS 120

SEQ ID NO: 30           moltype = AA  length = 107
FEATURE                 Location/Qualifiers
REGION                  1..107
                        note = Description of Artificial Sequence:
                        Syntheticpolypeptide
source                  1..107
                        mol_type = protein
                        organism = synthetic construct
SEQUENCE: 30
DIQMTQSPSS LSASIGDRVT ITCRASQGIS SWLAWYQQKP GKAPKLLIYA ASSLQSGVPS   60
RFSGSGSGTD FTLTISSLQP EDFATYYCQQ ANSFPLTFGG GTKVEIK                107
```

```
SEQ ID NO: 31              moltype = AA   length = 125
FEATURE                    Location/Qualifiers
REGION                     1..125
                           note = Description of Artificial Sequence:
                           Syntheticpolypeptide
source                     1..125
                           mol_type = protein
                           organism = synthetic construct
SEQUENCE: 31
EVQLVESGGG LVQPGGSLRL SCAVSGITFS NAWMSWVRQA PGKGLEWVGR IKSKTYGGTT   60
DYAAPVKGRF IISRDDSKDT LYLQMNSLKT EDTAIYYCTT DPWNYVNYNY FMDVWGKGTT  120
VTVSS                                                              125

SEQ ID NO: 32              moltype = AA   length = 107
FEATURE                    Location/Qualifiers
REGION                     1..107
                           note = Description of Artificial Sequence:
                           Syntheticpolypeptide
source                     1..107
                           mol_type = protein
                           organism = synthetic construct
SEQUENCE: 32
DIQMTQSPSS LSASVGDRVT ITCRASQDIR NYLAWYQQKP GKITHLLVYA ASTLQSGVPS   60
RFSGSGSGTD FTLTINSLQP EDVATYYCQN YFSVPLTFGG GTKVEIK                107

SEQ ID NO: 33              moltype = AA   length = 234
FEATURE                    Location/Qualifiers
REGION                     1..234
                           note = Description of Unknown:CD30L full length sequence
source                     1..234
                           mol_type = protein
                           organism = unidentified
SEQUENCE: 33
MDPGLQQALN GMAPPGDTAM HVPAGSVASH LGTTSRSYFY LTTATLALCL VFTVATIMVL   60
VVQRTDSIPN SPDNVPLKGG NCSEDLLCIL KRAPFKKSWA YLQVAKHLNK TKLSWNKDGI  120
LHGVRYQDGN LVIQFPGLYF IICQLQFLVQ CPNNSVDLKL ELLINKHIKK QALVTVCESG  180
MQTKHVYQNL SQFLLDYLQV NTTISVNVDT FQYIDTSTFP LENVLSIFLY SNSD        234

SEQ ID NO: 34              moltype = AA   length = 172
FEATURE                    Location/Qualifiers
REGION                     1..172
                           note = Description of Unknown:CD30L extracellular domain
                           sequence
source                     1..172
                           mol_type = protein
                           organism = unidentified
SEQUENCE: 34
QRTDSIPNSP DNVPLKGGNC SEDLLCILKR APFKKSWAYL QVAKHLNKTK LSWNKDGILH   60
GVRYQDGNLV IQFPGLYFII CQLQFLVQCP NNSVDLKLEL LINKHIKKQA LVTVCESGMQ  120
TKHVYQNLSQ FLLDYLQVNT TISVNVDTFQ YIDTSTFPLE NVLSIFLYSN SD          172

SEQ ID NO: 35              moltype =     length =
SEQUENCE: 35
000

SEQ ID NO: 36              moltype =     length =
SEQUENCE: 36
000

SEQ ID NO: 37              moltype =     length =
SEQUENCE: 37
000

SEQ ID NO: 38              moltype =     length =
SEQUENCE: 38
000

SEQ ID NO: 39              moltype =     length =
SEQUENCE: 39
000

SEQ ID NO: 40              moltype =     length =
SEQUENCE: 40
000

SEQ ID NO: 41              moltype =     length =
SEQUENCE: 41
000
```

| | | |
|---|---|---|
| SEQ ID NO: 42 SEQUENCE: 42 | moltype = | length = 000 |
| SEQ ID NO: 43 SEQUENCE: 43 | moltype = | length = 000 |
| SEQ ID NO: 44 SEQUENCE: 44 | moltype = | length = 000 |
| SEQ ID NO: 45 SEQUENCE: 45 | moltype = | length = 000 |
| SEQ ID NO: 46 SEQUENCE: 46 | moltype = | length = 000 |
| SEQ ID NO: 47 SEQUENCE: 47 | moltype = | length = 000 |
| SEQ ID NO: 48 SEQUENCE: 48 | moltype = | length = 000 |
| SEQ ID NO: 49 SEQUENCE: 49 | moltype = | length = 000 |
| SEQ ID NO: 50 SEQUENCE: 50 | moltype = | length = 000 |
| SEQ ID NO: 51 SEQUENCE: 51 | moltype = | length = 000 |
| SEQ ID NO: 52 SEQUENCE: 52 | moltype = | length = 000 |
| SEQ ID NO: 53 SEQUENCE: 53 | moltype = | length = 000 |
| SEQ ID NO: 54 SEQUENCE: 54 | moltype = | length = 000 |
| SEQ ID NO: 55 SEQUENCE: 55 | moltype = | length = 000 |
| SEQ ID NO: 56 SEQUENCE: 56 | moltype = | length = 000 |
| SEQ ID NO: 57 SEQUENCE: 57 | moltype = | length = 000 |
| SEQ ID NO: 58 SEQUENCE: 58 | moltype = | length = 000 |
| SEQ ID NO: 59 SEQUENCE: 59 | moltype = | length = 000 |
| SEQ ID NO: 60 SEQUENCE: 60 | moltype = | length = 000 |
| SEQ ID NO: 61 SEQUENCE: 61 | moltype = | length = 000 |

| | | |
|---|---|---|
| SEQ ID NO: 62 SEQUENCE: 62 000 | moltype = | length = |
| SEQ ID NO: 63 SEQUENCE: 63 000 | moltype = | length = |
| SEQ ID NO: 64 SEQUENCE: 64 000 | moltype = | length = |
| SEQ ID NO: 65 SEQUENCE: 65 000 | moltype = | length = |
| SEQ ID NO: 66 SEQUENCE: 66 000 | moltype = | length = |
| SEQ ID NO: 67 SEQUENCE: 67 000 | moltype = | length = |
| SEQ ID NO: 68 SEQUENCE: 68 000 | moltype = | length = |
| SEQ ID NO: 69 SEQUENCE: 69 000 | moltype = | length = |
| SEQ ID NO: 70 SEQUENCE: 70 000 | moltype = | length = |
| SEQ ID NO: 71 SEQUENCE: 71 000 | moltype = | length = |
| SEQ ID NO: 72 SEQUENCE: 72 000 | moltype = | length = |
| SEQ ID NO: 73 SEQUENCE: 73 000 | moltype = | length = |
| SEQ ID NO: 74 SEQUENCE: 74 000 | moltype = | length = |
| SEQ ID NO: 75 SEQUENCE: 75 000 | moltype = | length = |
| SEQ ID NO: 76 SEQUENCE: 76 000 | moltype = | length = |
| SEQ ID NO: 77 SEQUENCE: 77 000 | moltype = | length = |
| SEQ ID NO: 78 SEQUENCE: 78 000 | moltype = | length = |
| SEQ ID NO: 79 SEQUENCE: 79 000 | moltype = | length = |
| SEQ ID NO: 80 SEQUENCE: 80 000 | moltype = | length = |
| SEQ ID NO: 81 SEQUENCE: 81 | moltype = | length = |

```
000

SEQ ID NO: 82          moltype =    length =
SEQUENCE: 82
000

SEQ ID NO: 83          moltype =    length =
SEQUENCE: 83
000

SEQ ID NO: 84          moltype =    length =
SEQUENCE: 84
000

SEQ ID NO: 85          moltype =    length =
SEQUENCE: 85
000

SEQ ID NO: 86          moltype =    length =
SEQUENCE: 86
000

SEQ ID NO: 87          moltype =    length =
SEQUENCE: 87
000

SEQ ID NO: 88          moltype =    length =
SEQUENCE: 88
000

SEQ ID NO: 89          moltype =    length =
SEQUENCE: 89
000

SEQ ID NO: 90          moltype =    length =
SEQUENCE: 90
000

SEQ ID NO: 91          moltype =    length =
SEQUENCE: 91
000

SEQ ID NO: 92          moltype =    length =
SEQUENCE: 92
000

SEQ ID NO: 93          moltype =    length =
SEQUENCE: 93
000

SEQ ID NO: 94          moltype =    length =
SEQUENCE: 94
000

SEQ ID NO: 95          moltype =    length =
SEQUENCE: 95
000

SEQ ID NO: 96          moltype =    length =
SEQUENCE: 96
000

SEQ ID NO: 97          moltype =    length =
SEQUENCE: 97
000

SEQ ID NO: 98          moltype =    length =
SEQUENCE: 98
000

SEQ ID NO: 99          moltype =    length =
SEQUENCE: 99
000

SEQ ID NO: 100         moltype = AA  length = 7
FEATURE                Location/Qualifiers
REGION                 1..7
                       note = Description of Artificial Sequence: Syntheticpeptide
source                 1..7
```

```
                        mol_type = protein
                        organism = synthetic construct
SEQUENCE: 100
GGSISGY                                                              7

SEQ ID NO: 101          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 101
GGSISGYYWS                                                           10

SEQ ID NO: 102          moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 102
GYYWS                                                                5

SEQ ID NO: 103          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 103
SGYYWS                                                               6

SEQ ID NO: 104          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 104
GGSISGYY                                                             8

SEQ ID NO: 105          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 105
GGSISGY                                                              7

SEQ ID NO: 106          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 106
GGSISGYYWS                                                           10

SEQ ID NO: 107          moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 107
GYYWS                                                                5

SEQ ID NO: 108          moltype = AA  length = 6
FEATURE                 Location/Qualifiers
REGION                  1..6
                        note = Description of Artificial Sequence: Syntheticpeptide
```

```
source                  1..6
                        mol_type = protein
                        organism = synthetic construct
SEQUENCE: 108
SGYYWS                                                                    6

SEQ ID NO: 109          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 109
GGSISGYY                                                                  8

SEQ ID NO: 110          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 110
GFNFDDY                                                                   7

SEQ ID NO: 111          moltype = AA   length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 111
GFNFDDYAMH                                                               10

SEQ ID NO: 112          moltype = AA   length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 112
DYAMH                                                                     5

SEQ ID NO: 113          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 113
DDYAMH                                                                    6

SEQ ID NO: 114          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 114
GFNFDDYA                                                                  8

SEQ ID NO: 115          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 115
GFNFDDY                                                                   7

SEQ ID NO: 116          moltype = AA   length = 10
FEATURE                 Location/Qualifiers
REGION                  1..10
```

```
                    note = Description of Artificial Sequence: Syntheticpeptide
source              1..10
                    mol_type = protein
                    organism = synthetic construct
SEQUENCE: 116
GFNFDDYAMH                                                                    10

SEQ ID NO: 117      moltype = AA  length = 5
FEATURE             Location/Qualifiers
REGION              1..5
                    note = Description of Artificial Sequence: Syntheticpeptide
source              1..5
                    mol_type = protein
                    organism = synthetic construct
SEQUENCE: 117
DYAMH                                                                          5

SEQ ID NO: 118      moltype = AA  length = 6
FEATURE             Location/Qualifiers
REGION              1..6
                    note = Description of Artificial Sequence: Syntheticpeptide
source              1..6
                    mol_type = protein
                    organism = synthetic construct
SEQUENCE: 118
DDYAMH                                                                         6

SEQ ID NO: 119      moltype = AA  length = 8
FEATURE             Location/Qualifiers
REGION              1..8
                    note = Description of Artificial Sequence: Syntheticpeptide
source              1..8
                    mol_type = protein
                    organism = synthetic construct
SEQUENCE: 119
GFNFDDYA                                                                       8

SEQ ID NO: 120      moltype = AA  length = 7
FEATURE             Location/Qualifiers
REGION              1..7
                    note = Description of Artificial Sequence: Syntheticpeptide
source              1..7
                    mol_type = protein
                    organism = synthetic construct
SEQUENCE: 120
GGSISGY                                                                        7

SEQ ID NO: 121      moltype = AA  length = 10
FEATURE             Location/Qualifiers
REGION              1..10
                    note = Description of Artificial Sequence: Syntheticpeptide
source              1..10
                    mol_type = protein
                    organism = synthetic construct
SEQUENCE: 121
GGSISGYYWS                                                                    10

SEQ ID NO: 122      moltype = AA  length = 5
FEATURE             Location/Qualifiers
REGION              1..5
                    note = Description of Artificial Sequence: Syntheticpeptide
source              1..5
                    mol_type = protein
                    organism = synthetic construct
SEQUENCE: 122
GYYWS                                                                          5

SEQ ID NO: 123      moltype = AA  length = 6
FEATURE             Location/Qualifiers
REGION              1..6
                    note = Description of Artificial Sequence: Syntheticpeptide
source              1..6
                    mol_type = protein
                    organism = synthetic construct
SEQUENCE: 123
SGYYWS                                                                         6

SEQ ID NO: 124      moltype = AA  length = 8
FEATURE             Location/Qualifiers
```

```
REGION                   1..8
                         note = Description of Artificial Sequence: Syntheticpeptide
source                   1..8
                         mol_type = protein
                         organism = synthetic construct
SEQUENCE: 124
GGSISGYY                                                                    8

SEQ ID NO: 125           moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 125
GGSISGY                                                                     7

SEQ ID NO: 126           moltype = AA  length = 10
FEATURE                  Location/Qualifiers
REGION                   1..10
                         note = Description of Artificial Sequence: Syntheticpeptide
source                   1..10
                         mol_type = protein
                         organism = synthetic construct
SEQUENCE: 126
GGSISGYYWS                                                                 10

SEQ ID NO: 127           moltype = AA  length = 5
FEATURE                  Location/Qualifiers
REGION                   1..5
                         note = Description of Artificial Sequence: Syntheticpeptide
source                   1..5
                         mol_type = protein
                         organism = synthetic construct
SEQUENCE: 127
GYYWS                                                                       5

SEQ ID NO: 128           moltype = AA  length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 128
SGYYWS                                                                      6

SEQ ID NO: 129           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 129
GGSISGYY                                                                    8

SEQ ID NO: 130           moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 130
GFPFSSY                                                                     7

SEQ ID NO: 131           moltype = AA  length = 10
FEATURE                  Location/Qualifiers
REGION                   1..10
                         note = Description of Artificial Sequence: Syntheticpeptide
source                   1..10
                         mol_type = protein
                         organism = synthetic construct
SEQUENCE: 131
GFPFSSYGMH                                                                 10

SEQ ID NO: 132           moltype = AA  length = 5
```

```
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 132
SYGMH                                                                           5

SEQ ID NO: 133          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 133
SSYGMH                                                                          6

SEQ ID NO: 134          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 134
GFPFSSYG                                                                        8

SEQ ID NO: 135          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 135
GFPFSSY                                                                         7

SEQ ID NO: 136          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 136
GFPFSSYGMH                                                                     10

SEQ ID NO: 137          moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 137
SYGMH                                                                           5

SEQ ID NO: 138          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 138
SSYGMH                                                                          6

SEQ ID NO: 139          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 139
GFPFSSYG                                                                        8
```

```
SEQ ID NO: 140            moltype = AA   length = 5
FEATURE                   Location/Qualifiers
REGION                    1..5
                          note = Description of Artificial Sequence: Syntheticpeptide
source                    1..5
                          mol_type = protein
                          organism = synthetic construct
SEQUENCE: 140
FYSGY                                                                             5

SEQ ID NO: 141            moltype = AA   length = 9
FEATURE                   Location/Qualifiers
REGION                    1..9
                          note = Description of Artificial Sequence: Syntheticpeptide
source                    1..9
                          mol_type = protein
                          organism = synthetic construct
SEQUENCE: 141
YIFYSGYTK                                                                         9

SEQ ID NO: 142            moltype = AA   length = 16
FEATURE                   Location/Qualifiers
REGION                    1..16
                          note = Description of Artificial Sequence: Syntheticpeptide
source                    1..16
                          mol_type = protein
                          organism = synthetic construct
SEQUENCE: 142
YIFYSGYTKY NPSLKS                                                                 16

SEQ ID NO: 143            moltype = AA   length = 12
FEATURE                   Location/Qualifiers
REGION                    1..12
                          note = Description of Artificial Sequence: Syntheticpeptide
source                    1..12
                          mol_type = protein
                          organism = synthetic construct
SEQUENCE: 143
WIGYIFYSGY TK                                                                     12

SEQ ID NO: 144            moltype = AA   length = 7
FEATURE                   Location/Qualifiers
REGION                    1..7
                          note = Description of Artificial Sequence: Syntheticpeptide
source                    1..7
                          mol_type = protein
                          organism = synthetic construct
SEQUENCE: 144
IFYSGYT                                                                           7

SEQ ID NO: 145            moltype = AA   length = 5
FEATURE                   Location/Qualifiers
REGION                    1..5
                          note = Description of Artificial Sequence: Syntheticpeptide
source                    1..5
                          mol_type = protein
                          organism = synthetic construct
SEQUENCE: 145
FYSGY                                                                             5

SEQ ID NO: 146            moltype = AA   length = 9
FEATURE                   Location/Qualifiers
REGION                    1..9
                          note = Description of Artificial Sequence: Syntheticpeptide
source                    1..9
                          mol_type = protein
                          organism = synthetic construct
SEQUENCE: 146
YIFYSGYTK                                                                         9

SEQ ID NO: 147            moltype = AA   length = 16
FEATURE                   Location/Qualifiers
REGION                    1..16
                          note = Description of Artificial Sequence: Syntheticpeptide
source                    1..16
                          mol_type = protein
                          organism = synthetic construct
SEQUENCE: 147
YIFYSGYTKY NPSLKS                                                                 16
```

```
SEQ ID NO: 148          moltype = AA   length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 148
WIGYIFYSGY TK                                                           12

SEQ ID NO: 149          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 149
IFYSGYT                                                                 7

SEQ ID NO: 150          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 150
SWRSGN                                                                  6

SEQ ID NO: 151          moltype = AA   length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 151
GISWRSGNIG                                                              10

SEQ ID NO: 152          moltype = AA   length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 152
GISWRSGNIG YAGSVKG                                                      17

SEQ ID NO: 153          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 153
WVSGISWRSG NIG                                                          13

SEQ ID NO: 154          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 154
ISWRSGNI                                                                8

SEQ ID NO: 155          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 155
```

```
SWRSGN                                                                              6

SEQ ID NO: 156          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 156
GISWRSGNIG                                                                         10

SEQ ID NO: 157          moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 157
GISWRSGNIG YADSVKG                                                                 17

SEQ ID NO: 158          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 158
WVSGISWRSG NIG                                                                     13

SEQ ID NO: 159          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 159
ISWRSGNI                                                                            8

SEQ ID NO: 160          moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 160
FYSGY                                                                               5

SEQ ID NO: 161          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 161
YIFYSGYTK                                                                           9

SEQ ID NO: 162          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 162
YIFYSGYTKY NPSLKS                                                                  16

SEQ ID NO: 163          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
```

```
SEQUENCE: 163
WIGYIFYSGY TK                                                          12

SEQ ID NO: 164          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 164
IFYSGYT                                                                7

SEQ ID NO: 165          moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 165
FYSGY                                                                  5

SEQ ID NO: 166          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 166
YIFYSGYTK                                                              9

SEQ ID NO: 167          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 167
YIFYSGYTKY NPSLKS                                                      16

SEQ ID NO: 168          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 168
WIGYIFYSGY TK                                                          12

SEQ ID NO: 169          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 169
IFYSGYT                                                                7

SEQ ID NO: 170          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 170
WFDGNN                                                                 6

SEQ ID NO: 171          moltype = AA  length = 10
FEATURE                 Location/Qualifiers
REGION                  1..10
                        note = Description of Artificial Sequence: Syntheticpeptide
source                  1..10
                        mol_type = protein
```

```
                        organism = synthetic construct
SEQUENCE: 171
FIWFDGNNKD                                                                       10

SEQ ID NO: 172          moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 172
FIWFDGNNKD YADSVKG                                                               17

SEQ ID NO: 173          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 173
WVTFIWFDGN NKD                                                                   13

SEQ ID NO: 174          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 174
IWFDGNNK                                                                          8

SEQ ID NO: 175          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 175
WFDGNN                                                                            6

SEQ ID NO: 176          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 176
FIWFDGNNKD                                                                       10

SEQ ID NO: 177          moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 177
FIWFDGNNKD YADSVKG                                                               17

SEQ ID NO: 178          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 178
WVTFIWFDGN NKD                                                                   13

SEQ ID NO: 179          moltype = AA  length = 8
FEATURE                 Location/Qualifiers
REGION                  1..8
                        note = Description of Artificial Sequence: Syntheticpeptide
source                  1..8
```

```
                        mol_type = protein
                        organism = synthetic construct
SEQUENCE: 179
IWFDGNNK                                                                        8

SEQ ID NO: 180          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 180
DRWDFDY                                                                         7

SEQ ID NO: 181          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 181
DRWDFDY                                                                         7

SEQ ID NO: 182          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 182
DRWDFDY                                                                         7

SEQ ID NO: 183          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 183
ARDRWDFD                                                                        8

SEQ ID NO: 184          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 184
ARDRWDFDY                                                                       9

SEQ ID NO: 185          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 185
DRWDFDY                                                                         7

SEQ ID NO: 186          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 186
DRWDFDY                                                                         7

SEQ ID NO: 187          moltype = AA  length = 7
FEATURE                 Location/Qualifiers
REGION                  1..7
                        note = Description of Artificial Sequence: Syntheticpeptide
```

```
source                    1..7
                          mol_type = protein
                          organism = synthetic construct
SEQUENCE: 187
DRWDFDY                                                                  7

SEQ ID NO: 188            moltype = AA   length = 8
FEATURE                   Location/Qualifiers
REGION                    1..8
                          note = Description of Artificial Sequence: Syntheticpeptide
source                    1..8
                          mol_type = protein
                          organism = synthetic construct
SEQUENCE: 188
ARDRWDFD                                                                 8

SEQ ID NO: 189            moltype = AA   length = 9
FEATURE                   Location/Qualifiers
REGION                    1..9
                          note = Description of Artificial Sequence: Syntheticpeptide
source                    1..9
                          mol_type = protein
                          organism = synthetic construct
SEQUENCE: 189
ARDRWDFDY                                                                9

SEQ ID NO: 190            moltype = AA   length = 15
FEATURE                   Location/Qualifiers
REGION                    1..15
                          note = Description of Artificial Sequence: Syntheticpeptide
source                    1..15
                          mol_type = protein
                          organism = synthetic construct
SEQUENCE: 190
DKGIGFNWNY EGFDY                                                         15

SEQ ID NO: 191            moltype = AA   length = 15
FEATURE                   Location/Qualifiers
REGION                    1..15
                          note = Description of Artificial Sequence: Syntheticpeptide
source                    1..15
                          mol_type = protein
                          organism = synthetic construct
SEQUENCE: 191
DKGIGFNWNY EGFDY                                                         15

SEQ ID NO: 192            moltype = AA   length = 15
FEATURE                   Location/Qualifiers
REGION                    1..15
                          note = Description of Artificial Sequence: Syntheticpeptide
source                    1..15
                          mol_type = protein
                          organism = synthetic construct
SEQUENCE: 192
DKGIGFNWNY EGFDY                                                         15

SEQ ID NO: 193            moltype = AA   length = 16
FEATURE                   Location/Qualifiers
REGION                    1..16
                          note = Description of Artificial Sequence: Syntheticpeptide
source                    1..16
                          mol_type = protein
                          organism = synthetic construct
SEQUENCE: 193
AKDKGIGFNW NYEGFD                                                        16

SEQ ID NO: 194            moltype = AA   length = 17
FEATURE                   Location/Qualifiers
REGION                    1..17
                          note = Description of Artificial Sequence: Syntheticpeptide
source                    1..17
                          mol_type = protein
                          organism = synthetic construct
SEQUENCE: 194
AKDKGIGFNW NYEGFDY                                                       17

SEQ ID NO: 195            moltype = AA   length = 15
FEATURE                   Location/Qualifiers
REGION                    1..15
```

```
                        -continued note = Description of Artificial Sequence: Syntheticpeptide
source                  1..15
                        mol_type = protein
                        organism = synthetic construct
SEQUENCE: 195
DKGIGFNWNY EGFDY                                                            15

SEQ ID NO: 196          moltype = AA  length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 196
DKGIGFNWNY EGFDY                                                            15

SEQ ID NO: 197          moltype = AA  length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 197
DKGIGFNWNY EGFDY                                                            15

SEQ ID NO: 198          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 198
AKDKGIGFNW NYEGFD                                                           16

SEQ ID NO: 199          moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 199
AKDKGIGFNW NYEGFDY                                                          17

SEQ ID NO: 200          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 200
DRWDFDY                                                                      7

SEQ ID NO: 201          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 201
DRWDFDY                                                                      7

SEQ ID NO: 202          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 202
DRWDFDY                                                                      7

SEQ ID NO: 203          moltype = AA  length = 8
FEATURE                 Location/Qualifiers
```

```
REGION                  1..8
                        note = Description of Artificial Sequence: Syntheticpeptide
source                  1..8
                        mol_type = protein
                        organism = synthetic construct
SEQUENCE: 203
ARDRWDFD                                                                        8

SEQ ID NO: 204          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 204
ARDRWDFDY                                                                       9

SEQ ID NO: 205          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 205
DRWDFDY                                                                         7

SEQ ID NO: 206          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 206
DRWDFDY                                                                         7

SEQ ID NO: 207          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 207
DRWDFDY                                                                         7

SEQ ID NO: 208          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 208
ARDRWDFD                                                                        8

SEQ ID NO: 209          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 209
ARDRWDFDY                                                                       9

SEQ ID NO: 210          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 210
NGVYYGSGAY VDY                                                                  13

SEQ ID NO: 211          moltype = AA  length = 13
```

```
FEATURE              Location/Qualifiers
REGION               1..13
                     note = Description of Artificial Sequence: Syntheticpeptide
source               1..13
                     mol_type = protein
                     organism = synthetic construct
SEQUENCE: 211
NGVYYGSGAY VDY                                                              13

SEQ ID NO: 212       moltype = AA  length = 13
FEATURE              Location/Qualifiers
REGION               1..13
                     note = Description of Artificial Sequence: Syntheticpeptide
source               1..13
                     mol_type = protein
                     organism = synthetic construct
SEQUENCE: 212
NGVYYGSGAY VDY                                                              13

SEQ ID NO: 213       moltype = AA  length = 14
FEATURE              Location/Qualifiers
REGION               1..14
                     note = Description of Artificial Sequence: Syntheticpeptide
source               1..14
                     mol_type = protein
                     organism = synthetic construct
SEQUENCE: 213
ARNGVYYGSG AYVD                                                             14

SEQ ID NO: 214       moltype = AA  length = 15
FEATURE              Location/Qualifiers
REGION               1..15
                     note = Description of Artificial Sequence: Syntheticpeptide
source               1..15
                     mol_type = protein
                     organism = synthetic construct
SEQUENCE: 214
ARNGVYYGSG AYVDY                                                            15

SEQ ID NO: 215       moltype = AA  length = 13
FEATURE              Location/Qualifiers
REGION               1..13
                     note = Description of Artificial Sequence: Syntheticpeptide
source               1..13
                     mol_type = protein
                     organism = synthetic construct
SEQUENCE: 215
NGVYYGSGAY VDY                                                              13

SEQ ID NO: 216       moltype = AA  length = 13
FEATURE              Location/Qualifiers
REGION               1..13
                     note = Description of Artificial Sequence: Syntheticpeptide
source               1..13
                     mol_type = protein
                     organism = synthetic construct
SEQUENCE: 216
NGVYYGSGAY VDY                                                              13

SEQ ID NO: 217       moltype = AA  length = 13
FEATURE              Location/Qualifiers
REGION               1..13
                     note = Description of Artificial Sequence: Syntheticpeptide
source               1..13
                     mol_type = protein
                     organism = synthetic construct
SEQUENCE: 217
NGVYYGSGAY VDY                                                              13

SEQ ID NO: 218       moltype = AA  length = 14
FEATURE              Location/Qualifiers
REGION               1..14
                     note = Description of Artificial Sequence: Syntheticpeptide
source               1..14
                     mol_type = protein
                     organism = synthetic construct
SEQUENCE: 218
ARNGVYYGSG AYVD                                                             14
```

-continued

```
SEQ ID NO: 219          moltype = AA   length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 219
ARNGVYYGSG AYVDY                                                          15

SEQ ID NO: 220          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 220
GFTFSIY                                                                    7

SEQ ID NO: 221          moltype = AA   length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 221
GFTFSIYGMH                                                                10

SEQ ID NO: 222          moltype = AA   length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 222
IYGMH                                                                      5

SEQ ID NO: 223          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 223
SIYGMH                                                                     6

SEQ ID NO: 224          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 224
GFTFSIYG                                                                   8

SEQ ID NO: 225          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 225
GFAFNIY                                                                    7

SEQ ID NO: 226          moltype = AA   length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 226
GFAFNIYGMH                                                                10
```

```
SEQ ID NO: 227           moltype = AA   length = 5
FEATURE                  Location/Qualifiers
REGION                   1..5
                         note = Description of Artificial Sequence: Syntheticpeptide
source                   1..5
                         mol_type = protein
                         organism = synthetic construct
SEQUENCE: 227
IYGMH                                                                    5

SEQ ID NO: 228           moltype = AA   length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 228
NIYGMH                                                                   6

SEQ ID NO: 229           moltype = AA   length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 229
GFAFNIYG                                                                 8

SEQ ID NO: 230           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 230
GFSLSTSGV                                                                9

SEQ ID NO: 231           moltype = AA   length = 12
FEATURE                  Location/Qualifiers
REGION                   1..12
                         note = Description of Artificial Sequence: Syntheticpeptide
source                   1..12
                         mol_type = protein
                         organism = synthetic construct
SEQUENCE: 231
GFSLSTSGVG VG                                                           12

SEQ ID NO: 232           moltype = AA   length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 232
TSGVGVG                                                                  7

SEQ ID NO: 233           moltype = AA   length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 233
STSGVGVG                                                                 8

SEQ ID NO: 234           moltype = AA   length = 10
FEATURE                  Location/Qualifiers
REGION                   1..10
                         note = Description of Artificial Sequence: Syntheticpeptide
source                   1..10
                         mol_type = protein
                         organism = synthetic construct
SEQUENCE: 234
```

```
GFSLSTSGVG                                                                   10

SEQ ID NO: 235         moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 235
WYDGSN                                                                       6

SEQ ID NO: 236         moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 236
VIWYDGSNKY                                                                   10

SEQ ID NO: 237         moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 237
VIWYDGSNKY YVDSVKG                                                           17

SEQ ID NO: 238         moltype = AA  length = 13
FEATURE                Location/Qualifiers
REGION                 1..13
                       note = Description of Artificial Sequence: Syntheticpeptide
source                 1..13
                       mol_type = protein
                       organism = synthetic construct
SEQUENCE: 238
WVAVIWYDGS NKY                                                               13

SEQ ID NO: 239         moltype = AA  length = 8
FEATURE                Location/Qualifiers
REGION                 1..8
                       note = Description of Artificial Sequence: Syntheticpeptide
source                 1..8
                       mol_type = protein
                       organism = synthetic construct
SEQUENCE: 239
IWYDGSNK                                                                     8

SEQ ID NO: 240         moltype = AA  length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 240
SYDGSN                                                                       6

SEQ ID NO: 241         moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 241
VISYDGSNKV                                                                   10

SEQ ID NO: 242         moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
```

```
-continued

SEQUENCE: 242
VISYDGSNKV YADSVKG                                                          17

SEQ ID NO: 243          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 243
WVAVISYDGS NKV                                                              13

SEQ ID NO: 244          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 244
ISYDGSNK                                                                    8

SEQ ID NO: 245          moltype = AA   length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 245
YWNDD                                                                       5

SEQ ID NO: 246          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 246
LIYWNDDKR                                                                   9

SEQ ID NO: 247          moltype = AA   length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 247
LIYWNDDKRY SPSLKS                                                           16

SEQ ID NO: 248          moltype = AA   length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 248
WLALIYWNDD KR                                                               12

SEQ ID NO: 249          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 249
IYWNDDK                                                                     7

SEQ ID NO: 250          moltype = AA   length = 7
FEATURE                 Location/Qualifiers
REGION                  1..7
                        note = Description of Artificial Sequence: Syntheticpeptide
source                  1..7
                        mol_type = protein
```

```
                        organism = synthetic construct
SEQUENCE: 250
EGNLFDY                                                                            7

SEQ ID NO: 251          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 251
EGNLFDY                                                                            7

SEQ ID NO: 252          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 252
EGNLFDY                                                                            7

SEQ ID NO: 253          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 253
AREGNLFD                                                                           8

SEQ ID NO: 254          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 254
AREGNLFDY                                                                          9

SEQ ID NO: 255          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 255
SGGITMVRGV FDY                                                                    13

SEQ ID NO: 256          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 256
SGGITMVRGV FDY                                                                    13

SEQ ID NO: 257          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 257
SGGITMVRGV FDY                                                                    13

SEQ ID NO: 258          moltype = AA   length = 14
FEATURE                 Location/Qualifiers
REGION                  1..14
                        note = Description of Artificial Sequence: Syntheticpeptide
source                  1..14
```

```
                                mol_type = protein
                                organism = synthetic construct
SEQUENCE: 258
AKSGGITMVR GVFD                                                          14

SEQ ID NO: 259                  moltype = AA  length = 15
FEATURE                         Location/Qualifiers
REGION                          1..15
                                note = Description of Artificial Sequence: Syntheticpeptide
source                          1..15
                                mol_type = protein
                                organism = synthetic construct
SEQUENCE: 259
AKSGGITMVR GVFDY                                                         15

SEQ ID NO: 260                  moltype = AA  length = 15
FEATURE                         Location/Qualifiers
REGION                          1..15
                                note = Description of Artificial Sequence: Syntheticpeptide
source                          1..15
                                mol_type = protein
                                organism = synthetic construct
SEQUENCE: 260
RRTTTVTIYY YYMDV                                                         15

SEQ ID NO: 261                  moltype = AA  length = 15
FEATURE                         Location/Qualifiers
REGION                          1..15
                                note = Description of Artificial Sequence: Syntheticpeptide
source                          1..15
                                mol_type = protein
                                organism = synthetic construct
SEQUENCE: 261
RRTTTVTIYY YYMDV                                                         15

SEQ ID NO: 262                  moltype = AA  length = 15
FEATURE                         Location/Qualifiers
REGION                          1..15
                                note = Description of Artificial Sequence: Syntheticpeptide
source                          1..15
                                mol_type = protein
                                organism = synthetic construct
SEQUENCE: 262
RRTTTVTIYY YYMDV                                                         15

SEQ ID NO: 263                  moltype = AA  length = 16
FEATURE                         Location/Qualifiers
REGION                          1..16
                                note = Description of Artificial Sequence: Syntheticpeptide
source                          1..16
                                mol_type = protein
                                organism = synthetic construct
SEQUENCE: 263
AHRRTTTVTI YYYYMD                                                        16

SEQ ID NO: 264                  moltype = AA  length = 17
FEATURE                         Location/Qualifiers
REGION                          1..17
                                note = Description of Artificial Sequence: Syntheticpeptide
source                          1..17
                                mol_type = protein
                                organism = synthetic construct
SEQUENCE: 264
AHRRTTTVTI YYYYMDV                                                       17

SEQ ID NO: 265                  moltype =     length =
SEQUENCE: 265
000

SEQ ID NO: 266                  moltype =     length =
SEQUENCE: 266
000

SEQ ID NO: 267                  moltype =     length =
SEQUENCE: 267
000

SEQ ID NO: 268                  moltype =     length =
SEQUENCE: 268
```

000

SEQ ID NO: 269         moltype =    length =
SEQUENCE: 269
000

SEQ ID NO: 270         moltype =    length =
SEQUENCE: 270
000

SEQ ID NO: 271         moltype =    length =
SEQUENCE: 271
000

SEQ ID NO: 272         moltype =    length =
SEQUENCE: 272
000

SEQ ID NO: 273         moltype =    length =
SEQUENCE: 273
000

SEQ ID NO: 274         moltype =    length =
SEQUENCE: 274
000

SEQ ID NO: 275         moltype =    length =
SEQUENCE: 275
000

SEQ ID NO: 276         moltype =    length =
SEQUENCE: 276
000

SEQ ID NO: 277         moltype =    length =
SEQUENCE: 277
000

SEQ ID NO: 278         moltype =    length =
SEQUENCE: 278
000

SEQ ID NO: 279         moltype =    length =
SEQUENCE: 279
000

SEQ ID NO: 280         moltype =    length =
SEQUENCE: 280
000

SEQ ID NO: 281         moltype =    length =
SEQUENCE: 281
000

SEQ ID NO: 282         moltype =    length =
SEQUENCE: 282
000

SEQ ID NO: 283         moltype =    length =
SEQUENCE: 283
000

SEQ ID NO: 284         moltype =    length =
SEQUENCE: 284
000

SEQ ID NO: 285         moltype =    length =
SEQUENCE: 285
000

SEQ ID NO: 286         moltype =    length =
SEQUENCE: 286
000

SEQ ID NO: 287         moltype =    length =
SEQUENCE: 287
000

SEQ ID NO: 288         moltype =    length =

| | | |
|---|---|---|
| SEQUENCE: 288 000 | | |
| SEQ ID NO: 289 SEQUENCE: 289 000 | moltype = | length = |
| SEQ ID NO: 290 SEQUENCE: 290 000 | moltype = | length = |
| SEQ ID NO: 291 SEQUENCE: 291 000 | moltype = | length = |
| SEQ ID NO: 292 SEQUENCE: 292 000 | moltype = | length = |
| SEQ ID NO: 293 SEQUENCE: 293 000 | moltype = | length = |
| SEQ ID NO: 294 SEQUENCE: 294 000 | moltype = | length = |
| SEQ ID NO: 295 SEQUENCE: 295 000 | moltype = | length = |
| SEQ ID NO: 296 SEQUENCE: 296 000 | moltype = | length = |
| SEQ ID NO: 297 SEQUENCE: 297 000 | moltype = | length = |
| SEQ ID NO: 298 SEQUENCE: 298 000 | moltype = | length = |
| SEQ ID NO: 299 SEQUENCE: 299 000 | moltype = | length = |
| SEQ ID NO: 300 FEATURE REGION  source  SEQUENCE: 300 RASQGIRNNL G | moltype = AA   length = 11 Location/Qualifiers 1..11 note = Description of Artificial Sequence: Syntheticpeptide 1..11 mol_type = protein organism = synthetic construct | 11 |
| SEQ ID NO: 301 FEATURE REGION  source  SEQUENCE: 301 RASQGIRNNL G | moltype = AA   length = 11 Location/Qualifiers 1..11 note = Description of Artificial Sequence: Syntheticpeptide 1..11 mol_type = protein organism = synthetic construct | 11 |
| SEQ ID NO: 302 FEATURE REGION  source  SEQUENCE: 302 RASQGIRNNL G | moltype = AA   length = 11 Location/Qualifiers 1..11 note = Description of Artificial Sequence: Syntheticpeptide 1..11 mol_type = protein organism = synthetic construct | 11 |
| SEQ ID NO: 303 FEATURE | moltype = AA   length = 7 Location/Qualifiers | |

-continued

```
REGION                  1..7
                        note = Description of Artificial Sequence: Syntheticpeptide
source                  1..7
                        mol_type = protein
                        organism = synthetic construct
SEQUENCE: 303
RNNLGWY                                                                        7

SEQ ID NO: 304          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 304
QGIRNN                                                                         6

SEQ ID NO: 305          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 305
RASQGIRNNL G                                                                  11

SEQ ID NO: 306          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 306
RASQGIRNNL G                                                                  11

SEQ ID NO: 307          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 307
RASQGIRNNL G                                                                  11

SEQ ID NO: 308          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 308
RNNLGWY                                                                        7

SEQ ID NO: 309          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 309
QGIRNN                                                                         6

SEQ ID NO: 310          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 310
RASQGISNHL A                                                                  11

SEQ ID NO: 311          moltype = AA  length = 11
```

```
                         -continued

FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 311
RASQGISNHL A                                                                  11

SEQ ID NO: 312           moltype = AA  length = 11
FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 312
RASQGISNHL A                                                                  11

SEQ ID NO: 313           moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 313
SNHLAWF                                                                        7

SEQ ID NO: 314           moltype = AA  length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 314
QGISNH                                                                         6

SEQ ID NO: 315           moltype = AA  length = 11
FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 315
RASQGISNHL A                                                                  11

SEQ ID NO: 316           moltype = AA  length = 11
FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 316
RASQGISNHL A                                                                  11

SEQ ID NO: 317           moltype = AA  length = 11
FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 317
RASQGISNHL A                                                                  11

SEQ ID NO: 318           moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 318
SNHLAWF                                                                        7
```

| | |
|---|---|
| SEQ ID NO: 319<br>FEATURE<br>REGION<br><br>source | moltype = AA  length = 6<br>Location/Qualifiers<br>1..6<br>note = Description of Artificial Sequence: Syntheticpeptide<br>1..6<br>mol_type = protein<br>organism = synthetic construct |
| SEQUENCE: 319<br>QGISNH | 6 |
| SEQ ID NO: 320<br>FEATURE<br>REGION<br><br>source | moltype = AA  length = 16<br>Location/Qualifiers<br>1..16<br>note = Description of Artificial Sequence: Syntheticpeptide<br>1..16<br>mol_type = protein<br>organism = synthetic construct |
| SEQUENCE: 320<br>RSSQSLLHSN GYNYLD | 16 |
| SEQ ID NO: 321<br>FEATURE<br>REGION<br><br>source | moltype = AA  length = 16<br>Location/Qualifiers<br>1..16<br>note = Description of Artificial Sequence: Syntheticpeptide<br>1..16<br>mol_type = protein<br>organism = synthetic construct |
| SEQUENCE: 321<br>RSSQSLLHSN GYNYLD | 16 |
| SEQ ID NO: 322<br>FEATURE<br>REGION<br><br>source | moltype = AA  length = 16<br>Location/Qualifiers<br>1..16<br>note = Description of Artificial Sequence: Syntheticpeptide<br>1..16<br>mol_type = protein<br>organism = synthetic construct |
| SEQUENCE: 322<br>RSSQSLLHSN GYNYLD | 16 |
| SEQ ID NO: 323<br>FEATURE<br>REGION<br><br>source | moltype = AA  length = 12<br>Location/Qualifiers<br>1..12<br>note = Description of Artificial Sequence: Syntheticpeptide<br>1..12<br>mol_type = protein<br>organism = synthetic construct |
| SEQUENCE: 323<br>LHSNGYNYLD WY | 12 |
| SEQ ID NO: 324<br>FEATURE<br>REGION<br><br>source | moltype = AA  length = 11<br>Location/Qualifiers<br>1..11<br>note = Description of Artificial Sequence: Syntheticpeptide<br>1..11<br>mol_type = protein<br>organism = synthetic construct |
| SEQUENCE: 324<br>QSLLHSNGYN Y | 11 |
| SEQ ID NO: 325<br>FEATURE<br>REGION<br><br>source | moltype = AA  length = 16<br>Location/Qualifiers<br>1..16<br>note = Description of Artificial Sequence: Syntheticpeptide<br>1..16<br>mol_type = protein<br>organism = synthetic construct |
| SEQUENCE: 325<br>RSSQSLLHSN GYNYLD | 16 |
| SEQ ID NO: 326<br>FEATURE<br>REGION<br><br>source | moltype = AA  length = 16<br>Location/Qualifiers<br>1..16<br>note = Description of Artificial Sequence: Syntheticpeptide<br>1..16<br>mol_type = protein<br>organism = synthetic construct |
| SEQUENCE: 326<br>RSSQSLLHSN GYNYLD | 16 |

```
SEQ ID NO: 327          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 327
RSSQSLLHSN GYNYLD                                                           16

SEQ ID NO: 328          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 328
LHSNGYNYLD WY                                                               12

SEQ ID NO: 329          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 329
QSLLHSNGYN Y                                                                11

SEQ ID NO: 330          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 330
RSSQSLLHSN GYNYLD                                                           16

SEQ ID NO: 331          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 331
RSSQSLLHSN GYNYLD                                                           16

SEQ ID NO: 332          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 332
RSSQSLLHSN GYNYLD                                                           16

SEQ ID NO: 333          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 333
LHSNGYNYLD WY                                                               12

SEQ ID NO: 334          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 334
```

QSLLHSNGYN Y                                                                                  11

SEQ ID NO: 335          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 335
RSSQSLLHSN GYNYLD                                                                             16

SEQ ID NO: 336          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 336
RSSQSLLHSN GYNYLD                                                                             16

SEQ ID NO: 337          moltype = AA  length = 16
FEATURE                 Location/Qualifiers
REGION                  1..16
                        note = Description of Artificial Sequence: Syntheticpeptide
source                  1..16
                        mol_type = protein
                        organism = synthetic construct
SEQUENCE: 337
RSSQSLLHSN GYNYLD                                                                             16

SEQ ID NO: 338          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 338
LHSNGYNYLD WY                                                                                 12

SEQ ID NO: 339          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 339
QSLLHSNGYN Y                                                                                  11

SEQ ID NO: 340          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 340
AESSLQS                                                                                        7

SEQ ID NO: 341          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 341
AESSLQS                                                                                        7

SEQ ID NO: 342          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct -continued

```
SEQUENCE: 342
AESSLQS                                                                 7

SEQ ID NO: 343          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 343
LLIYAESSLQ                                                              10

SEQ ID NO: 344          moltype =   length =
SEQUENCE: 344
000

SEQ ID NO: 345          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 345
AESSLQS                                                                 7

SEQ ID NO: 346          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 346
AESSLQS                                                                 7

SEQ ID NO: 347          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 347
AESSLQS                                                                 7

SEQ ID NO: 348          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 348
LLIYAESSLQ                                                              10

SEQ ID NO: 349          moltype =   length =
SEQUENCE: 349
000

SEQ ID NO: 350          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 350
AASSLQS                                                                 7

SEQ ID NO: 351          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 351
```

```
                                                           -continued

AASSLQS                                                                  7

SEQ ID NO: 352         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 352
AASSLQS                                                                  7

SEQ ID NO: 353         moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 353
SLIYAASSLQ                                                              10

SEQ ID NO: 354         moltype =     length =
SEQUENCE: 354
000

SEQ ID NO: 355         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 355
AASSLQS                                                                  7

SEQ ID NO: 356         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 356
AASSLQS                                                                  7

SEQ ID NO: 357         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 357
AASSLQS                                                                  7

SEQ ID NO: 358         moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 358
SLIYAASSLQ                                                              10

SEQ ID NO: 359         moltype =     length =
SEQUENCE: 359
000

SEQ ID NO: 360         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 360
LGSNRAS                                                                  7
```

```
SEQ ID NO: 361         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 361
LGSNRAS                                                                          7

SEQ ID NO: 362         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 362
LGSNRAS                                                                          7

SEQ ID NO: 363         moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 363
LLIYLGSNRA                                                                      10

SEQ ID NO: 364         moltype =     length =
SEQUENCE: 364
000

SEQ ID NO: 365         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 365
LGSNRAS                                                                          7

SEQ ID NO: 366         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 366
LGSNRAS                                                                          7

SEQ ID NO: 367         moltype = AA  length = 7
FEATURE                Location/Qualifiers
REGION                 1..7
                       note = Description of Artificial Sequence: Syntheticpeptide
source                 1..7
                       mol_type = protein
                       organism = synthetic construct
SEQUENCE: 367
LGSNRAS                                                                          7

SEQ ID NO: 368         moltype = AA  length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 368
LLIYLGSNRA                                                                      10

SEQ ID NO: 369         moltype =     length =
SEQUENCE: 369
000
```

| | | |
|---|---|---|
| SEQ ID NO: 370<br>FEATURE<br>REGION<br><br>source | moltype = AA  length = 7<br>Location/Qualifiers<br>1..7<br>note = Description of Artificial Sequence: Syntheticpeptide<br>1..7<br>mol_type = protein<br>organism = synthetic construct | |
| SEQUENCE: 370<br>LGSNRAS | | 7 |
| SEQ ID NO: 371<br>FEATURE<br>REGION<br><br>source | moltype = AA  length = 7<br>Location/Qualifiers<br>1..7<br>note = Description of Artificial Sequence: Syntheticpeptide<br>1..7<br>mol_type = protein<br>organism = synthetic construct | |
| SEQUENCE: 371<br>LGSNRAS | | 7 |
| SEQ ID NO: 372<br>FEATURE<br>REGION<br><br>source | moltype = AA  length = 7<br>Location/Qualifiers<br>1..7<br>note = Description of Artificial Sequence: Syntheticpeptide<br>1..7<br>mol_type = protein<br>organism = synthetic construct | |
| SEQUENCE: 372<br>LGSNRAS | | 7 |
| SEQ ID NO: 373<br>FEATURE<br>REGION<br><br>source | moltype = AA  length = 10<br>Location/Qualifiers<br>1..10<br>note = Description of Artificial Sequence: Syntheticpeptide<br>1..10<br>mol_type = protein<br>organism = synthetic construct | |
| SEQUENCE: 373<br>LLIYLGSNRA | | 10 |
| SEQ ID NO: 374<br>SEQUENCE: 374<br>000 | moltype =   length = | |
| SEQ ID NO: 375<br>FEATURE<br>REGION<br><br>source | moltype = AA  length = 7<br>Location/Qualifiers<br>1..7<br>note = Description of Artificial Sequence: Syntheticpeptide<br>1..7<br>mol_type = protein<br>organism = synthetic construct | |
| SEQUENCE: 375<br>LGSNRAS | | 7 |
| SEQ ID NO: 376<br>FEATURE<br>REGION<br><br>source | moltype = AA  length = 7<br>Location/Qualifiers<br>1..7<br>note = Description of Artificial Sequence: Syntheticpeptide<br>1..7<br>mol_type = protein<br>organism = synthetic construct | |
| SEQUENCE: 376<br>LGSNRAS | | 7 |
| SEQ ID NO: 377<br>FEATURE<br>REGION<br><br>source | moltype = AA  length = 7<br>Location/Qualifiers<br>1..7<br>note = Description of Artificial Sequence: Syntheticpeptide<br>1..7<br>mol_type = protein<br>organism = synthetic construct | |
| SEQUENCE: 377<br>LGSNRAS | | 7 |
| SEQ ID NO: 378<br>FEATURE<br>REGION<br><br>source | moltype = AA  length = 10<br>Location/Qualifiers<br>1..10<br>note = Description of Artificial Sequence: Syntheticpeptide<br>1..10 | |

```
SEQUENCE: 378
LLIYLGSNRA                                                                10

SEQ ID NO: 379          moltype =    length =
SEQUENCE: 379
000

SEQ ID NO: 380          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 380
LQDFNYPYT                                                                 9

SEQ ID NO: 381          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 381
LQDFNYPYT                                                                 9

SEQ ID NO: 382          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 382
LQDFNYPYT                                                                 9

SEQ ID NO: 383          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 383
LQDFNYPY                                                                  8

SEQ ID NO: 384          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 384
LQDFNYPYT                                                                 9

SEQ ID NO: 385          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 385
LQDFNYPYT                                                                 9

SEQ ID NO: 386          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 386
LQDFNYPYT                                                                 9
```

| | | |
|---|---|---|
| SEQ ID NO: 387<br>FEATURE<br>REGION<br>source | moltype = AA  length = 9<br>Location/Qualifiers<br>1..9<br>note = Description of Artificial Sequence: Syntheticpeptide<br>1..9<br>mol_type = protein<br>organism = synthetic construct | |
| SEQUENCE: 387<br>LQDFNYPYT | | 9 |
| SEQ ID NO: 388<br>FEATURE<br>REGION<br>source | moltype = AA  length = 8<br>Location/Qualifiers<br>1..8<br>note = Description of Artificial Sequence: Syntheticpeptide<br>1..8<br>mol_type = protein<br>organism = synthetic construct | |
| SEQUENCE: 388<br>LQDFNYPY | | 8 |
| SEQ ID NO: 389<br>FEATURE<br>REGION<br>source | moltype = AA  length = 9<br>Location/Qualifiers<br>1..9<br>note = Description of Artificial Sequence: Syntheticpeptide<br>1..9<br>mol_type = protein<br>organism = synthetic construct | |
| SEQUENCE: 389<br>LQDFNYPYT | | 9 |
| SEQ ID NO: 390<br>FEATURE<br>REGION<br>source | moltype = AA  length = 9<br>Location/Qualifiers<br>1..9<br>note = Description of Artificial Sequence: Syntheticpeptide<br>1..9<br>mol_type = protein<br>organism = synthetic construct | |
| SEQUENCE: 390<br>QQYVTYPLT | | 9 |
| SEQ ID NO: 391<br>FEATURE<br>REGION<br>source | moltype = AA  length = 9<br>Location/Qualifiers<br>1..9<br>note = Description of Artificial Sequence: Syntheticpeptide<br>1..9<br>mol_type = protein<br>organism = synthetic construct | |
| SEQUENCE: 391<br>QQYVTYPLT | | 9 |
| SEQ ID NO: 392<br>FEATURE<br>REGION<br>source | moltype = AA  length = 9<br>Location/Qualifiers<br>1..9<br>note = Description of Artificial Sequence: Syntheticpeptide<br>1..9<br>mol_type = protein<br>organism = synthetic construct | |
| SEQUENCE: 392<br>QQYVTYPLT | | 9 |
| SEQ ID NO: 393<br>FEATURE<br>REGION<br>source | moltype = AA  length = 8<br>Location/Qualifiers<br>1..8<br>note = Description of Artificial Sequence: Syntheticpeptide<br>1..8<br>mol_type = protein<br>organism = synthetic construct | |
| SEQUENCE: 393<br>QQYVTYPL | | 8 |
| SEQ ID NO: 394<br>FEATURE<br>REGION<br>source | moltype = AA  length = 9<br>Location/Qualifiers<br>1..9<br>note = Description of Artificial Sequence: Syntheticpeptide<br>1..9<br>mol_type = protein<br>organism = synthetic construct | |
| SEQUENCE: 394<br>QQYVTYPLT | | 9 |

```
SEQ ID NO: 395          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 395
QQYVTYPLT                                                                        9

SEQ ID NO: 396          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 396
QQYVTYPLT                                                                        9

SEQ ID NO: 397          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 397
QQYVTYPLT                                                                        9

SEQ ID NO: 398          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 398
QQYVTYPL                                                                         8

SEQ ID NO: 399          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 399
QQYVTYPLT                                                                        9

SEQ ID NO: 400          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 400
MQALQTPRT                                                                        9

SEQ ID NO: 401          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 401
MQALQTPRT                                                                        9

SEQ ID NO: 402          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 402
```

```
MQALQTPRT                                                                                    9

SEQ ID NO: 403         moltype = AA  length = 8
FEATURE                Location/Qualifiers
REGION                 1..8
                       note = Description of Artificial Sequence: Syntheticpeptide
source                 1..8
                       mol_type = protein
                       organism = synthetic construct
SEQUENCE: 403
MQALQTPR                                                                                     8

SEQ ID NO: 404         moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 404
MQALQTPRT                                                                                    9

SEQ ID NO: 405         moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 405
MQALQTPRT                                                                                    9

SEQ ID NO: 406         moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 406
MQALQTPRT                                                                                    9

SEQ ID NO: 407         moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 407
MQALQTPRT                                                                                    9

SEQ ID NO: 408         moltype = AA  length = 8
FEATURE                Location/Qualifiers
REGION                 1..8
                       note = Description of Artificial Sequence: Syntheticpeptide
source                 1..8
                       mol_type = protein
                       organism = synthetic construct
SEQUENCE: 408
MQALQTPR                                                                                     8

SEQ ID NO: 409         moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
SEQUENCE: 409
MQALQTPRT                                                                                    9

SEQ ID NO: 410         moltype = AA  length = 9
FEATURE                Location/Qualifiers
REGION                 1..9
                       note = Description of Artificial Sequence: Syntheticpeptide
source                 1..9
                       mol_type = protein
                       organism = synthetic construct
```

```
SEQUENCE: 410
MQALQTPRT                                                                  9

SEQ ID NO: 411        moltype = AA  length = 9
FEATURE               Location/Qualifiers
REGION                1..9
                      note = Description of Artificial Sequence: Syntheticpeptide
source                1..9
                      mol_type = protein
                      organism = synthetic construct
SEQUENCE: 411
MQALQTPRT                                                                  9

SEQ ID NO: 412        moltype = AA  length = 9
FEATURE               Location/Qualifiers
REGION                1..9
                      note = Description of Artificial Sequence: Syntheticpeptide
source                1..9
                      mol_type = protein
                      organism = synthetic construct
SEQUENCE: 412
MQALQTPRT                                                                  9

SEQ ID NO: 413        moltype = AA  length = 8
FEATURE               Location/Qualifiers
REGION                1..8
                      note = Description of Artificial Sequence: Syntheticpeptide
source                1..8
                      mol_type = protein
                      organism = synthetic construct
SEQUENCE: 413
MQALQTPR                                                                   8

SEQ ID NO: 414        moltype = AA  length = 9
FEATURE               Location/Qualifiers
REGION                1..9
                      note = Description of Artificial Sequence: Syntheticpeptide
source                1..9
                      mol_type = protein
                      organism = synthetic construct
SEQUENCE: 414
MQALQTPRT                                                                  9

SEQ ID NO: 415        moltype = AA  length = 9
FEATURE               Location/Qualifiers
REGION                1..9
                      note = Description of Artificial Sequence: Syntheticpeptide
source                1..9
                      mol_type = protein
                      organism = synthetic construct
SEQUENCE: 415
MQALQTPRT                                                                  9

SEQ ID NO: 416        moltype = AA  length = 9
FEATURE               Location/Qualifiers
REGION                1..9
                      note = Description of Artificial Sequence: Syntheticpeptide
source                1..9
                      mol_type = protein
                      organism = synthetic construct
SEQUENCE: 416
MQALQTPRT                                                                  9

SEQ ID NO: 417        moltype = AA  length = 9
FEATURE               Location/Qualifiers
REGION                1..9
                      note = Description of Artificial Sequence: Syntheticpeptide
source                1..9
                      mol_type = protein
                      organism = synthetic construct
SEQUENCE: 417
MQALQTPRT                                                                  9

SEQ ID NO: 418        moltype = AA  length = 8
FEATURE               Location/Qualifiers
REGION                1..8
                      note = Description of Artificial Sequence: Syntheticpeptide
source                1..8
                      mol_type = protein
```

```
                        -continued organism = synthetic construct
SEQUENCE: 418
MQALQTPR                                                                        8

SEQ ID NO: 419          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 419
MQALQTPRT                                                                       9

SEQ ID NO: 420          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 420
RASQSISSWL A                                                                   11

SEQ ID NO: 421          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 421
RASQSISSWL A                                                                   11

SEQ ID NO: 422          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 422
RASQSISSWL A                                                                   11

SEQ ID NO: 423          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 423
SSWLAWY                                                                         7

SEQ ID NO: 424          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 424
QSISSW                                                                          6

SEQ ID NO: 425          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 425
RASQGIRNDL G                                                                   11

SEQ ID NO: 426          moltype = AA   length = 11
FEATURE                 Location/Qualifiers
REGION                  1..11
                        note = Description of Artificial Sequence: Syntheticpeptide
source                  1..11
```

```
                        mol_type = protein
                        organism = synthetic construct
SEQUENCE: 426
RASQGIRNDL G                                                            11

SEQ ID NO: 427          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 427
RASQGIRNDL G                                                            11

SEQ ID NO: 428          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 428
RNDLGWY                                                                 7

SEQ ID NO: 429          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 429
QGIRND                                                                  6

SEQ ID NO: 430          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 430
RASQSVSSNL A                                                            11

SEQ ID NO: 431          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 431
RASQSVSSNL A                                                            11

SEQ ID NO: 432          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 432
RASQSVSSNL A                                                            11

SEQ ID NO: 433          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 433
SSNLAWY                                                                 7

SEQ ID NO: 434          moltype = AA   length = 6
FEATURE                 Location/Qualifiers
REGION                  1..6
                        note = Description of Artificial Sequence: Syntheticpeptide
```

```
                                      -continued source                  1..6
                        mol_type = protein
                        organism = synthetic construct
SEQUENCE: 434
QSVSSN                                                                        6

SEQ ID NO: 435          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 435
KASSLES                                                                       7

SEQ ID NO: 436          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 436
KASSLES                                                                       7

SEQ ID NO: 437          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 437
KASSLES                                                                       7

SEQ ID NO: 438          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 438
LLIYKASSLE                                                                   10

SEQ ID NO: 439          moltype =     length =
SEQUENCE: 439
000

SEQ ID NO: 440          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 440
AASSLHS                                                                       7

SEQ ID NO: 441          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 441
AASSLHS                                                                       7

SEQ ID NO: 442          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 442
AASSLHS                                                                       7
```

```
SEQ ID NO: 443          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 443
RLIHAASSLH                                                                          10

SEQ ID NO: 444          moltype =   length =
SEQUENCE: 444
000

SEQ ID NO: 445          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 445
GASTRAT                                                                              7

SEQ ID NO: 446          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 446
GASTRAT                                                                              7

SEQ ID NO: 447          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 447
GASTRAT                                                                              7

SEQ ID NO: 448          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 448
LLIYGASTRA                                                                          10

SEQ ID NO: 449          moltype =   length =
SEQUENCE: 449
000

SEQ ID NO: 450          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 450
QQYKSYYT                                                                             8

SEQ ID NO: 451          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 451
QQYKSYYT                                                                             8
```

```
SEQ ID NO: 452           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 452
QQYKSYYT                                                                      8

SEQ ID NO: 453           moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 453
QQYKSYY                                                                       7

SEQ ID NO: 454           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 454
QQYKSYYT                                                                      8

SEQ ID NO: 455           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 455
LQHNRYPIT                                                                     9

SEQ ID NO: 456           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 456
LQHNRYPIT                                                                     9

SEQ ID NO: 457           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 457
LQHNRYPIT                                                                     9

SEQ ID NO: 458           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 458
LQHNRYPI                                                                      8

SEQ ID NO: 459           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 459
LQHNRYPIT                                                                     9
```

```
SEQ ID NO: 460          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 460
QQYNNWPFT                                                                         9

SEQ ID NO: 461          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 461
QQYNNWPFT                                                                         9

SEQ ID NO: 462          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 462
QQYNNWPFT                                                                         9

SEQ ID NO: 463          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 463
QQYNNWPF                                                                          8

SEQ ID NO: 464          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 464
QQYNNWPFT                                                                         9

SEQ ID NO: 465          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 465
GFMFSSY                                                                           7

SEQ ID NO: 466          moltype = AA   length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 466
GFMFSSYSMN                                                                       10

SEQ ID NO: 467          moltype = AA   length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 467
```

```
SYSMN                                                                    5

SEQ ID NO: 468        moltype = AA  length = 6
FEATURE               Location/Qualifiers
REGION                1..6
                      note = Description of Artificial Sequence: Syntheticpeptide
source                1..6
                      mol_type = protein
                      organism = synthetic construct
SEQUENCE: 468
SSYSMN                                                                   6

SEQ ID NO: 469        moltype = AA  length = 8
FEATURE               Location/Qualifiers
REGION                1..8
                      note = Description of Artificial Sequence: Syntheticpeptide
source                1..8
                      mol_type = protein
                      organism = synthetic construct
SEQUENCE: 469
GFMFSSYS                                                                 8

SEQ ID NO: 470        moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 470
GFTFSNY                                                                  7

SEQ ID NO: 471        moltype = AA  length = 10
FEATURE               Location/Qualifiers
REGION                1..10
                      note = Description of Artificial Sequence: Syntheticpeptide
source                1..10
                      mol_type = protein
                      organism = synthetic construct
SEQUENCE: 471
GFTFSNYAMT                                                              10

SEQ ID NO: 472        moltype = AA  length = 5
FEATURE               Location/Qualifiers
REGION                1..5
                      note = Description of Artificial Sequence: Syntheticpeptide
source                1..5
                      mol_type = protein
                      organism = synthetic construct
SEQUENCE: 472
NYAMT                                                                    5

SEQ ID NO: 473        moltype = AA  length = 6
FEATURE               Location/Qualifiers
REGION                1..6
                      note = Description of Artificial Sequence: Syntheticpeptide
source                1..6
                      mol_type = protein
                      organism = synthetic construct
SEQUENCE: 473
SNYAMT                                                                   6

SEQ ID NO: 474        moltype = AA  length = 8
FEATURE               Location/Qualifiers
REGION                1..8
                      note = Description of Artificial Sequence: Syntheticpeptide
source                1..8
                      mol_type = protein
                      organism = synthetic construct
SEQUENCE: 474
GFTFSNYA                                                                 8

SEQ ID NO: 475        moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
```

```
SEQUENCE: 475
GFTFSNY                                                               7

SEQ ID NO: 476          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 476
GFTFSNYAMT                                                           10

SEQ ID NO: 477          moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 477
NYAMT                                                                 5

SEQ ID NO: 478          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 478
SNYAMT                                                                6

SEQ ID NO: 479          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 479
GFTFSNYA                                                              8

SEQ ID NO: 480          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 480
GFTFSSY                                                               7

SEQ ID NO: 481          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 481
GFTFSSYDMH                                                           10

SEQ ID NO: 482          moltype = AA  length = 5
FEATURE                 Location/Qualifiers
REGION                  1..5
                        note = Description of Artificial Sequence: Syntheticpeptide
source                  1..5
                        mol_type = protein
                        organism = synthetic construct
SEQUENCE: 482
SYDMH                                                                 5

SEQ ID NO: 483          moltype = AA  length = 6
FEATURE                 Location/Qualifiers
REGION                  1..6
                        note = Description of Artificial Sequence: Syntheticpeptide
source                  1..6
                        mol_type = protein
```

```
                         -continued organism = synthetic construct
SEQUENCE: 483
SSYDMH                                                                    6

SEQ ID NO: 484           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 484
GFTFSSYD                                                                  8

SEQ ID NO: 485           moltype = AA  length = 7
FEATURE                  Location/Qualifiers
REGION                   1..7
                         note = Description of Artificial Sequence: Syntheticpeptide
source                   1..7
                         mol_type = protein
                         organism = synthetic construct
SEQUENCE: 485
GITFSNA                                                                   7

SEQ ID NO: 486           moltype = AA  length = 10
FEATURE                  Location/Qualifiers
REGION                   1..10
                         note = Description of Artificial Sequence: Syntheticpeptide
source                   1..10
                         mol_type = protein
                         organism = synthetic construct
SEQUENCE: 486
GITFSNAWMS                                                               10

SEQ ID NO: 487           moltype = AA  length = 5
FEATURE                  Location/Qualifiers
REGION                   1..5
                         note = Description of Artificial Sequence: Syntheticpeptide
source                   1..5
                         mol_type = protein
                         organism = synthetic construct
SEQUENCE: 487
NAWMS                                                                     5

SEQ ID NO: 488           moltype = AA  length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 488
SNAWMS                                                                    6

SEQ ID NO: 489           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 489
GITFSNAW                                                                  8

SEQ ID NO: 490           moltype = AA  length = 6
FEATURE                  Location/Qualifiers
REGION                   1..6
                         note = Description of Artificial Sequence: Syntheticpeptide
source                   1..6
                         mol_type = protein
                         organism = synthetic construct
SEQUENCE: 490
SSSSST                                                                    6

SEQ ID NO: 491           moltype = AA  length = 10
FEATURE                  Location/Qualifiers
REGION                   1..10
                         note = Description of Artificial Sequence: Syntheticpeptide
source                   1..10
```

```
                        mol_type = protein
                        organism = synthetic construct
SEQUENCE: 491
YISSSSSTIY                                                               10

SEQ ID NO: 492          moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 492
YISSSSSTIY DADSVKG                                                       17

SEQ ID NO: 493          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 493
WVSYISSSSS TIY                                                           13

SEQ ID NO: 494          moltype = AA  length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 494
ISSSSSTI                                                                 8

SEQ ID NO: 495          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 495
SGFGGS                                                                   6

SEQ ID NO: 496          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 496
AISGFGGSTY                                                               10

SEQ ID NO: 497          moltype = AA  length = 17
FEATURE                 Location/Qualifiers
REGION                  1..17
                        note = Description of Artificial Sequence: Syntheticpeptide
source                  1..17
                        mol_type = protein
                        organism = synthetic construct
SEQUENCE: 497
AISGFGGSTY YADSVKG                                                       17

SEQ ID NO: 498          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 498
WVSAISGFGG STY                                                           13

SEQ ID NO: 499          moltype = AA  length = 8
FEATURE                 Location/Qualifiers
REGION                  1..8
                        note = Description of Artificial Sequence: Syntheticpeptide
```

```
source                      1..8
                            mol_type = protein
                            organism = synthetic construct
SEQUENCE: 499
ISGFGGST                                                                  8

SEQ ID NO: 500              moltype = AA  length = 330
FEATURE                     Location/Qualifiers
REGION                      1..330
                            note = Description of Artificial Sequence:
                              Syntheticpolypeptide
source                      1..330
                            mol_type = protein
                            organism = synthetic construct
SEQUENCE: 500
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 501              moltype = AA  length = 330
FEATURE                     Location/Qualifiers
REGION                      1..330
                            note = Description of Artificial Sequence:
                              Syntheticpolypeptide
source                      1..330
                            mol_type = protein
                            organism = synthetic construct
SEQUENCE: 501
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELEGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 502              moltype = AA  length = 330
FEATURE                     Location/Qualifiers
REGION                      1..330
                            note = Description of Artificial Sequence:
                              Syntheticpolypeptide
source                      1..330
                            mol_type = protein
                            organism = synthetic construct
SEQUENCE: 502
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 503              moltype = AA  length = 330
FEATURE                     Location/Qualifiers
REGION                      1..330
                            note = Description of Artificial Sequence:
                              Syntheticpolypeptide
source                      1..330
                            mol_type = protein
                            organism = synthetic construct
SEQUENCE: 503
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAEGA   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 504              moltype = AA  length = 330
FEATURE                     Location/Qualifiers
REGION                      1..330
                            note = Description of Artificial Sequence:
                              Syntheticpolypeptide
source                      1..330
                            mol_type = protein
                            organism = synthetic construct
SEQUENCE: 504
```

```
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LAAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 505            moltype = AA  length = 330
FEATURE                   Location/Qualifiers
REGION                    1..330
                          note = Description of Artificial Sequence:
                          Syntheticpolypeptide
source                    1..330
                          mol_type = protein
                          organism = synthetic construct
SEQUENCE: 505
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LAAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 506            moltype = AA  length = 330
FEATURE                   Location/Qualifiers
REGION                    1..330
                          note = Description of Artificial Sequence:
                          Syntheticpolypeptide
source                    1..330
                          mol_type = protein
                          organism = synthetic construct
SEQUENCE: 506
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LAAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 507            moltype = AA  length = 330
FEATURE                   Location/Qualifiers
REGION                    1..330
                          note = Description of Artificial Sequence:
                          Syntheticpolypeptide
source                    1..330
                          mol_type = protein
                          organism = synthetic construct
SEQUENCE: 507
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEEFGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPASIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 508            moltype = AA  length = 330
FEATURE                   Location/Qualifiers
REGION                    1..330
                          note = Description of Artificial Sequence:
                          Syntheticpolypeptide
source                    1..330
                          mol_type = protein
                          organism = synthetic construct
SEQUENCE: 508
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVAVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 509            moltype = AA  length = 330
FEATURE                   Location/Qualifiers
REGION                    1..330
                          note = Description of Artificial Sequence:
                          Syntheticpolypeptide
source                    1..330
                          mol_type = protein
                          organism = synthetic construct
```

```
SEQUENCE: 509
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYG   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 510         moltype = AA   length = 327
FEATURE                Location/Qualifiers
REGION                 1..327
                       note = Description of Artificial Sequence:
                        Syntheticpolypeptide
source                 1..327
                       mol_type = protein
                       organism = synthetic construct
SEQUENCE: 510
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 511         moltype = AA   length = 327
FEATURE                Location/Qualifiers
REGION                 1..327
                       note = Description of Artificial Sequence:
                        Syntheticpolypeptide
source                 1..327
                       mol_type = protein
                       organism = synthetic construct
SEQUENCE: 511
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 512         moltype = AA   length = 327
FEATURE                Location/Qualifiers
REGION                 1..327
                       note = Description of Artificial Sequence:
                        Syntheticpolypeptide
source                 1..327
                       mol_type = protein
                       organism = synthetic construct
SEQUENCE: 512
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEAAGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 513         moltype = AA   length = 6
FEATURE                Location/Qualifiers
REGION                 1..6
                       note = Description of Artificial Sequence: Syntheticpeptide
source                 1..6
                       mol_type = protein
                       organism = synthetic construct
SEQUENCE: 513
SGYGGS                                                               6

SEQ ID NO: 514         moltype = AA   length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 514
AISGYGGSTY                                                          10

SEQ ID NO: 515         moltype = AA   length = 17
FEATURE                Location/Qualifiers
REGION                 1..17
```

```
                    note = Description of Artificial Sequence: Syntheticpeptide
source              1..17
                    mol_type = protein
                    organism = synthetic construct
SEQUENCE: 515
AISGYGGSTY YAASVKG                                                          17

SEQ ID NO: 516      moltype = AA   length = 13
FEATURE             Location/Qualifiers
REGION              1..13
                    note = Description of Artificial Sequence: Syntheticpeptide
source              1..13
                    mol_type = protein
                    organism = synthetic construct
SEQUENCE: 516
WVSAISGYGG STY                                                              13

SEQ ID NO: 517      moltype = AA   length = 8
FEATURE             Location/Qualifiers
REGION              1..8
                    note = Description of Artificial Sequence: Syntheticpeptide
source              1..8
                    mol_type = protein
                    organism = synthetic construct
SEQUENCE: 517
ISGYGGST                                                                     8

SEQ ID NO: 518      moltype = AA   length = 5
FEATURE             Location/Qualifiers
REGION              1..5
                    note = Description of Artificial Sequence: Syntheticpeptide
source              1..5
                    mol_type = protein
                    organism = synthetic construct
SEQUENCE: 518
GIGGD                                                                        5

SEQ ID NO: 519      moltype = AA   length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 519
SIGIGGDTY                                                                    9

SEQ ID NO: 520      moltype = AA   length = 16
FEATURE             Location/Qualifiers
REGION              1..16
                    note = Description of Artificial Sequence: Syntheticpeptide
source              1..16
                    mol_type = protein
                    organism = synthetic construct
SEQUENCE: 520
SIGIGGDTYY PGSVKG                                                           16

SEQ ID NO: 521      moltype = AA   length = 12
FEATURE             Location/Qualifiers
REGION              1..12
                    note = Description of Artificial Sequence: Syntheticpeptide
source              1..12
                    mol_type = protein
                    organism = synthetic construct
SEQUENCE: 521
WVSSIGIGGD TY                                                               12

SEQ ID NO: 522      moltype = AA   length = 7
FEATURE             Location/Qualifiers
REGION              1..7
                    note = Description of Artificial Sequence: Syntheticpeptide
source              1..7
                    mol_type = protein
                    organism = synthetic construct
SEQUENCE: 522
IGIGGDT                                                                      7

SEQ ID NO: 523      moltype = AA   length = 8
FEATURE             Location/Qualifiers
```

```
REGION                  1..8
                        note = Description of Artificial Sequence: Syntheticpeptide
source                  1..8
                        mol_type = protein
                        organism = synthetic construct
SEQUENCE: 523
KSKTYGGT                                                                         8

SEQ ID NO: 524          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 524
RIKSKTYGGT TD                                                                   12

SEQ ID NO: 525          moltype = AA  length = 19
FEATURE                 Location/Qualifiers
REGION                  1..19
                        note = Description of Artificial Sequence: Syntheticpeptide
source                  1..19
                        mol_type = protein
                        organism = synthetic construct
SEQUENCE: 525
RIKSKTYGGT TDYAAPVKG                                                            19

SEQ ID NO: 526          moltype = AA  length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 526
WVGRIKSKTY GGTTD                                                                15

SEQ ID NO: 527          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 527
IKSKTYGGTT                                                                      10

SEQ ID NO: 528          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 528
EAYPGYYYNY MDV                                                                  13

SEQ ID NO: 529          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 529
EAYPGYYYNY MDV                                                                  13

SEQ ID NO: 530          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 530
EAYPGYYYNY MDV                                                                  13

SEQ ID NO: 531          moltype = AA  length = 14
```

```
                         -continued

FEATURE                  Location/Qualifiers
REGION                   1..14
                         note = Description of Artificial Sequence: Syntheticpeptide
source                   1..14
                         mol_type = protein
                         organism = synthetic construct
SEQUENCE: 531
TREAYPGYYY NYMD                                                                14

SEQ ID NO: 532           moltype = AA  length = 15
FEATURE                  Location/Qualifiers
REGION                   1..15
                         note = Description of Artificial Sequence: Syntheticpeptide
source                   1..15
                         mol_type = protein
                         organism = synthetic construct
SEQUENCE: 532
TREAYPGYYY NYMDV                                                               15

SEQ ID NO: 533           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 533
DHDYYAFDY                                                                       9

SEQ ID NO: 534           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 534
DHDYYAFDY                                                                       9

SEQ ID NO: 535           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 535
DHDYYAFDY                                                                       9

SEQ ID NO: 536           moltype = AA  length = 10
FEATURE                  Location/Qualifiers
REGION                   1..10
                         note = Description of Artificial Sequence: Syntheticpeptide
source                   1..10
                         mol_type = protein
                         organism = synthetic construct
SEQUENCE: 536
AKDHDYYAFD                                                                     10

SEQ ID NO: 537           moltype = AA  length = 11
FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 537
AKDHDYYAFD Y                                                                   11

SEQ ID NO: 538           moltype = AA  length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 538
DHDYYAFDY                                                                       9
```

```
SEQ ID NO: 539          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 539
DHDYYAFDY                                                                         9

SEQ ID NO: 540          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 540
DHDYYAFDY                                                                         9

SEQ ID NO: 541          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 541
AKDHDYYAFD                                                                       10

SEQ ID NO: 542          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 542
AKDHDYYAFD Y                                                                     11

SEQ ID NO: 543          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 543
GEWDLLWYFM DV                                                                    12

SEQ ID NO: 544          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 544
GEWDLLWYFM DV                                                                    12

SEQ ID NO: 545          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 545
GEWDLLWYFM DV                                                                    12

SEQ ID NO: 546          moltype = AA  length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 546
ARGEWDLLWY FMD                                                                   13
```

```
SEQ ID NO: 547           moltype = AA   length = 14
FEATURE                  Location/Qualifiers
REGION                   1..14
                         note = Description of Artificial Sequence: Syntheticpeptide
source                   1..14
                         mol_type = protein
                         organism = synthetic construct
SEQUENCE: 547
ARGEWDLLWY FMDV                                                              14

SEQ ID NO: 548           moltype = AA   length = 14
FEATURE                  Location/Qualifiers
REGION                   1..14
                         note = Description of Artificial Sequence: Syntheticpeptide
source                   1..14
                         mol_type = protein
                         organism = synthetic construct
SEQUENCE: 548
DPWNYVNYNY FMDV                                                              14

SEQ ID NO: 549           moltype = AA   length = 14
FEATURE                  Location/Qualifiers
REGION                   1..14
                         note = Description of Artificial Sequence: Syntheticpeptide
source                   1..14
                         mol_type = protein
                         organism = synthetic construct
SEQUENCE: 549
DPWNYVNYNY FMDV                                                              14

SEQ ID NO: 550           moltype = AA   length = 14
FEATURE                  Location/Qualifiers
REGION                   1..14
                         note = Description of Artificial Sequence: Syntheticpeptide
source                   1..14
                         mol_type = protein
                         organism = synthetic construct
SEQUENCE: 550
DPWNYVNYNY FMDV                                                              14

SEQ ID NO: 551           moltype = AA   length = 15
FEATURE                  Location/Qualifiers
REGION                   1..15
                         note = Description of Artificial Sequence: Syntheticpeptide
source                   1..15
                         mol_type = protein
                         organism = synthetic construct
SEQUENCE: 551
TTDPWNYVNY NYFMD                                                             15

SEQ ID NO: 552           moltype = AA   length = 16
FEATURE                  Location/Qualifiers
REGION                   1..16
                         note = Description of Artificial Sequence: Syntheticpeptide
source                   1..16
                         mol_type = protein
                         organism = synthetic construct
SEQUENCE: 552
TTDPWNYVNY NYFMDV                                                            16

SEQ ID NO: 553           moltype = AA   length = 11
FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 553
RASQSISSRL A                                                                 11

SEQ ID NO: 554           moltype = AA   length = 11
FEATURE                  Location/Qualifiers
REGION                   1..11
                         note = Description of Artificial Sequence: Syntheticpeptide
source                   1..11
                         mol_type = protein
                         organism = synthetic construct
SEQUENCE: 554
```

```
RASQSISSRL A                                                               11

SEQ ID NO: 555        moltype = AA  length = 11
FEATURE               Location/Qualifiers
REGION                1..11
                      note = Description of Artificial Sequence: Syntheticpeptide
source                1..11
                      mol_type = protein
                      organism = synthetic construct
SEQUENCE: 555
RASQSISSRL A                                                               11

SEQ ID NO: 556        moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 556
SSRLAWY                                                                    7

SEQ ID NO: 557        moltype = AA  length = 6
FEATURE               Location/Qualifiers
REGION                1..6
                      note = Description of Artificial Sequence: Syntheticpeptide
source                1..6
                      mol_type = protein
                      organism = synthetic construct
SEQUENCE: 557
QSISSR                                                                     6

SEQ ID NO: 558        moltype = AA  length = 11
FEATURE               Location/Qualifiers
REGION                1..11
                      note = Description of Artificial Sequence: Syntheticpeptide
source                1..11
                      mol_type = protein
                      organism = synthetic construct
SEQUENCE: 558
RASQSISSYL N                                                               11

SEQ ID NO: 559        moltype = AA  length = 11
FEATURE               Location/Qualifiers
REGION                1..11
                      note = Description of Artificial Sequence: Syntheticpeptide
source                1..11
                      mol_type = protein
                      organism = synthetic construct
SEQUENCE: 559
RASQSISSYL N                                                               11

SEQ ID NO: 560        moltype = AA  length = 11
FEATURE               Location/Qualifiers
REGION                1..11
                      note = Description of Artificial Sequence: Syntheticpeptide
source                1..11
                      mol_type = protein
                      organism = synthetic construct
SEQUENCE: 560
RASQSISSYL N                                                               11

SEQ ID NO: 561        moltype = AA  length = 7
FEATURE               Location/Qualifiers
REGION                1..7
                      note = Description of Artificial Sequence: Syntheticpeptide
source                1..7
                      mol_type = protein
                      organism = synthetic construct
SEQUENCE: 561
SSYLNWY                                                                    7

SEQ ID NO: 562        moltype = AA  length = 6
FEATURE               Location/Qualifiers
REGION                1..6
                      note = Description of Artificial Sequence: Syntheticpeptide
source                1..6
                      mol_type = protein
                      organism = synthetic construct
```

```
SEQUENCE: 562
QSISSY                                                                          6

SEQ ID NO: 563          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 563
RASQSINSYL N                                                                   11

SEQ ID NO: 564          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 564
RASQSINSYL N                                                                   11

SEQ ID NO: 565          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 565
RASQSINSYL N                                                                   11

SEQ ID NO: 566          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 566
NSYLNWY                                                                         7

SEQ ID NO: 567          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 567
QSINSY                                                                          6

SEQ ID NO: 568          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 568
RASQGISSWL A                                                                   11

SEQ ID NO: 569          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 569
RASQGISSWL A                                                                   11

SEQ ID NO: 570          moltype = AA  length = 11
FEATURE                 Location/Qualifiers
REGION                  1..11
                        note = Description of Artificial Sequence: Syntheticpeptide
source                  1..11
                        mol_type = protein
```

```
                        organism = synthetic construct
SEQUENCE: 570
RASQGISSWL A                                                                 11

SEQ ID NO: 571          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 571
SSWLAWY                                                                      7

SEQ ID NO: 572          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 572
QGISSW                                                                       6

SEQ ID NO: 573          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 573
RASQDIRNYL A                                                                 11

SEQ ID NO: 574          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 574
RASQDIRNYL A                                                                 11

SEQ ID NO: 575          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 575
RASQDIRNYL A                                                                 11

SEQ ID NO: 576          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 576
RNYLAWY                                                                      7

SEQ ID NO: 577          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 577
QDIRNY                                                                       6

SEQ ID NO: 578          moltype = AA   length = 7
FEATURE                 Location/Qualifiers
REGION                  1..7
                        note = Description of Artificial Sequence: Syntheticpeptide
source                  1..7
```

```
                        mol_type = protein
                        organism = synthetic construct
SEQUENCE: 578
KASNLES                                                                 7

SEQ ID NO: 579          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 579
KASNLES                                                                 7

SEQ ID NO: 580          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 580
KASNLES                                                                 7

SEQ ID NO: 581          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 581
LLIYKASNLE                                                             10

SEQ ID NO: 582          moltype =   length =
SEQUENCE: 582
000

SEQ ID NO: 583          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 583
AVSSLQS                                                                 7

SEQ ID NO: 584          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 584
AVSSLQS                                                                 7

SEQ ID NO: 585          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 585
AVSSLQS                                                                 7

SEQ ID NO: 586          moltype = AA  length = 10
FEATURE                 Location/Qualifiers
REGION                  1..10
                        note = Description of Artificial Sequence: Syntheticpeptide
source                  1..10
                        mol_type = protein
                        organism = synthetic construct
SEQUENCE: 586
LLIYAVSSLQ                                                             10
```

| | | |
|---|---|---|
| SEQ ID NO: 587<br>SEQUENCE: 587<br>000 | moltype =   length = | |
| SEQ ID NO: 588<br>FEATURE<br>REGION<br><br>source | moltype = AA   length = 7<br>Location/Qualifiers<br>1..7<br>note = Description of Artificial Sequence: Syntheticpeptide<br>1..7<br>mol_type = protein<br>organism = synthetic construct | |
| SEQUENCE: 588<br>SASSLQS | | 7 |
| SEQ ID NO: 589<br>FEATURE<br>REGION<br><br>source | moltype = AA   length = 7<br>Location/Qualifiers<br>1..7<br>note = Description of Artificial Sequence: Syntheticpeptide<br>1..7<br>mol_type = protein<br>organism = synthetic construct | |
| SEQUENCE: 589<br>SASSLQS | | 7 |
| SEQ ID NO: 590<br>FEATURE<br>REGION<br><br>source | moltype = AA   length = 7<br>Location/Qualifiers<br>1..7<br>note = Description of Artificial Sequence: Syntheticpeptide<br>1..7<br>mol_type = protein<br>organism = synthetic construct | |
| SEQUENCE: 590<br>SASSLQS | | 7 |
| SEQ ID NO: 591<br>FEATURE<br>REGION<br><br>source | moltype = AA   length = 10<br>Location/Qualifiers<br>1..10<br>note = Description of Artificial Sequence: Syntheticpeptide<br>1..10<br>mol_type = protein<br>organism = synthetic construct | |
| SEQUENCE: 591<br>LLIYSASSLQ | | 10 |
| SEQ ID NO: 592<br>SEQUENCE: 592<br>000 | moltype =   length = | |
| SEQ ID NO: 593<br>FEATURE<br>REGION<br><br>source | moltype = AA   length = 7<br>Location/Qualifiers<br>1..7<br>note = Description of Artificial Sequence: Syntheticpeptide<br>1..7<br>mol_type = protein<br>organism = synthetic construct | |
| SEQUENCE: 593<br>AASSLQS | | 7 |
| SEQ ID NO: 594<br>FEATURE<br>REGION<br><br>source | moltype = AA   length = 7<br>Location/Qualifiers<br>1..7<br>note = Description of Artificial Sequence: Syntheticpeptide<br>1..7<br>mol_type = protein<br>organism = synthetic construct | |
| SEQUENCE: 594<br>AASSLQS | | 7 |
| SEQ ID NO: 595<br>FEATURE<br>REGION<br><br>source | moltype = AA   length = 7<br>Location/Qualifiers<br>1..7<br>note = Description of Artificial Sequence: Syntheticpeptide<br>1..7<br>mol_type = protein<br>organism = synthetic construct | |
| SEQUENCE: 595<br>AASSLQS | | 7 |
| SEQ ID NO: 596 | moltype = AA   length = 10 | |

```
FEATURE              Location/Qualifiers
REGION               1..10
                     note = Description of Artificial Sequence: Syntheticpeptide
source               1..10
                     mol_type = protein
                     organism = synthetic construct
SEQUENCE: 596
LLIYAASSLQ                                                                    10

SEQ ID NO: 597       moltype =    length =
SEQUENCE: 597
000

SEQ ID NO: 598       moltype = AA   length = 7
FEATURE              Location/Qualifiers
REGION               1..7
                     note = Description of Artificial Sequence: Syntheticpeptide
source               1..7
                     mol_type = protein
                     organism = synthetic construct
SEQUENCE: 598
AASTLQS                                                                        7

SEQ ID NO: 599       moltype = AA   length = 7
FEATURE              Location/Qualifiers
REGION               1..7
                     note = Description of Artificial Sequence: Syntheticpeptide
source               1..7
                     mol_type = protein
                     organism = synthetic construct
SEQUENCE: 599
AASTLQS                                                                        7

SEQ ID NO: 600       moltype = AA   length = 7
FEATURE              Location/Qualifiers
REGION               1..7
                     note = Description of Artificial Sequence: Syntheticpeptide
source               1..7
                     mol_type = protein
                     organism = synthetic construct
SEQUENCE: 600
AASTLQS                                                                        7

SEQ ID NO: 601       moltype = AA   length = 10
FEATURE              Location/Qualifiers
REGION               1..10
                     note = Description of Artificial Sequence: Syntheticpeptide
source               1..10
                     mol_type = protein
                     organism = synthetic construct
SEQUENCE: 601
LLVYAASTLQ                                                                    10

SEQ ID NO: 602       moltype =    length =
SEQUENCE: 602
000

SEQ ID NO: 603       moltype = AA   length = 9
FEATURE              Location/Qualifiers
REGION               1..9
                     note = Description of Artificial Sequence: Syntheticpeptide
source               1..9
                     mol_type = protein
                     organism = synthetic construct
SEQUENCE: 603
QQYNSYSRT                                                                      9

SEQ ID NO: 604       moltype = AA   length = 9
FEATURE              Location/Qualifiers
REGION               1..9
                     note = Description of Artificial Sequence: Syntheticpeptide
source               1..9
                     mol_type = protein
                     organism = synthetic construct
SEQUENCE: 604
QQYNSYSRT                                                                      9

SEQ ID NO: 605       moltype = AA   length = 9
FEATURE              Location/Qualifiers
```

```
REGION              1..9
                    note = Description of Artificial Sequence: Syntheticpeptide
source              1..9
                    mol_type = protein
                    organism = synthetic construct
SEQUENCE: 605
QQYNSYSRT                                                                    9

SEQ ID NO: 606      moltype = AA  length = 8
FEATURE             Location/Qualifiers
REGION              1..8
                    note = Description of Artificial Sequence: Syntheticpeptide
source              1..8
                    mol_type = protein
                    organism = synthetic construct
SEQUENCE: 606
QQYNSYSR                                                                     8

SEQ ID NO: 607      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 607
QQYNSYSRT                                                                    9

SEQ ID NO: 608      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 608
QQSYSTPYT                                                                    9

SEQ ID NO: 609      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 609
QQSYSTPYT                                                                    9

SEQ ID NO: 610      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 610
QQSYSTPYT                                                                    9

SEQ ID NO: 611      moltype = AA  length = 8
FEATURE             Location/Qualifiers
REGION              1..8
                    note = Description of Artificial Sequence: Syntheticpeptide
source              1..8
                    mol_type = protein
                    organism = synthetic construct
SEQUENCE: 611
QQSYSTPY                                                                     8

SEQ ID NO: 612      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 612
QQSYSTPYT                                                                    9

SEQ ID NO: 613      moltype = AA  length = 9
```

```
                        -continued
FEATURE             Location/Qualifiers
REGION              1..9
                    note = Description of Artificial Sequence: Syntheticpeptide
source              1..9
                    mol_type = protein
                    organism = synthetic construct
SEQUENCE: 613
QQSYSTPYT                                                                  9

SEQ ID NO: 614      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 614
QQSYSTPYT                                                                  9

SEQ ID NO: 615      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 615
QQSYSTPYT                                                                  9

SEQ ID NO: 616      moltype = AA  length = 8
FEATURE             Location/Qualifiers
REGION              1..8
                    note = Description of Artificial Sequence: Syntheticpeptide
source              1..8
                    mol_type = protein
                    organism = synthetic construct
SEQUENCE: 616
QQSYSTPY                                                                   8

SEQ ID NO: 617      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 617
QQSYSTPYT                                                                  9

SEQ ID NO: 618      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 618
QQANSFPLT                                                                  9

SEQ ID NO: 619      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 619
QQANSFPLT                                                                  9

SEQ ID NO: 620      moltype = AA  length = 9
FEATURE             Location/Qualifiers
REGION              1..9
                    note = Description of Artificial Sequence: Syntheticpeptide
source              1..9
                    mol_type = protein
                    organism = synthetic construct
SEQUENCE: 620
QQANSFPLT                                                                  9
```

```
SEQ ID NO: 621           moltype = AA   length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 621
QQANSFPL                                                                  8

SEQ ID NO: 622           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 622
QQANSFPLT                                                                 9

SEQ ID NO: 623           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 623
QNYFSVPLT                                                                 9

SEQ ID NO: 624           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 624
QNYFSVPLT                                                                 9

SEQ ID NO: 625           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 625
QNYFSVPLT                                                                 9

SEQ ID NO: 626           moltype = AA   length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 626
QNYFSVPL                                                                  8

SEQ ID NO: 627           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 627
QNYFSVPLT                                                                 9

SEQ ID NO: 628           moltype = AA   length = 10
FEATURE                  Location/Qualifiers
REGION                   1..10
                         note = Description of Artificial Sequence: Syntheticpeptide
source                   1..10
                         mol_type = protein
                         organism = synthetic construct
SEQUENCE: 628
VSGGSISGYY                                                               10
```

```
SEQ ID NO: 629         moltype = AA   length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 629
ASGFNFDDYA                                                                  10

SEQ ID NO: 630         moltype = AA   length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 630
VSGFTFSSYD                                                                  10

SEQ ID NO: 631         moltype = AA   length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 631
ASGFMFSSYS                                                                  10

SEQ ID NO: 632         moltype = AA   length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 632
ASGFTFSNYA                                                                  10

SEQ ID NO: 633         moltype = AA   length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 633
ASGFTFSNYA                                                                  10

SEQ ID NO: 634         moltype = AA   length = 10
FEATURE                Location/Qualifiers
REGION                 1..10
                       note = Description of Artificial Sequence: Syntheticpeptide
source                 1..10
                       mol_type = protein
                       organism = synthetic construct
SEQUENCE: 634
VSGITFSNAW                                                                  10

SEQ ID NO: 635         moltype = AA   length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 635
GYYWS                                                                        5

SEQ ID NO: 636         moltype = AA   length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 636
```

```
DYAMH                                                              5

SEQ ID NO: 637         moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 637
SYDMH                                                              5

SEQ ID NO: 638         moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 638
SYSMN                                                              5

SEQ ID NO: 639         moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 639
NYAMT                                                              5

SEQ ID NO: 640         moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 640
NYAMT                                                              5

SEQ ID NO: 641         moltype = AA  length = 5
FEATURE                Location/Qualifiers
REGION                 1..5
                       note = Description of Artificial Sequence: Syntheticpeptide
source                 1..5
                       mol_type = protein
                       organism = synthetic construct
SEQUENCE: 641
NAWMS                                                              5

SEQ ID NO: 642         moltype = AA  length = 16
FEATURE                Location/Qualifiers
REGION                 1..16
                       note = Description of Artificial Sequence: Syntheticpeptide
source                 1..16
                       mol_type = protein
                       organism = synthetic construct
SEQUENCE: 642
IFYSGYTKYN PSLKSR                                                  16

SEQ ID NO: 643         moltype = AA  length = 17
FEATURE                Location/Qualifiers
REGION                 1..17
                       note = Description of Artificial Sequence: Syntheticpeptide
source                 1..17
                       mol_type = protein
                       organism = synthetic construct
SEQUENCE: 643
ISWRSGNIGY ADSVKGR                                                 17

SEQ ID NO: 644         moltype = AA  length = 16
FEATURE                Location/Qualifiers
REGION                 1..16
                       note = Description of Artificial Sequence: Syntheticpeptide
source                 1..16
                       mol_type = protein
                       organism = synthetic construct
```

-continued

```
SEQUENCE: 644
IGIGGDTYYP GSVKGR                                                         16

SEQ ID NO: 645           moltype = AA   length = 17
FEATURE                  Location/Qualifiers
REGION                   1..17
                         note = Description of Artificial Sequence: Syntheticpeptide
source                   1..17
                         mol_type = protein
                         organism = synthetic construct
SEQUENCE: 645
ISSSSSTIYD ADSVKGR                                                        17

SEQ ID NO: 646           moltype = AA   length = 17
FEATURE                  Location/Qualifiers
REGION                   1..17
                         note = Description of Artificial Sequence: Syntheticpeptide
source                   1..17
                         mol_type = protein
                         organism = synthetic construct
SEQUENCE: 646
ISGFGGSTYY ADSVKGR                                                        17

SEQ ID NO: 647           moltype = AA   length = 17
FEATURE                  Location/Qualifiers
REGION                   1..17
                         note = Description of Artificial Sequence: Syntheticpeptide
source                   1..17
                         mol_type = protein
                         organism = synthetic construct
SEQUENCE: 647
ISGYGGSTYY AASVKGR                                                        17

SEQ ID NO: 648           moltype = AA   length = 19
FEATURE                  Location/Qualifiers
REGION                   1..19
                         note = Description of Artificial Sequence: Syntheticpeptide
source                   1..19
                         mol_type = protein
                         organism = synthetic construct
SEQUENCE: 648
IKSKTYGGTT DYAAPVKGR                                                      19

SEQ ID NO: 649           moltype = AA   length = 12
FEATURE                  Location/Qualifiers
REGION                   1..12
                         note = Description of Artificial Sequence: Syntheticpeptide
source                   1..12
                         mol_type = protein
                         organism = synthetic construct
SEQUENCE: 649
WIGYIFYSGY TK                                                             12

SEQ ID NO: 650           moltype = AA   length = 13
FEATURE                  Location/Qualifiers
REGION                   1..13
                         note = Description of Artificial Sequence: Syntheticpeptide
source                   1..13
                         mol_type = protein
                         organism = synthetic construct
SEQUENCE: 650
WVSGISWRSG NIG                                                            13

SEQ ID NO: 651           moltype = AA   length = 12
FEATURE                  Location/Qualifiers
REGION                   1..12
                         note = Description of Artificial Sequence: Syntheticpeptide
source                   1..12
                         mol_type = protein
                         organism = synthetic construct
SEQUENCE: 651
WVSSIGIGGD TY                                                             12

SEQ ID NO: 652           moltype = AA   length = 13
FEATURE                  Location/Qualifiers
REGION                   1..13
                         note = Description of Artificial Sequence: Syntheticpeptide
source                   1..13
                         mol_type = protein
```

```
                        organism = synthetic construct
SEQUENCE: 652
WVSYISSSSS TIY                                                                 13

SEQ ID NO: 653          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 653
WVSAISGFGG STY                                                                 13

SEQ ID NO: 654          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 654
WVSAISGYGG STY                                                                 13

SEQ ID NO: 655          moltype = AA   length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 655
WVGRIKSKTY GGTTD                                                               15

SEQ ID NO: 656          moltype = AA   length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 656
DRWDFD                                                                          6

SEQ ID NO: 657          moltype = AA   length = 14
FEATURE                 Location/Qualifiers
REGION                  1..14
                        note = Description of Artificial Sequence: Syntheticpeptide
source                  1..14
                        mol_type = protein
                        organism = synthetic construct
SEQUENCE: 657
DKGIGFNWNY EGFD                                                                14

SEQ ID NO: 658          moltype = AA   length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 658
GEWDLLWYFM D                                                                   11

SEQ ID NO: 659          moltype = AA   length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 659
EAYPGYYYNY MD                                                                  12

SEQ ID NO: 660          moltype = AA   length = 8
FEATURE                 Location/Qualifiers
REGION                  1..8
                        note = Description of Artificial Sequence: Syntheticpeptide
source                  1..8
```

```
                        mol_type = protein
                        organism = synthetic construct
SEQUENCE: 660
DHDYYAFD                                                                 8

SEQ ID NO: 661          moltype = AA   length = 8
FEATURE                 Location/Qualifiers
REGION                  1..8
                        note = Description of Artificial Sequence: Syntheticpeptide
source                  1..8
                        mol_type = protein
                        organism = synthetic construct
SEQUENCE: 661
DHDYYAFD                                                                 8

SEQ ID NO: 662          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 662
DPWNYVNYNY FMD                                                          13

SEQ ID NO: 663          moltype = AA   length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 663
DRWDFDY                                                                  7

SEQ ID NO: 664          moltype = AA   length = 15
FEATURE                 Location/Qualifiers
REGION                  1..15
                        note = Description of Artificial Sequence: Syntheticpeptide
source                  1..15
                        mol_type = protein
                        organism = synthetic construct
SEQUENCE: 664
DKGIGFNWNY EGFDY                                                        15

SEQ ID NO: 665          moltype = AA   length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 665
GEWDLLWYFM DV                                                           12

SEQ ID NO: 666          moltype = AA   length = 13
FEATURE                 Location/Qualifiers
REGION                  1..13
                        note = Description of Artificial Sequence: Syntheticpeptide
source                  1..13
                        mol_type = protein
                        organism = synthetic construct
SEQUENCE: 666
EAYPGYYYNY MDV                                                          13

SEQ ID NO: 667          moltype = AA   length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 667
DHDYYAFDY                                                                9

SEQ ID NO: 668          moltype = AA   length = 9
FEATURE                 Location/Qualifiers
REGION                  1..9
                        note = Description of Artificial Sequence: Syntheticpeptide
```

```
source                   1..9
                         mol_type = protein
                         organism = synthetic construct
SEQUENCE: 668
DHDYYAFDY                                                                       9

SEQ ID NO: 669           moltype = AA  length = 14
FEATURE                  Location/Qualifiers
REGION                   1..14
                         note = Description of Artificial Sequence: Syntheticpeptide
source                   1..14
                         mol_type = protein
                         organism = synthetic construct
SEQUENCE: 669
DPWNYVNYNY FMDV                                                                 14

SEQ ID NO: 670           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 670
ASQGIRNN                                                                        8

SEQ ID NO: 671           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 671
ASQGISNH                                                                        8

SEQ ID NO: 672           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 672
ASQGISSW                                                                        8

SEQ ID NO: 673           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 673
ASQSISSR                                                                        8

SEQ ID NO: 674           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 674
ASQSISSY                                                                        8

SEQ ID NO: 675           moltype = AA  length = 8
FEATURE                  Location/Qualifiers
REGION                   1..8
                         note = Description of Artificial Sequence: Syntheticpeptide
source                   1..8
                         mol_type = protein
                         organism = synthetic construct
SEQUENCE: 675
ASQSINSY                                                                        8

SEQ ID NO: 676           moltype = AA  length = 8
FEATURE                  Location/Qualifiers
REGION                   1..8
```

```
                        note = Description of Artificial Sequence: Syntheticpeptide
source                  1..8
                        mol_type = protein
                        organism = synthetic construct
SEQUENCE: 676
ASQDIRNY                                                                        8

SEQ ID NO: 677          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 677
RASQGIRNNL G                                                                   11

SEQ ID NO: 678          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 678
RASQGISNHL A                                                                   11

SEQ ID NO: 679          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 679
RASQGISSWL A                                                                   11

SEQ ID NO: 680          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 680
RASQSISSRL A                                                                   11

SEQ ID NO: 681          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 681
RASQSISSYL N                                                                   11

SEQ ID NO: 682          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 682
RASQSINSYL N                                                                   11

SEQ ID NO: 683          moltype = AA  length = 11
FEATURE                 Location/Qualifiers
REGION                  1..11
                        note = Description of Artificial Sequence: Syntheticpeptide
source                  1..11
                        mol_type = protein
                        organism = synthetic construct
SEQUENCE: 683
RASQDIRNYL A                                                                   11

SEQ ID NO: 684          moltype = AA  length = 12
FEATURE                 Location/Qualifiers
```

```
REGION                  1..12
                        note = Description of Artificial Sequence: Syntheticpeptide
source                  1..12
                        mol_type = protein
                        organism = synthetic construct
SEQUENCE: 684
AESSLQSGVP SR                                                                  12

SEQ ID NO: 685          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 685
AASSLQSGVP SR                                                                  12

SEQ ID NO: 686          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 686
AASSLQSGVP SR                                                                  12

SEQ ID NO: 687          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 687
KASNLESGVP SR                                                                  12

SEQ ID NO: 688          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 688
AVSSLQSGVP SR                                                                  12

SEQ ID NO: 689          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 689
SASSLQSGVP SR                                                                  12

SEQ ID NO: 690          moltype = AA  length = 12
FEATURE                 Location/Qualifiers
REGION                  1..12
                        note = Description of Artificial Sequence: Syntheticpeptide
source                  1..12
                        mol_type = protein
                        organism = synthetic construct
SEQUENCE: 690
AASTLQSGVP SR                                                                  12

SEQ ID NO: 691          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 691
AESSLQS                                                                         7

SEQ ID NO: 692          moltype = AA  length = 7
```

```
                          -continued

FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 692
AASSLQS                                                                         7

SEQ ID NO: 693          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 693
AASSLQS                                                                         7

SEQ ID NO: 694          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 694
KASNLES                                                                         7

SEQ ID NO: 695          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 695
AVSSLQS                                                                         7

SEQ ID NO: 696          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 696
SASSLQS                                                                         7

SEQ ID NO: 697          moltype = AA  length = 7
FEATURE                 Location/Qualifiers
REGION                  1..7
                        note = Description of Artificial Sequence: Syntheticpeptide
source                  1..7
                        mol_type = protein
                        organism = synthetic construct
SEQUENCE: 697
AASTLQS                                                                         7

SEQ ID NO: 698          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 698
DFNYPY                                                                          6

SEQ ID NO: 699          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 699
YVTYPL                                                                          6
```

```
SEQ ID NO: 700          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 700
ANSFPL                                                                   6

SEQ ID NO: 701          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 701
YNSYSR                                                                   6

SEQ ID NO: 702          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 702
SYSTPY                                                                   6

SEQ ID NO: 703          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 703
SYSTPY                                                                   6

SEQ ID NO: 704          moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 704
YFSVPL                                                                   6

SEQ ID NO: 705          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 705
LQDFNYPYT                                                                9

SEQ ID NO: 706          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 706
QQYVTYPLT                                                                9

SEQ ID NO: 707          moltype = AA  length = 9
FEATURE                 Location/Qualifiers
REGION                  1..9
                        note = Description of Artificial Sequence: Syntheticpeptide
source                  1..9
                        mol_type = protein
                        organism = synthetic construct
SEQUENCE: 707
QQANSFPLT                                                                9
```

```
SEQ ID NO: 708           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 708
QQYNSYSRT                                                                        9

SEQ ID NO: 709           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 709
QQSYSTPYT                                                                        9

SEQ ID NO: 710           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 710
QQSYSTPYT                                                                        9

SEQ ID NO: 711           moltype = AA   length = 9
FEATURE                  Location/Qualifiers
REGION                   1..9
                         note = Description of Artificial Sequence: Syntheticpeptide
source                   1..9
                         mol_type = protein
                         organism = synthetic construct
SEQUENCE: 711
QNYFSVPLT                                                                        9

SEQ ID NO: 712           moltype =      length =
SEQUENCE: 712
000

SEQ ID NO: 713           moltype =      length =
SEQUENCE: 713
000

SEQ ID NO: 714           moltype =      length =
SEQUENCE: 714
000

SEQ ID NO: 715           moltype =      length =
SEQUENCE: 715
000

SEQ ID NO: 716           moltype =      length =
SEQUENCE: 716
000

SEQ ID NO: 717           moltype =      length =
SEQUENCE: 717
000

SEQ ID NO: 718           moltype =      length =
SEQUENCE: 718
000

SEQ ID NO: 719           moltype =      length =
SEQUENCE: 719
000

SEQ ID NO: 720           moltype =      length =
SEQUENCE: 720
000

SEQ ID NO: 721           moltype =      length =
SEQUENCE: 721
```

```
000

SEQ ID NO: 722         moltype =    length =
SEQUENCE: 722
000

SEQ ID NO: 723         moltype =    length =
SEQUENCE: 723
000

SEQ ID NO: 724         moltype = AA  length = 17
FEATURE                Location/Qualifiers
REGION                 1..17
                       note = Description of Artificial Sequence: Syntheticpeptide
VARIANT                1
                       note = Y, G, or S
VARIANT                3
                       note = S, G, or absent
VARIANT                4
                       note = F, W, or I
VARIANT                5
                       note = Y, R, or absent
VARIANT                6
                       note = G or S
VARIANT                8
                       note = Y, N, or D
VARIANT                9
                       note = T or I
VARIANT                10
                       note = K, G, or Y
VARIANT                12
                       note = N, A, or P
VARIANT                13
                       note = P, D, or G
VARIANT                15
                       note = L or V
VARIANT                17
                       note = S or G
source                 1..17
                       mol_type = protein
                       organism = synthetic construct
SEQUENCE: 724
XIXXXXGXXX YXXSXKX                                                     17

SEQ ID NO: 725         moltype =    length =
SEQUENCE: 725
000

SEQ ID NO: 726         moltype =    length =
SEQUENCE: 726
000

SEQ ID NO: 727         moltype =    length =
SEQUENCE: 727
000

SEQ ID NO: 728         moltype =    length =
SEQUENCE: 728
000

SEQ ID NO: 729         moltype =    length =
SEQUENCE: 729
000

SEQ ID NO: 730         moltype =    length =
SEQUENCE: 730
000

SEQ ID NO: 731         moltype =    length =
SEQUENCE: 731
000

SEQ ID NO: 732         moltype =    length =
SEQUENCE: 732
000

SEQ ID NO: 733         moltype =    length =
SEQUENCE: 733
000
```

| | |
|---|---|
| SEQ ID NO: 734 | moltype = AA  length = 17 |
| FEATURE | Location/Qualifiers |
| REGION | 1..17 |
| | note = Description of Artificial Sequence: Syntheticpeptide |
| VARIANT | 2 |
| | note = S, G, or absent |
| VARIANT | 3 |
| | note = F, W, or I |
| VARIANT | 4 |
| | note = Y, R, or absent |
| VARIANT | 5 |
| | note = G or S |
| VARIANT | 7 |
| | note = Y, N, or D |
| VARIANT | 8 |
| | note = T or I |
| VARIANT | 9 |
| | note = K, G, or Y |
| VARIANT | 11 |
| | note = N, A, or P |
| VARIANT | 12 |
| | note = P, D, or G |
| VARIANT | 14 |
| | note = L or V |
| VARIANT | 16 |
| | note = G or S |
| source | 1..17 |
| | mol_type = protein |
| | organism = synthetic construct |
| SEQUENCE: 734 | |
| IXXXXGXXXY XXSXKXR | 17 |
| | |
| SEQ ID NO: 735 | moltype =   length = |
| SEQUENCE: 735 | |
| 000 | |
| | |
| SEQ ID NO: 736 | moltype =   length = |
| SEQUENCE: 736 | |
| 000 | |
| | |
| SEQ ID NO: 737 | moltype =   length = |
| SEQUENCE: 737 | |
| 000 | |
| | |
| SEQ ID NO: 738 | moltype = AA  length = 17 |
| FEATURE | Location/Qualifiers |
| REGION | 1..17 |
| | note = Description of Artificial Sequence: Syntheticpeptide |
| VARIANT | 2 |
| | note = K or R |
| VARIANT | 3 |
| | note = D or absent |
| VARIANT | 4 |
| | note = R, K, or G |
| VARIANT | 5 |
| | note = G, E, or absent |
| VARIANT | 6 |
| | note = I, W, or absent |
| VARIANT | 7 |
| | note = G, D, or absent |
| VARIANT | 8 |
| | note = F, L, or absent |
| VARIANT | 9 |
| | note = N, L, or absent |
| VARIANT | 11 |
| | note = N, Y, or absent |
| VARIANT | 12 |
| | note = Y or absent |
| VARIANT | 13 |
| | note = D, E, or absent |
| VARIANT | 14 |
| | note = G or absent |
| VARIANT | 16 |
| | note = M or absent |
| source | 1..17 |
| | mol_type = protein |
| | organism = synthetic construct |
| SEQUENCE: 738 | |

```
                                       AXXXXXXXXW XXXXFXD                                  17

SEQ ID NO: 739          moltype =   length =
SEQUENCE: 739
000

SEQ ID NO: 740          moltype = AA  length = 18
FEATURE                 Location/Qualifiers
REGION                  1..18
                        note = Description of Artificial Sequence: Syntheticpeptide
VARIANT                 2
                        note = K or R
VARIANT                 3
                        note = D or absent
VARIANT                 4
                        note = R, K, or G
VARIANT                 5
                        note = G, E, or absent
VARIANT                 6
                        note = I, W, or absent
VARIANT                 7
                        note = G, D, or absent
VARIANT                 8
                        note = F, L, or absent
VARIANT                 9
                        note = N, L, or absent
VARIANT                 11
                        note = N, Y, or absent
VARIANT                 12
                        note = Y or absent
VARIANT                 13
                        note = D, E, or absent
VARIANT                 14
                        note = G or absent
VARIANT                 16
                        note = M or absent
VARIANT                 18
                        note = Y or V
source                  1..18
                        mol_type = protein
                        organism = synthetic construct
SEQUENCE: 740
                                       AXXXXXXXXW XXXXFXDX                                 18

SEQ ID NO: 741          moltype =   length =
SEQUENCE: 741
000

SEQ ID NO: 742          moltype =   length =
SEQUENCE: 742
000

SEQ ID NO: 743          moltype =   length =
SEQUENCE: 743
000

SEQ ID NO: 744          moltype = AA  length = 11
FEATURE                 Location/Qualifiers
REGION                  1..11
                        note = Description of Artificial Sequence: Syntheticpeptide
VARIANT                 7
                        note = R or S
VARIANT                 8
                        note = N or S
VARIANT                 9
                        note = N, H, or W
VARIANT                 11
                        note = G or A
source                  1..11
                        mol_type = protein
                        organism = synthetic construct
SEQUENCE: 744
                                       RASQGIXXXL X                                        11

SEQ ID NO: 745          moltype = AA  length = 11
FEATURE                 Location/Qualifiers
REGION                  1..11
                        note = Description of Artificial Sequence: Syntheticpeptide
VARIANT                 5
```

```
                        note = G, S, or D
VARIANT                 7
                        note = R, S, or N
VARIANT                 8
                        note = N or S
VARIANT                 9
                        note = N, H, W, R, or Y
VARIANT                 11
                        note = G, A, or N
source                  1..11
                        mol_type = protein
                        organism = synthetic construct
SEQUENCE: 745
RASQXIXXXL X                                                              11

SEQ ID NO: 746          moltype =    length =
SEQUENCE: 746
000

SEQ ID NO: 747          moltype =    length =
SEQUENCE: 747
000

SEQ ID NO: 748          moltype =    length =
SEQUENCE: 748
000

SEQ ID NO: 749          moltype =    length =
SEQUENCE: 749
000

SEQ ID NO: 750          moltype = AA   length = 8
FEATURE                 Location/Qualifiers
REGION                  1..8
                        note = Description of Artificial Sequence: Syntheticpeptide
VARIANT                 6
                        note = R or S
VARIANT                 7
                        note = N or S
VARIANT                 8
                        note = N, H, or W
source                  1..8
                        mol_type = protein
                        organism = synthetic construct
SEQUENCE: 750
ASQGIXXX                                                                   8

SEQ ID NO: 751          moltype = AA   length = 8
FEATURE                 Location/Qualifiers
REGION                  1..8
                        note = Description of Artificial Sequence: Syntheticpeptide
VARIANT                 4
                        note = G, S, or D
VARIANT                 6
                        note = R, S, or N
VARIANT                 7
                        note = N or S
VARIANT                 8
                        note = N, H, W, R, or Y
source                  1..8
                        mol_type = protein
                        organism = synthetic construct
SEQUENCE: 751
ASQXIXXX                                                                   8

SEQ ID NO: 752          moltype = AA   length = 7
FEATURE                 Location/Qualifiers
REGION                  1..7
                        note = Description of Artificial Sequence: Syntheticpeptide
VARIANT                 2
                        note = A or E
source                  1..7
                        mol_type = protein
                        organism = synthetic construct
SEQUENCE: 752
AXSSLQS                                                                    7

SEQ ID NO: 753          moltype =    length =
SEQUENCE: 753
```

```
SEQ ID NO: 754          moltype = AA  length = 10
FEATURE                 Location/Qualifiers
REGION                  1..10
                        note = Description of Artificial Sequence: Syntheticpeptide
VARIANT                 1
                        note = L or S
VARIANT                 6
                        note = A or E
source                  1..10
                        mol_type = protein
                        organism = synthetic construct
SEQUENCE: 754
XLIYAXSSLQ                                                                    10

SEQ ID NO: 755          moltype = AA  length = 10
FEATURE                 Location/Qualifiers
REGION                  1..10
                        note = Description of Artificial Sequence: Syntheticpeptide
VARIANT                 1
                        note = L or S
VARIANT                 3
                        note = I or V
VARIANT                 5
                        note = A, K, or S
VARIANT                 6
                        note = A, E, or V
VARIANT                 8
                        note = S, N, or T
VARIANT                 10
                        note = Q or E
source                  1..10
                        mol_type = protein
                        organism = synthetic construct
SEQUENCE: 755
XLXYXXSXLX                                                                    10

SEQ ID NO: 756          moltype =    length =
SEQUENCE: 756
000

SEQ ID NO: 757          moltype =    length =
SEQUENCE: 757
000

SEQ ID NO: 758          moltype = AA  length = 12
FEATURE                 Location/Qualifiers
REGION                  1..12
                        note = Description of Artificial Sequence: Syntheticpeptide
VARIANT                 2
                        note = A or E
source                  1..12
                        mol_type = protein
                        organism = synthetic construct
SEQUENCE: 758
AXSSLQSGVP SR                                                                 12

SEQ ID NO: 759          moltype = AA  length = 12
FEATURE                 Location/Qualifiers
REGION                  1..12
                        note = Description of Artificial Sequence: Syntheticpeptide
VARIANT                 1
                        note = A, K, or S
VARIANT                 2
                        note = A, E, or V
VARIANT                 4
                        note = S, N, or T
VARIANT                 6
                        note = Q or E
source                  1..12
                        mol_type = protein
                        organism = synthetic construct
SEQUENCE: 759
XXSXLXSGVP SR                                                                 12

SEQ ID NO: 760          moltype =    length =
SEQUENCE: 760
000
```

```
SEQ ID NO: 761           moltype =    length =
SEQUENCE: 761
000

SEQ ID NO: 762           moltype =    length =
SEQUENCE: 762
000

SEQ ID NO: 763           moltype =    length =
SEQUENCE: 763
000

SEQ ID NO: 764           moltype =    length =
SEQUENCE: 764
000

SEQ ID NO: 765           moltype =    length =
SEQUENCE: 765
000

SEQ ID NO: 766           moltype = AA   length = 124
FEATURE                  Location/Qualifiers
REGION                   1..124
                         note = Description of Artificial Sequence:
                          Syntheticpolypeptide
source                   1..124
                         mol_type = protein
                         organism = synthetic construct
SEQUENCE: 766
QVQLQESGPG LVKPSETLSL TCTVSGGSIS SYIWSWIRQP AGKGLEWIGR IYASGNTNYN   60
PSLKSRVTIS VDTSKNQFSL KLSSMTAADT AVYYCARDYR VAGTYYYYYG LDVWGQGTTV  120
TVSS                                                              124

SEQ ID NO: 767           moltype = AA   length = 110
FEATURE                  Location/Qualifiers
REGION                   1..110
                         note = Description of Artificial Sequence:
                          Syntheticpolypeptide
source                   1..110
                         mol_type = protein
                         organism = synthetic construct
SEQUENCE: 767
QSALTQPASV SGSPGQSITI SCTGTSSDVG VYDYVSWYQQ HPGKAPKLMI YEVSNRPSGV   60
SNRFSGSKSG NTASLTISGL QTEDEADYYC SSYTSRSTWV FGGGTKLTVL            110

SEQ ID NO: 768           moltype = AA   length = 454
FEATURE                  Location/Qualifiers
REGION                   1..454
                         note = Description of Artificial Sequence:
                          Syntheticpolypeptide
source                   1..454
                         mol_type = protein
                         organism = synthetic construct
SEQUENCE: 768
QVQLQESGPG LVKPSETLSL TCTVSGGSIS SYIWSWIRQP AGKGLEWIGR IYASGNTNYN   60
PSLKSRVTIS VDTSKNQFSL KLSSMTAADT AVYYCARDYR VAGTYYYYYG LDVWGQGTTV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
AAGAPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 769           moltype = AA   length = 216
FEATURE                  Location/Qualifiers
REGION                   1..216
                         note = Description of Artificial Sequence:
                          Syntheticpolypeptide
source                   1..216
                         mol_type = protein
                         organism = synthetic construct
SEQUENCE: 769
QSALTQPASV SGSPGQSITI SCTGTSSDVG VYDYVSWYQQ HPGKAPKLMI YEVSNRPSGV   60
SNRFSGSKSG NTASLTISGL QTEDEADYYC SSYTSRSTWV FGGGTKLTVL GQPKAAPSVT  120
LFPPSSEELQ ANKATLVCLI SDFYPGAVTV AWKADSSPVK AGVETTTPSK QSNNKYAASS  180
YLSLTPEQWK SHKSYSCQVT HEGSTVEKTV APTECS                           216

SEQ ID NO: 770           moltype = AA   length = 15
```

```
FEATURE             Location/Qualifiers
source              1..15
                    mol_type = protein
                    organism = synthetic construct
SEQUENCE: 770
KGGNCSEDLL CILKR                                                    15

SEQ ID NO: 771      moltype = AA  length = 17
FEATURE             Location/Qualifiers
source              1..17
                    mol_type = protein
                    organism = synthetic construct
SEQUENCE: 771
KTKLSWNKDG ILHGVRY                                                  17

SEQ ID NO: 772      moltype = AA  length = 12
FEATURE             Location/Qualifiers
source              1..12
                    mol_type = protein
                    organism = synthetic construct
SEQUENCE: 772
ATYYCQQYVT YP                                                       12

SEQ ID NO: 773      moltype = AA  length = 24
FEATURE             Location/Qualifiers
source              1..24
                    mol_type = protein
                    organism = synthetic construct
SEQUENCE: 773
QRTDSIPNSP DNVPLKGGNC SEDL                                          24

SEQ ID NO: 774      moltype = AA  length = 11
FEATURE             Location/Qualifiers
source              1..11
                    mol_type = protein
                    organism = synthetic construct
SEQUENCE: 774
GLEWVSGISW R                                                        11

SEQ ID NO: 775      moltype = AA  length = 13
FEATURE             Location/Qualifiers
source              1..13
                    mol_type = protein
                    organism = synthetic construct
SEQUENCE: 775
GGNCSEDLLC ILK                                                      13

SEQ ID NO: 776      moltype = AA  length = 16
FEATURE             Location/Qualifiers
source              1..16
                    mol_type = protein
                    organism = synthetic construct
SEQUENCE: 776
SLIYAASSLQ SGVPSR                                                   16

SEQ ID NO: 777      moltype = AA  length = 9
FEATURE             Location/Qualifiers
source              1..9
                    mol_type = protein
                    organism = synthetic construct
SEQUENCE: 777
IGFNWNYEG                                                            9

SEQ ID NO: 778      moltype = AA  length = 12
FEATURE             Location/Qualifiers
source              1..12
                    mol_type = protein
                    organism = synthetic construct
SEQUENCE: 778
LKGGNCSEDL LC                                                       12

SEQ ID NO: 779      moltype = AA  length = 22
FEATURE             Location/Qualifiers
source              1..22
                    mol_type = protein
                    organism = synthetic construct
SEQUENCE: 779
SLRLSCAASG FNFDDYAMHW VR                                            22
```

```
SEQ ID NO: 780            moltype = AA  length = 5
FEATURE                   Location/Qualifiers
source                    1..5
                          mol_type = protein
                          organism = synthetic construct
SEQUENCE: 780
RAPFK                                                                    5

SEQ ID NO: 781            moltype = AA  length = 5
FEATURE                   Location/Qualifiers
source                    1..5
                          mol_type = protein
                          organism = synthetic construct
SEQUENCE: 781
FDYWG                                                                    5

SEQ ID NO: 782            moltype = AA  length = 9
FEATURE                   Location/Qualifiers
source                    1..9
                          mol_type = protein
                          organism = synthetic construct
SEQUENCE: 782
KHLNKTKLS                                                                9

SEQ ID NO: 783            moltype = AA  length = 8
FEATURE                   Location/Qualifiers
source                    1..8
                          mol_type = protein
                          organism = synthetic construct
SEQUENCE: 783
LQSGVPSR                                                                 8

SEQ ID NO: 784            moltype = AA  length = 8
FEATURE                   Location/Qualifiers
source                    1..8
                          mol_type = protein
                          organism = synthetic construct
SEQUENCE: 784
AKHLNKTK                                                                 8

SEQ ID NO: 785            moltype = AA  length = 13
FEATURE                   Location/Qualifiers
source                    1..13
                          mol_type = protein
                          organism = synthetic construct
SEQUENCE: 785
ISWRSGNIGY ADS                                                          13

SEQ ID NO: 786            moltype = AA  length = 9
FEATURE                   Location/Qualifiers
source                    1..9
                          mol_type = protein
                          organism = synthetic construct
SEQUENCE: 786
VRYQDGNLV                                                                9
```

The invention claimed is:

1. An antibody or antigen binding fragment thereof that binds CD30L, wherein the antibody or antigen binding fragment thereof comprises:

(a) a heavy chain variable region complementarity determining region 1 (CDR-H1) comprising the amino acid sequence set forth in SEQ ID NO: 119; a heavy chain variable region complementarity determining region 2 (CDR-H2) comprising the amino acid sequence set forth in SEQ ID NO: 159; a heavy chain variable region complementarity determining region 3 (CDR-H3) comprising the amino acid sequence set forth in SEQ ID NO: 199; a light chain variable region complementarity determining region 1 (CDR-L1) comprising the amino acid sequence set forth in SEQ ID NO: 319; a light chain variable region complementarity determining region 2 (CDR-L2) comprising the amino acid sequence set forth in SEQ ID NO: 359; and a light chain variable region complementarity determining region 3 (CDR-L3) comprising the amino acid sequence set forth in SEQ ID NO: 399;

(b) a CDR-H1 comprising the amino acid sequence set forth in SEQ ID NO: 118; a CDR-H2 comprising the amino acid sequence set forth in SEQ ID NO: 158; a CDR-H3 comprising the amino acid sequence set forth in SEQ ID NO: 198; a CDR-L1 comprising the amino acid sequence setforthin SEQ IDNO: 318, a CDR-L2 comprising the amino acid sequence set forth in SEQ ID NO: 358; and a CDR-L3 comprising the amino acid sequence set forth in SEQ ID NO: 398.

(c) a CDR-H1 comprising the amino acid sequence setforthin SEQ ID NO: 117; a CDR-H2 comprising the amino acid sequence set forth in SEQ ID NO: 157; a CDR-H3 comprising the amino acid sequence set forth in SEQ ID NO: 197; a CDR-L1 comprising the amino acid sequence setforthin SEQ ID NO: 317, a CDR-L2 comprising the amino acid sequence set forth in SEQ ID NO: 357; and a CDR-L3 comprising the amino acid sequence set forth in SEQ ID NO: 397;
(d) a CDR-H1 comprising the amino acid sequence set forth in SEQ ID NO: 116; a CDR-H2 comprising the amino acid sequence set forth in SEQ ID NO: 156; a CDR-H3 comprising the amino acid sequence set forth in SEQ ID NO: 196; a CDR-L1 comprising the amino acid sequence set forth in SEQ ID NO: 316, a CDR-L2 comprising the amino acid sequence set forth in SEQ ID NO: 356; and a CDR-L3 comprising the amino acid sequence set forth in SEQ ID NO: 396;
(e) a CDR-H1 comprising the amino acid sequence set forth in SEQ ID NO: 115; a CDR-H2 comprising the amino acid sequence set forth in SEQ ID NO: 155; a CDR-H3 comprising the amino acid sequence set forth in SEQ ID NO: 195; a CDR-L1 comprising the amino acid sequence setforthin SEQ ID NO: 315, a CDR-L2 comprising the amino acid sequence set forth in SEQ ID NO: 355; and a CDR-L3 comprising the amino acid sequence set forth in SEQ ID NO: 395; or
(f) a CDR-H1 comprising the amino acid sequence set forth in SEQ ID NO: 629; a CDR-H2 comprising the amino acid sequence set forth in SEQ ID NO: 643; a CDR-H3 comprising the amino acid sequence set forth in SEQ ID NO: 657; a CDR-L1 comprising the amino acid sequence setforthin SEQ IDNO: 671, a CDR-L2 comprising the amino acid sequence set forth in SEQ ID NO: 685; and a CDR-L3 comprising the amino acid sequence set forth in SEQ ID NO: 699.

2. The antibody or antigen binding fragment thereof of claim 1, wherein the CDR-H1 comprises the amino acid sequence set forth in SEQ ID NO: 117, the CDR-H2 comprises the amino acid sequence set forth in SEQ ID NO: 157, the CDR-H3 comprises the amino acid sequence set forth in SEQ ID NO: 197, the CDR-L1 comprises the amino acid sequence set forth in SEQ ID NO: 317, the CDR-L2 comprises the amino acid sequence set forth in SEQ ID NO: 357, and the CDR-L3 comprises the amino acid sequence set forth in SEQ ID NO: 397.

3. The antibody or antigen binding fragment thereof of claim 1, wherein the CDR-H1 comprises the amino acid sequence set forth in SEQ ID NO: 115, the CDR-H2 comprises the amino acid sequence set forth in SEQ ID NO: 155, the CDR-H3 comprises the amino acid sequence set forth in SEQ ID NO: 195, the CDR-L1 comprises the amino acid sequence set forth in SEQ ID NO: 315, the CDR-L2 comprises the amino acid sequence set forth in SEQ ID NO: 355, and the CDR-L3 comprises the amino acid sequence set forth in SEQ ID NO: 395.

4. The antibody or antigen binding fragment thereof of claim 1, wherein the CDR-H1 comprises the amino acid sequence set forth in SEQ ID NO: 116, the CDR-H2 comprises the amino acid sequence set forth in SEQ ID NO: 156, the CDR-H3 comprises the amino acid sequence set forth in SEQ ID NO: 196, the CDR-L1 comprises the amino acid sequence set forth in SEQ ID NO: 316, the CDR-L2 comprises the amino acid sequence set forth in SEQ ID NO: 356, and the CDR-L3 comprises the amino acid sequence set forth in SEQ ID NO: 396.

5. The antibody or antigen binding fragment thereof of claim 1, wherein the CDR-H1 comprises the amino acid sequence set forth in SEQ ID NO: 118, the CDR-H2 comprises the amino acid sequence set forth in SEQ ID NO: 158, the CDR-H3 comprises the amino acid sequence set forth in SEQ ID NO: 198, the CDR-L1 comprises the amino acid sequence set forth in SEQ ID NO: 318, the CDR-L2 comprises the amino acid sequence set forth in SEQ ID NO: 358, and the CDR-L3 comprises the amino acid sequence set forth in SEQ ID NO: 398.

6. The antibody or antigen binding fragment thereof of claim 1, wherein the CDR-H1 comprises the amino acid sequence set forth in SEQ ID NO: 119, the CDR-H2 comprises the amino acid sequence set forth in SEQ ID NO: 159, the CDR-H3 comprises the amino acid sequence set forth in SEQ ID NO: 199, the CDR-L1 comprises the amino acid sequence set forth in SEQ ID NO: 319, the CDR-L2 comprises the amino acid sequence set forth in SEQ ID NO: 359, and the CDR-L3 comprises the amino acid sequence set forth in SEQ ID NO: 399.

7. The antibody or antigen binding fragment thereof of claim 1, wherein the CDR-H1 comprises the amino acid sequence set forth in SEQ ID NO: 629, the CDR-H2 comprises the amino acid sequence set forth in SEQ ID NO: 643, the CDR-H3 comprises the amino acid sequence set forth in SEQ ID NO: 657, the CDR-L1 comprises the amino acid sequence set forth in SEQ ID NO: 671, the CDR-L2 comprises the amino acid sequence set forth in SEQ ID NO: 685, and the CDR-L3 comprises the amino acid sequence set forth in SEQ ID NO: 699.

8. The antibody or antigen binding fragment thereof of claim 1, comprising a VH and a VL, wherein:
(a) the VH comprises an amino acid sequence having at least about 90% sequence identity to SEQ ID NO: 6; and
(b) the VL comprises an amino acid sequence having at least about 90% sequence identity to SEQ ID NO: 8.

9. The antibody or antigen binding fragment thereof of claim 1, wherein the antibody or antigen binding fragment thereof comprises:
(a) a VH comprising an amino acid sequence set forth in SEQ ID NO: 6; and (b) a VL comprising an amino acid sequence set forth in SEQ ID NO: 8.

10. The antibody or antigen binding fragment thereof of claim 6, wherein the antibody or antigen binding fragment thereof comprises:
(a) a VH comprising an amino acid sequence set forth in SEQ ID NO: 5; and (b) a VL comprising an amino acid sequence set forth in SEQ ID NO: 7.

11. The antibody or antigen binding fragment thereof of claim 9, further comprising an IgG constant region.

12. The antibody or antigen binding fragment thereof of claim 11, wherein the IgG constant region comprises an amino acid sequence having 95% sequence identity to the amino acid sequence set forth by any one of SEQ ID NOs: 500-512.

13. The antibody or antigen binding fragment thereof of claim 12, wherein the IgG constant region comprises the amino acid sequence set forth by any one of SEQ ID NOs: 500-512.

14. The antibody or antigen binding fragment thereof of claim 11, wherein the IgG constant region comprises the amino acid sequence set forth by SEQ ID NO: 504.

15. The antibody or antigen binding fragment thereof of claim 13, wherein the IgG constant region has reduced antibody-dependent cell-mediated cytotoxicity (ADCC) function as compared to human IgG1, reduced complement-dependent cytotoxicity (CDC) as compared to human IgG1, or both reduced ADCC and reduced CDC as compared to human IgG1.

16. The antibody or antigen binding fragment thereof of claim 1, wherein the antibody or antigen binding fragment thereof is an antibody and the antibody is an IgG antibody.

17. The antibody of claim 16, wherein the IgG antibody is IgG1, IgG2, IgG3, or IgG4.

18. The antibody or antigen binding fragment thereof of claim 2, wherein the antibody or antigen binding fragment thereof is an antibody and the antibody is an IgG antibody.

19. The antibody of claim 18, wherein the IgG antibody is IgG1, IgG2, IgG3, or IgG4.

20. The antibody or antigen binding fragment thereof of claim 3, wherein the antibody or antigen binding fragment thereof is an antibody and the antibody is an IgG antibody.

21. The antibody of claim 20, wherein the IgG antibody is IgG1, IgG2, IgG3, or IgG4.

22. The antibody or antigen binding fragment thereof of claim 4, wherein the antibody or antigen binding fragment thereof is an antibody and the antibody is an IgG antibody.

23. The antibody of claim 22, wherein the IgG antibody is IgG1, IgG2, IgG3, or IgG4.

24. The antibody or antigen binding fragment thereof of claim 5, wherein the antibody or antigen binding fragment thereof is an antibody and the antibody is an IgG antibody.

25. The antibody of claim 24, wherein the IgG antibody is IgG1, IgG2, IgG3, or IgG4.

26. The antibody or antigen binding fragment thereof of claim 6, wherein the antibody or antigen binding fragment thereof is an antibody and the antibody is an IgG antibody.

27. The antibody of claim 26, wherein the IgG antibody is IgG1, IgG2, IgG3, or IgG4.

28. The antibody or antigen binding fragment thereof of claim 7, wherein the antibody or antigen binding fragment thereof is an antibody and the antibody is an IgG antibody.

29. The antibody of claim 28, wherein the IgG antibody is IgG1, IgG2, IgG3, or IgG4.

30. The antibody or antigen binding fragment thereof of claim 1, wherein the antibody or antigen binding fragment thereof is human, chimeric, or humanized.

\* \* \* \* \*